United States Patent
Kwon et al.

(10) Patent No.: US 11,325,952 B2
(45) Date of Patent: May 10, 2022

(54) LIGHT-GATED SIGNALING MODULATION

(71) Applicant: Korea University Research and Business Foundation, Seoul (KR)

(72) Inventors: Hyungbae Kwon, Jupiter, FL (US); Dongmin Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 724 days.

(21) Appl. No.: 16/079,773

(22) PCT Filed: Feb. 23, 2017

(86) PCT No.: PCT/EP2017/054246
§ 371 (c)(1),
(2) Date: Aug. 24, 2018

(87) PCT Pub. No.: WO2017/144620
PCT Pub. Date: Aug. 31, 2017

(65) Prior Publication Data
US 2020/0010513 A1 Jan. 9, 2020

Related U.S. Application Data

(60) Provisional application No. 62/299,214, filed on Feb. 24, 2016.

(30) Foreign Application Priority Data

May 17, 2016 (EP) ..................................... 16169851

(51) Int. Cl.
| | |
|---|---|
| C07K 14/415 | (2006.01) |
| A61K 49/00 | (2006.01) |
| C12N 9/64 | (2006.01) |
| C12N 15/62 | (2006.01) |
| G01N 33/50 | (2006.01) |

(52) U.S. Cl.
CPC ........ *C07K 14/415* (2013.01); *A61K 49/0004* (2013.01); *A61K 49/0045* (2013.01); *C12N 9/6472* (2013.01); *C12N 15/62* (2013.01); *C12Y 304/22044* (2013.01); *G01N 33/5008* (2013.01); *C07K 2319/03* (2013.01); *C07K 2319/22* (2013.01); *C07K 2319/41* (2013.01); *C07K 2319/43* (2013.01); *C07K 2319/50* (2013.01)

(58) Field of Classification Search
CPC ........ C07H 21/00; C07H 21/02; C07H 21/04; A61K 49/0047; A61K 49/0004; A61K 49/0045; C07K 2319/03; C07K 14/415; C07K 2319/50; C07K 2319/22; C07K 2319/43; C07K 2319/41; C12N 9/6472; C12N 15/62; G01N 33/542; G01N 33/5008; C12Y 304/22044
USPC ..................................... 536/23.1, 23.2, 23.3
See application file for complete search history.

*Primary Examiner* — Jana A Hines
(74) *Attorney, Agent, or Firm* — NSIP Law

(57) ABSTRACT

The present invention relates to a nucleic acid molecule encoding a fusion protein, wherein the nucleic acid molecule comprises: (a) a first nucleic acid sequence encoding a first biosensor, wherein said first biosensor is a first molecule capable of interacting with a second molecule; (b) a second nucleic acid sequence encoding an effector-activating module, wherein the effector-activating module comprises a nucleic acid sequence encoding a first part of a protease, wherein said first part of the protease is capable of interacting with a second part of said protease to form an active form of said protease; (c) a third nucleic acid sequence encoding a third biosensor comprising a protease cleavage site, wherein the protease cleavage site is sterically occluded in the absence of a stimulus for said third biosensor and wherein the protease cleavage site becomes accessible in the presence of said stimulus.

17 Claims, 30 Drawing Sheets

Figure 1:
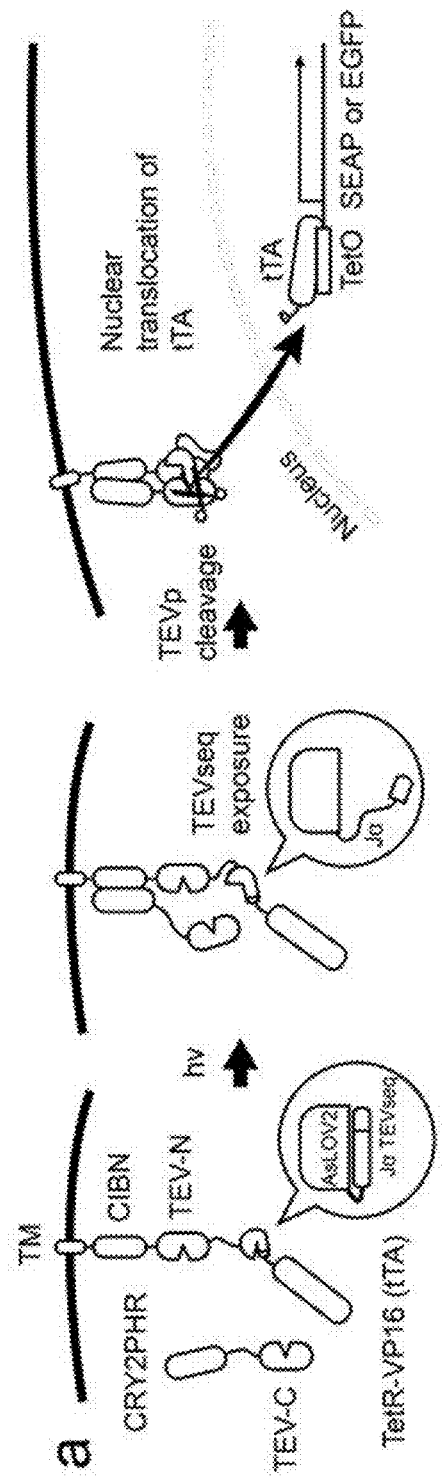
Figure 1:
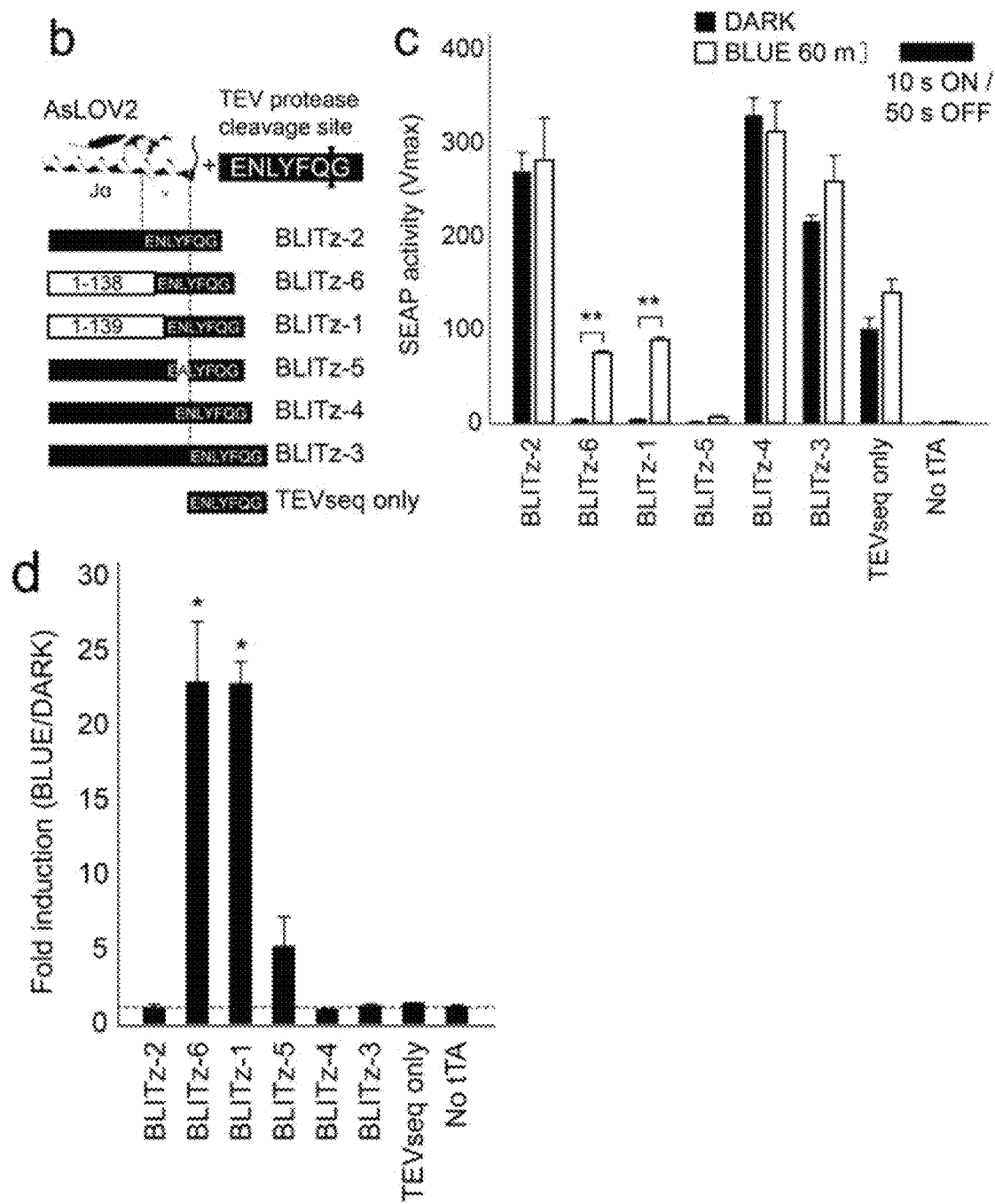
Figure 1:
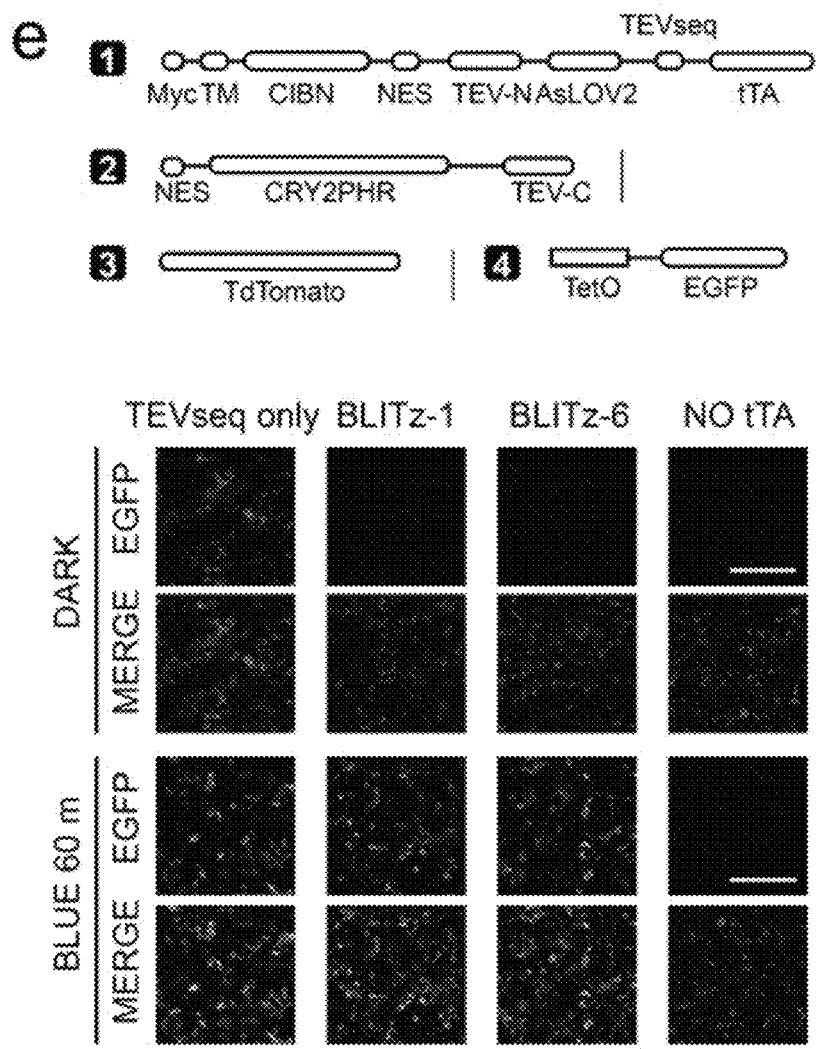
Figure 1:
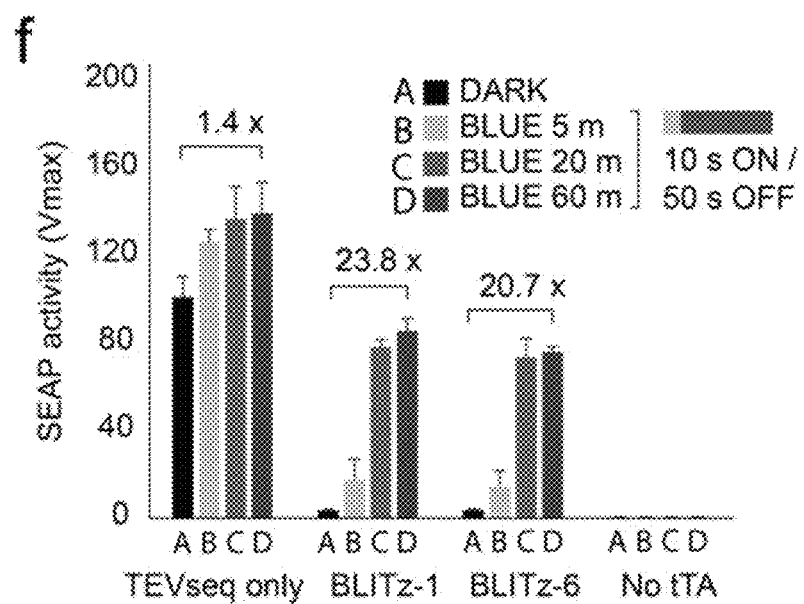
Figure 1:
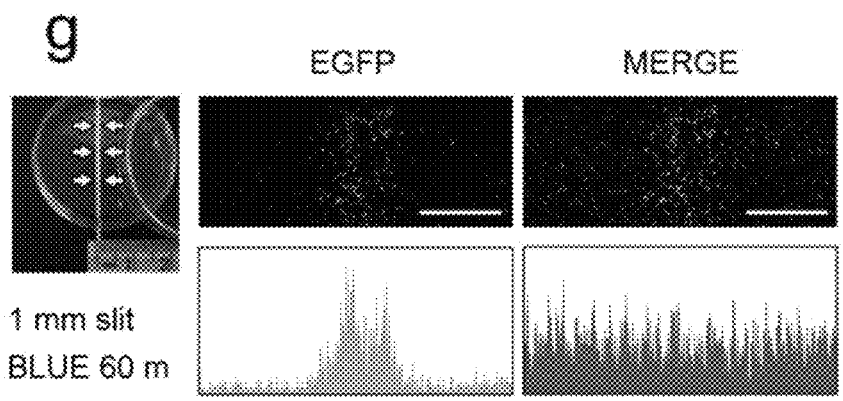

Specification includes a Sequence Listing.

CMV:: NES-CRY2PHR-TEV-C
5961 bp

▣ Synthesized neucleotides
synthesized from Eurofins Genomics (USA)

❶ PCR amplification of CRY2PHR

Template:
pCRY2PHR-mCherryN1
Addgene #26866

Primer list (5'-3')

❶ XhoI-CRY2PHR-FW - AAACTCGAGGCCACCATGAAGATGGACAAAAAGAC
CRY2PHR-PstI-RV - TTTGCTAGCTGCTGCTCCGATCATGATCTG

A)

LIGHT-GATED SIGNALING MODULATION

The present invention relates to a nucleic acid molecule encoding a fusion protein, wherein the nucleic acid molecule comprises: (a) a first nucleic acid sequence encoding a transmembrane domain linked to a first biosensor, wherein said first biosensor is a first molecule capable of interacting with a second molecule to form part of a first inducible interaction module, and wherein said first biosensor is linked to the transmembrane domain such that the first biosensor is located intracellularly upon expression of the fusion protein in a cell; (b) a second nucleic acid sequence encoding an effector-activating module, wherein the effector-activating module comprises: (i) a nucleic acid sequence encoding a first part of a protease, wherein said first part of the protease is capable of interacting with a second part of said protease to form an active form of said protease; or (ii) a nucleic acid sequence encoding a second biosensor, wherein said second biosensor is a first molecule capable of interacting with a second molecule to form part of a second inducible interaction module; (c) a third nucleic acid sequence encoding a third biosensor comprising a protease cleavage site, wherein the protease cleavage site is sterically occluded in the absence of a stimulus for said third biosensor and wherein the protease cleavage site becomes accessible in the presence of said stimulus; and (d) a fourth nucleic acid sequence encoding an effector molecule. The present invention further relates to a vector comprising the nucleic acid molecule of the invention, to sets of nucleic acid molecules, to the sets of nucleic acid molecules of the invention comprised in one or more vectors, to a cell expressing a set of nucleic acid molecules according to the invention as well as to a cell comprising the one or more vectors of the invention. Furthermore, the present invention relates to a method for inducing intracellular signaling, as well as to a method for monitoring intracellular signaling.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

One of the ongoing challenges in scientific research is the analysis of complex networks underlying cellular functions. In the last decade, a wide variety of methods to study protein-protein interactions ranging from biochemical to genetic or cell-based approaches, such as affinity purification, co-immunoprecipitation as well as yeast two-hybrid systems, have been developed. In addition, fluorescence-based methods for in-cell visualization of protein-protein-interactions have been introduced, including e.g. fluorescence resonance energy transfer (FRET) and bimolecular fluorescence complementation (BiFC), both of which are based on the expression of fluorescently labeled proteins or fragments thereof. However, the analysis of live events in cells still remains a challenge.

In particular the visualization of brain function has been a long-lasting challenge. Imaging neuromodulation is as important as mapping neuronal activity in a brain. Visualizing neuromodulatory states in specific neural circuits is critical to understanding the diversity of animal behavior, sensation, and cognitive functions. In recent decades, a large array of genetic or optical techniques has been developed to label neuronal structure and activities (Alvarez, V. A. & Sabatini, B. L. Anatomical and physiological plasticity of dendritic spines. *Annual review of neuroscience* 30, 79-97 (2007); Bhatt, D. H., Zhang, S. & Gan, W. B. Dendritic spine dynamics. *Annual review of physiology* 71, 261-282, (2009); Chen, T. W. et al. Ultrasensitive fluorescent proteins for imaging neuronal activity. *Nature* 499, 295-300, (2013)). However, no useful genetically-encoded neuromodulation mapping techniques have been developed so far and none of the previous efforts have led to useful methods for visualizing modulatory actions in the brain.

Also the identification and manipulation of active neural circuits that are indispensable for specific actions or perception has been a long-lasting challenge in modern neuroscience. The possible approach should label a subset of neurons selectively in the pool of thousands of neurons that have similar structural and functional characteristics. The recently developed genetically encoded calcium indicators (GECIs) enable the monitoring of active populations of neurons while animals are performing a particular task (Chen, T. W. et al. Ultrasensitive fluorescent proteins for imaging neuronal activity. *Nature* 499, 295-300, (2013)). The degree of sensitivity of this approach is sufficient to detect a $Ca^{2+}$ rise elicited by a single action potential as well as at individual synapses (Chen, T. W. et al. Ultrasensitive fluorescent proteins for imaging neuronal activity. *Nature* 499, 295-300, (2013)). However, all GECI signals decay back to the basal level within short time window of a few seconds and, therefore, only limited brain areas are available for visualization at a time. To supplement this limitation, a designed calcium integrator named CAMPARI has recently been developed (Fosque, B. F. et al. Neural circuits. Labeling of active neural circuits in vivo with designed calcium integrators. *Science* 347, 755-760, (2015)). This technique uses irreversible photo-conversion of an EosFP upon high $Ca^{2+}$ and violet light, such that a group of active neurons can be captured at a specific time point with high temporal resolution. However, fluorescence can only be visualized under low calcium concentrations, so the sample needs to be incubated in the presence of a calcium buffer such as ethylene glycol tetraacetic acid (EGTA). This fact limits the applicability of this system to post-hoc analysis of sampled tissues or neuronal cultures. Furthermore, photo-conversion does not modify or amend downstream protein signaling or gene expression, and thus does not enable for the testing of a causal relationship between neuronal function and behavior.

As alternative approaches, a couple of activity-dependent gene expression systems have been developed to label functional neuronal ensembles. One method that is widely used is the visualization of immediate-early gene (IEG) expression such as c-fos or Arc (Barth, A. L., Gerkin, R. C. & Dean, K. L. Alteration of neuronal firing properties after in vivo experience in a FosGFP transgenic mouse. *The Journal of neuroscience: the official journal of the Society for Neuroscience* 24, 6466-6475, (2004); Inoue, M. et al. Synaptic activity-responsive element (SARE): A unique genomic structure with an unusual sensitivity to neuronal activity. *Communicative & integrative biology* 3, 443-446, (2010); Okuno, H. et al. Inverse synaptic tagging of inactive synapses via dynamic interaction of Arc/Arg3.1 with CaM-KIIbeta. *Cell* 149, 886-898, (2012); Smeyne, R. J. et al. fos-lacZ transgenic mice: mapping sites of gene induction in the central nervous system. *Neuron* 8, 13-23 (1992).).

IEG expression is induced by transcription factors converged from various calcium-dependent signaling cascades (Bito, H., Deisseroth, K. & Tsien, R. W. Ca2+-dependent regulation in neuronal gene expression. *Current opinion in neurobiology* 7, 419-429 (1997); Flavell, S. W. & Greenberg, M. E. Signaling mechanisms linking neuronal activity to gene expression and plasticity of the nervous system. *Annual review of neuroscience* 31, 563-590, (2008)). Taking advantage of the gene expression, this technique was further engineered to express various reporter genes under IEG promoters. Using these approaches, recent studies successfully triggered artificial memory by manipulating a labeled neuronal ensemble, thus demonstrating evidence of sufficiency for specific behavior (Garner, A. R. et al. Generation of a synthetic memory trace. *Science* 335, 1513-1516, (2012); Liu, X. et al. Optogenetic stimulation of a hippocampal engram activates fear memory recall. *Nature* 484, 381-385, (2012)). Furthermore, the magnitude of gene expression was highly enhanced by putting several activity-dependent transcription factors together (Kawashima, T. et al. Functional labeling of neurons and their projections using the synthetic activity-dependent promoter E-SARE. *Nature methods* 10, 889-895, (2013)). Although IEG system and its derivatives have the capability of gene manipulation, all these activity-dependent gene markers are nonetheless not able to faithfully reflect individual neuronal activity as precisely as GECIs, and the quantitative correlation with neuronal activity is weak.

Furthermore, there exists a plethora of general systems based on reporter activation for investigating protein-protein interactions and compounds affecting same. For example, U.S. Pat. No. 8,574,865 describes general methods and assays for identifying a compound that modulates a protein-protein interaction. These methods and assays make use of an inactive reporter activating protein, which becomes activated as the consequence of protease-mediated cleavage of a protease cleavage site interposed between two portions of the inactive reporter activating protein. If protein-protein interaction is induced by a test compound, this interaction will lead to activation of the reporter activating protein and the respective signal produced by the reporter can be detected.

Light-inducible gene expression is another approach that is currently employed in the art. For example, WO92/19724 describes light-regulated DNA sequences that are capable of promoting the expression of heterologous genes in transgenic plants. The method makes use of light-inducible promoters, in particular the chalcone synthase promoter.

Kennedy et al. 2010 (Kennedy, M. J. et al. Rapid blue-light-mediated induction of protein interactions in living cells. *Nature methods* 7, 973-975, (2010)) describe the use of genetically encoded light-inducible protein interaction modules based on *Arabidopsis thaliana* cryptochrome 2 (CRY2) and CIB1, in combination with split effector molecules, such as the Gal4 transcription factor or Cre recombinase. Upon light induction, the photosensor CRY2 binds to the HLH protein CIB1 without the need for an exogenous chromophore, thereby reconstituting the split parts of the respective effector molecule.

Motta-Mena et al. 2014 describe an inducible promoter system based on the EL222 bacterial transcription factor. This transcription factor contains two minimal elements: a photosensory LOV domain and a helix-turn-helix DNA-binding domain. In the dark, both domains are bound to each other, which results in the covering of the HTH-DNA-binding domain, thereby preventing dimerisation and DNA-binding. Blue light illumination leads to the formation of protein/flavin adduct within the LOV domain, which disrupts the inhibitory LOV/HTH interaction and allows EL222 to dimerise and bind DNA.

Guntas et al. 2015 (Guntas, G. et al. Engineering an improved light-induced dimer (iLID) for controlling the localization and activity of signaling proteins. *Proceedings of the National Academy of Sciences of the United States of America* 112, 112-117, (2015)) describe the engineering of the AsLOV2 domain to make it more light-sensitive, i.e. reducing the amount of activity in the dark (leakiness) and, thus, increasing the effect seen upon light-activation. The AsLOV2 domain is used as a fusion construct with the SsrA peptide. In the dark, binding to the binding partner SspB is prevented by steric occlusion, but upon light activation, SsrA becomes sterically available due to the conformational change in AsLOV2 and binds to SspB, making this system a light-inducible heterodimer pair.

WO 2015/120548 describes proteins derived from fluorescent proteins that are photocleavable, i.e. they dissociated into two distinct fragments or release one end of an internal loop upon illumination. As a consequent, the proteins change their fluorescence or become non-fluorescent.

The currently best gene-based method among the known methods suitable for neuromodulation mapping is the so-called "Tango" system, a tool for visualizing brain states by labeling neuromodulator-sensitive neuronal populations (Barnea, G. et al. The genetic design of signaling cascades to record receptor activation. *Proceedings of the National Academy of Sciences of the United States of America* 105, 64-69, (2008); Inagaki, H. K. et al. Visualizing neuromodulation in vivo: TANGO-mapping of dopamine signaling reveals appetite control of sugar sensing. *Cell* 148, 583-595, (2012); Jagadish, S., Barnea, G., Clandinin, T. R. & Axel, R. Identifying functional connections of the inner photoreceptors in *Drosophila* using Tango-Trace. *Neuron* 83, 630-644, (2014)). This genetic-based labeling technique was originally designed to monitor metabotropic G-coupled receptor activation (Barnea, G. et al. The genetic design of signaling cascades to record receptor activation. *Proceedings of the National Academy of Sciences of the United States of America* 105, 64-69, (2008)), but has also been used to map neuromodulation in *Drosophila* (Inagaki, H. K. et al. Visualizing neuromodulation in vivo: TANGO-mapping of dopamine signaling reveals appetite control of sugar sensing. *Cell* 148, 583-595, (2012); Jagadish, S., Barnea, G., Clandinin, T. R. & Axel, R. Identifying functional connections of the inner photoreceptors in *Drosophila* using Tango-Trace. *Neuron* 83, 630-644, (2014)), examine lipid metabolism (Kono, M. et al. Sphingosine-1-phosphate receptor 1 reporter mice reveal receptor activation sites in vivo. *The Journal of clinical investigation* 124, 2076-2086, (2014)), and perform drug screens of human GPCRs (Kroeze, W. K. et al. PRESTO-Tango as an open-source resource for interrogation of the druggable human GPCRome. *Nature structural & molecular biology* 22, 362-369, (2015)). However, the Tango system has never been used in a mammalian brain, mainly because of high level of ligand-independent background signals and poor signal-to-noise ratio. These technical limitations as well as the inability of specific antagonists to block ligand-induced gene expression (Inagaki, H. K. et al. Visualizing neuromodulation in vivo: TANGO-mapping of dopamine signaling reveals appetite control of sugar sensing. *Cell* 148, 583-595, (2012)) have limited the application of the Tango system to studies of phasic neuromodulatory states.

Thus, despite the fact that a lot of effort is currently being invested into the development of methods for monitoring and modulating cell signaling, in particular for neuromodulation mapping, these methods typically suffer from poor signal-to-noise ratios, usually because of ligand-independent background signals. Accordingly, there is still a need to provide alternative methods for monitoring and/or modulating cell signaling, for tagging neuromodulatory action, and in particular for monitoring and/or modulating behaviorally-related neuromodulatory action. Such methods would represent valuable research tools and would offer tremendous value to the field.

This need is addressed by the provision of the embodiments characterized in the claims.

Accordingly, the present invention relates to a nucleic acid molecule encoding a fusion protein, wherein the nucleic acid molecule comprises: (a) a first nucleic acid sequence encoding a transmembrane domain linked to a first biosensor, wherein said first biosensor is a first molecule capable of interacting with a second molecule to form part of a first inducible interaction module, and wherein said first biosensor is linked to the transmembrane domain such that the first biosensor is located intracellularly upon expression of the fusion protein in a cell; (b) a second nucleic acid sequence encoding an effector-activating module, wherein the effector-activating module comprises: (i) a nucleic acid sequence encoding a first part of a protease, wherein said first part of the protease is capable of interacting with a second part of said protease to form an active form of said protease; or (ii) a nucleic acid sequence encoding a second biosensor, wherein said second biosensor is a first molecule capable of interacting with a second molecule to form part of a second inducible interaction module; (c) a third nucleic acid sequence encoding a third biosensor comprising a protease cleavage site, wherein the protease cleavage site is sterically occluded in the absence of a stimulus for said third biosensor and wherein the protease cleavage site becomes accessible in the presence of said stimulus; and (d) a fourth nucleic acid sequence encoding an effector molecule.

In accordance with the present invention, the term "nucleic acid molecule", also referred to as nucleic acid sequence or polynucleotide herein, includes DNA, such as cDNA or genomic DNA, and RNA. It is understood that the term "RNA" as used herein comprises all forms of RNA including mRNA. Both, single-strand as well as double-strand nucleic acid molecules are encompassed by this term.

The nucleic acid molecules of the invention can e.g. be synthesized by standard chemical synthesis methods, produced semi-synthetically, i.e. by combining parts synthesized by chemical synthesis with parts that are isolated from natural sources, or produced recombinantly, i.e. by combining parts that are isolated from natural sources. Ligation of the coding sequences to transcriptional regulatory elements and/or to other amino acid encoding sequences can be carried out using established methods, such as restriction digests, ligations and molecular cloning.

In accordance with the present invention, the nucleic acid molecule encodes a fusion protein. The term "fusion protein", as used herein, relates to a construct in which (poly)peptides are fused together that do not naturally occur in such a combination. For example, the (poly)peptides may naturally occur as separate molecules. Such a fusion is achieved by the joining of two or more nucleic acid sequences that originally coded for separate molecules, i.e. the fusion protein of the invention is produced by recombinant DNA technology, i.e. genetic engineering. Translation of these fused nucleic acid sequences results in a fusion protein, with functional properties derived from each of the original molecules. Suitable methods for creating such fused nucleic acid sequences by recombinant DNA technology as well as suitable vectors for expression of the fusion proteins are well established in the art, e.g. in Molecular Cloning: A laboratory Manual (Fourth Edition) by Michael R. Green and Joseph Sambrook. In accordance with the present invention, the term "fusion protein" does not encompass conjugate proteins obtained by chemically linking two (or more) separate (poly)peptides, i.e. by expressing the separate (poly)peptides and, after their expression, chemically linking them to form a conjugate.

The term "comprising", as used herein, denotes that further components and/or steps can be included in addition to the specifically recited components and/or steps. However, this term also encompasses that the claimed subject-matter consists of exactly the recited components and/or steps.

In those embodiments where the nucleic acid molecule encoding the fusion protein includes more than the recited sequences, additional sequences may include for example sequences introduced for purification, to ensure correct intracellular translocation or to enable appropriate processing of the transcript as well as peptide linker sequences. Purification sequences typically encoding peptides that confer on the resulting fusion protein an affinity to certain chromatography column materials. Typical examples for such peptides include, without being limiting, the T7 tag, the Xpress tag, myc tags, oligohistidine-tags, Strep-tags, FLAG-tags, glutathione S-transferase, maltose-binding protein or the albumin-binding domain of protein G. Particularly preferred sequences are the T7 tag (having the sequence MASMTGGQQMG (SEQ ID NO:26)), the Xpress tag (having the sequence DLYDDDDK (SEQ ID NO:27)) or the myc tag (having the sequence EQKLISEEDL (SEQ ID NO:28)). Non-limiting examples of sequences that ensure correct intracellular translocation include nuclear export sequences, such as e.g. the sequence LQLPPLERLTLE (SEQ ID NO:29) or the IgK leader sequence (e.g. METDTLLLWVLLL-WVPGSTGD; SEQ ID NO:30) employed in the appended examples. Non-limiting examples of sequences that enable appropriate processing of the transcript e.g. in bicistronic systems include a P2A, such as e.g. the sequence ATNFSLLKQAGDVEENPGP (SEQ ID NO: 31) employed in the appended examples. Linker sequences are sequences that connect the individual amino acid sequences encoded by the nucleic acid molecule with each other. A peptide linker as envisaged by the present invention is a linker of at least 1 amino acid in length. Preferably, the linker is 1 to 100 amino acids in length. More preferably, the linker is 2 to 50 amino acids in length and even more preferably, the linker is 5 to 20 amino acids in length. Preferably, the linker is a flexible linker comprising or consisting of the amino acids glycine, serine, arginine, leucine and/or glutamic acid. Preferably the linker sequences comprise or consist of a sequence selected from the group consisting of GGGGSGGGGSGGGGRSGGS (SEQ ID NO:32), GGSGGLEG (SEQ ID NO:33), GGGGRSGGGGS (SEQ ID NO:34), GGGGSGGGGSGGGG (SEQ ID NO:35) and GSGSG (SEQ ID NO:36). More preferably, the linker comprises or consists of the sequence GSGSG or GGGGSGGGGSGGGG. The length and sequence of a suitable linker depends on the composition of the respective fusion protein. Methods to test the suitability of different linkers are well known in the art and include e.g. the comparison of the binding affinity or the protein stability or the production yield of the fusion protein of the invention to the same fusion proteins that comprise different linkers.

In accordance with the present invention, the nucleic acid molecule encoding the fusion protein comprises at least the specifically recited elements (a) to (d), preferably in the recited order, i.e. (a), (b), (c) and (d). This order can be either starting from the N-terminal residue and ending with the most C-terminal residue (N→C) or vice versa, i.e. starting from the C-terminal residue and ending with the most N-terminal residue (C→N). Preferably, the order is from N- to C-terminal, i.e. N→C. More preferably, the nucleic acid molecule of the invention comprises additional linker sequences between each of (a), (b), (c) and (d).

In accordance with the present invention, the nucleic acid molecule encoding the fusion protein comprises a first nucleic acid sequence encoding a transmembrane domain linked to a first biosensor, wherein said first biosensor is linked to the transmembrane domain such that the first biosensor is located intracellularly upon expression of the fusion protein in a cell.

The "transmembrane domain", in accordance with the present invention, relates to an amino acid sequence, typically a hydrophobic amino acid sequence, that forms a polypeptide that spans once or several times through the phospholipid membrane of cell. In those cases where the transmembrane domain spans only once through the membrane, one part of the transmembrane domain is located on the outside of the cell and another part of the transmembrane domain is located at the inside of the cell, i.e. intracellularly. There is no particular restriction as to which part of the transmembrane domain is intracellular and which part is extracellular. However, typically, the N-terminal part is located extracellularly and the C-terminal part is located intracellularly. Preferably, the intracellular part is the C-terminus. In those cases where the transmembrane domain spans several times through the membrane, situations can arise wherein both ends of the transmembrane domain are located on the same side of the cell, i.e. either intra- or extracellularly. In that case it is necessary that a transmembrane domain is chosen for which, upon expression in a cell, both the N- and the C-terminus are located intracellularly.

The transmembrane domain can be a functional, naturally occurring molecule, such as e.g. a receptor or channel. Alternatively, the transmembrane domain can be an amino acid sequence that does not naturally occur as such in a cell but that forms a polypeptide that spans through the membrane, thereby forming an anchor at the internal surface of the cell.

Non limiting examples of transmembrane domains include G-protein coupled receptors (GPCR), such as e.g. DRD2 or part of the PDGF receptor as shown in the appended examples, as well as e.g. the CD28 transmembrane domain (represented in SEQ ID NO:37 and 38) or the CD8a transmembrane domain (represented in SEQ ID NO:39 and 40). A preferred transmembrane domain including parts of the PDGF receptor is shown in SEQ ID NOs:41 and 42, including an IgK leader sequence, a myc tag, parts of the PDGF receptor and a C-terminal linker sequence.

The main function of the transmembrane domain is to keep the fusion protein encoded by the nucleic acid molecule of the invention at a particular location within the cell by anchoring same in the membrane. In this way, the effector molecule is also kept at this location until its release, as described further below.

Linked to the part of the transmembrane domain that is located intracellularly upon expression in a cell is a first biosensor. The biosensor can be linked to any portion of the transmembrane domain that, after expression in a cell, is located intracellularly, preferably to the intracellular terminus of the amino acid sequence representing the transmembrane domain. If both termini are present inside the cell upon expression, the biosensor is preferably linked to the C-terminal end of the transmembrane domain.

The term "linked", as used herein, refers to the covalent connection of two sequences, either directly via a peptide bond between one amino acid of the transmembrane domain and one amino acid of the first biosensor, or indirectly via a peptide linker, as described above. Preferably, a linking sequence is encompassed between the transmembrane domain and the first biosensor. Non-limiting examples of linking amino acid sequences have been provided above. Additional examples include the sequence ACGGGGSGGGGSGGGGRSGGSMLQLPPLERLTLE (SEQ ID NO:43) as employed in the construct shown in SEQ ID NO:1, the sequence LQLPPLERLTLGGSGGLE (SEQ ID NO:44) as employed in the construct shown in SEQ ID NO:3, the sequence LQLPPLERLTLGGSGGLEG (SEQ ID NO:45) as employed in the construct shown in SEQ ID NO:5 or the sequence ACGGGGSGGGGSGGGGR (SEQ ID NO:46) as employed in the construct shown in SEQ ID NO:8.

The term "biosensor", as used herein, relates to a molecule capable of sensing, i.e. detecting, a biological stimulus. Non-limiting examples of such stimuli are light, pharmacological drugs, chemicals, the binding of an interaction partner such as e.g. a ligand, as well as the presence of molecules such as e.g. ions, in particular calcium.

In the presence of the respective stimulus, said first biosensor interacts with a second molecule to form part of a first inducible interaction module. Such interaction modules are referred to herein as "inducible" interaction modules, because the interaction between the respective individual molecules only occurs in the presence of the respective stimulus, i.e. it is induced in the presence of the stimulus. It will be appreciated that this interaction is reversible, i.e. in the absence of the stimulus the interaction partners can separate again and, thus, can subsequently again be induced to interact should the stimulus be present again.

Examples of such inducible interaction modules are well known in the art and include, without being limiting, light inducible interaction modules, such as e.g. CRY2PHR and CIBN, PIF and PhyB or LOV and LOV; ligand-inducible interaction modules, such as e.g. G protein-coupled receptors or parts thereof, such as e.g. V2tail, and β-arrestin2; calcium-inducible modules such as e.g. calmodulin with M13 or M13 variants with different calcium affinities; as well as drug inducible systems, such as e.g. rapamycin or kinase/phosphatase-inducible systems, e.g. MAPK or receptor tyrosine kinases. These systems have been described in the art, e.g. in Chen, T. W. et al. Ultrasensitive fluorescent proteins for imaging neuronal activity. *Nature* 499, 295-300, doi:10.1038/nature12354 (2013); Zhang, K. & Cui, B. Optogenetic control of intracellular signaling pathways. *Trends in biotechnology* 33, 92-100, doi:10.1016/j.tibtech.2014.11.007 (2015); Barnea, G. et al. The genetic design of signaling cascades to record receptor activation. *Proceedings of the National Academy of Sciences of the United States of America* 105, 64-69, doi:10.1073/pnas.0710487105 (2008).

In accordance with the present invention, the nucleic acid molecule encoding the fusion protein further comprises a second nucleic acid sequence encoding an effector-activating module.

The term "effector-activating module" relates to a molecule that is capable of activating the effector molecule of (d) under specific, pre-determined circumstances and when the protease cleavage site of (c) is accessible. Depending on the nature of the effector-activating module, these conditions leading to effector activation differ, as detailed in the following.

In the first option (i), the effector-activating module comprises a first part of a protease, wherein said first part of the protease is capable of interacting with a second part of said protease to form an active form of said protease.

The choice of protease is not particularly limited, as long as the protease can be split into two molecules that are capable of exerting the enzymatic activity of the protease upon interaction of the two molecules. Preferably, the protease is the Tobacco Etch Virus nuclear-inclusion-a endopeptidase (TEV).

Also with regard to the length and composition of the first part of the protease (and consequently of the resulting second part of the protease), there is not particular limitation. It will be appreciated that the two parts of the protease should be stable and should be able to interact with the respective other part. With regard to TEV, preferred N-terminal and a C-terminal TEV molecules as employed in the appended examples are shown in SEQ ID NO:24 and SEQ ID NO:25, respectively. There is further no particular limitation as to which part of the protease is included in the effector-activating module. For example, for TEV protease, either the N-terminal part or the C-terminal part can be included in the effector-activating module. Preferably, the N-terminal part of TEV is included in the effector-activating module, as shown in the appended examples.

In accordance with this first option (i), the conditions that enable effector activation when the protease cleavage site of (c) is accessible are conditions that enable the interaction of the two parts of the protease. For example, where the first inducible interaction module is e.g. a light-inducible interaction module, the presence of a corresponding light stimulus leads to the interaction of the first biosensor with its respective second molecule. By providing within the cell a further fusion protein comprising said second molecule fused to the second part of the protease, the interaction of the first biosensor with this second molecule results in that the two parts of the protease can interact and, thus, will be able to enzymatically cleave the fusion protein at the protease cleavage site of (c). This approach is described herein below in more detail with regard to the BLITz system, iTango2 system and Cal-Light system of the invention.

In the second option (ii), the effector-activating module comprises a second biosensor, wherein said second biosensor is a first molecule capable of interacting with a second molecule to form part of a second inducible interaction module.

The definitions and preferred embodiments provided herein above with regard to the first biosensor apply mutatis mutandis. It will be appreciate that the second biosensor has to be different from the first biosensor. Preferably, the first biosensor is part of a ligand- or calcium-inducible interaction module (such as e.g. a GPCR or part thereof, such as V2tail, or a calcium-sensor, such as e.g. CaM) and the second biosensor is part if a light-inducible interaction module, such as e.g. CIBN.

In accordance with this second option (ii), the conditions that enable effector activation when the protease cleavage site of (c) is accessible are also conditions that enable the interaction of the two parts of the protease. However, as opposed to option (i) above, the binding of two interacting molecules is required, each carrying one part of the protease. Here, the first inducible interaction module brings one part of the protease into the vicinity of the protease cleavage site of (c) and the second inducible interaction module brings the second part of the protease into the vicinity of the protease cleavage site of (c). Once both modules are induced, the two parts of the protease interact and are able to enzymatically cleave the fusion protein at the protease cleavage site of (c). This approach is described herein below in more detail with regard to the iTango system.

In accordance with the present invention, the nucleic acid molecule encoding the fusion protein further comprises a third nucleic acid sequence encoding a third biosensor.

Again, the definitions and preferred embodiments provided herein above with regard to the first biosensor apply mutatis mutandis, unless otherwise defined. In accordance with the invention, the third biosensor is capable of undergoing a conformational change in its 3D structure in response to a stimulus. Thus, the protease cleavage site is sterically occluded in the absence of a stimulus for said third biosensor, i.e. it is protected from cleavage, but becomes accessible in the presence of said stimulus, i.e. the cleavage site can now serve as a target for the protease. It will be appreciated that the protease cleavage site is a cleavage site for the protease to be used in the intended system, i.e. the protease formed by the interaction of the individual modules described herein. Thus, where the protease employed e.g. in option (b)(i) is TEV, the cleavage site is a TEV cleavage site. Moreover, where the first and second inducible interaction module bring a first and a second part of TEV in the vicinity of the cleavage site, as described above for option (b)(ii), the cleavage site is a cleavage site for TEV protease. Suitable cleavage sites for a variety of proteases of choice are well known in the art and can be selected by the skilled person without further ado. Preferably, the third biosensor is a biosensor derived from *Avena sativa* phototropin1 light-oxygen-voltage 2 (AsLOV2).

The stimulus for the third biosensor can be the same or different than the stimuli for the first and/or second biosensor. Preferably, the stimulus for the third biosensor is chosen such as to enable the use of two different stimuli when employing the nucleic acid molecule of the invention. Accordingly, where the effector-activating module is as defined in (b)(i), it is preferred that the stimulus for the third biosensor differs from the stimulus for the first biosensor. Most preferably in this regard, the stimulus for the first biosensor is either ligand binding or calcium binding and the stimulus for the third biosensor is light. Where the effector-activating module is as defined in (b)(ii), biosensors for two different inducible interaction modules requiring two different stimuli are already present, as discussed above. In that case, it is preferred that the stimulus for the third biosensor is identical to one of the stimuli that induce either the first or the second biosensor. Most preferably in this regard, the stimulus for the first biosensor is either ligand binding or calcium binding and the stimulus for the second and for the third biosensor is light.

Further in accordance with the present invention, the nucleic acid molecule encoding the fusion protein additionally comprises a fourth nucleic acid sequence encoding an effector molecule.

The term "effector molecule", as used herein, relates to a molecule capable of eliciting a desired and detectable effect within a cell. Non-limiting examples include the activation of gene transcription, e.g. of a reporter gene, the inactivation of expression of a constitutively active gene; or the modulation of the genome within the cell, e.g. by inducing strand breaks in the DNA and subsequent homologous or non-homologous recombination; or protease induced protein inactivation, e.g. by employing a dormant N-degron as described in more detail herein below. The effector molecule can also be e.g. a reporter molecule or an enzyme.

Due to the incorporation of the effector molecule into the fusion protein encoded by the nucleic acid molecule of the invention, the effector molecule is kept at a location within the cell where it cannot exert its action. For example, by keeping a transcription or genome modulator anchored at the cell membrane, it cannot exert its effect on the genome, which is located in the cell nucleus. Upon cleavage of the protease cleavage site of (c), the effector molecule is released and can translocate to the relevant subcellular compartment. It will be appreciated that additional sequences, such as e.g. a nucleus localizing signal (NLS) can be fused to the effector molecule to ensure its translocation to the correct compartment. Preferably, an effector molecule is chosen that translocates on its own, i.e. that does not requires such additional sequences.

In accordance with the present invention, a novel approach to converting signaling events into a detectable output, such as e.g. gene expression, is provided. This approach offers a high spatiotemporal resolution while at the same time having a reduced signal-to-noise ratio. Previous approaches, such as e.g. the Tango system, suffered from the drawback of high levels of ligand-independent background signals and poor signal-to-noise ratios. These technical limitations have severely limited the application of these systems in the past, in particular when the aim was the study of phasic neuromodulatory states.

These fundamental problems have been solved herein by developing a dual control system, named Blue-Light Inducible TEV protease (BLITz), which makes use of the nucleic acid molecule of the invention. In short, based on TEV as an exemplary protease, the TEV protease recognition sequence has been made photocleavable and the reconstitution of split TEV protease has been rendered either light-inducible or inducible by other stimuli, including ligands or calcium. The original split TEV system was first published in Nature Methods (Wehr, M. C. et al. Monitoring regulated protein-protein interactions using split TEV. Nature methods 3, 985-993, (2006)) and was widely used in various fields including neuroscience and cell biology. However, so far no light-inducible split TEV system has been developed. By providing a light-inducible split TEV system for the first time, a noninvasive, fast reactive, spatially precise and also reversible system is provided that does not require any pharmacological drugs for its regulation. By implementing this BLITz system into the original Tango system, an induced Tango system (referred to as "iTango") is provided herein with significantly improved spatiotemporal resolution. In iTango2-transfected neurons, which are transfected with a simplified version of iTango, background signals were nearly undetectable, but light- and ligand-inducibility was very robust, with a SNR corresponding to roughly 900% fold change. The same experiments using the conventional Tango system yielded only a 50% fold change (Djannatian, M. S., Galinski, S., Fischer, T. M. & Rossner, M. J. Studying G protein-coupled receptor activation using split-tobacco etch virus assays. Analytical biochemistry 412, 141-152, (2011)).

Due to the improvement of spatiotemporal resolution and signal-to-noise ratio the new techniques can now be applied in a timely precise way to mammalian brains (e.g. in transgenic animals), which are typically difficult to investigate because subtle neuromodulatory signals are constantly flowing in and out. Thus, the present invention allows to investigate the neuromodulation code in a complex neuronal network, which has not been attainable before. Furthermore, the present invention also provides a good template for a light-inducible G-protein coupled signaling monitoring platform. Simply exchanging GPCR parts from the system shown in the appended example allows to build whole library of GPCRs and to image individual's action as shown in a recent study (Kroeze, W. K. et al. PRESTO-Tango as an open-source resource for interrogation of the druggable human GPCRome. Nature structural & molecular biology 22, 362-369, (2015)). So far, no technique linking GPCR activation to gene expression in a light-dependent way has been described.

Moreover, the nucleic acid molecule of the present invention further enables a novel activity-dependent labeling system that reliably and quantitatively relays neuronal activity to gene expression. The basic principle of this technique is to render gene expression dependent on calcium and light. For example, whenever neurons fire, calcium enters neurons, but gene expression will not begin until a light stimulus is provided. When light is illuminated, gene expression will be initiated only in active neurons because calcium influx will occur in active neurons. Because this labeling system is designed to turn on gene transcription initiation when both light and calcium present, this technique was named Calcium and Light-Induced Gene Handling Tookit, "Cal-Light". This Cal-Light system reliably translates functions to gene expression, so its application will be diverse in circuit level studies. As is shown in the appended examples (see example 4), the Cal-Light system expresses reporter genes in a calcium- and light-dependent manner in cultured neurons. When Cal-Light was introduced in vivo, a functional neuronal group in the motor cortex could be selectively labeled. Successful visualization of long-range axonal trajectory in the basal ganglia area can also be achieved. It will be further possible to control the behavior of an animal by activating labeled neurons selectively by the Cal-Light constructs.

In a preferred embodiment of the nucleic acid molecule of the invention, the first inducible interaction module and the second inducible interaction module are independently selected from a light-inducible interaction module, a ligand-inducible interaction module and a calcium-inducible module.

The term "are independently selected", as used herein, relates to the fact that the first inducible interaction module and the second inducible interaction module have to be different. Nonetheless, both may be selected from the same class, as long as they respond to a different stimulus. For example, the first inducible interaction module may respond to blue light, while the second inducible interaction module may be responsive to red light. Also the use of different ligands is explicitly envisaged herein. Most preferably, however, the first inducible interaction module and the second inducible interaction module are selected from different groups, e.g. one is a light-inducible interaction module and the other is either a ligand-inducible interaction module or a calcium-inducible module; or one is a ligand-inducible interaction module and the other is either a light-inducible interaction module or a calcium-inducible module; or one is a calcium-inducible module and the other is either a ligand-inducible interaction module or a light-inducible interaction module.

The module is inducible by the respective stimulus, i.e. light, ligand or calcium, if the presence or absence of the stimulus is capable of initiating a modification of the module. Preferably, the individual parts of the module interact in the presence of the stimulus and do not interact in the absence of the stimulus, or vice versa, or the molecules of the module undergo a conformational change in the presence of the stimulus and return to the original confirmation in the absence of the stimulus.

It will be appreciated that any kind of light capable of inducing such a modification might be used in the light-inducible interaction module. Preferably, the light is selected from blue light, UV light or red/far red light. Most preferably, the light is blue light. It is further preferred that light-inducible interaction module is CIBN/CRY2PHR.

It will further be appreciated that any kind of ligand capable of inducing such a modification might be used in the ligand-inducible interaction module. Preferably, the ligand is a ligand for a GPCR. It is further preferred that the ligand-inducible interaction module is GPCR/β-arrestin2.

It will also be appreciated that in those cases where the module is a calcium-inducible module, such that the modification is induced by calcium, any method of increasing intracellular calcium might be used. For example, as is well known, upon stimulation of neurons, they become depolarized. This depolarization in turn leads to the opening of voltage-sensitive calcium channels, thereby resulting in a calcium influx into neurons. Accordingly, one approach is to stimulate neurons, for example by electrical stimulation, optogenetic activation of neurons, blocking inhibition by GABA receptor antagonists, KCl application, or any pharmacological application that causes neuronal depolarization. In in vivo conditions, neurons fire spontaneously or are activated by synaptic inputs, which does not need extrinsic stimulation. Behaviorally relevant neurons will fire and calcium will enter into neurons while animals are behaving. It is particularly preferred that the calcium-inducible module is CaM/M13.

In a further preferred embodiment of the nucleic acid molecule of the invention, the effector molecule is a transcriptional modulator, a genome modulator, a reporter molecule, an enzyme, or degron.

The term "transcriptional modulator", as used herein, relates to one or more molecules capable of activating or inactivating the transcription of a particular gene, or capable of altering the amount of transcription of a particular gene. Transcriptional modulators are well known in the art and have been described e.g. in Gossen, M. & Bujard, H. Tight control of gene expression in mammalian cells by tetracycline-responsive promoters. *Proceedings of the National Academy of Sciences of the United States of America* 89, 5547-5551 (1992). Non-limiting examples of transcriptional modulators in accordance with the present invention include TetR-VP16(tTA), as well as TetR-VP15, TetR-VP64, GAL4-VP16 or GAL4-VP64. Preferably, the transcriptional modulator is the TetR-VP16(tTA) molecule employed in the appended examples (see e.g. SEQ ID NO:10 and 11).

The term "genome modulator", as used herein, relates to one or more molecules capable of altering the genomic constitution within a target cell, for example by inducing double-strand breaks and, subsequently, inducing non-homologous or homologous recombination. Genome modulators and gene editing mediated by such modulators are well known in the art and have been described e.g. in Hsu, P. D., Lander, E. S. & Zhang, F. Development and applications of CRISPR-Cas9 for genome engineering. *Cell* 157, 1262-1278, (2014); Nagy, A. Cre recombinase: the universal reagent for genome tailoring. Genesis 26, 99-109 (2000). Non-limiting examples of genome modulators in accordance with the present invention include the Crispr-Cas9 system as well as the Cre recombinase. A schematic overview of these system incorporated into the nucleic acid molecule of the present invention is presented in FIG. 18 below.

The effector molecule can also be a reporter molecule, such as e.g. a fluorescent or bioluminescent molecule fused to a nuclear localization sequence. Upon release of the reporter molecule from the fusion protein, i.e. after cleavage of the protease cleavage site, the reporter molecule can translocate to a different site within the cell. This translocation can be observed and used as a read-out. Suitable fluorescent proteins include, without being limiting, green fluorescent protein (GFP), yellow fluorescent protein (YFP), red fluorescent protein (RFP), cyan fluorescent protein (CFP) or infrared fluorescent protein (IFP) as well as fluorescent dyes such as e.g. Fluorescein, Alexa Fluor or Cy dyes. Suitable bioluminescent proteins include, amongst others, luciferase, in particular bacterial luciferase (luxAB), Photinus luciferase and *Renilla* luciferase.

Furthermore, the effector molecule can also be an enzyme. For example, the enzyme can be an enzyme capable of catalyzing chromogenic, chemiluminescent or fluorescent reactions, such as e.g. horseradish peroxidase (HRP), luciferase, β-galactosidase and alkaline phosphatase (AP). Also envisaged herein are genetically engineered enzymes, such as for example, a procaspase that has been modified to contain a TEV cleavage site (TEVseq), such that the procaspase is inactive. Upon cleavage of the TEVseq the procaspases switches to an active caspase, causing apoptosis (Gray, D. C., Mahrus, S. & Wells, J. A. Activation of specific apoptotic caspases with an engineered small-molecule-activated protease. *Cell* 142, 637-646, (2010)).

A further type of molecule suitable for use as an effector molecule in accordance with the present invention is degron, in particular N-degron. N-degrons are natural or artificial tags that can be added to the N-terminal end of a protein of interest. Because N-degrons are proteolytically processed, amino acids other than methionine form the N-terminus of the protein, which serve as recognition signal for poly-ubiquitinylation and the subsequent proteasomal degradation through the N-end rule pathway in eukaryotes. By attaching a further protein to the N-terminal end of the N-degron, the N-degron can be rendered dormant, i.e. it is protected from proteolytic processing. In accordance with the nucleic acid molecule of the present invention, said further protein is the nucleic acid sequence of (a) to (c). Upon cleavage at the protease cleavage site of (c), the N-terminal end of N-degron becomes exposed, thus initiating the degradation of the protein of interest. This method is well known in the art and has been described, e.g. in Taxis, C., Stier, G., Spadaccini, R. & Knop, M. Efficient protein depletion by genetically controlled deprotection of a dormant N-degron. *Molecular systems biology* 5, 267, (2009). Because this method regulates protein level by accelerating protein degradation, the use of degron can be beneficial in defining cellular functions that require sustained protein activity.

Yet another effector molecule suitable for use as an effector molecule in accordance with the present invention is Tetanus Toxin Light Chain (TeTxLC). TeTxLC cleaves synaptobrevin 2, an essential protein mediating vesicle release. Therefore, when TeTxLC is expressed in a cell, all vesicular fusion events in that cell are prevented, such that neurotransmitters such as glutamate and GABA are not released. TeTxLC is a non-toxic protein that retains the enzymatic activity encoded by the holotoxin and that is—as a protein—unable to gain access to intracellular targets without microinjection. Moreover, there is no chance of contamination by the heavy chain since only the light chain is encoded and expressed.

By employing TeTxLC as an effector molecule in accordance with the invention, it becomes possible to investigate functions associated with vesicular activity within a selective group of cells without killing or damaging these cells.

Furthermore, it is envisaged that the effector molecule is composed of a split system, preferably making use of the SpyTag/SpyCatcher system. This system is well known in the art and has been described e.g. in Bedbrook, C. N. et al. Genetically Encoded Spy Peptide Fusion System to Detect Plasma Membrane-Localized Proteins In Vivo. *Chemistry & biology* 22, 1108-1121, (2015). By combining the one part of an effector molecule, such as of e.g. Cre recombinase or Cas9, with a SpyTag, the activity of the effector molecule can be further controlled. This is because the effector molecule will only be active once the SpyTag interacts with the SpyCatcher, to which the second part of the effector molecule will be attached. Thus, particularly envisaged is the use of the fusion protein SpyTag-Cre-N (i.e. the N-terminal part of Cre recombinase) as part (d) of the nucleic acid molecule of the invention, wherein the fusion protein SpyCatcher-Cre-C (i.e. the C-terminal part of Cre recombinase) is to provided to the cell as the interaction partner. Alternatively envisaged is the use of the fusion protein SpyTag-Cas9-N (i.e. the N-terminal part of Cas9) as part (d) of the nucleic acid molecule of the invention, wherein the fusion protein SpyCatcher-Cas9-C (i.e. the C-terminal part Cas9) is to provided to the cell as the interaction partner. A schematic overview of such an approach is provided in FIG. 19 below.

Incorporation of the SpyTag/SpyCatcher system is particularly advantageous for use in combination with Cre recombinase or the CRISPR/Cas system, because in theory, a single protein of Cre or Cas9 can initiate gene editing. Thus, even the smallest amount of light-independent Cas9 or Cre protein release can cause non-specific gene editing. To prevent this possibility, split Cas9 and Cre proteins can be employed as described, such that these proteins are not functional on their own. In the presence of the respective stimulus, sufficiently large amounts of the split proteins will be released and will relocate to the nucleus, where they interact with the second half of the protein to form a functional molecule. By employing the SpyTag/SpyCatcher system, the binding of the two halves of the split protein to each other is facilitated.

In a further preferred embodiment of the nucleic acid molecule of the invention, the third nucleic acid sequence comprises (i) a nucleic acid sequence encoding the N-terminal amino acids 1 to 138 or 1 to 139 of *Avena sativa* phototropin1 light-oxygen-voltage 2 (AsLOV2), linked at its C-terminus to (ii) a protease cleavage site.

The N-terminal amino acids 1 to 138 of AsLOV2 are represented in the sequence listing as SEQ ID NO:49 and the corresponding nucleic acid sequence is represented in SEQ ID NO:50. Further, the N-terminal amino acids 1 to 139 of AsLOV2 are represented in the sequence listing as SEQ ID NO:51 and the corresponding nucleic acid sequence is represented in SEQ ID NO:52. These sequences are fused at their C-terminal end to a protease cleavage site, preferably a TEV cleavage site as described below.

AsLOV2 acts as a biosensor for light which changes its conformation upon a light stimulation, thereby making the protease cleavage site accessible. The two preferred AsLOV2 constructs according to this preferred embodiment have been identified in the appended examples as particularly useful light-sensors with a low back-ground activation in the absence of a light stimulus and a high activation in the presence of the stimulus, i.e. a particularly good signal-to-noise-ratio.

In a particularly preferred embodiment of the nucleic acid molecule of the invention, the protease cleavage site is a TEV protease cleavage site.

Any site that can be cleaved by TEV protease can be employed in accordance with this embodiment. Thus, the TEV protease cleavage can be a naturally existing cleavage site for TEV protease, or a modified cleavage site, as long as the TEV protease can still cleave said site. Preferably, the cleavage site is specific for TEV protease, i.e. it is only cleaved by TEV protease, but not by any other protease. Preferably, the TEV cleavage site has the amino acid sequence ENLYFQG (SEQ ID NO:53) or EALYFQG (SEQ ID NO:54). Furthermore, the most C-terminal G in these sequences can be replaced by any one of the other 19 proteinogenic amino acids, i.e. by S, A, M, C, N, H, Y, K, D, Q, F, T, W, R, L, E, I, V, or P (Kapust, R. B., Tozser, J., Copeland, T. D. & Waugh, D. S. The P1' specificity of tobacco etch virus protease. *Biochemical and biophysical research communications* 294, 949-955, (2002). The nucleic acid sequences encoding the preferred two TEV protease cleavage sites ENLYFQG and EALYFQG, are represented by SEQ ID NOs: 55 and 56, respectively.

In another preferred embodiment of the nucleic acid molecule of the invention, the nucleic acid molecule comprises (i) a nucleic acid sequence encoding a transmembrane domain linked to a nucleic acid sequence selected from: SEQ ID NO:1, SEQ ID NO:3, SEQ ID NO:5, and SEQ ID NO:8 such that the nucleic acid sequence selected from: SEQ ID NO:1, SEQ ID NO:3, SEQ ID NO:5, and SEQ ID NO:8 is located intracellularly upon expression of the protein in a cell; and (ii) a nucleic acid sequence encoding an effector molecule, wherein the effector molecule is selected from TetR-VP16(tTA), Cas9 or Cre recombinase.

In accordance with this embodiment, a nucleic acid sequence encoding a transmembrane domain of interest is linked with one of the nucleic acid sequences cited, wherein SEQ ID NO:1 represents a nucleic acid sequence comprising, in the recited order, CIBN-TEV-N-AsLOV2-TEVseq; SEQ ID NO:3 represents a nucleic acid sequence comprising, in the recited order, V2tail-TEV-N-AsLOV2-TEVseq; SEQ ID NO:5 represents a nucleic acid sequence comprising, in the recited order, V2tail-CIBN-AsLOV2-TEVseq; and SEQ ID NO:8 represents a nucleic acid sequence comprising, in the recited order, CaM-TEV-N-AsLOV2-TEVseq. Accordingly, SEQ ID NO:1 represents a sequence suitable for use in the BLITz system, SEQ ID NO:3 represents a sequence suitable for use in the iTango2 system, SEQ ID NO:5 represents a sequence suitable for use in the iTango1 system and SEQ ID NO:8 represents a sequence suitable for use in the Cal-Light system. The amino acid sequences encoded by these nucleic acid sequences are represented in SEQ ID NOs:2, 4, 6 and 9.

The effector, in accordance with this embodiment, is selected from TetR-VP16(tTA), Cas9 or Cre recombinase. Suitable nucleic acid sequence encoding such effectors, as well as the respective amino acid sequences, are represented in SEQ ID NO:10 and 11 for TetR-VP16(tTA), SEQ ID NO:12 and 13 for Cas9 and SEQ ID NO:14 and 15 for Cre recombinase.

In a more preferred embodiment of the nucleic acid molecule of the invention, the nucleic acid molecule comprises a nucleic acid sequence encoding a transmembrane domain linked to a nucleic acid encoding the effector (tTa). Therefore, the nucleic acid molecule may be selected from SEQ ID NO:16 (CIBN-TEV-N-AsLOV2-TEVseq-TetR-VP16(tTA)), SEQ ID NO:18 (V2tail-TEV-N-AsLOV2-TEVseq-TetR-VP16(tTA)), SEQ ID NO:20 (V2tail-CIBN-AsLOV2-TEVseq-TetR-VP16(tTA)) and SEQ ID NO:22 (CaM-TEV-N-AsLOV2-TEVseq-TetR-VP16(tTA)), such that the nucleic acid molecule selected from: SEQ ID NO:16, SEQ ID NO:18, SEQ ID NO:20, and SEQ ID NO:22 is located intracellularly upon expression of the protein in a cell. The amino acid sequences corresponding to these nucleic acid sequences are represented in SEQ ID NOs: 17, 19, 21 and 23, respectively.

The present invention further relates to a vector comprising the nucleic acid molecule of the invention.

Usually, the vector is a plasmid, cosmid, virus, bacteriophage or another vector used conventionally e.g. in genetic engineering. Preferably, the vector is a plasmid, more preferably a plasmid based on the multipurpose expression vector pCS2+(Addgene), which is suitable for expressing proteins in *Xenopus* embryos, zebrafish embryos as well as a wide variety of mammalian and avian cells. Another suitable mammalian expression vector is the pCS4+ vector derived from pCS2+ as described in Yeo C and Whitman M, 2001 (Nodal signals to Smads through Cripto-dependent and Cripto-independent mechanisms. Mol Cell 7(5):949-957), which has been employed in the appended examples.

Alternative vectors include, without being limiting, plasmid vectors, such as pQE-12, the pUC-series, pBluescript (Stratagene), the pET-series of expression vectors (Novagen) or pCRTOPO (Invitrogen), lambda gt11, pJOE, the pBBR1-MCS series, pJB861, pBSMuL, pBC2, pUCPKS, pTACT1 and vectors compatible with expression in mammalian cells like E-027 pCAG Kosak-Cherry (L45a) vector system, pREP (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, plZD35, Okayama-Berg cDNA expression vector pcDV1 (Pharmacia), pRc/CMV, pcDNA1, pcDNA3 (Invitrogen), pcDNA3.1, pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Non-limiting examples for plasmid vectors suitable for *Pichia pastoris* comprise e.g. the plasmids pAO815, pPIC9K and pPIC3.5K (all Invitrogen).

Generally, vectors can contain one or more origins of replication (ori) and inheritance systems for cloning or expression, one or more markers for selection in the host, e.g., antibiotic resistance, and one or more expression cassettes. In addition, the coding sequences comprised in the vector can be ligated to transcriptional regulatory elements and/or to other amino acid encoding sequences using established methods. Such regulatory sequences are well known to those skilled in the art and include, without being limiting, regulatory sequences ensuring the initiation of transcription, internal ribosomal entry sites (IRES) (Owens, G. C. et al. [2001] Proc. Natl. Acad. Sci. U.S.A. 98:1471-1476) and optionally regulatory elements ensuring termination of transcription and stabilization of the transcript. Non-limiting examples for such regulatory elements ensuring the initiation of transcription comprise promoters, a translation initiation codon, enhancers, insulators and/or regulatory elements ensuring transcription termination, which are to be included downstream of the nucleic acid molecules of the invention. Further examples include Kozak sequences and intervening sequences flanked by donor and acceptor sites for RNA splicing, nucleotide sequences encoding secretion signals or, depending on the expression system used, signal sequences capable of directing the expressed protein to a cellular compartment or to the culture medium. The vectors may also contain an additional expressible polynucleotide coding for one or more chaperones to facilitate correct protein folding. Suitable bacterial expression hosts comprise e.g. strains derived from JM83, W3110, KS272, TG1, BL21 (such as BL21 (DE3), BL21 (DE3)PlysS, BL21 (DE3)RIL, BL21 (DE3)PRARE) or Rosettaâ. For vector modification, PCR amplification and ligation techniques, see Sambrook & Russel [2001] (Cold Spring Harbor Laboratory, NY).

Examples of suitable origins of replication include, for example, the full length ColE1, truncated ColE1, the SV40 viral and the M13 origins of replication, while examples of suitable promoters include, without being limiting, the cytomegalovirus (CMV) promoter, in particular the CMV IE94 promoter employed in the appended examples, SV40-promoter, the tetracycline promoter/operator (tet$^{\%}$), which is chemically inducible with anhydrotetracycline, RSV-promoter (Rous sarcoma virus), the lacZ promoter, chicken β-actin promoter, CAG-promoter (a combination of chicken β-actin promoter and cytomegalovirus immediate-early enhancer), the gai10 promoter, human elongation factor 1α-promoter, AOX1 promoter, GAL1 promoter CaM-kinase promoter, the lac, trp or tac promoter, the T7 or T5 promoter, the lacUV5 promoter, the *Autographa californica* multiple nuclear polyhedrosis virus (AcMNPV) polyhedral promoter or a globin intron in mammalian and other animal cells. One example of an enhancer is e.g. the SV40-enhancer. Non-limiting examples for regulatory elements ensuring transcription termination include the SV40-poly-A site, the tk-poly-A site, the rho-independent lpp terminator or the AcMNPV polyhedral polyadenylation signals. Non-limiting examples of selectable markers include the ampicillin-resistance gene (β-lactamase), dhfr, gpt, neomycin, hygromycin, blasticidin or geneticin.

Preferably, the vector of the present invention is an expression vector. An expression vector according to this invention is capable of directing the replication and the expression of the nucleic acid molecule of the invention and, accordingly, of the fusion protein of the present invention encoded thereby.

The nucleic acid molecules and/or vectors of the invention as described herein above may be designed for introduction into cells by e.g. chemical based methods (calcium phosphate, liposomes, DEAE-dextrane, polyethylenimine, nucleofection), non chemical methods (electroporation, sonoporation, optical transfection, gene electrotransfer, hydrodynamic delivery or naturally occurring transformation upon contacting cells with the nucleic acid molecule of the invention), particle-based methods (gene gun, magnetofection, impalefection) phage vector-based methods and viral methods. For example, expression vectors derived from viruses such as retroviruses, vaccinia virus, adeno-associated virus, herpes viruses, Semliki Forest Virus or bovine papilloma virus, may be used for delivery of the nucleic acid molecules into targeted cell population. Additionally, baculoviral systems can also be used as vector in eukaryotic expression system for the nucleic acid molecules of the invention. Preferably, the nucleic acid molecules and/or vectors of the invention are designed for viral infection methods.

The present invention further relates to a set of nucleic acid molecules comprising: (a) the nucleic acid molecule of the invention, wherein the effector-activating module comprises a first part of a protease, wherein said first part of the protease is capable of interacting with a second part of said protease to form an active form of said protease; and (b) a second nucleic acid molecule encoding a second fusion protein, the second nucleic acid molecule comprising (i) a first nucleic acid sequence encoding a molecule that represents the corresponding second molecule of the first inducible interaction module according to the nucleic acid molecule of the invention; and (ii) a second nucleic acid sequence encoding the second part of a protease, capable of interacting with the first part of said protease to form an active form of said protease.

This set of nucleic acid molecules is also referred to herein as the "first set of nucleic acid molecules of the invention".

The term "set", as used herein, relates to a combination of at least the recited nucleic acid molecules. In other words, the set of the present invention requires that more than one molecular species of nucleic acid molecules is present. However, the term "set" does not require the presence of any other compounds, vials, containers, manuals and the like. The term "comprising" in the context of the set(s) of the invention denotes that further components can be present in the set. The various components of the set may be present in isolation or combination. For example, the recited nucleic acid molecules of the set may be packaged in one or more containers such as one or more vials.

The set in accordance with this embodiment comprises at least the nucleic acid molecule of the invention, i.e. a nucleic acid molecule encoding a fusion protein as described herein above. The effector-activating module is as defined in the first alternative, i.e. it is a first part of a protease that is capable of interacting with a second part of said protease to form an active form of said protease. As described herein above, a particularly preferred protease is TEV protease and said first part of the protease is preferably the N-terminal part of TEV (TEV-N) and the second part is preferably the C-terminal part of TEV (TEV-C).

The set in accordance with this embodiment further comprises a second nucleic acid molecule encoding a second fusion protein. The nucleic acid molecule encoding said second fusion protein comprises two nucleic acid sequences: a first sequence that encodes the counterpart of the first inducible interaction module; and a second sequence that encodes the second part of the protease, such as e.g. TEV-C. The order of the first and second sequence within the second nucleic acid molecule from 5' to 3' is not particularly limited and may be first (i) and then (ii) or, alternatively, first (ii) and then (i).

As described herein above, the first inducible interaction module may be chosen from a plethora of suitable inducible systems. Depending on the choice made in constructing the nucleic acid molecule of the invention, the respective corresponding interaction partner has to be included in this nucleic acid molecule encoding the second fusion protein of the invention. For example, if CIBN is present in the nucleic acid molecule of the invention as the first biosensor, then CRY2PHR has to be present in the nucleic acid molecule encoding the second fusion protein in accordance with the present embodiment. Alternatively, if either PIF or PhyB is present in the first fusion protein, the respective partner (i.e. either PhyB or PIF) has to be present in the second fusion protein. Further combinations have been recited above, e.g. LOV and LOV, GPCR and β-arrestin2, CaM and M13 and so forth.

Exemplary nucleic acid sequences encoding for such a second fusion protein are represented by SEQ ID NOs:57, 59 and 61, wherein SEQ ID NO:57 represents a fusion protein of CRY2PHR with TEV-C (for use when the first fusion protein is e.g. the protein encoded by the nucleic acid molecule of SEQ ID NO:1); SEQ ID NO:59 represents a fusion protein of β-arrestin2 with TEV-C (for use when the first fusion protein is e.g. the protein encoded by the nucleic acid molecule of SEQ ID NO:3) and, additionally, TdTomato (the same sequence without TdTomato is represented in SEQ ID NO:63 and 64); and SEQ ID NO:61 represents a fusion protein of TEV-C with M13 (for use when the first fusion protein is e.g. the protein encoded by the nucleic acid molecule of SEQ ID NO:8). The corresponding amino acid sequences are represented by SEQ ID NOs: 58, 60 and 62, respectively.

Also in accordance with the second nucleic acid molecule of this embodiment, the term "comprising" means that additional nucleic acid sequences may be encompassed in said nucleic acid molecule. Such additional sequences include for example transfections control sequences, such as the TdTomato sequence employed in the appended examples and as shown in combination with β-arrestin2 and TEV-C in SEQ ID NO:59.

The set of nucleic acid molecules according to this embodiment provides suitable nucleic acid molecules for carrying out methods of monitoring or inducing intracellular signaling, as described in more detail herein below. Thus, the methods described herein as the BLITz system, the iTango2 system and the Cal-Light system can all be carried out by employing the set of nucleic acid molecules in accordance with this embodiment. Exemplary schematic representations of first and second nucleic acid molecules in accordance with this embodiment are shown e.g. in FIG. 1(e) for the BLITz system, in FIG. 3(b) for the iTango2 system and in FIG. 16 for the Cal-Light system.

The present invention further relates to a set of nucleic acid molecules comprising: (a) the nucleic acid molecule according to the invention, wherein the effector-activating module is as defined in option (b)(ii); (b) a second nucleic acid molecule encoding a second fusion protein, the second nucleic acid molecule comprising (i) a first nucleic acid sequence encoding a molecule that represents the corresponding second molecule of the first inducible interaction module according to option (a); and (ii) a second nucleic acid sequence encoding a first part of a protease, wherein said first part of the protease is capable of interacting with a second part of said protease to form an active form of said protease; and (c) a third nucleic acid molecule encoding a third fusion protein, the third nucleic acid molecule comprising (i) a first nucleic acid sequence encoding a molecule that represents the corresponding second molecule of the second inducible interaction module according to option (b)(ii); and (ii) a second nucleic acid sequence encoding the second part of a protease, capable of interacting with the first part of the protease in accordance with (b)(ii) to form an active form of said protease.

This set of nucleic acid molecules is also referred to herein as the "second set of nucleic acid molecules of the invention".

The definitions and preferred embodiments provided herein above for the term "set" and the meaning of "comprising" apply mutatis mutandis also to this alternative set of nucleic acid molecules.

This set of nucleic acid molecules comprises, in accordance with the present invention, at least the nucleic acid molecule of the invention, i.e. a nucleic acid molecule encoding a fusion protein as described herein above. The effector-activating module is as defined in the second alternative, i.e. it is a second biosensor, wherein said second biosensor is a first molecule capable of interacting with a second molecule to form part of a second inducible interaction module. Preferred molecules for this second biosensor and this second inducible interaction module have been described herein above and include, without being limiting, CIBN and CRY2PHR, PIF and PhyB or LOV and LOV. It will be appreciated that the second inducible interaction module is composed of different molecules than the first inducible interaction module.

The set in accordance with this embodiment further comprises a second nucleic acid molecule encoding a second fusion protein. The nucleic acid molecule encoding said second fusion protein comprises two nucleic acid sequences: a first sequence that encodes for the counterpart of the first inducible interaction module; and a second sequence that encodes a first part of a protease that is capable of interacting with a second part of said protease to form an active form of said protease. As described herein above, a particularly preferred protease is TEV protease and said first part of the protease is preferably the N-terminal part of TEV (TEV-N) and the second part is preferably the C-terminal part of TEV (TEV-C).

The set in accordance with this embodiment further comprises a third nucleic acid molecule encoding a third fusion protein. The nucleic acid molecule encoding said third fusion protein also comprises two nucleic acid sequences: a first sequence that encodes the counterpart of the second inducible interaction module; and a second sequence that encodes the second part of the protease, such as e.g. TEV-C.

The order of the first and second nucleic acid sequence within the nucleic acid molecule encoding the second fusion protein and within the nucleic acid molecule encoding the third fusion protein from 5' to 3' is not particularly limited and may be first (i) and then (ii) or, alternatively, first (ii) and then (i).

As described herein above, the first as well as the second inducible interaction module may be chosen from a plethora of suitable inducible systems, with the proviso that two different modules are chosen. Depending on the choice made in constructing the nucleic acid molecule of the invention, the respective corresponding interaction partners have to be included in the second and third fusion proteins in accordance with the invention. For example, if GPCR (in particular V2tail as shown in the appended examples) is present in the nucleic acid molecule of the invention as the first biosensor, then β-arrestin2 has to be present in the second fusion protein. To continue with this example, β-arrestin2 would be present in said second fusion protein with a first part of a protease, preferably TEV-N. The third fusion protein would then comprise the second part of said protease, e.g. TEV-C, together with the second part of the first inducible interaction system. If the first part of said first inducible interaction system present in the nucleic acid molecule of the invention is e.g. CIBN, then CRY2PHR will have to be present in the nucleic acid molecule encoding the third fusion protein.

An exemplary nucleic acid sequence encoding for such a second fusion protein is represented by SEQ ID NO:65, which represents a fusion protein of β-arrestin2 with TEV-N and, additionally, TdTomato (the same sequence without TdTomato is represented in SEQ ID NO:67 and 68). An exemplary nucleic acid sequence encoding for such a third fusion protein is represented by SEQ ID NO:69, which represents a fusion protein of CRY2PHR with TEV-C. These two exemplary sequences may e.g. be employed together with the nucleic acid molecule of the invention represented in SEQ ID NO:5. The amino acid sequence encoded by these nucleic acid sequences are represented in SEQ ID NOs: 66 and 70, respectively.

This set of nucleic acid molecules according to the invention also provides suitable nucleic acid molecules for carrying out methods of monitoring or inducing intracellular signaling, as described in more detail herein below. More specifically, the method described herein as the iTango system can be carried out by employing this set of nucleic acid molecules. An exemplary schematic representation of first, second and third nucleic acid molecules in accordance with this embodiment are shown e.g. in FIG. 2(c) for the iTango2 system.

In a preferred embodiment of the set of nucleic acid molecule, the set of nucleic acid molecules is comprised in one or more vectors.

All definitions and preferred embodiments provided herein above regarding the term "vectors" apply mutatis mutandis also with regard to this embodiment.

The term "one or more", as used herein, refers to exactly one but also to more than one, such as e.g. two, three, four, five, six, seven and so on. Moreover, the term "one or more" does not define the actual number of one type of molecule present, but refers to the number of distinct molecules of the recited class. For example, the term "one or more vectors" refers to exactly one vector, i.e. one vector carrying for example the first nucleic acid molecule encoding the first fusion protein, the second nucleic acid molecule encoding the second nucleic acid molecule as well as, where applicable, the third nucleic acid molecule encoding the third fusion protein. The term, however, also refers to more than one vector, such as e.g. two or three different vectors, carrying the different nucleic acid molecules.

The present invention further relates to a host cell or host expressing the set of nucleic acid molecules of the invention. The present invention further relates to a host cell or host comprising (and expressing) the one or more vectors of the invention. Preferably, the host is a non-human host.

The "host cell", in accordance with the present invention, can be any cell in which signal transduction events are to be investigated. In a preferred embodiment, the host cell is/are (an) isolated cell(s) which may be part of a cell culture.

For example, suitable mammalian host cells include, without being limiting, HEK293, Hela, H9, Per.C6 and Jurkat cells, mouse NIH3T3, NS0 and C127 cells, COS 1, COS 7 and CV1, quail QC1-3 cells, mouse L cells, mouse sarcoma cells, Bowes melanoma cells and Chinese hamster ovary (CHO) cells. Also within the scope of the present invention are primary mammalian cells or cell lines. Primary cells are cells which are directly obtained from an organism. Suitable primary cells are, for example, human dermal and pulmonary fibroblasts, human epithelial cells (nasal, tracheal, renal, placental, intestinal, bronchial epithelial cells), human secretory cells (from salivary, sebaceous and sweat glands), human endocrine cells (thyroid cells), human adipose cells, human smooth muscle cells, human skeletal muscle cells, human leucocytes such as B-cells, T-cells, NK-cells or dendritic cells and stable, immortalized cell lines derived thereof (for example hTERT or oncogene immortalized cells), mouse neuronal cells, mouse embryonic fibroblasts (MEF), mouse primary hepatocytes, cardiomyocytes as well as mouse muscle stem cells (satellite cells).

Other suitable eukaryotic host cells are e.g. chicken cells, such as e.g. DT40 cells, or yeasts such as *Saccharomyces cerevisiae*, *Pichia pastoris*, *Schizosaccharomyces pombe* and *Kluyveromyces lactis*. Insect cells suitable for expression are e.g. *Drosophila* S2, *Drosophila* Kc, *Spodoptera* Sf9 and Sf21 or *Trichoplusia* Hi5 cells. Suitable zebrafish cell lines include, without being limiting, ZFL, SJD or ZF4.

Particularly preferred host cells in accordance with the present invention are HEK293T cells and neuronal cells, such as e.g. the primary hippocampal cells employed in the appended examples.

Appropriate culture media and conditions for the above described host cells are known in the art. For example, for HEK293T cells, an exemplary suitable medium is high glucose Dulbecco's Modified Eagle Medium (DMEM) comprising 10% fetal bovine serum and 1% penicillin-streptomycin. Suitable culture conditions include e.g. incubation at 37° C. under 10% $CO_2$ conditions. For neuronal cells, in particular hippocampal cells, an exemplary suitable medium is neurobasal medium (Invitrogen) comprising: 1% (v/v) FBS, 1% (v/v) Glutamax supplement, 2% (v/v) B27 supplement, and 1% (v/v) penicillin-streptomycin. Exemplary culture conditions for primary hippocampal neuron culture are 37° C. at 10% $CO_2$ conditions with a media-change for fresh FBS-free medium every four days.

It will be appreciated that the "host cell comprising the one or more vectors of the invention", in accordance with the present invention, expresses the fusion proteins encoded by the nucleic acid molecules comprised in said one or more vectors.

Transgenic (non-human) animals as hosts transfected with and/or expressing the set of nucleic acid molecules of the invention or the one or more vector(s) of the present invention also lie within the scope of the invention. In a preferred embodiment, the transgenic animal is a mammal or a fish, more preferably the transgenic animal is selected from the group consisting of a mouse, rat, hamster, cow, cat, pig, dog, horse, rabbit, monkey or fish.

Methods for the production of a transgenic animal include for example methods for the production of transgenic mice or other mammals, which usually comprise introduction of the nucleic acid molecule or targeting vector(s) of the present invention into a germ cell, an embryonic cell, stem cell or an egg or a cell derived therefrom. Production of transgenic embryos and screening of those can be performed, e.g., as described by A. L. Joyner Ed., Gene Targeting, A Practical Approach (1993), Oxford University Press. The DNA of the embryonic membranes of embryos can be analyzed using, e.g., Southern blots with an appropriate probe. A general method for making transgenic animals is described in the art; see for example WO 94/24274. For making transgenic organisms (which include homologously targeted non-human animals), embryonal stem cells (ES cells) are preferred. Murine ES cells, such as AB-1 line grown on mitotically inactive SNL76/7 cell feeder layers (McMahon and Bradley, Cell 62:1073-1085 (1990)) essentially as described (Robertson, E. J. (1987) in Teratocarcinomas and Embryonic Stem Cells: A Practical Approach. E. J. Robertson, ed. (Oxford: IRL Press), p. 71-112) may be used for homologous gene targeting. Other suitable ES lines include, but are not limited to, the E14 line (Hooper et al., Nature 326:292-295 (1987)), the D3 line (Doetschman et al., J. Embryol. Exp. Morph. 87:27-45 (1985)), the CCE line (Robertson et al., Nature 323:445-448 (1986)), the AK-7 line (Zhuang et al., Cell 77:875-884 (1994)). The success of generating a mouse line from ES cells bearing a specific modification depends on the pluripotency of the ES cells (i.e., their ability, once injected into a host developing embryo, such as a blastocyst or formula, to participate in embryogenesis and contribute to the germ cells of the resulting animal). The blastocysts containing the injected ES cells are allowed to develop in the uteri of pseudopregnant non-human females and are born, e.g. as chimeric mice. The resultant chimeric transgenic mice are backcrossed and screened for the presence of the correctly targeted transgene(s) by PCR or Southern blot analysis on tail biopsy DNA of offspring so as to identify heterozygous transgenic mice.

The host cells or hosts in accordance with these embodiments may e.g. be employed in the methods of monitoring or inducing intracellular signaling described herein below.

The present invention further relates to a method for inducing intracellular signaling, the method comprising: (a-i) providing a cell expressing the first set of nucleic acid molecules according to the invention; (a-ii) applying a first stimulus to the cell of (a-i), wherein the first stimulus is capable of inducing the first inducible interaction module; and (a-iii) applying a second stimulus to the cell of (a-i), wherein the second stimulus is capable of inducing the third biosensor such that the protease cleavage site becomes accessible; or (b-i) providing a cell expressing the second set of nucleic acid molecules according to the invention; (b-ii) applying a first stimulus to the cell of (b-i), wherein the first stimulus is capable of inducing the first inducible interaction module; (b-iii) applying a second stimulus to the cell of (b-i), wherein the second stimulus is capable of inducing the second inducible interaction module; and (b-iv) applying a third stimulus to the cell of (b-i), wherein the third stimulus is capable of inducing the third biosensor in accordance with claim 1(c) such that the protease cleavage site becomes accessible; thereby effecting a biological response due to the activation of the effector molecule.

The term "intracellular signaling", as used herein, is not particularly limited and encompasses various kinds of signal transduction events that occur within a particular cell of interest. Non-limiting examples of such signal transduction events are receptor activation-dependent activation of downstream signaling pathways, protein translocation, ion-dependent activation of downstream signaling. By employing the method of the present invention, these signals can be activated in a targeted manner due to high temporal blue light sensitivity and will result in gene expression only in the group of cells targeted, such as cells in an experiment in vitro setting as well as cells involved in vivo in an animal's perception, action, or emotion. Once cells express reporter genes, their expression can be monitored. Moreover, their expression can be used to create e.g. artificial behavior, sensation, emotion, or memory within a live animal.

In accordance with this method of the invention, a cell is provided that expresses either the first set of nucleic acid molecules of the invention (option (a)) or the second set of nucleic acid molecules of the intention (option (b)).

The term "a cell", as used herein, refers to one type of cells, such as e.g. HEK293 cells or hippocampal neurons, but is not limited to one cell, but also encompasses a plurality of cells of this one cell type.

In those cases where the cell expresses the first set of nucleic acid molecules of the invention, a first and a second stimulus are then applied to the cell. The first stimulus is chosen such that it is capable of inducing the first inducible interaction module. In other words, where the first inducible interaction module is e.g. a light-inducible interaction module, the first stimulus to be applied is light; where the first inducible interaction module is e.g. a ligand-inducible interaction module, the first stimulus to be applied is a ligand and where the first inducible interaction module is e.g. a calcium-inducible interaction module, the first stimulus to be applied is calcium, e.g. via providing a stimulus that leads to an increase in intracellular calcium. Preferably, the first stimulus is a ligand or calcium.

In addition, either simultaneously or prior or after the first stimulus, a second stimulus is applied to the cell, wherein this second stimulus is chosen such that it is capable of inducing the third biosensor in the nucleic acid molecule of the invention (i.e. the third biosensor encoded by the nucleic acid molecule of (c)), such that the protease cleavage site becomes accessible. Preferably, the second stimulus is light.

In those cases where the cell expresses the second set of nucleic acid molecules of the invention, three stimuli are applied to the cell. The first stimulus is chosen such that it is capable of inducing the first inducible interaction module, as described above for the first alternative of this method. Preferably, the first stimulus is a ligand or calcium.

In addition, either simultaneously or prior or after the first stimulus, a second stimulus is applied to the cell, wherein this second stimulus is chosen such that it is capable of inducing the second inducible interaction module of the nucleic acid molecule of the invention (i.e. according to option (b)(ii) in the nucleic acid molecule of the invention). If the second inducible interaction module is inducible by a different stimulus than the first inducible interaction module, which is preferred as detailed above, then it will be appreciated that the second stimulus is different from the first stimulus. Preferably, the second stimulus is light, most preferably blue light.

Furthermore, simultaneously or prior or after the first stimulus and/or the second stimulus, a third stimulus is applied to the cell. This third stimulus is chosen such that it capable of inducing the third biosensor in the nucleic acid molecule of the invention (i.e. the third biosensor encoded by the nucleic acid molecule of (c)), such that the protease cleavage site becomes accessible. Preferably, the third stimulus is identical to either the first or the second stimulus. More preferably, the third stimulus is identical to the second stimulus, and most preferably the third stimulus is light. It will be appreciated that where the third stimulus is identical to the first or second stimulus, said stimulus does not have to be provided separately.

Particularly preferred is that the first stimulus is a ligand or calcium and the second and third stimulus are a light stimulus, preferably blue light.

Once a cell expressing either the first or the second set of nucleic acid molecules of the invention has been exposed to the recited stimuli, all interaction partners will interact with each other, thereby bringing the individual parts of the protease together, such that the protease can exert its enzymatic action on the protease cleavage site that has become accessible due to the respective stimulus. As a consequence, the effector molecule is released from the fusion protein and can now exert its action.

All other definitions and preferred embodiments provided herein above with regard to the nucleic acid molecule and the sets of nucleic acid molecules of the invention, in particular with regard to the individual components of the fusion protein and their combinations, apply mutatis mutandis to this aspect of the invention.

The present invention further relates to a method for monitoring intracellular signaling, the method comprising: (a-i) providing a cell expressing the first set of nucleic acid molecules according to the invention; (a-ii) applying a first stimulus to the cell of (a-i), wherein the first stimulus is capable of inducing the first inducible interaction module; and (a-iii) applying a second stimulus to the cell of (a-i), wherein the second stimulus is capable of inducing the third biosensor such that the protease cleavage site becomes accessible; or (b-i) providing a cell expressing the second set of nucleic acid molecules according to the invention; (b-ii) applying a first stimulus to the cell of (b-i), wherein the first stimulus is capable of inducing the first inducible interaction module; (b-iii) applying a second stimulus to the cell of (b-i), wherein the second stimulus is capable of inducing the second inducible interaction module; and (b-iv) applying a third stimulus to the cell of (b-i), wherein the third stimulus is capable of inducing the third biosensor such that the protease cleavage site becomes accessible; and (c) detecting the biological response effected by the effector molecule.

Signaling events that can be monitored have been described herein above.

The term "monitoring" refers to tracking the events within the cell upon a stimulus based on the activity of the effector molecule. Depending on the choice of effector molecule, said monitoring can for example be carried out by observing the cells by microscopy, e.g. two-photon or confocal microscopy imaging by use of fluorescent labeling; by detecting gene expression levels in e.g. western blots, chemiluminescent assays, or immunohistochemical staining; as well as by measuring receptor-mediated currents in e.g. electrophysiological recordings.

The steps (a) and (b) in accordance with this method of the invention of monitoring intracellular signaling are identical to the steps (a) and (b) in accordance with the method of the invention of inducing intracellular signaling. Thus, the definitions and preferred embodiments provided above with regard to the method of the invention of inducing intracellular signaling apply mutatis mutandis to this method of the invention of monitoring intracellular signaling.

In addition, in a further step (c), the biological response effected by the effector molecule employed is detected.

Detection of the biological response can be carried out by any of a plethora of methods well known in the art. For example, if the biological response is an increase (e.g. in case of using a transcriptional activator) or decrease (e.g. in case of employing degron) in transcription or a change in transcription due to genome modulation (e.g. in case of employing Cre recombinase or the CRISPR/Cas system), detection can be carried out on the nucleic acid level or on the amino acid level. Methods for detecting transcription on the nucleic acid level include, but are not limited to, northern blotting, PCR, RT-PCR or real time RT-PCR. These methods are well known in the art. Methods for the detecting transcription on the amino acid level include but are not limited to western blotting or polyacrylamide gel electrophoresis in conjunction with protein staining techniques such as Coomassie Brilliant blue or silver-staining. Also of use in protein quantification is the Agilent Bioanalyzer technique. Where the biological response is an increase in the transcription of a fluorescently or bioluminescently labeled reporter molecule, or a change in the location of such a molecule within the cell, the detection can, in addition to the above techniques, also be carried out by microscopy or electrophysiological approaches such as whole-cell current or voltage clamp recording in combination with two-photon photolysis, or electrical or optogenetic neuronal stimulation. Electrophysiological recording will in particular be used when monitoring ionotrophic or metabotrophic receptor level changes. Furthermore, immunohistochemistry offers a further suitable approach for detecting the biological response effected by the effector molecule employed. Further aspects that can be monitored, in particular when the method is carried out in vivo in a host animal, include, without being limiting, sensory perception, motor planning/execution, emotional expression, psychiatric disorder symptoms such as schizophrenia or depression, as well as higher level cognitive functions such as motivation or learning.

Preferably, the method is carried out in vitro, most preferably in (an) isolated cell(s).

As is shown in the appended examples, the provision of the nucleic acid molecule of the invention now enables the performance of various improved methods for inducing and/or monitoring intracellular signaling events, in particular the iTango or iTango2 system or the Cal-Light system. Due to the two-step verification system employed in these methods, they represent ideal templates for multi-protein interaction induction and/or monitoring platforms. The methods of the present invention have an improved spatiotemporal resolution and signal-to-noise ratio compared to established techniques in the art and, thus, they can be applied even in environments such as the brain, that are difficult to investigate because of the subtle neuromodulatory signals that are constantly flowing in and out.

Unless otherwise defined, all technical and scientific terms used herein have the same meaning as commonly understood by one of ordinary skill in the art to which this invention belongs. In case of conflict, the patent specification, including definitions, will prevail.

All the sequences accessible through the Database Accession Numbers cited herein are within the scope of the present invention and also include potential future updates in the database, in order to account for future corrections and modifications in the entries of the respective databases, which might occur due to the continuing progress of science.

All amino acid sequences provided herein are presented starting with the most N-terminal residue and ending with the most C-terminal residue (N→C), as customarily done in the art, and the one-letter or three-letter code abbreviations as used to identify amino acids throughout the present invention correspond to those commonly used for amino acids.

Regarding the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims. To give a non-limiting example, the combination of claims 12, 9 and 4 is clearly and unambiguously envisaged in view of the claim structure. The same applies for example to the combination of claims 12, 9 and 7, etc.

The figures show:

FIG. 1: Development of BLITz system. (a) Schematic drawing of BLITz proteins and simple diagram of light-induced gene expression. The major protein body, TM-CIBN-TEV-N-AsLOV2-TEVseq-TetR-VP16 (tTA), is targeted to a membrane with a transmembrane domain (TM). CRY2PHR-TEV-C is localized in the cytosol. Blue light causes interaction of CRY2PHR with CIBN, and TEV-C and TEV-N subsequently interact with each other. At the same time, TEVseq is unmasked due to conformational changes of AsLOV2 Jα-helix. When these two light-dependent processes are satisfied, TEVseq cleaves TetR-VP16, which translocates to the nucleus and causes targeted gene expression. (b) Design of TEVseq insertion into Jα-helix. The C-terminal end of Jα-helix was serially deleted and replaced by the TEV cleavage sequence (TEVseq; sequence ENLYFQG (SEQ ID NO:24)). The TEV cleavage site (after "Q" and before "G") is labeled by arrowheads. Note that numbering of different BLITz constructs is independent of deletion length. (c) Average of SEAP activity assay when transfected with different types of BLITz constructs. ** indicates p<0.01. (d) Fold induction changes when blue light was illuminated. * indicates p<0.05 (e) Schematic of DNA plasmids transfected into cells (top). EGFP and TdTomato expression when different BLITz constructs were transfected. When TEVseq was not hidden, a significant amount of EGFP expression is visible even in dark condition. When BLITz-1 and -6 were transfected, EGFP signals were detected only when blue light was illuminated. The control without tTA (No tTA) did not trigger any gene expression even in the light condition. TdTomato is a transfection marker. (f) Light exposure time-dependent gene expression fold changes. (g) Representative images of region-specific gene expression controlled by light. Scale bars, 200 μm (e) and 1 mm (g).

Figure 2:
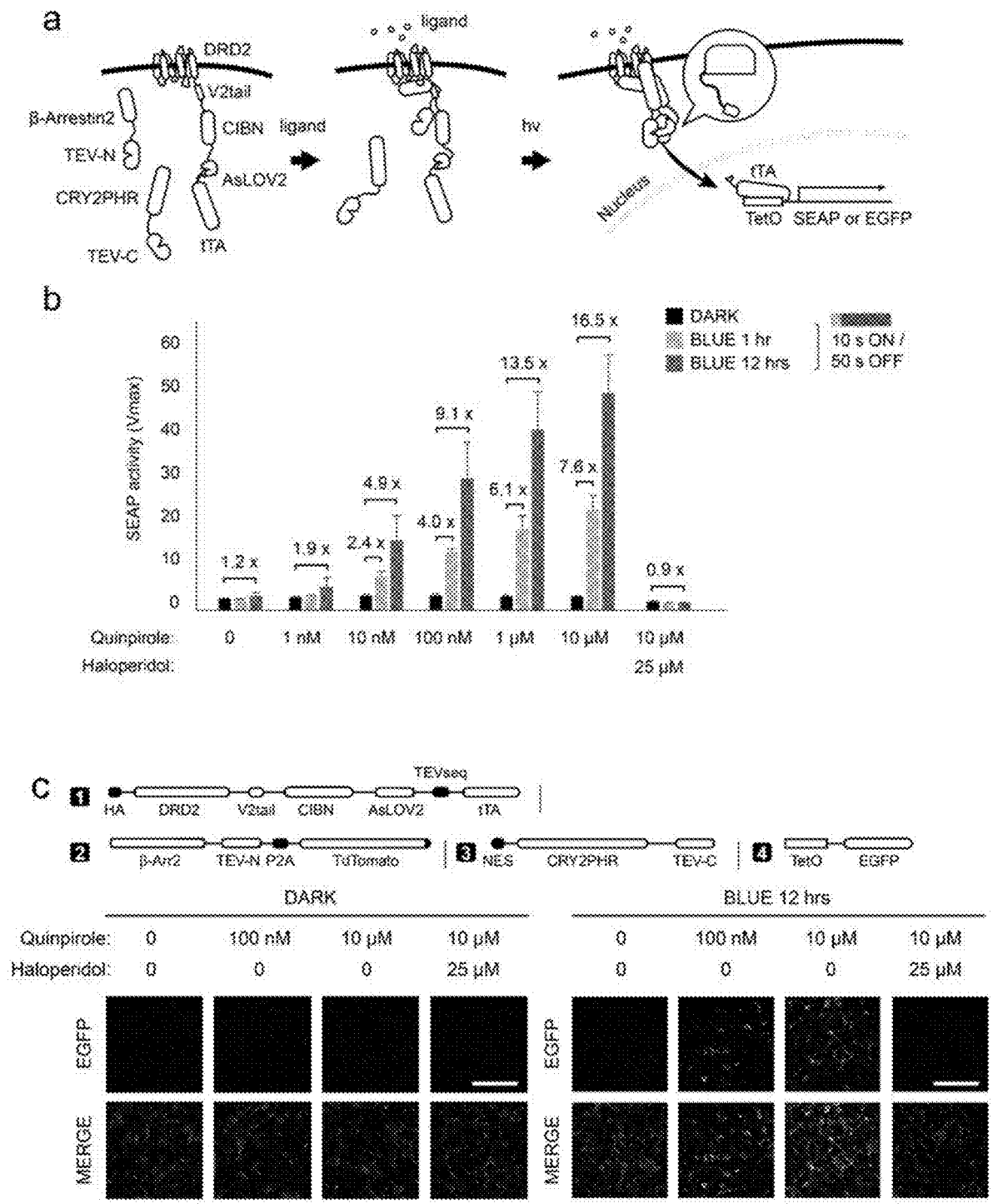

FIG. 2: Development of the iTango platform. (a) Graphical illustration of the iTango system. DRD2-V2tail (Vasopressin 2 tail)-CIBN-AsLOV2-tTA functions as the main platform. Two more modules co-operate together to cleave TEVseq by reacting to either light or ligand. DRD2 activation by an agonist leads to β-arrestin-2-TEV-N fusion protein translocation and binding to V2tail. The other part of TEV, TEV-C, is recruited by blue light via CRY2PHR-CIBN binding. When all iTango modules combine, released tTA translocates into the nucleus to cause gene expression. (b) The level of gene expression quantified by SEAP assay. Concentration of quinpirole (1 nM~10 μM) and period of blue light was varied. SEAP activity was proportionally increased by the concentration of quinpirole and the duration of light exposure. (c) The DRD2-iTango system monitored by EGFP expression. EGFP expression was prominent only when both light and ligand are present. No EGFP was expressed even by high concentration of quinpirole if blue light was off. Blue light only was not sufficient to induce EGFP expression. TdTomato is used as a transfection marker. Scale bar, 200 μm.

Figure 3:
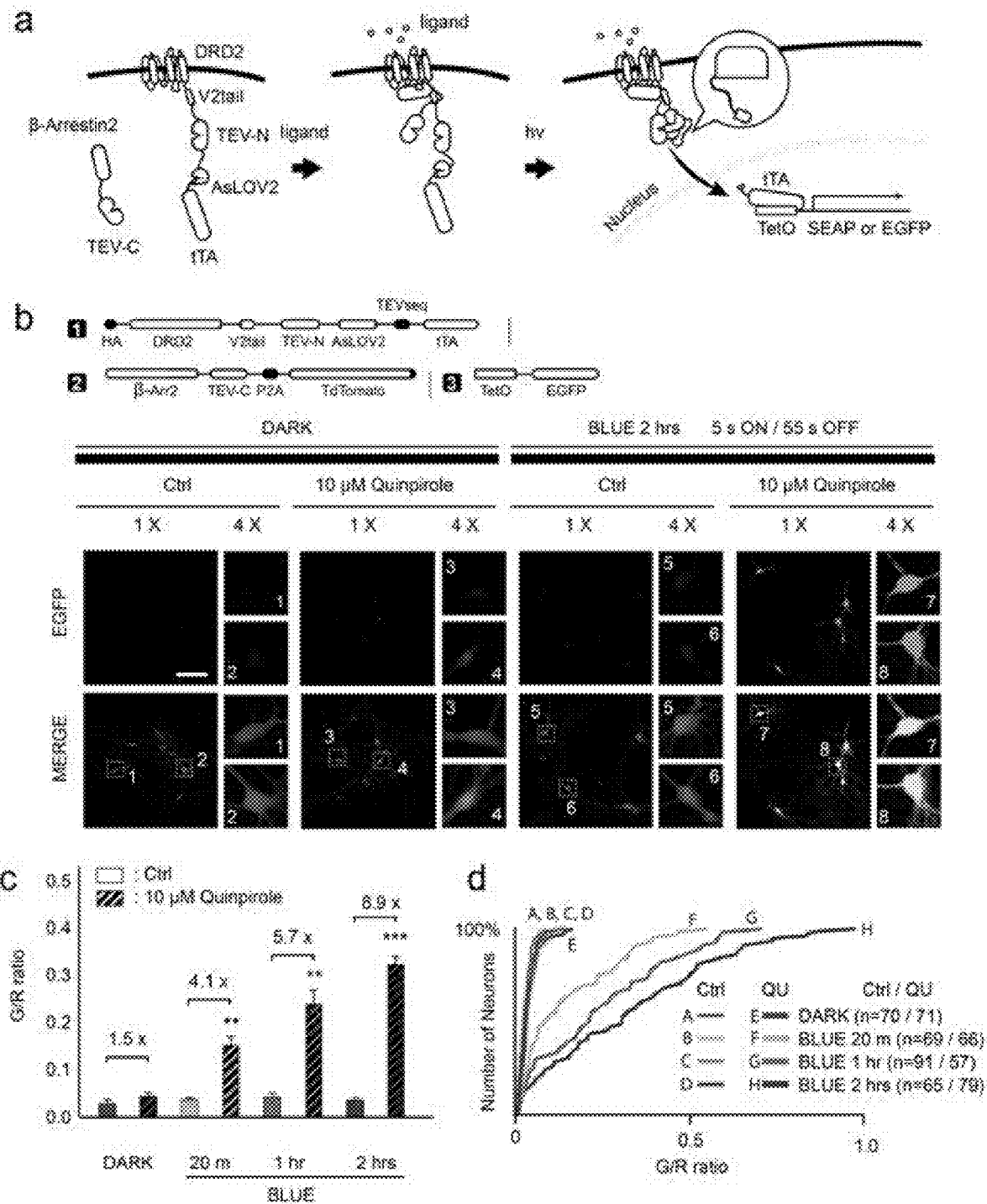

FIG. 3: Light- and ligand-inducibility of gene expression in neurons using iTango2. (a) Schematic design of iTango2 system. Dopamine binding to DRD2 causes β-arrestin-2 recruitment to V2tail. Light exposes TEVseq, leading to the release of tTA and subsequent gene expression. (b) Light- and ligand-dependent gene expression pattern tested in hippocampal culture neurons. iTango2 constructs and EGFP reporter genes were transfected and gene expression levels were compared between the dark and blue light conditions. Two representative neurons from each condition are magnified for clear visualization of expression. (c) Summary graph showing that EGFP expression is increased depending on the blue light exposure time and the presence of the DRD2 agonist, quinpirole. Gene expression level was measured by calculating the ratio of green to red fluorescence intensities. (d) Cumulative plot of EGFP expressing neurons. Blue light shifted the curve to the right direction significantly, indicating that more neurons display high level of green fluorescence. Note that blue light alone could not elicit any EGFP expression. Quinpirole without blue light also failed to cause gene expression at all, while a short period of blue light robustly enhanced EGFP expression. Scale bar, 100 μm (b).

Figure 4:
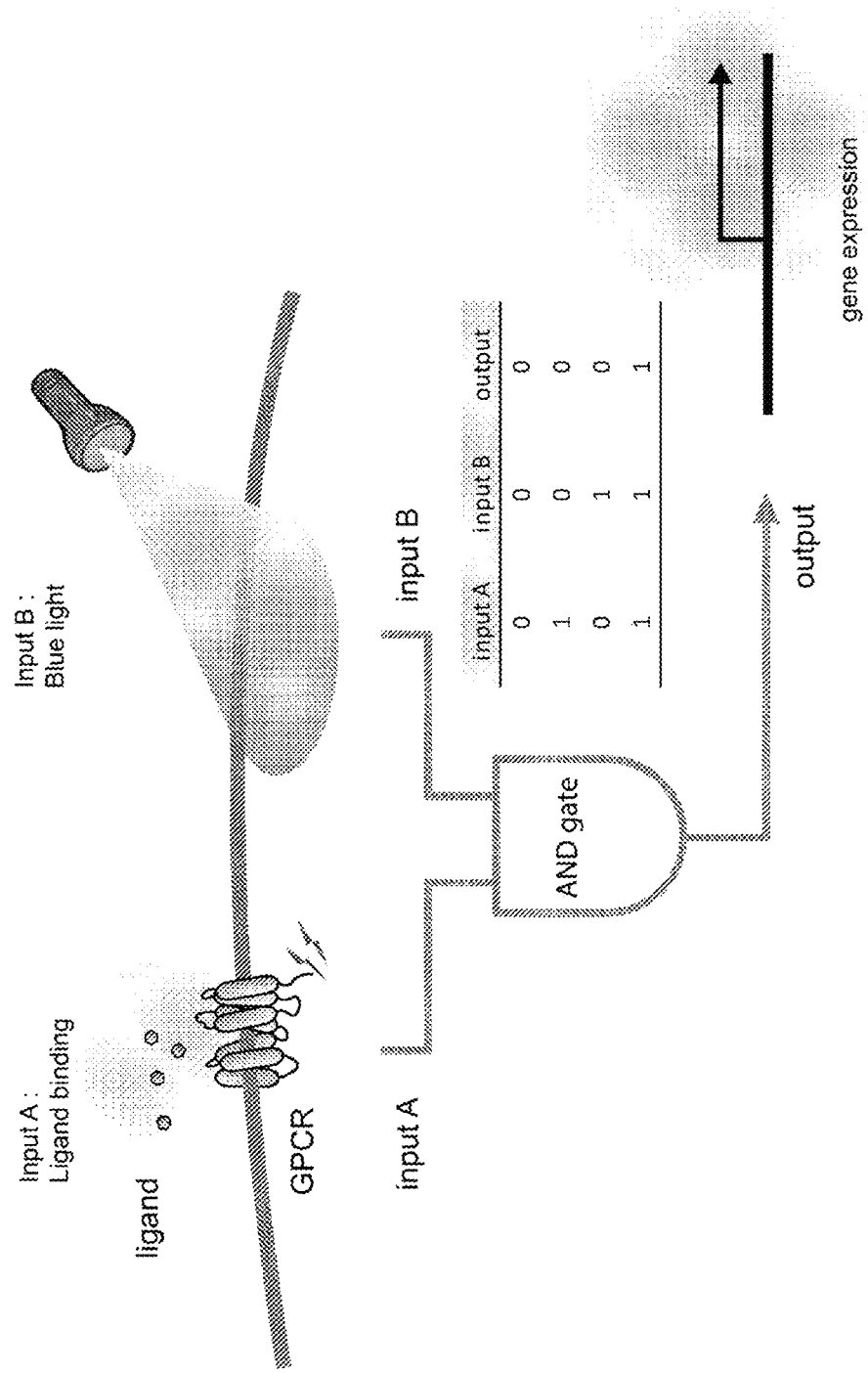

FIG. 4: A general strategy for a ligand-mediated gene expression system gated by light. Schematic illustration of a ligand-mediated gene expression system gated by blue light. The strategy is similar to "AND logic gate". Ligand binding event or blue light provide independent signaling inputs to the system and the final output (target gene expression) is only turned on when both signals are concomitantly triggered. Gene expression level becomes proportional to the strength and the duration of ligand-mediated signaling in the presence of blue light.

Figure 5:
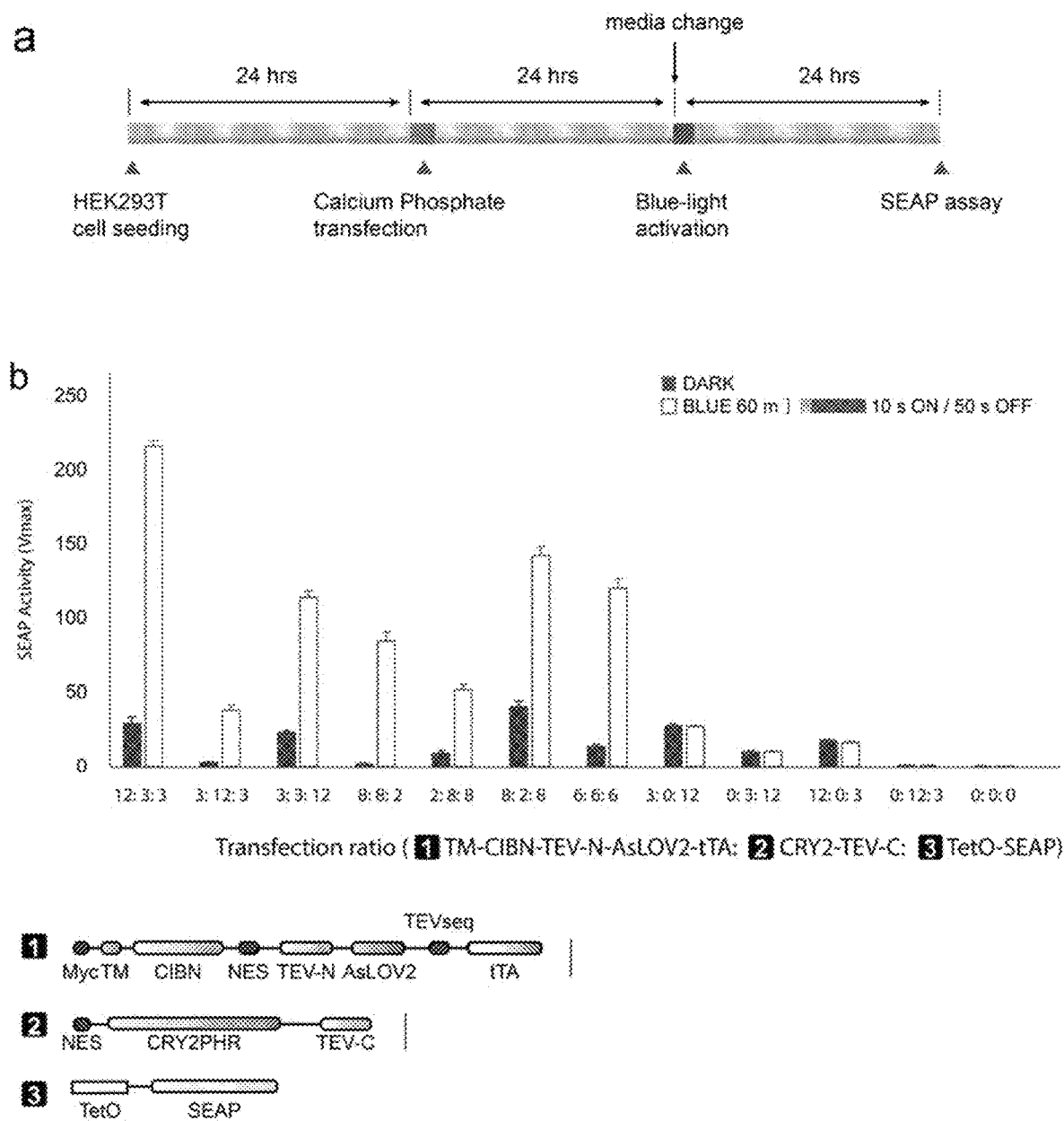

FIG. 5: Optimization of BLITz in various condition of transfection ratio. (a) Schematic experimental procedures in HEK293T cells. Right before blue light activation, media was replaced by fresh DMEM containing 10% FBS. (b) Summary graph of SEAP assay at different ratios of BLITz constructs. The best fold change was observed for the 8:8:2 (TM-CIBN-TEV-N-AsLOV2-tTA: CRY2-TEV-C: TetO-SEAP) ratio. Error bar represents±S.D. of three independent experiments.

Figure 6:
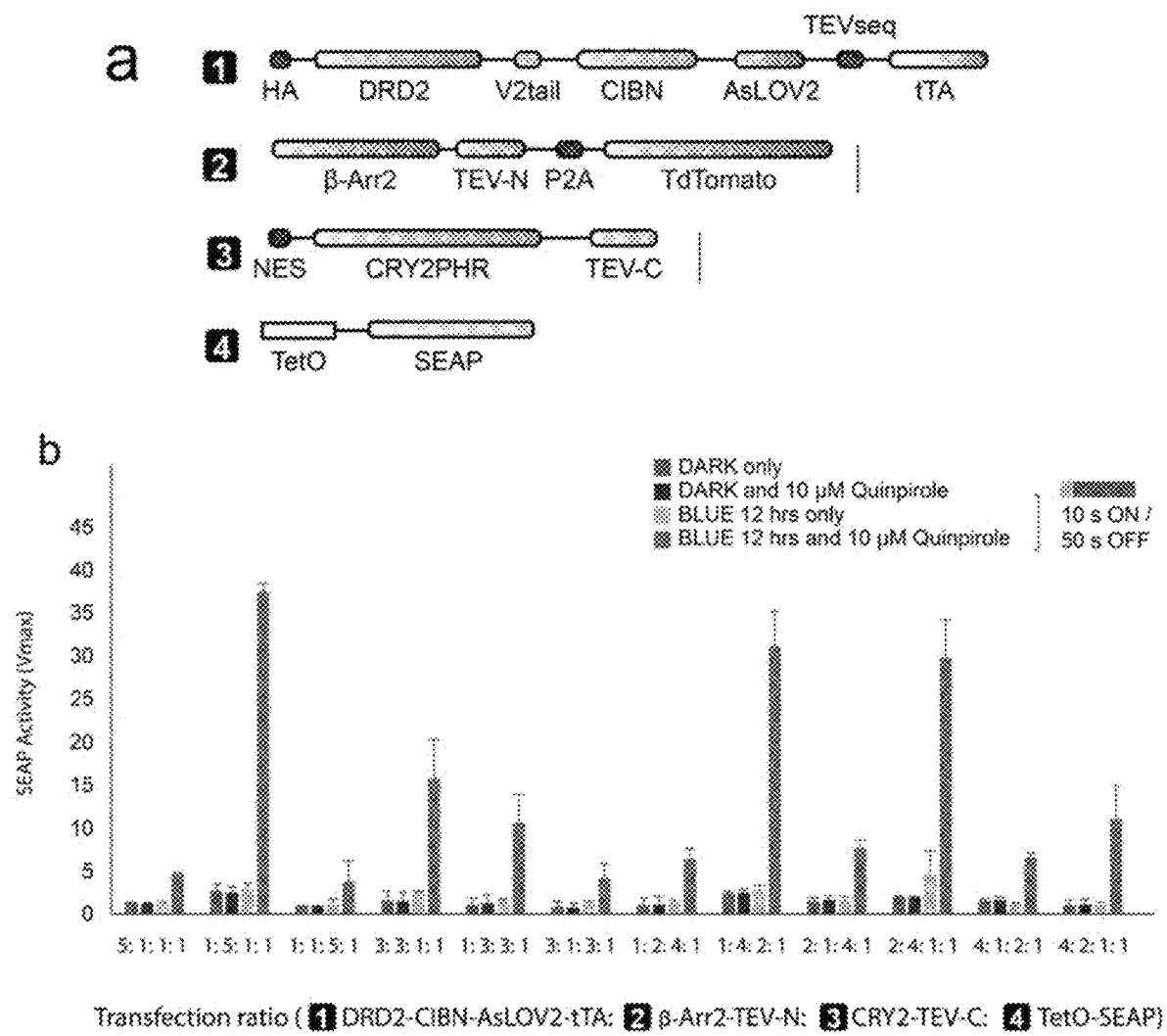

FIG. 6: Optimization of DRD2-iTango1 (prototype of iTango) at various transfection ratios. (a) Schematics of DNA constructs of DRD2-iTango1. (b) SEAP assay shows different gene expression level of DRD2-iTango1 at various transfection ratios. To test DRD2-iTango1, 10 μM Quinpirole were treated and a 10-second pulsed blue light was given for 12 hrs. The summary graph is represented by means±S.D. of three independent measurements.

Figure 7:
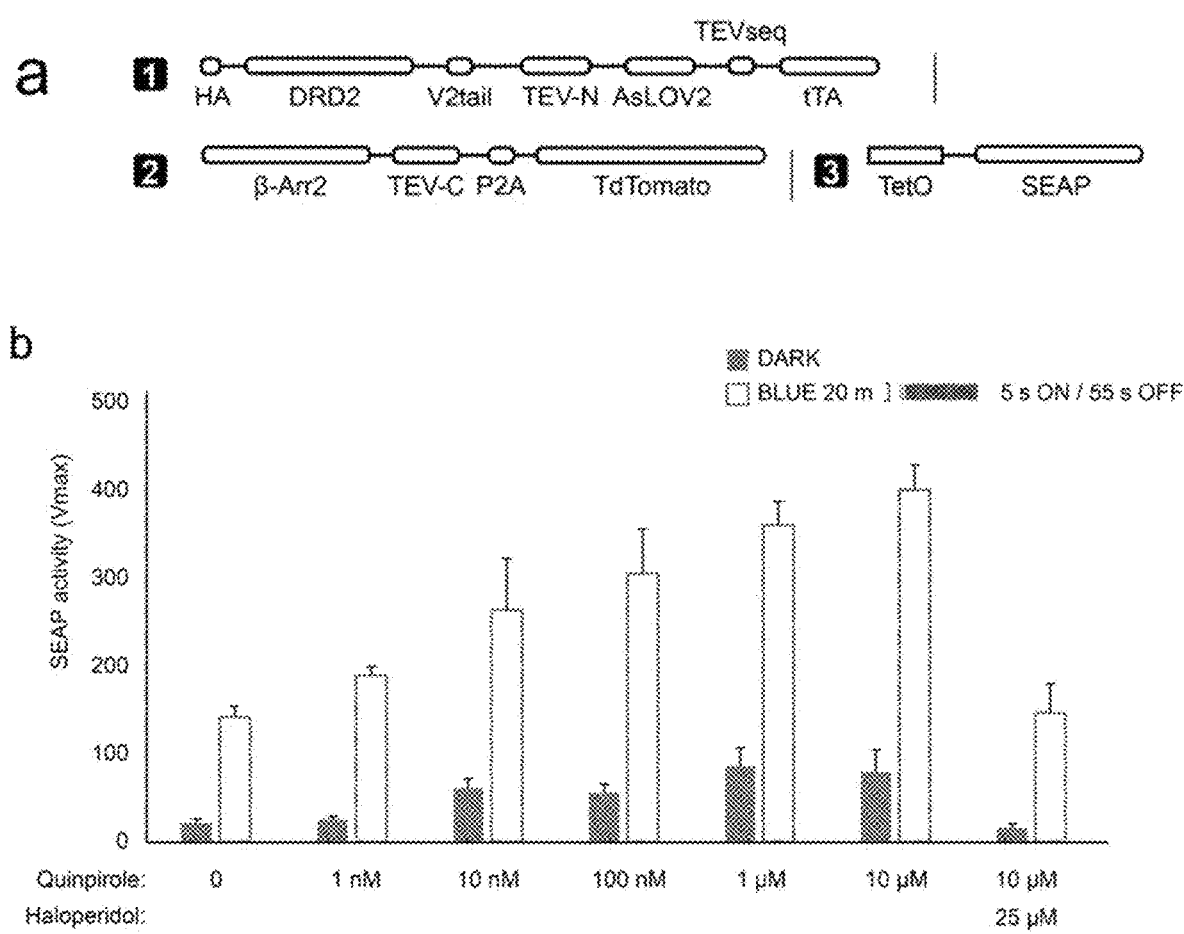

FIG. 7: Blue light- and ligand-dependent gene expression of DRD2-iTango2 in HEK293T cells. (a) Simplified illustration of DNA constructs containing individual protein modules. (b) Summary graph of dose-dependent gene expression pattern of DRD2-iTango2 in HEK293T cells. Various concentration of quinpirole was applied in the presence of blue light (5 sec on/55 sec off) for 20 min.

Figure 8:
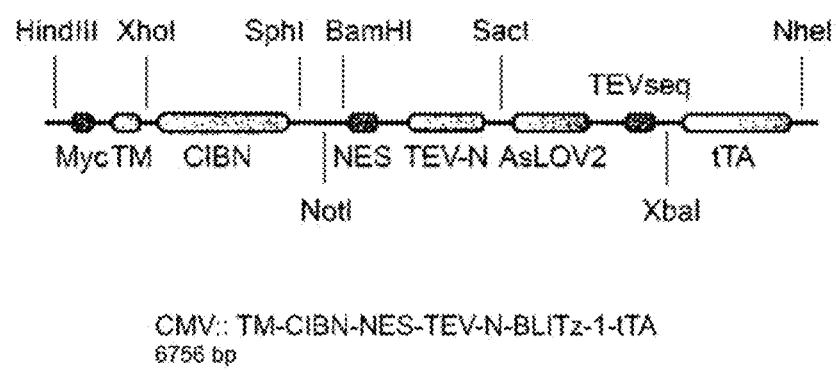
Figure 8:
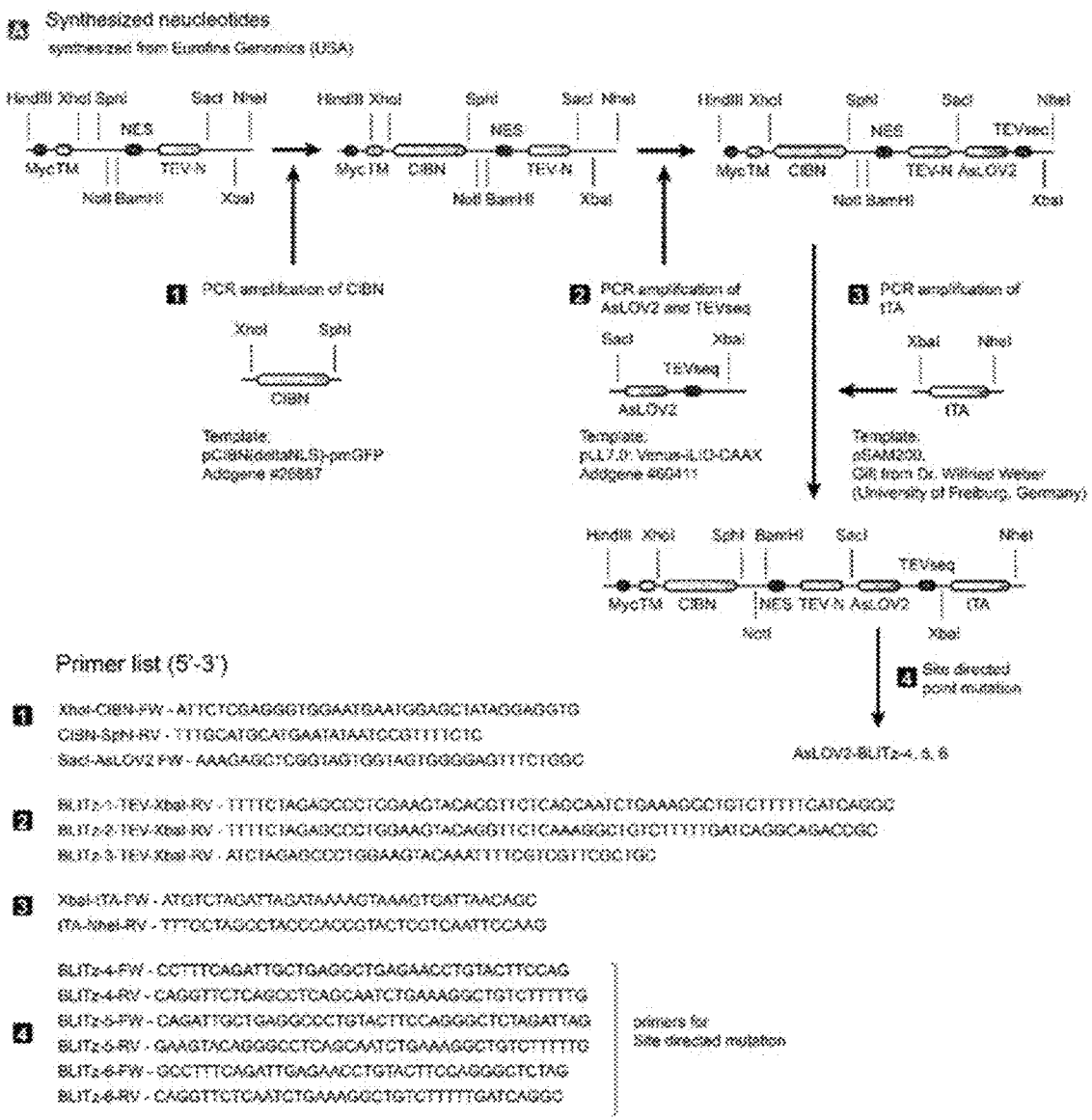

FIG. 8: Schematic figure representing a workflow to clone CMV::TM-CIBN-NES-TEV-N-BLITz-1-tTA and a primer list (SEQ ID NOs: 75 to 88) used in the cloning process.

Figure 9:
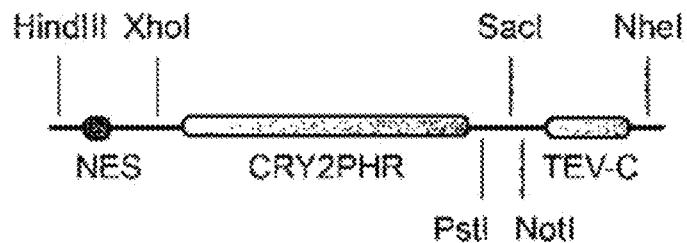
Figure 9:
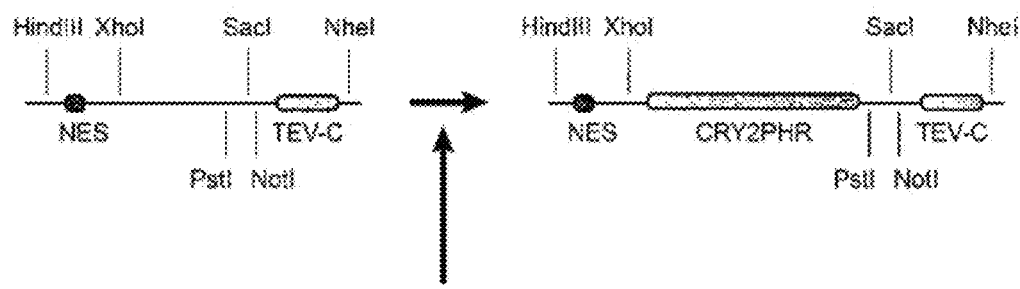
Figure 9:
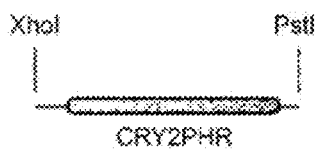

FIG. 9: Schematic figure represents a workflow to clone CMV::NES-CRY2PHR-TEV-C and a primer list (SEQ ID NOs: 89 and 90) used in the cloning process.

Figure 10:
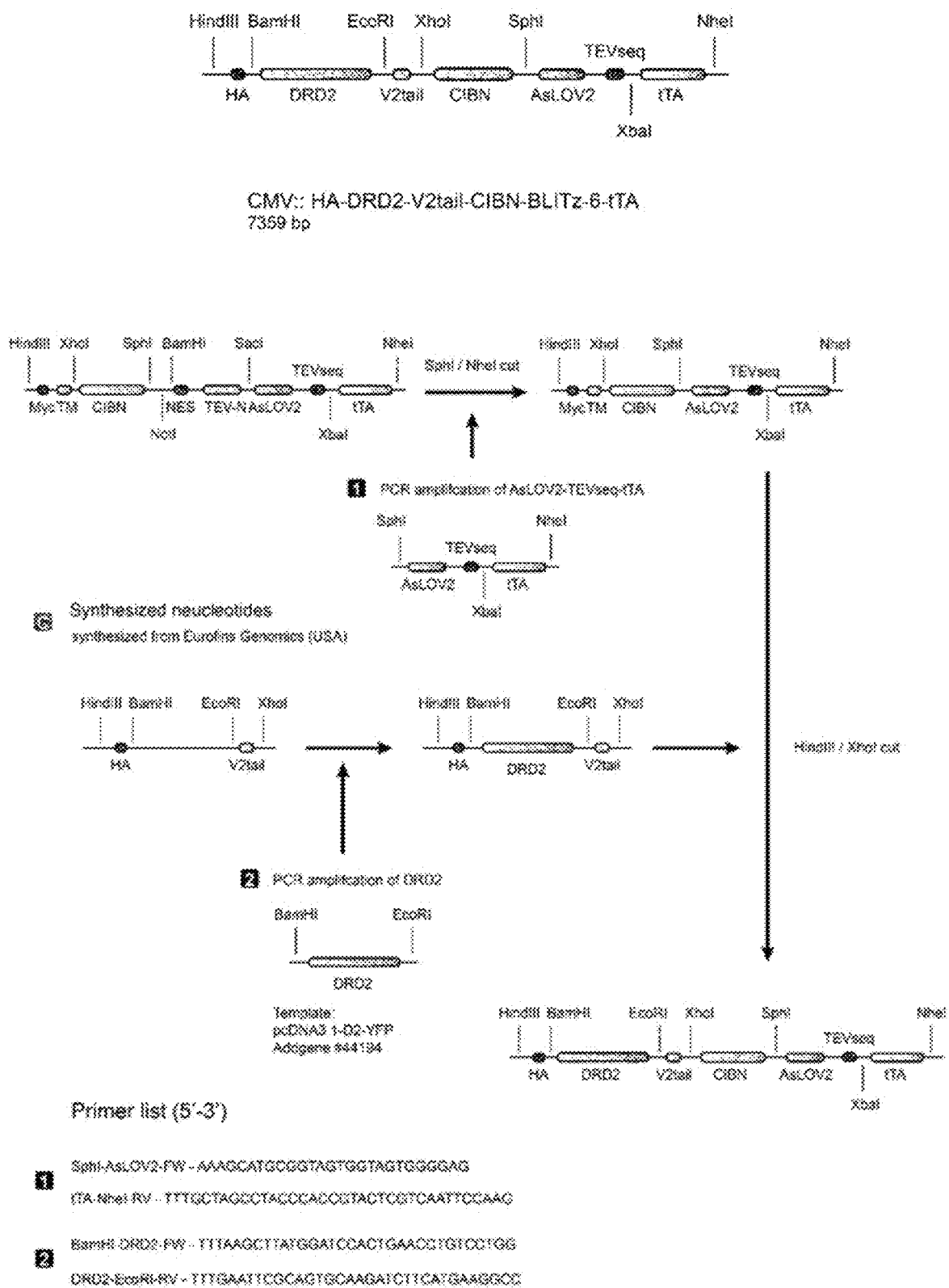

FIG. 10: Schematic figure represents a workflow to clone CMV::HA-DRD2-V2tail-CIBN-BLITz-6-tTA and a primer list (SEQ ID NOs: 91 to 94) used in the cloning process.

Figure 11:
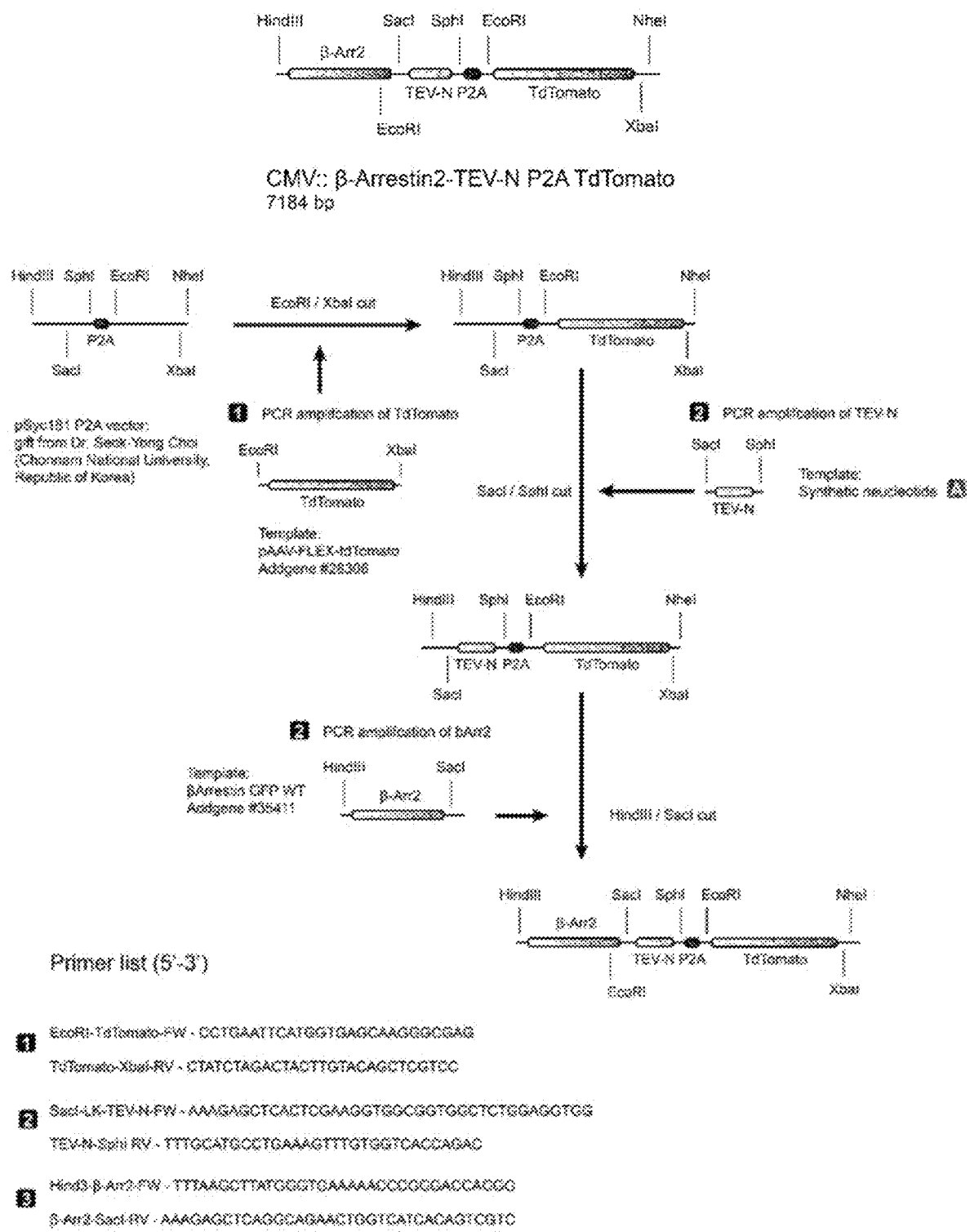

FIG. 11: Schematic figure represents a workflow to clone CMV::β-Arr2-TEV-N P2A TdTomato and a primer list (SEQ ID NOs: 95 to 100) used in the cloning process.

Figure 12:
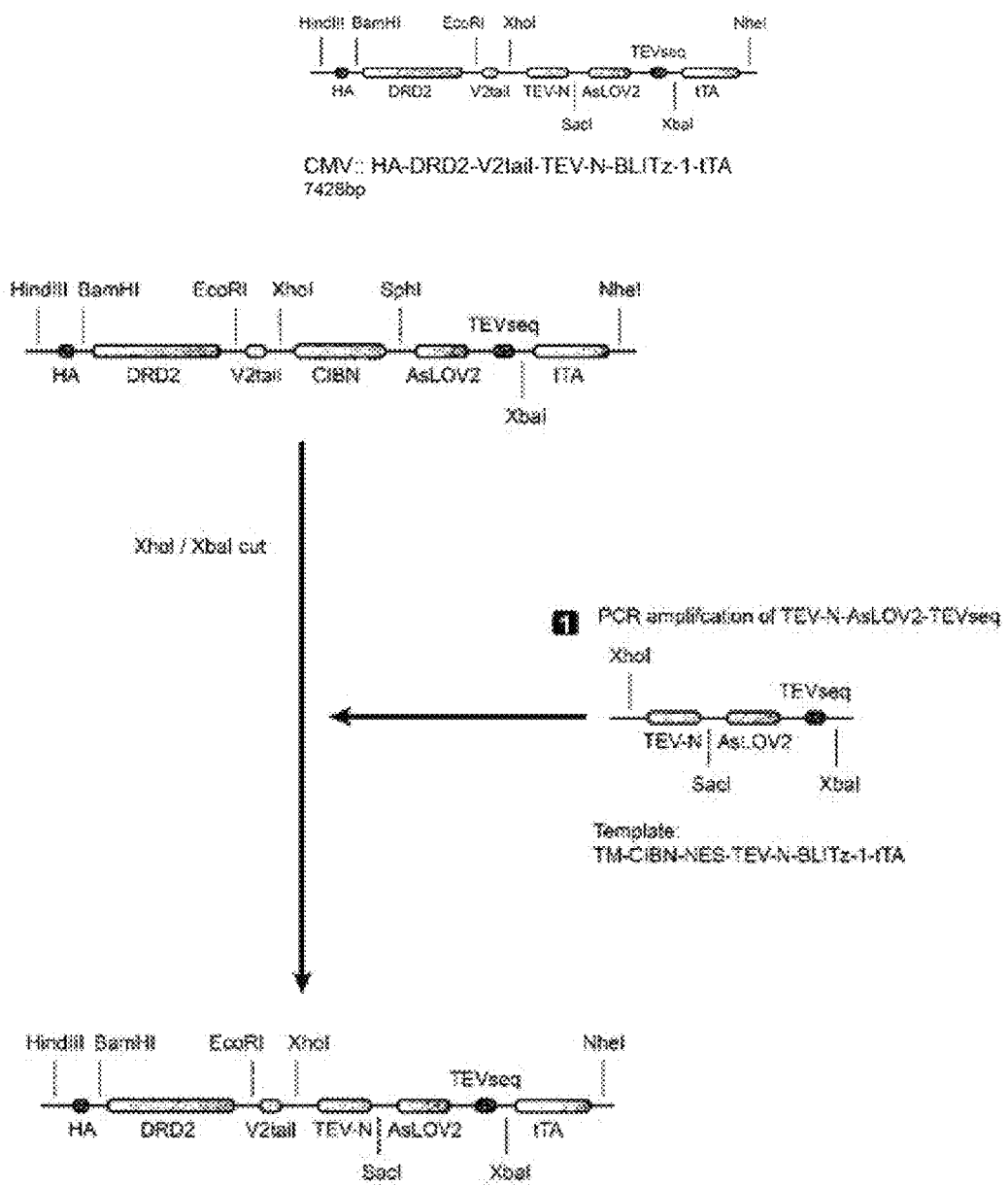

FIG. 12: Schematic figure represents a workflow to clone CMV::HA-DRD2-V2tail-TEV-N-BLITz-1-tTA and a primer list (SEQ ID NOs: 101 and 102) used in the cloning process.

Figure 13:
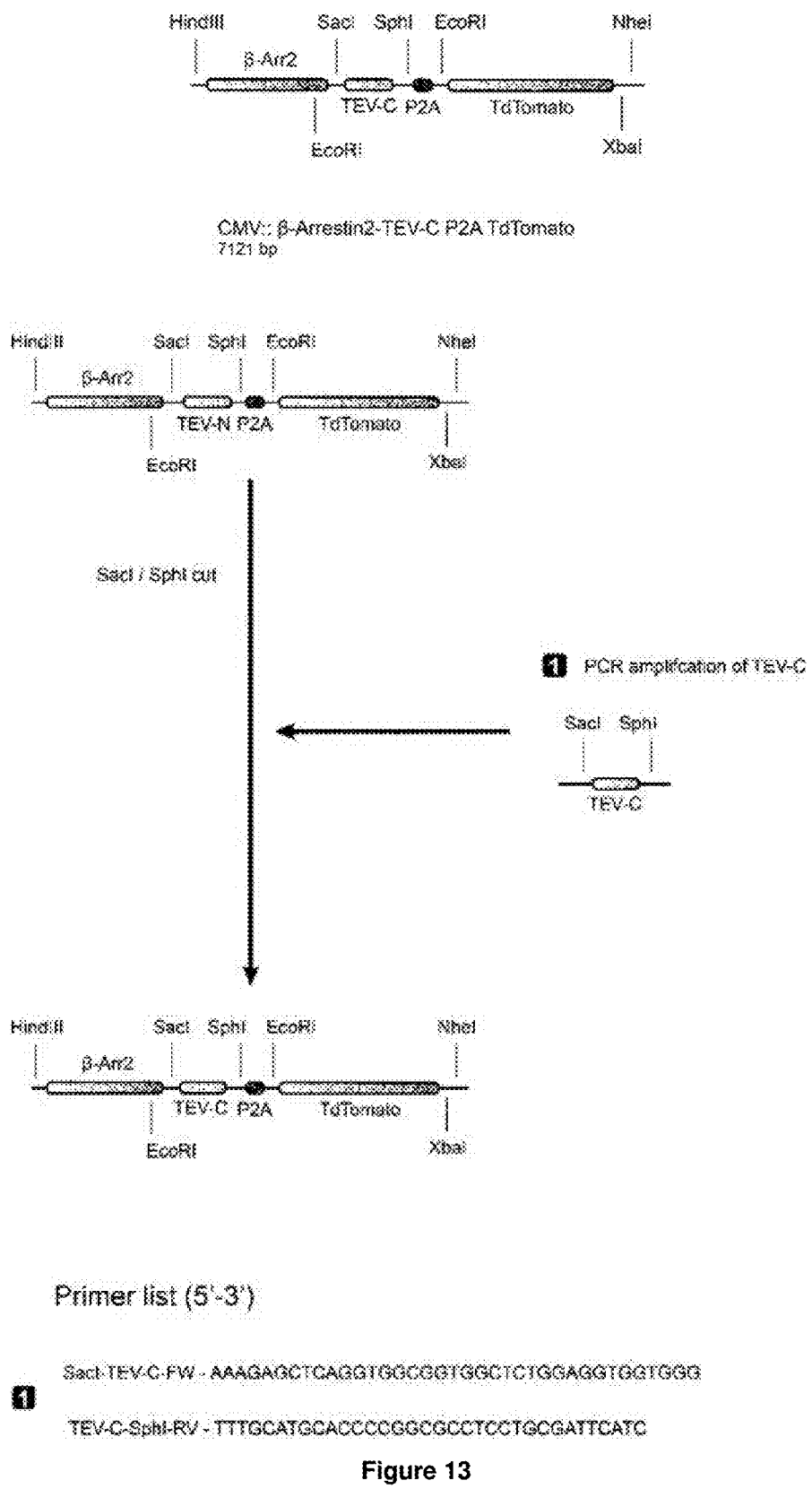

FIG. 13: Schematic figure represents a workflow to clone CMV::β-Arr2-TEV-C P2A TdTomato and a primer list (SEQ ID NOs: 103 and 104) used in the cloning process.

Figure 14:
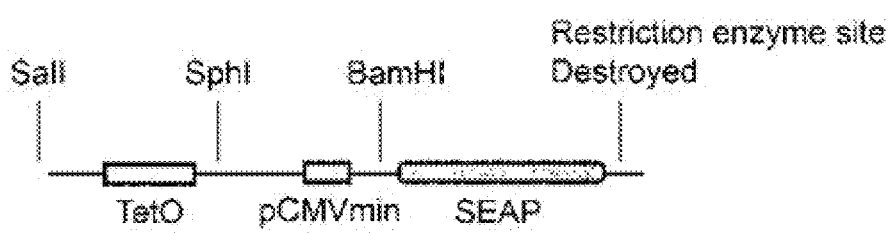
Figure 14:
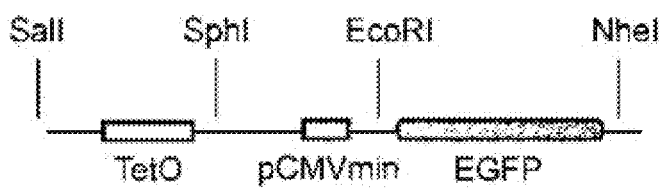
Figure 14:
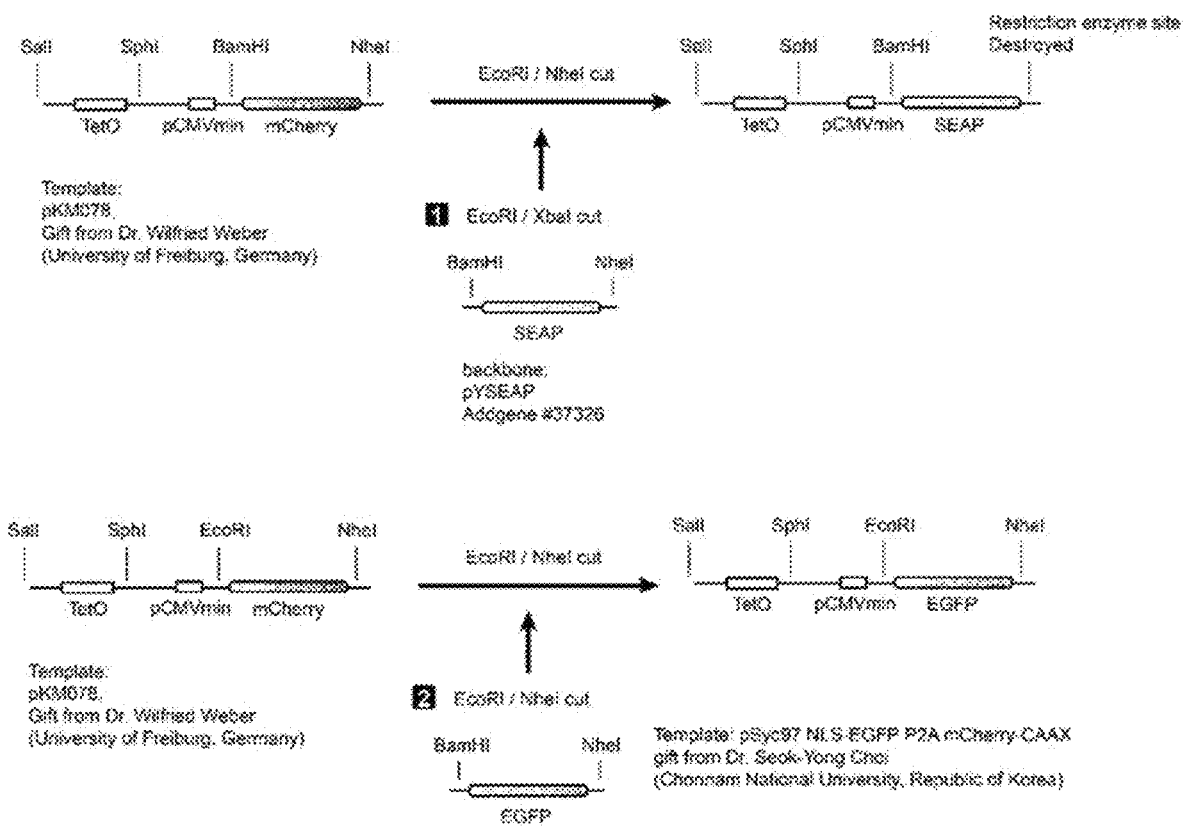

FIG. 14: Schematic figure represents a workflow to clone both TetO-SEAP and TetO-EGFP and a primer list (SEQ ID NOs: 105 and 106) used in the cloning process.

Figure 15:
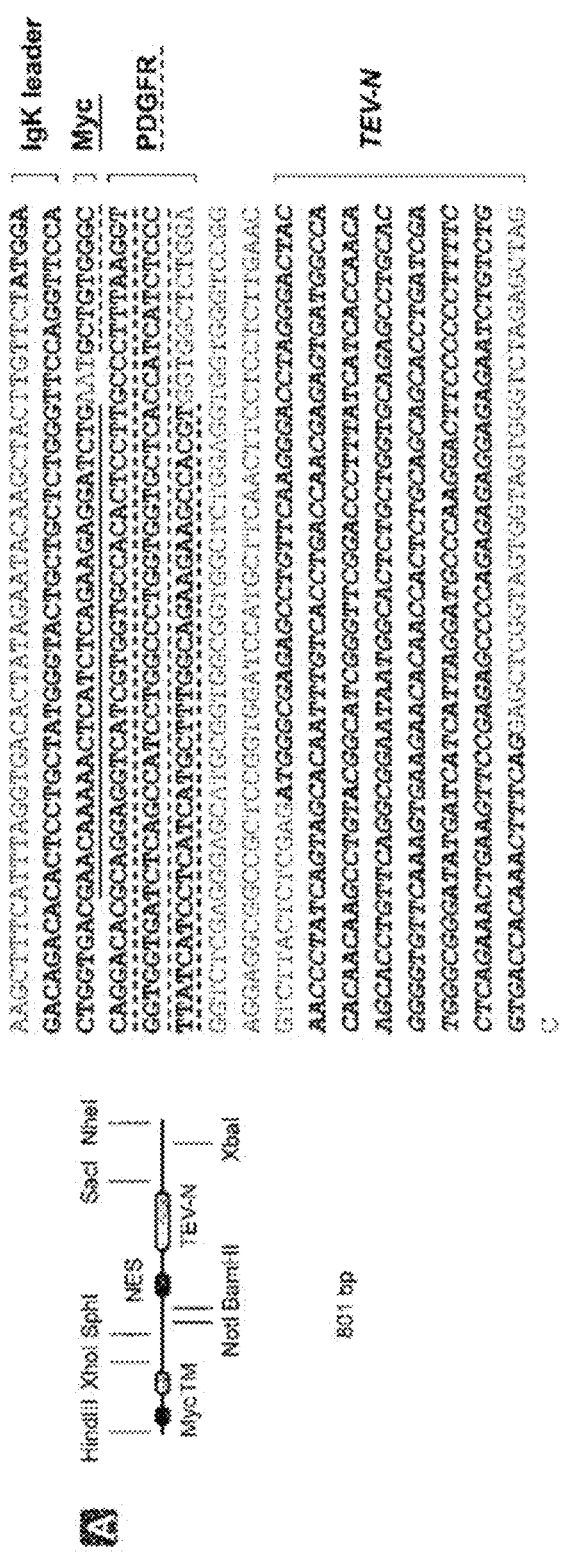
Figure 15:
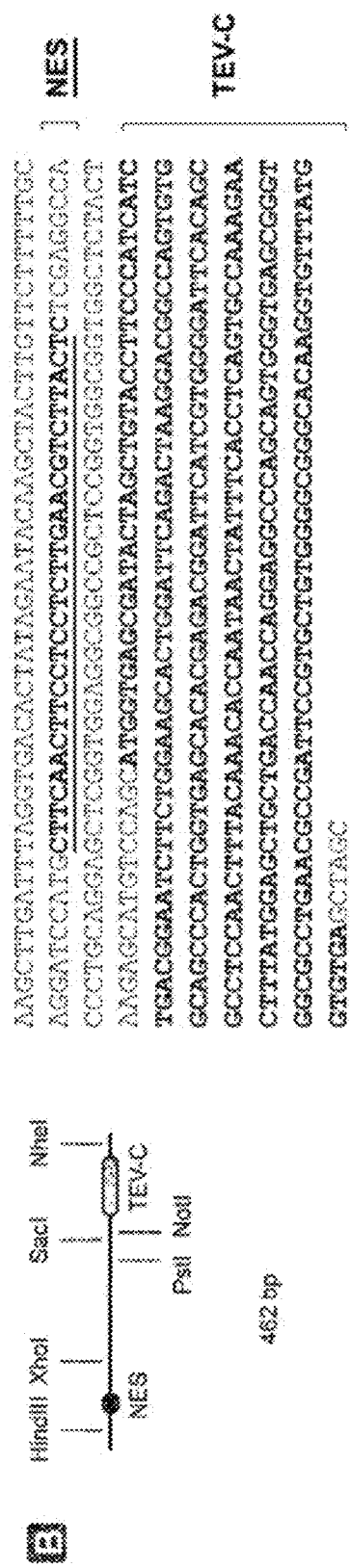
Figure 15:
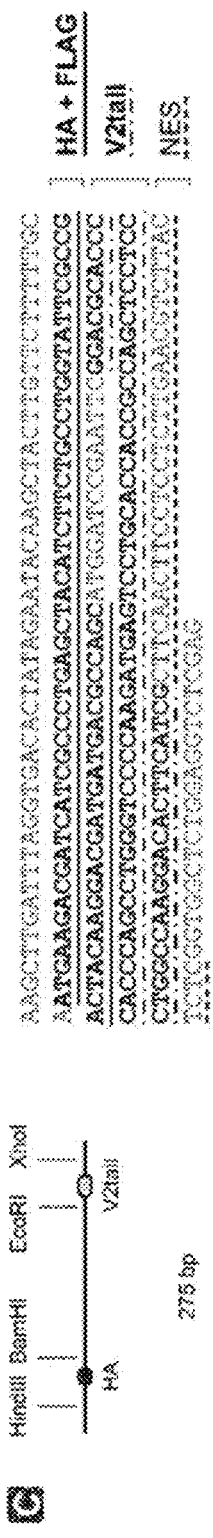

FIG. 15: Synthetic nucleotide backbone to develop the BLITz and iTango systems. Backbone "A" (SEQ ID NO:7) (IgK leader sequence: bold, Myc sequence: solid line, PDGFR transmembrane domain: dashed line, TEV-N sequence: bold italic) is used to clone CMV::TM-CIBN-NES-TEV-N-BLITz-1-tTA as described in FIG. 8; Backbone "B" (SEQ ID NO:47) (NES sequence: solid line, TEV-C: bold) is used to clone CMV::NES-CRY2PHR-TEV-C as described in FIG. 9; Backbone "C" (SEQ ID NO:48) (HA+FLAG sequences: solid line, V2tail: dashed dotted line, NES sequence: dashed line) is used to clone CMV::HA-DRD2-V2tail-CIBN-BLITz-6-tTA as described in FIG. 10.

Figure 16:
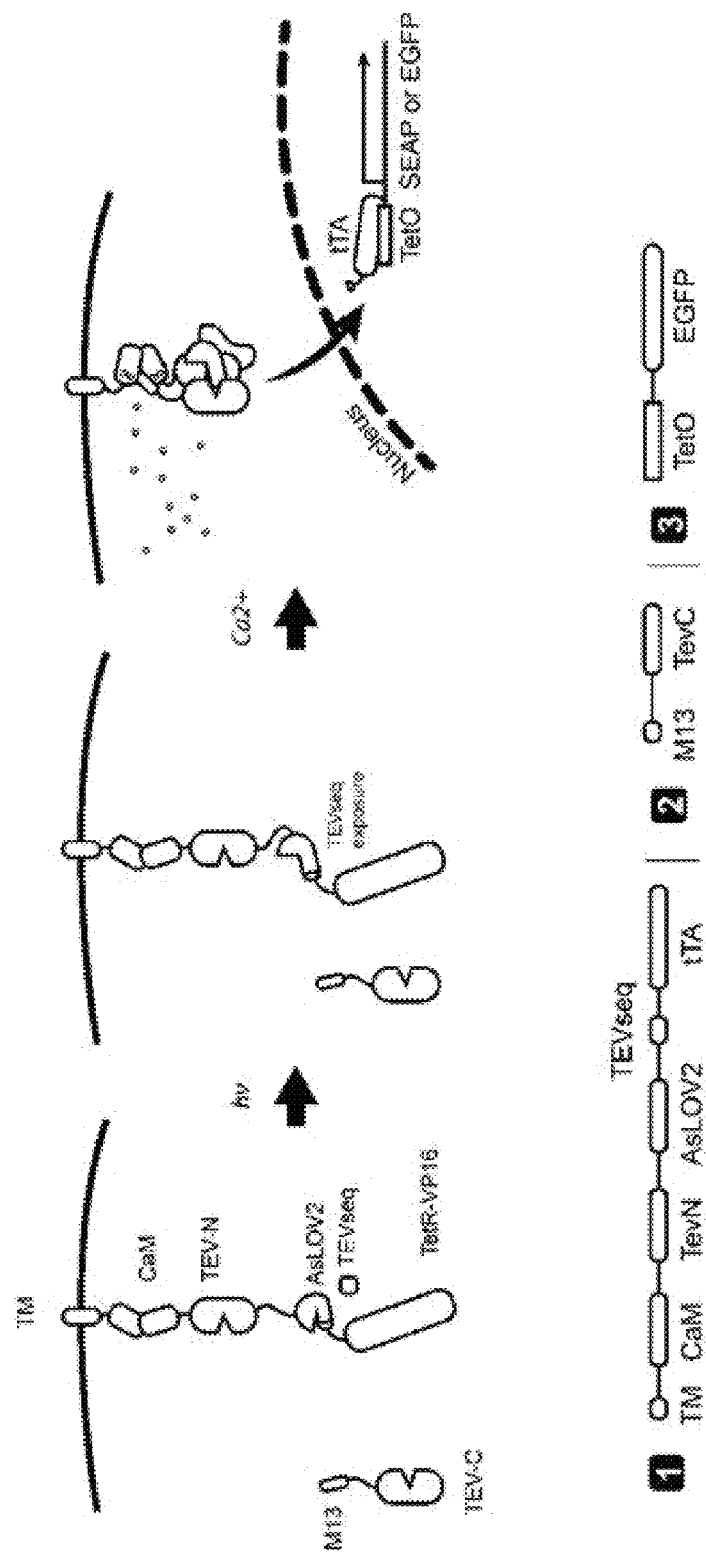

FIG. 16: Principles of Cal-Light. Schematic overview showing the principle of calcium- and light-induced signaling in the Cal-Light system.

Figure 17:
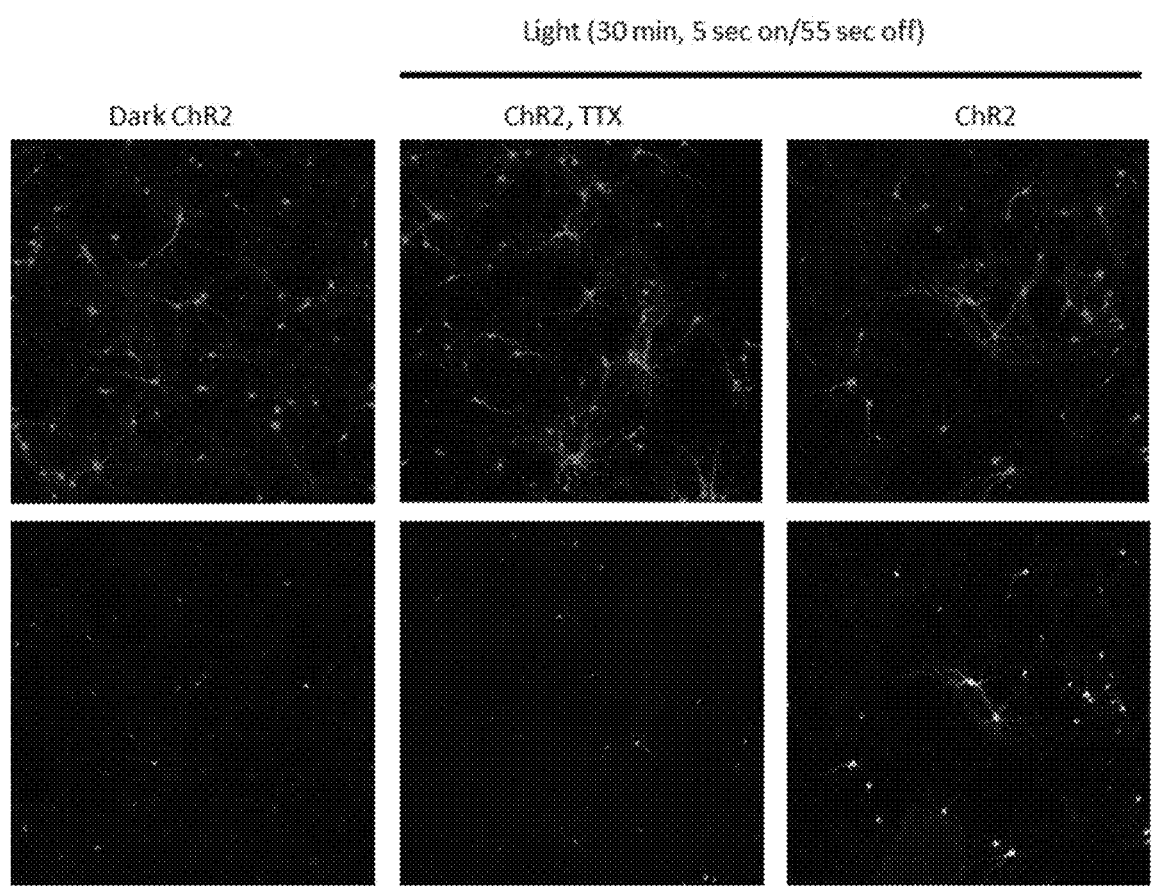

FIG. 17. Cal-Light test in dissociated culture neurons. Cal-Light constructs and EGFP reporter plasmid were transfected to hippocampal culture neurons. After 5 days of expression, a short pulse of blue light (5 sec on/55 sec off) was illuminated for 30 min in the presence or absence of tetrodotoxin (TTX). Two days later, slices were fixed and images were taken by confocal microscopy. EGFP expression was robustly increased only in a condition when blue light was illuminated and neuronal activity was not inhibited by TTX.

Figure 18:
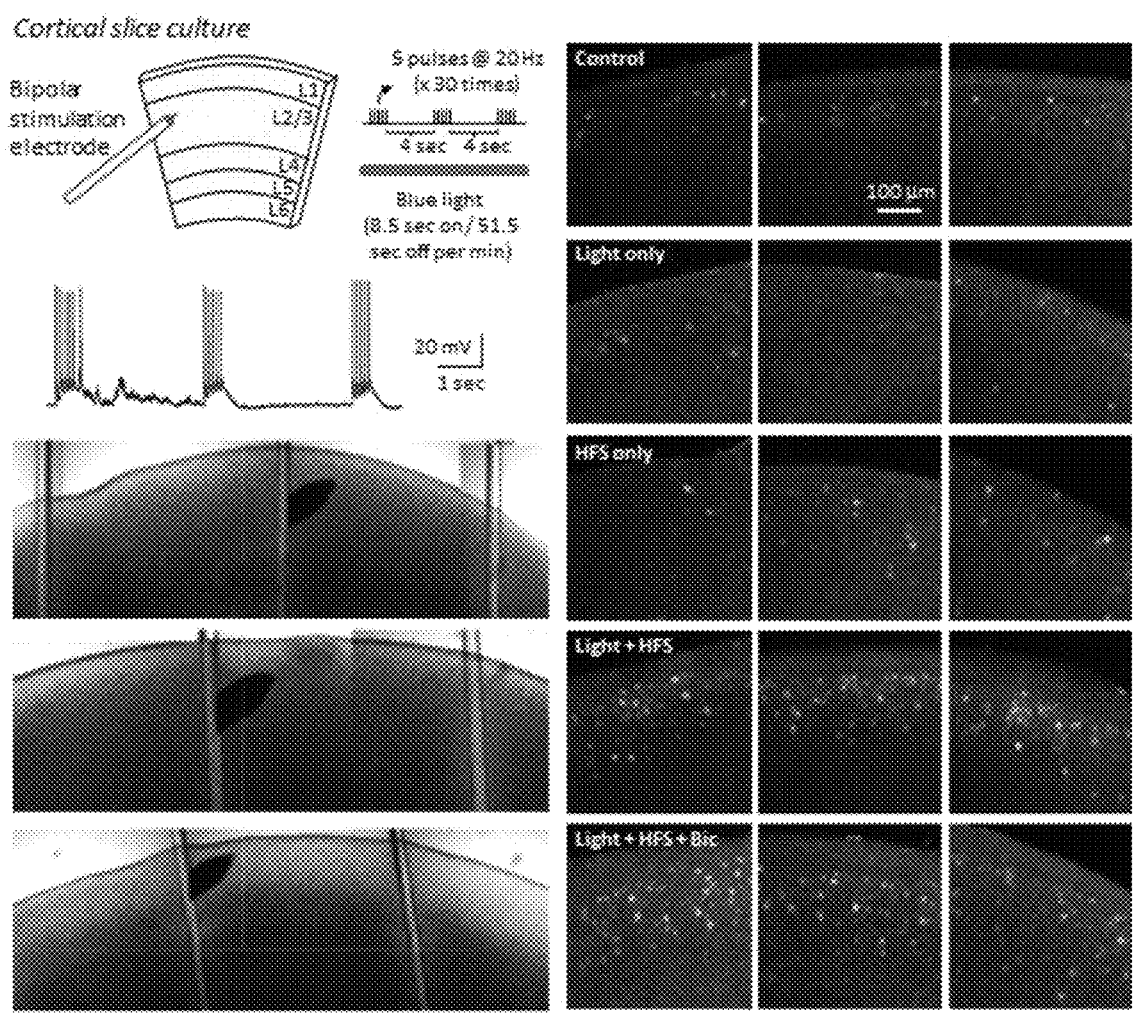

FIG. 18. Cal-Light test in cortical slice culture. AAV expressing Cal-Light constructs and EGFP reporter were infected to cortical slice culture at DIV3 (Days in vitro). After 12 days of expression, a short pulse of blue light (8.5 sec on/51.5 sec off) was illuminated for 30 min while a short burst of electrical stimulation was given. Examples of action potentials were plotted at the top left panel. Electrical stimulation reliably triggered action potentials measured in layer 2/3 pyramidal neurons. Two days later, slices were fixed and images were taken by confocal microscopy. EGFP expression was robustly increased in a condition when blue light and high frequency stimulation were given. Blue light or high frequency stimuli alone was not able to increase the level of EGFP expression.

Figure 19:
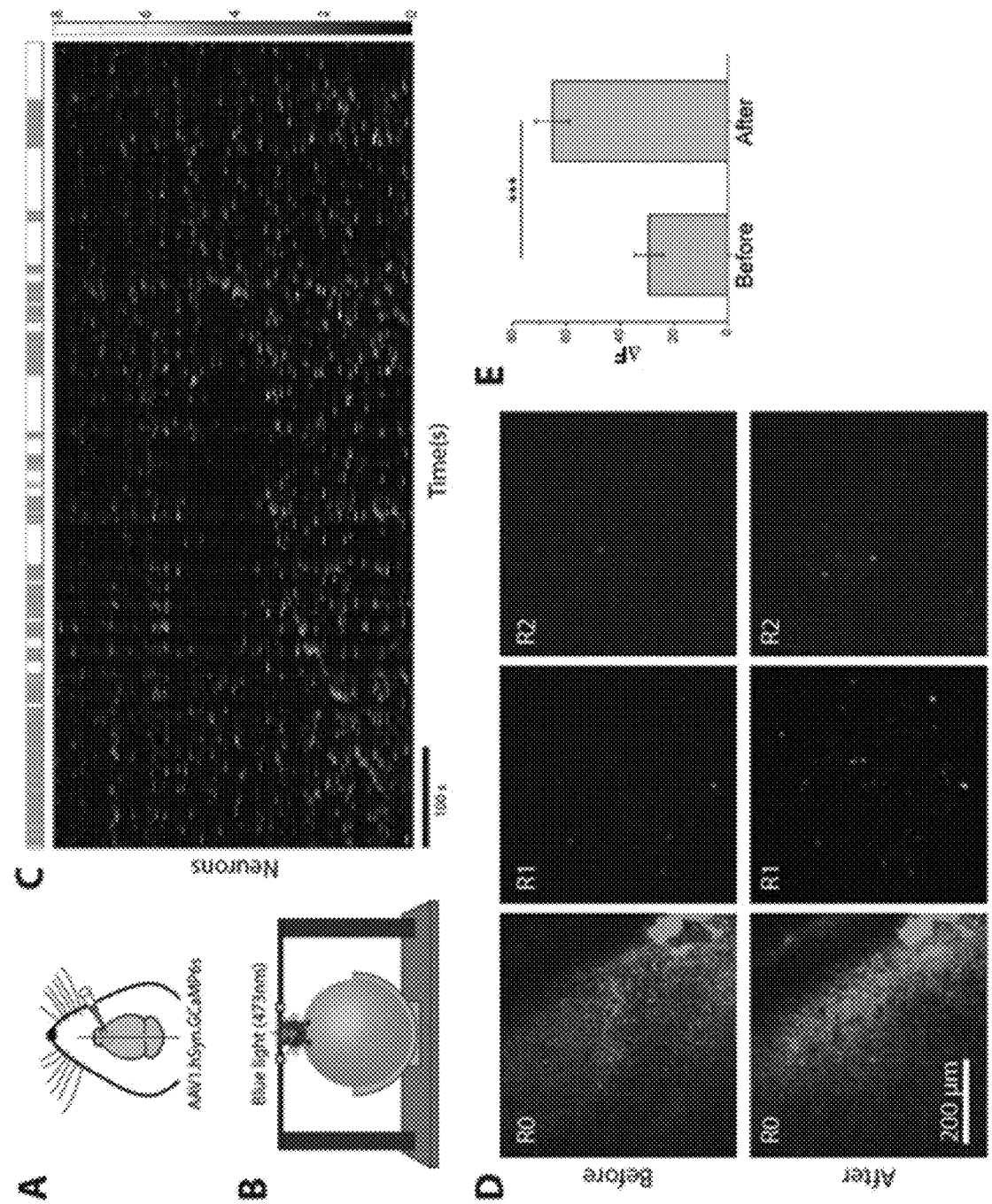

FIG. 19: In vivo labeling of an active neuronal population in awake behaving mice with Cal-Light. 2 weeks expression of AAV Cal-Light (400 nl) with GFP reporter (100 nl). (a) AAV injection and cranial window site. AAV-GCaMP6s was injected into mouse motor cortex to monitor neuronal activity by Ca2+ imaging. (b) Task schematics. A mouse is head-fixed sitting on the air-floating styrofoam ball. In this setup, the mouse can freely run on the ball. Blue light (473 nm) is delivered for 5 sec whenever the mouse start to run. (c) Calcium imaging (plotted as Delta F/F) from individual layer 2/3 neurons in motor cortex while a mouse runs on the ball. Whenever mice move, many neurons fire simultaneously as detected by calcium imaging. Because we illuminated blue light only while mice move, only active neuronal population related movements is supposed to be labeled by Cal-Light constructs. (d) In vivo imaging of Cal-light positive neurons. R0: reference plane (to identify exactly same brain area before and after blue light from the same mice, we imaged the landmark on the brain surface). Fluorescent intensity of cells in two regions (R1 and R2) is compared before and after (48 hours) blue light exposure. (e) Fluorescent intensity of cells before and after blue light exposure.

Figure 20:
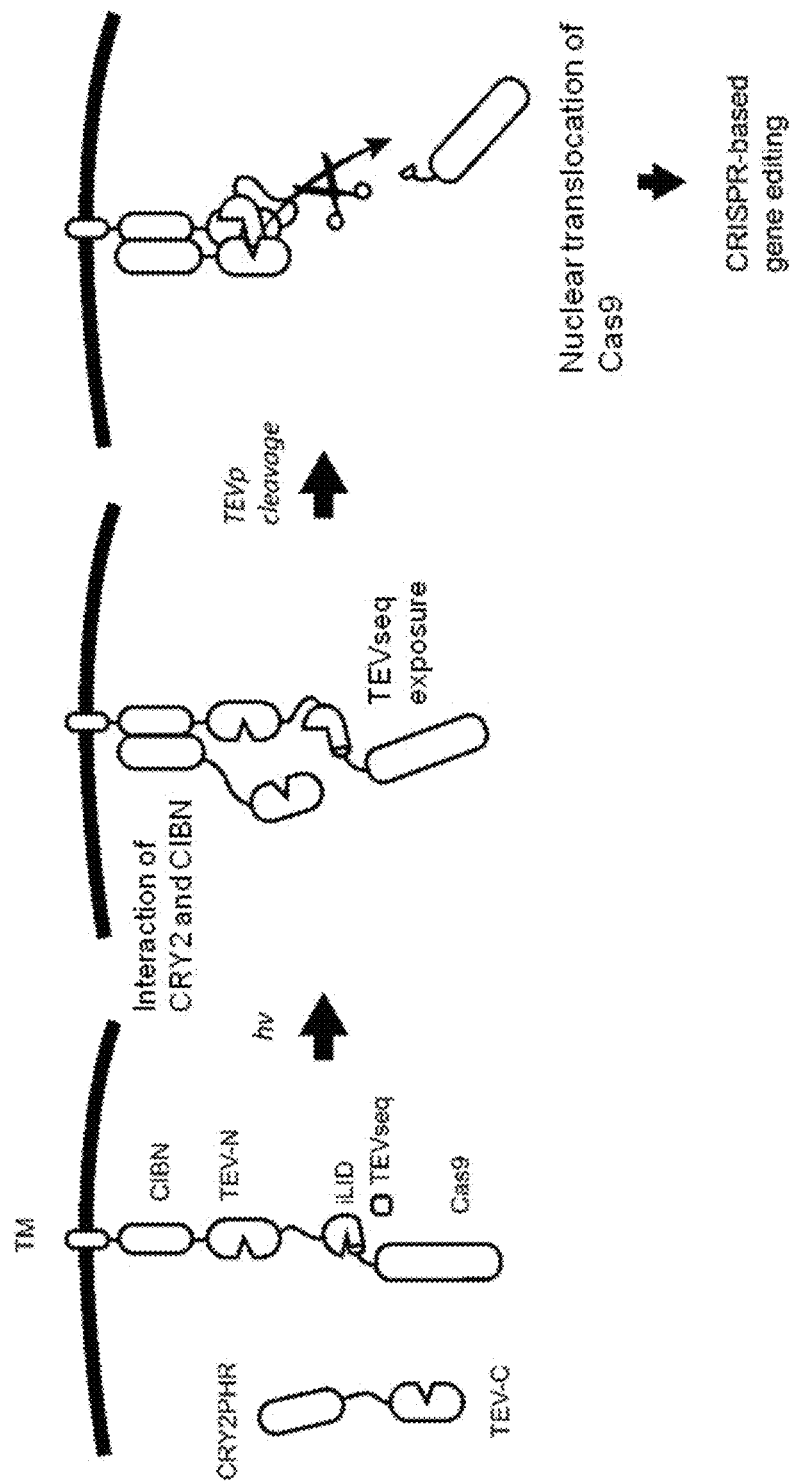
Figure 20:
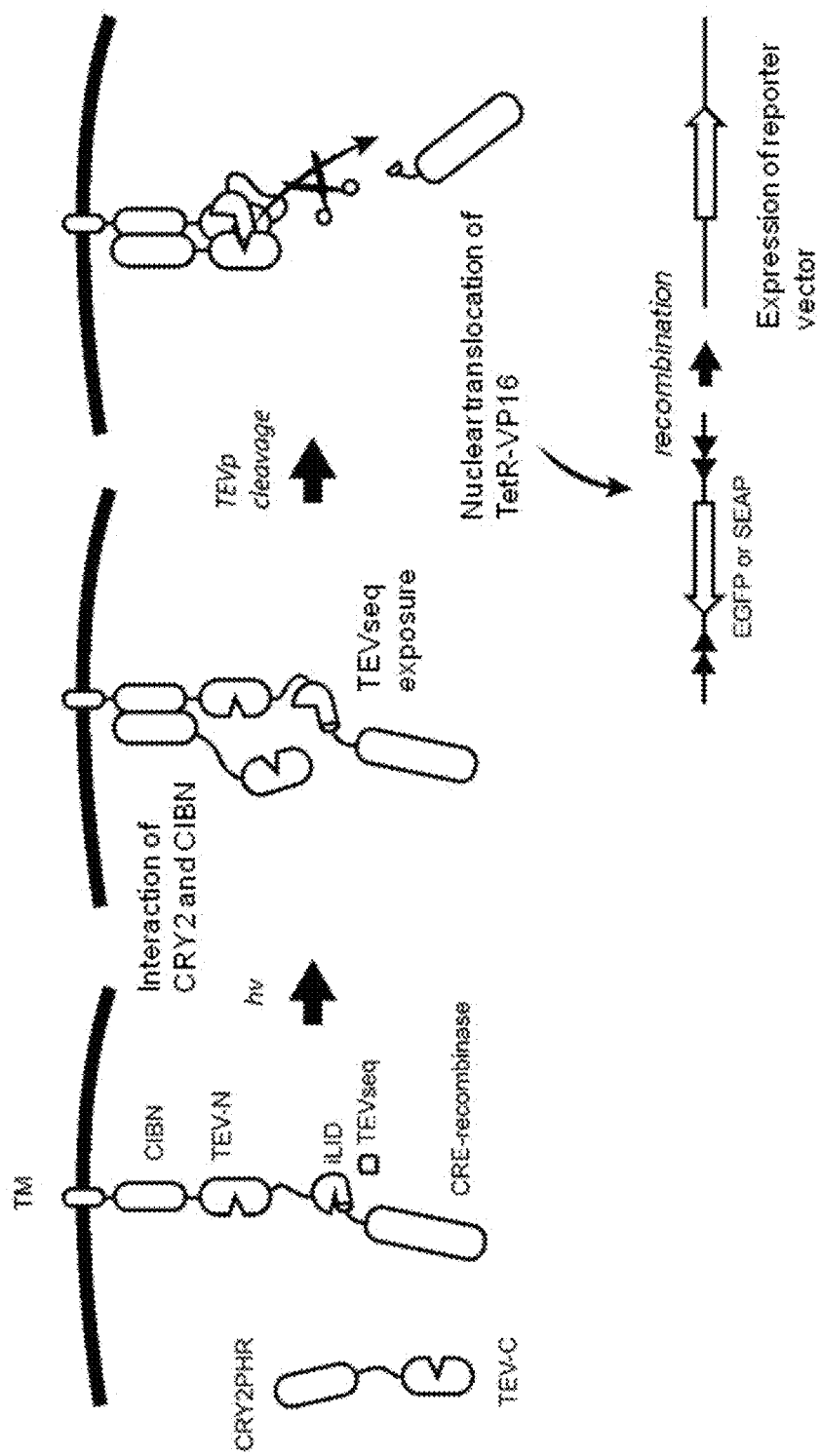

FIG. 20: Schematic representation of incorporation of alternative effector molecules. A) Schematic representation of a combination with the CRISPR-Cas system. B) Schematic representation of a combination with the Cre recombinase system.

Figure 21:
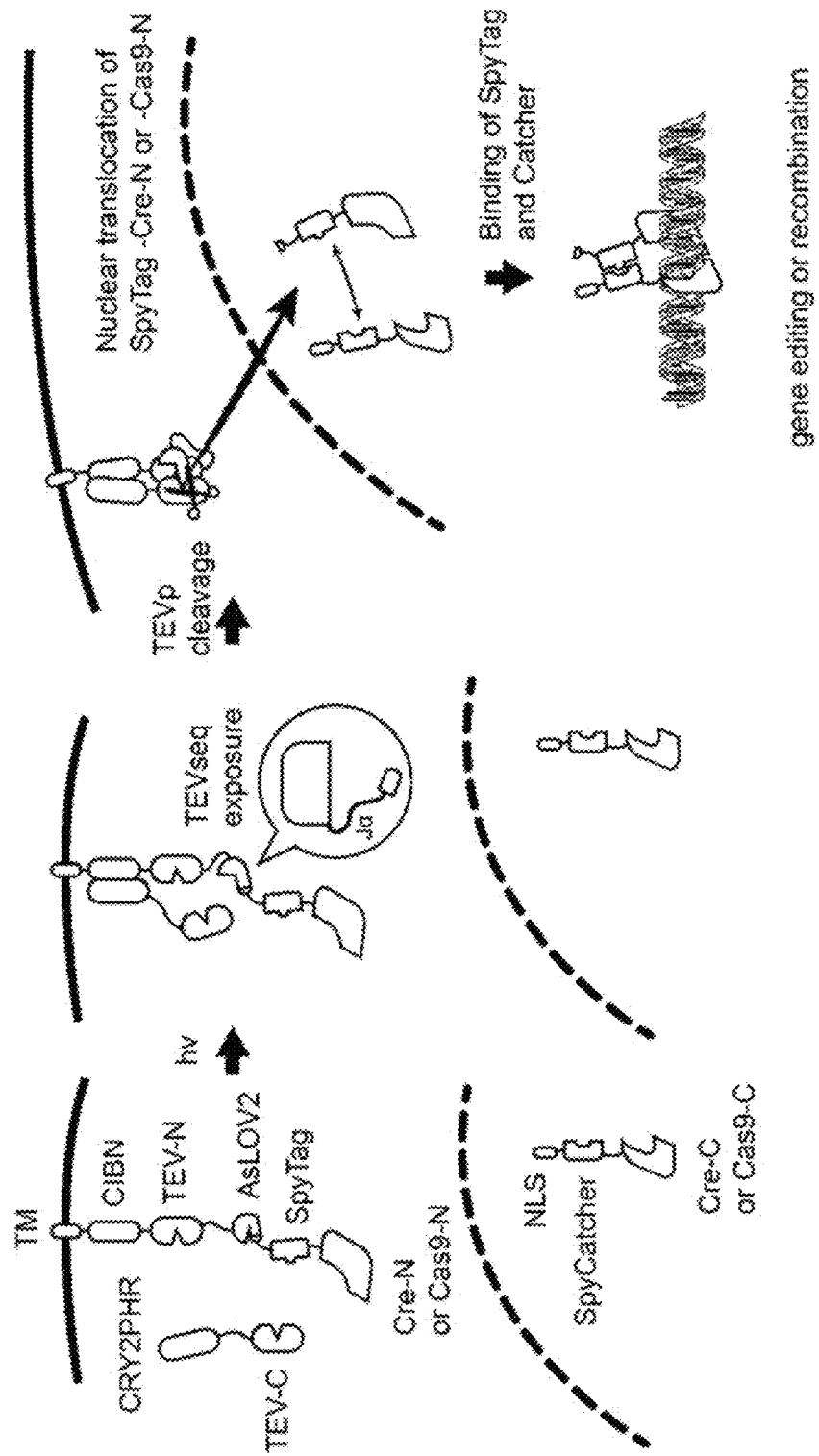

FIG. 21: Schematic representation of light-inducible, Spy-tagged CRISPR-Cas9 and CRE recombinase system. Both CRISPR-Cas9 and Cre systems are gene editing system. Cas9 or Cre proteins are split, so that N- or C-terminal fragment are obtained that are not functional on their own. In the scheme, Cre-N or Cas9-N have been designed such that they are expressed in the cytosol, while Cre-C or Cas9-C are expressed in the nucleus, in order to avoid stimulus-independent activation of the CRISPR-Cas9 or CRE system. When the Cre-N or Cas9-N is released by TEV cleavage, they can bind to the C-terminal part of the respective protein, because each N- and C-terminal fragment are linked to SpyTag and SpyCatcher, respectively. SpyTag and SpyCatcher can interact by themselves without any additional triggers.

Figure 22:
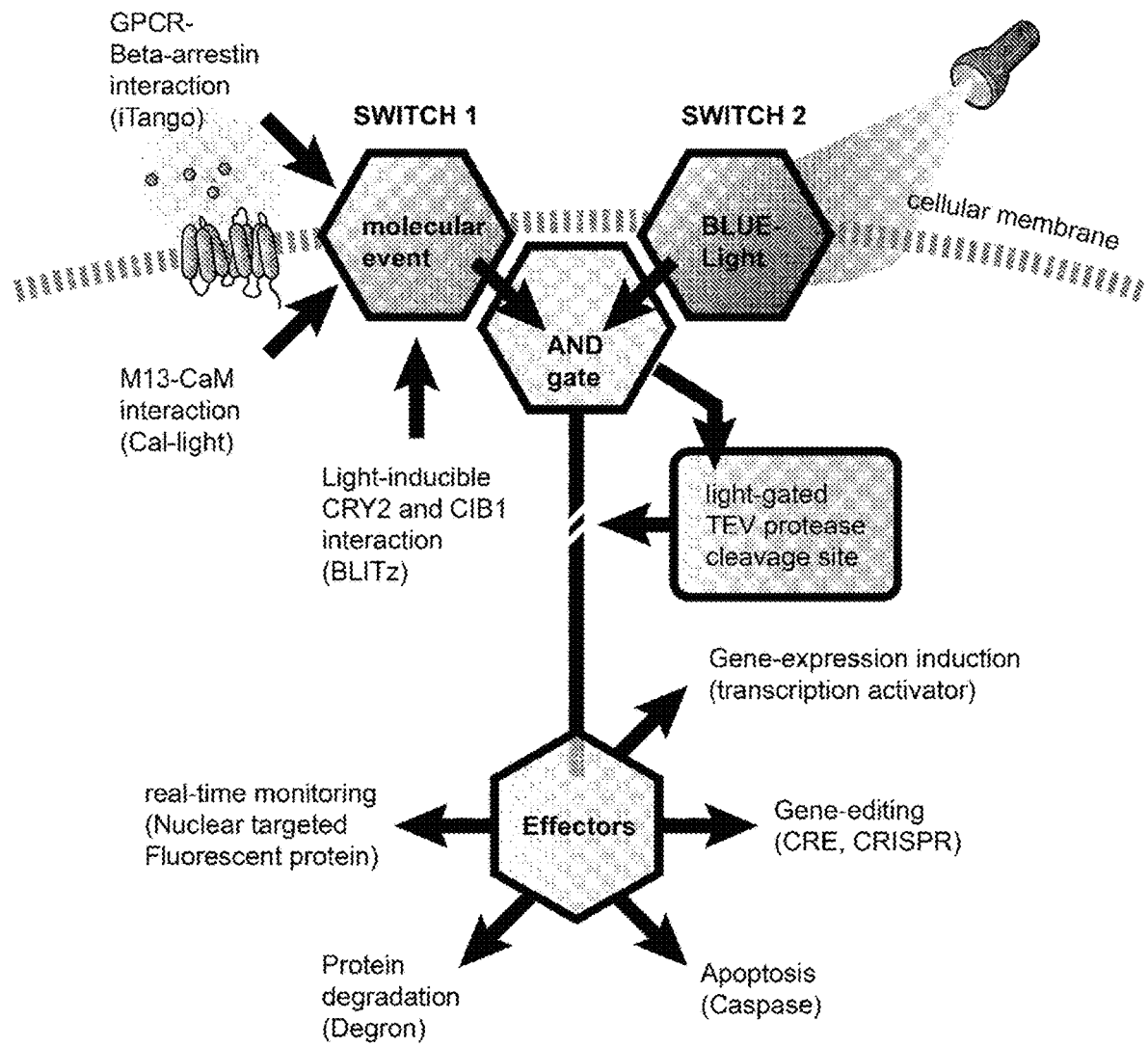

FIG. 22: Schematic overview of the various methods.

The following examples illustrate the invention:

EXAMPLE 1: GENERAL METHODS

Design and Construction of Plasmid Vectors

All plasmid vectors were constructed using a mammalian expression pCS4+ vector containing CMV IE94 promoter and ampicillin resistant sequence. Construction strategies and primers are fully described in FIGS. 8 to 15. Sequences encoding TEV-N, TEV-C, and V2tail were chemically synthesized by Eurofin Genomics (Huntsville, Ala., USA) and their full sequences are provided in FIG. 15.

To generate CMV::TM-CIBN-NES-TEV-N-BLITz-1-tTA (FIG. 8), CIBN, AsLOV2, and tTA sequences were amplified from pCIBN (ΔNLS)-pmGFP (Addgene #26867), pLL7.0: Venus-ILID-CAAX (Addgene #60411), and pSAM200 (provided by Dr. Wilfried Weber, University of Freiburg, Germany; tTA can be obtained from the pUHD15-1 vector described in Gossen, M. & Bujard, H. Tight control of gene expression in mammalian cells by tetracycline-responsive promoters. *Proceedings of the National Academy of Sciences of the United States of America* 89, 5547-5551 (1992), which is commercially available from Clontech, Cat No 631017), respectively. Amplified PCR products were digested by suitable combination of restriction enzymes and each PCR product was sub-cloned into synthesized TEV-N backbone as described in FIG. 15.

CMV::NES-CRY2PHR-TEV-C (FIG. 9) was generated by ligating the synthesized TEV-C backbone and the amplified CRY2PHR from Pcry2PHR-mCherryN1 (Addgene #26866).

CMV::HA-DRD2-V2tail-CIBN-BLITz-6-tTA (FIG. 10) was produced by a series of ligation of V2tail, AsLOV2-tTA, and DRD2. The sequence encoding HA signal and V2tail backbone originated from Presto-Tango sequences except for modifications of several restriction enzyme sites (Kroeze, W. K. et al. PRESTO-Tango as an open-source resource for interrogation of the druggable human GPCRome. *Nature structural & molecular biology* 22, 362-369, doi:10.1038/nsmb.3014 (2015)). DRD2 was amplified from pcDNA3.1-D2-YFP (Addgene #44194) with BamHI and EcoRI sites.

CMV::β-Arrestin2-TEV-N-P2A-TdTomato (FIG. 11) was produced with a simple subcloning method. β-Arrestin2 sequence was amplified from β-Arrestin GFP WT (Addgene #35411).

All cloning enzymes and reagents were purchased from New England Biolabs (MA, USA). All plasmid vectors generated in this study were confirmed once again by DNA sequencing (Eurofin Genomics).

Site-Directed Mutagenesis for BLITz Constructs

To generate BLITz variants, small nucleotides were inserted or deleted from the original AsLOV2 sequence through site-directed mutagenesis. Whole amplification of vector was performed by KOD polymerase (Cat #71086-3, EMD Millipore, Billerica, Mass., USA) which allows high speed and accurate PCR amplification. To remove parental templates, DpnI (Cat #R0176, New England Biolabs) restriction enzyme was used at 37° C. for 1 hr. This mixture was directly added to competent cells (*E. coli* DH5α strain, Zymo Research, CA, USA). Primers used for mutagenesis are described in FIG. 8 and shown in SEQ ID NOs: 75 to 88.

HEK293T Cell Culture and DNA Transfections

HEK293T cells were grown in high glucose Dulbecco's Modified Eagle Medium (DMEM) (Gibco, CA, USA) containing 10% fetal bovine serum (Cat #10438-018, Gibco) and 1% penicillin-streptomycin (Invitrogen, NY, USA). Cells were incubated at 37° C. and under 10% $CO_2$ conditions. For the experiment, all dishes and coverslip were pre-coated with a 1 mg/ml Poly-D-Lysine hydrobromide (Cat #P0899, Sigma-Aldrich, St. Louis, Mo., USA) solution for 2 hrs. After 0.25% trypsin (Cat #25200, Gibco) treatment for 2 min, detached cells were collected and the total cell numbers were counted. Dissociated cells were plated at $2 \times 10^5$ cells per 12 mm coverslip. 24 hrs later, DNA plasmid vectors were transfected using the calcium phosphate transfection kit (Clontech, CA, USA). The mixture of the DNA solution was slowly added into 2× Hepes Buffered Saline. After 1 hr incubation, precipitated solutions were added into each well.

Preparation of Dissociated Hippocampal Cultures and DNA Transfections

Primary hippocampal neuron culture was performed as previously described (Lee, D. et al. Inositol 1,4,5-trisphosphate 3-kinase A is a novel microtubule-associated protein: PKA-dependent phosphoregulation of microtubule binding affinity. *J Biol Chem* 287, 15981-15995, doi:10.1074/jbc.M112.344101 (2012)). Briefly, rat hippocampus (embryonic 18 days) was rapidly dissected and digested with 0.25% trypsin-EDTA (Invitrogen) for 10 m at 37° C. After trypsin-EDTA was removed, trypsinized cells were carefully triturated with 1,000 μL-sized pipet tip for 10 times. Dissociated cells were counted and plated at $10^5$ cells onto 12 mm PDL-coated coverslips. Plating media consisted of neurobasal medium (Invitrogen) and the following reagents: 1% (v/v) FBS, 1% (v/v) Glutamax Supplement (Gibco), 2% (v/v) B27 supplement (Gibco), and 1% (v/v) penicillin-streptomycin. Primary hippocampal neuron culture was grown in 37° C. temperature and 10% $CO_2$ conditions. Every 4 days, one third of the volume of media was replaced with fresh maintaining media lacking FBS. DNA was transfected by using a neuronal calcium phosphate transfection method as previously described (Jiang, M. & Chen, G. High Ca2+-phosphate transfection efficiency in low-density neuronal cultures. *Nat Protoc* 1, 695-700, doi:10.1038/nprot.2006.86 (2006)). Three days later (DIV 10), a short period of blue light was illuminated for 2 hrs (5 s ON/55 s OFF) and quinpirole and/or haloperidol were added into media when needed. After 2 hrs of incubation, the media were replaced to fresh ones. Neurons were fixed at DIV 12 for image acquisition.

Blue-Light Illumination

Blue light was illuminated by 465 nm wavelength blue LED array (LED wholesalers, Hayward, Calif., USA) that was controlled by a high-accuracy digital electronic timer (Model 451, GraLab, Centerville, Ohio, USA). The LED array was installed inside the 37° C. and 10% $CO_2$ incubator. One transparent blank plate with 2 cm height was inserted between the LED source and the sample to inhibit potential undesirable heating caused by the direct contact of the LED. In the experimental setup, the power of blue light at the specimen was 1.7 mW, measured by a power meter (PM100D, ThorLabs, Newton, N.J., USA). To make a dark condition, all lights were prevented by wrapping culture plates with an aluminum foil, and all experimental procedures were carried out under dim red light.

SEAP Chemiluminescent Assay

For the quantification of gene-expression levels, a secreted embryonic alkaline phosphatase (SEAP) chemiluminescent assay was used. All reagents for the SEAP assay were purchased from InvivoGen (San Diego, Calif., USA). 40 μl of sample was collected from the medium of each well and transferred into 96-wells plate. Samples were pre-heated in a 60° C. incubator for 10 m to inhibit the activity of endogenous alkaline phosphatase. All mixtures were added into a single master tube including SEAP substrates and L-homoarginine. The mixed solutions were carefully added into each sample onto 96-wells plate without bubbles. The chemiluminescence of each sample was measured by a micro-plate reader (SpectraMax Plus 384, Molecular Devices, Sunnyvale, Calif., USA) at 37° C. at 405 nm. Assays were made at every 30 s for 2 hrs. All data and the calculation of $V_{max}$ were acquired by a SoftMax Pro 5.4.1 (Molecular Devices).

Preparation and Acquisition of Images

Cells were fixed by pre-warmed 4% paraformaldehyde (Santa Cruz Biotechnology, Dallas, Tex., USA) for 10-15 min. Fixed cells were rinsed with PBS three times. Coverslips were mounted using mounting solution (Electron Microscopy Science, PA, USA). Imaging was performed using an upright confocal laser-scanning microscope (LSM780, Zeiss, Oberkochen, Germany) with 20×/0.8 M27 objective lens.

Pharmacological Drugs and Statistics

Quinpirole and haloperidol were purchased from Tocris Bioscience (Minneapolis, Minn., USA). Statistical significance was calculated by one-way ANOVA with post hoc Games Howell test using SPSS 12.0 (IBM) software.

EXAMPLE 2: DESIGN OF THE BLUE-LIGHT INDUCIBLE TEV PROTEASE (BLITZ) SYSTEM

Initial experiments showed that most photoactivatable proteins employed, such as CRY2 (cryptochrome 2) and CIB1 (cryptochrome-interacting basic-helix-loop-helix 1) (Zhang, K. & Cui, B. Optogenetic control of intracellular signaling pathways. *Trends in biotechnology* 33, 92-100, (2015)), provided a certain degree of light-independent background signals. Without wishing to be bound by theory, it is believed that this was due to the intrinsic promiscuity of protein-protein interactions. As this would prove problematic in an environment like the brain, where only subtle amounts of neuromodulators are flowing in and out, a novel two-step light switch control system was developed and named Blue-Light Inducible TEV protease (BLITz) (FIG. 1a). The BLITz system consists of two synthetic proteins and a single reporter vector with a tetracycline response element (TRE). The first synthetic protein is a membrane-tethered protein consisting of multiple light-sensitive modules: 1) CIBN (a truncated form of CIB1) (Kennedy, M. J. et al. Rapid blue-light-mediated induction of protein interactions in living cells. *Nature methods* 7, 973-975, (2010)); 2) TEV-N(N-terminal region of TEV protease) (Wehr, M. C. et al. Monitoring regulated protein-protein interactions using split TEV. *Nature methods* 3, 985-993, (2006)); 3) TEV protease cleavage sequence (TEVseq) inserted in a truncated form of *Avena sativa* phototropin1 light-oxygen-voltage 2 domains (AsLOV2) (Guntas, G. et al. Engineering an improved light-induced dimer (iLID) for controlling the localization and activity of signaling proteins. *Proceedings of the National Academy of Sciences of the United States of America* 112, 112-117, (2015)); and 4) TetR-VP16 (tetracycline-controlled transcriptional activator) (FIG. 1a). The second synthetic protein is a fusion protein of TEV-C(C-terminal region of TEV protease) and CRY2PHR (cryptochrome 2 photolyase homology region) ((Kennedy, M. J. et al. Rapid blue-light-mediated induction of protein interactions in living cells. *Nature methods* 7, 973-975, (2010); Wehr, M. C. et al. Monitoring regulated protein-protein interactions using split TEV. *Nature methods* 3, 985-993, (2006)) (FIG. 1a). In this set-up, TEV-C and TEV-N are separated into two different proteins and cannot bind each other in the absence of light (dark state). In the presence blue light, CRY2PHR and CIBN interact causing TEV-C and TEV-N to interact, regain protease function, and cleave TEVseq. Although the split TEV system reduced light-independent noise signals, some background cleavage was nonetheless observed due to the diffusion-mediated interaction between TEV-C and TEV-N (Williams, D. J., Puhl, H. L., 3rd & Ikeda, S. R. Rapid modification of proteins using a rapamycin-inducible tobacco etch virus protease system. *PloS one* 4, e7474, (2009)).

To abolish spontaneous TEVseq cleavage, the crystal structure of AsLOV2 protein was consulted, which shows that the Jα-helix is tightly associated with the Per-ARNT-Sim (PAS) core domain in the dark state, but becomes released upon blue light illumination (Harper, S. M., Neil, L. C. & Gardner, K. H. Structural basis of a phototropin light switch. *Science* 301, 1541-1544, (2003)). Thus, to prevent access by TEV protease in the dark state, but to allow complete access upon blue light illumination, the C-terminal region of the Jα-helix on AsLOV2 with the TEVseq was modified (FIG. 1a, b). To screen for light-inducible molecules with optimal SNR, serial deletion mutations were generated in the C-terminal region of the Jα-helix, including a point mutation within the TEVseq (FIG. 1b). It was observed that background gene expression levels were high when TEVseq was inserted close to the Jα-helix C-terminus (BLITz-3 and -4) (FIG. 1c), indicating TEVseq was accessible to TEV protease. Removing two more amino acids from the Jα-helix (BLITz-1 and -6), completely abolished baseline gene expression, while maintaining high light-induced gene expression. Removing amino acids 137 and 138 (BLITz-2) restored the baseline gene expression, suggesting those amino acids are tied to the light-dependent conformational changes (FIG. 1c). When the intact TEVseq was tested without a fusion to the AsLOV2 protein, similar to the classical Tango system, basal gene expression was high, as expected, and subsequent fold change was minimal (~1.4 fold) (FIGS. 1c, and 1f,). Upon removal of TetR-VP16 (No tTA), signals were nearly undetectable, suggesting background gene expression did not originate from the reporter itself (FIG. 1c). Based on a secreted embryonic alkaline phosphatase (SEAP) assay, BLITz-1 and -6 were found to be the best light-induced constructs, both with over 20-fold gene expression by blue light (FIG. 1d). Since the BLITz system is operated by protein-protein interactions, fold changes were found to be variable by the ratio of individual modules (FIG. 5). The results of the SEAP assay were in agreement with EGFP expression reporter data (FIG. 1e). BLITz-6 was selected for use in the neuromodulation mapping system.

Gene expression was also dependent on duration of blue light exposure. When a short light pulse (10 sec ON/50 sec OFF) was repeated for 5 min, gene expression was significantly increased, and the fold change was dramatically increased with longer exposure times (FIG. 1f). Because the light cycle was 10 sec ON/50 sec OFF per minute, just 50 seconds of total light exposure was sufficient to induce high gene expression and 5 minutes light caused fold changes higher than 20 folds (FIG. 1f). Additionally, this light-dependency greatly improved spatial resolution, enabling the limitation of EGFP expression only to the cells exposed to blue light (FIG. 1g). Thus, a light-inducible gene-coupled reporter system representing transitory protein interaction with a high SNR and precise spatiotemporal resolution has been developed.

EXAMPLE 3: DESIGN OF THE ITANGO SYSTEMS

Unlike the BLITz system, the original Tango system lacks an external control switch, resulting in constitutive activation and poor temporal resolution. To overcome these drawbacks, the original Tango system was reengineered by combining it with the BLITz system, such that gene expression is initiated only when both ligand and light are present (FIG. 2a). In this inducible Tango system (referred to herein as iTango), the binding of ligands to receptors causes β-arrestin-2/TEV-N recruitment, but does not cause TEVseq cleavage. Blue light illumination then recruits CRY2/TEV-C to form a functional protease that cleaves TEVseq. The two-step verification system of iTango makes it the ideal template for a multi-protein interaction monitoring platform. Furthermore, by simply exchanging the GPCR components of the iTango a whole library of GPCRs can be build, as shown in a recent study (Kroeze, W. K. et al. PRESTO-Tango as an open-source resource for interrogation of the druggable human GPCRome. *Nature structural & molecular biology* 22, 362-369, (2015)).

To verify that the iTango system reliably labels neuromodulatory actions, dopamine action was tested by using dopamine 2 receptor (DRD2). iTango constructs were expressed in HEK293T cells, and a DRD2 agonist, quinpirole, was introduced into the culture media. In the dark state, there was no noticeable spontaneous gene expression, but upon blue light illumination, gene expression was observed in a dose-dependent manner. Conversely, a complete block was observed with the DRD2 antagonist haloperidol (FIG. 2b). Interestingly, after transfecting a high amount of β-arrestin-2-TEV-N plasmid, SNR was robustly increased, suggesting that a reserved pool of β-arrestin-2 protein in the cytosol is critical (FIG. 6). An EGFP expression reporter assay revealed the same quinpirole- and light-dependent pattern (FIG. 2c).

These results indicate that gene expression was very selective to DRD2 activation, and ligand-independent background signals are almost negligible as expected from the two-step activation design. The temporal resolution was increased by about ~100 fold (calculated by net light exposure time, 10 min) as compared to the classical Tango system, which requires 12~24 hours of ligand incubation (Inagaki, H. K. et al. Visualizing neuromodulation in vivo: TANGO-mapping of dopamine signaling reveals appetite control of sugar sensing. *Cell* 148, 583-595, (2012)). More importantly, the constitutive presence of quinpirole, even at high concentration, did not cause any background signals and only gated by light. Thus, the new iTango system is a fast and reliable light-inducible technique with a high SNR for monitoring behaviorally-related phasic neuromodulatory action.

A further challenge is presented by neurons due to their morphology. For example, the probability of all three iTango proteins coming together in a thin and long space (e.g., dendrites or axons) is much lower than that of a compact, round space (e.g., HEK293 cells). Additionally, even if tTA is successfully released after TEVseq cleavage, it must travel a long distance through the dendrite to the cell body. To overcome these limitations, a simplified version of iTango was generated and called iTango2. This system lacks the CRY2PHR/CIBN light switch, allowing easier formation of the light- and ligand-induced protein complex. Transfecting iTango2 into HEK cells greatly increased the overall density of gene expression (FIG. 7). Background signals were slightly elevated due to the lack of one light-sensitive module, but both light- and ligand-inducible features were still preserved. In iTango2-transfected neurons, background signals were nearly undetectable, but light- and ligand-inducibility was very robust, with a SNR corresponding to roughly 900% fold change (FIG. 3b-d). The same experiments using the conventional Tango system yielded only a 50% fold change (Djannatian, M. S., Galinski, S., Fischer, T. M. & Rossner, M. J. Studying G protein-coupled receptor activation using split-tobacco etch virus assays. *Analytical biochemistry* 412, 141-152, (2011)).

Thus, the iTango systems enable visualization of neuromodulation codes in a precise time and space, which will allow to understand neural network topology of internal brain states underlying behavioral diversity.

EXAMPLE 4: THE CAL-LIGHT SYSTEM

First, it was tested whether the Cal-Light system expresses reporter genes in a calcium- and light-dependent manner in cultured neurons. Cal-Light constructs (FIG. 17) and Channelrhodopsin 2 (ChR2) were co-transfected into hippocampal culture neurons. After five days of expression, a short pulse of blue light (5 second on/55 second off) was repetitively illuminated for 30 minutes.

Two days later, neurons kept in a dark condition did not show high levels of EGFP expression although tdTomato expression (transfection marker) was confirmed to be very high (FIG. 17). This result indicates that Cal-Light proteins did not cause a target reporter gene expression in the absence of light stimulation. When Blue light was shone onto the neurons, but neuronal activity was completely blocked by TTX, reporter EGFP gene expression level was kept low as similar as in the dark condition (FIG. 17).

Robust EGFP expression was only observed in a condition when both blue light was given and when neuronal activity was not blocked (FIG. 17). These data demonstrate that the Cal-Light system reliably converts neuronal activity to gene expression in a light-dependent manner.

To control neuronal activity independent of blue light, action potentials were then triggered by electrical stimulation. Cortical slice culture were made at postnatal day 3 and AAV expressing Cal-Light constructs including an EGFP reporter were infected to slices at DIV 3 (Days in vitro). After 12 days of expression, a bipolar stimulation electrode was placed in layer 2/3. Three repeats of brief high-frequency electric pulses were delivered (5 pulses at 20 Hz) at 4 second intervals, while blue light was continuously shining for 8.5 seconds (FIG. 18). This stimulation protocol was repeated 30 times, resulting in triggering about 300 action potentials in total. Two days later, slices were fixed and gene expression pattern was imaged by confocal microscopy. Similar to the ChR2 experiments above, it was found that either blue light or high-frequency stimulation alone did not lead to high levels of EGFP expression, but when both light and stimulation occurred together, EGFP expressing neurons were robustly increased and their expression level was also increased (FIG. 18). Further increase of neuronal activity by bicuculine application also resulted in significant increase of EGFP expression (FIG. 18).

Because the Cal-Light technique reliably label active neurons upon light exposure, it is now possible to identify a population of neurons that is active during a specific behavior period in vivo. Based on light- and activity-dependent gene expression in slice experiments, the Cal-Light technique can further label active population of neurons that are involved in specific animal behavior. To monitor the level of neuronal activity during behavior in awake behaving mouse, AAV expressing Cal-Lights and GCaMP6s were injected into motor cortex in mouse (FIG. 19A). After 2 week of viral expression, a head fixed mouse was placed on a floating styroform ball, such that the mouse can freely run on the ball (FIG. 19B). Whenever mice started running, many neurons in motor cortex were firing, which were monitored by calcium imaging (FIG. 19C). Next, blue light was illuminated through a glass cranial window for 5 seconds whenever the mouse ran. In this experiment, active neurons during running should be labeled when blue light is applied. The same population of neurons was imaged before and after blue light exposure to directly compare how much the gene expression is increased in the same neurons (FIG. 19D). A significant increase in EGFP expression was observed two days after blue light exposure (FIG. 19E). These data indicate that Cal-Light is also functioning in vivo.

The invention claimed is:

1. A nucleic acid molecule encoding a fusion protein, wherein the nucleic acid molecule comprises:
   (a) a first nucleic acid sequence encoding a transmembrane domain linked to a first biosensor, wherein said first biosensor is a first molecule interacting with a second molecule to form part of a first inducible interaction module, and wherein said first biosensor is linked to the transmembrane domain such that the first biosensor is located intracellularly upon expression of the fusion protein in a cell;
   (b) a second nucleic acid sequence encoding an effector-activating module, wherein the effector-activating module comprises:
      (i) a first part of a protease, wherein said first part of the protease interacts with a second part of said protease to form an active form of said protease; or
      (ii) a second biosensor, wherein said second biosensor is a third molecule interacting with a fourth molecule to form part of a second inducible interaction module;
   (c) a third nucleic acid sequence encoding a third biosensor comprising a protease cleavage site, wherein the protease cleavage site is sterically occluded in the absence of a stimulus for said third biosensor and wherein the protease cleavage site becomes accessible in the presence of said stimulus; and
   (d) a fourth nucleic acid sequence encoding an effector molecule.

2. The nucleic acid molecule according to claim 1, wherein the first inducible interaction module and the second inducible interaction module are independently selected from the group consisting of a light-inducible interaction module, a ligand-inducible interaction module and a calcium-inducible module.

3. The nucleic acid molecule according to claim 1, wherein the effector molecule is a transcriptional modulator, a genome modulator, a reporter molecule, an enzyme, or degron.

4. The nucleic acid molecule according to claim 1, wherein the third nucleic acid sequence comprises (i) a nucleic acid sequence encoding N-terminal amino acids 1 to 138 (SEQ ID NO:49) or 1 to 139 (SEQ ID NO:51) of *Avena sativa* phototropin1 light-oxygen-voltage 2 (AsLOV2) comprising a light sensor which changes its conformation upon a light stimulation, linked at its C-terminus to (ii) a protease cleavage site.

5. The nucleic acid molecule according to claim 4, wherein the protease cleavage site is a TEV protease cleavage site.

6. The nucleic acid molecule according to claim 1,
wherein the first nucleic acid sequence is selected from the group consisting of SEQ ID NO:1, SEQ ID NO:3, SEQ ID NO:5, and SEQ ID NO:8, and wherein
the effector molecule is selected from the group consisting of TetR-VP16(tTA), Cas9, and Cre recombinase.

7. The nucleic acid molecule according to claim 1, wherein the first nucleic acid sequence is linked intracellularly to the fourth nucleic acid sequence to form a nucleic acid sequence selected from the group consisting of SEQ ID NO:16, SEQ ID NO:18, SEQ ID NO:20, and SEQ ID NO:22.

8. A vector comprising the nucleic acid molecule according to claim 1.

9. A set of nucleic acid molecules comprising: (a) the nucleic acid molecule according to claim 1, wherein the effector-activating module is as defined in claim 1; and (b) a fifth nucleic acid sequence encoding a second fusion protein, the fifth nucleic acid sequence comprising (i) a sixth nucleic acid sequence encoding a molecule comprising the second molecule of the first inducible interaction module of claim 1; and (ii) a seventh nucleic acid sequence encoding the second part of the protease interacting with the first part of said protease of claim 1 to form the active form of said protease.

10. A set of nucleic acid molecules comprising: (a) the nucleic acid molecule according to claim 1, wherein the effector-activating module is as defined in claim 1; (b) a fifth nucleic acid sequence encoding a second fusion protein, the fifth nucleic acid sequence comprising (i) a sixth nucleic acid sequence encoding a molecule comprising the second molecule of the first inducible interaction module of claim 1; and (ii) a seventh nucleic acid sequence encoding the first part of the first protease, wherein said first part of the protease interacts with the second part of said protease to form the active form of said protease; and (c) a eighth nucleic acid sequence encoding a third fusion protein, the eighth nucleic acid sequence comprising (i) a ninth nucleic acid sequence encoding a molecule comprising the second molecule of the second inducible interaction module of claim 1; and (ii) a tenth nucleic acid sequence encoding the second part of the protease interacting with the first part of the protease to form the active form of said protease.

11. The set of nucleic acid molecules according to claim 9, comprised in one or more vectors.

12. A host cell or host expressing the set of nucleic acid molecules according to claim 9.

13. A host cell or host comprising the one or more vectors according to claim 11.

14. A method for inducing intracellular signaling, the method comprising:
- (a-i) providing a cell expressing the set of nucleic acid molecules of claim 9;
- (a-ii) applying a first stimulus to the cell of (a-i), wherein the first stimulus induces the first inducible interaction module of claim 1; and
- (a-iii) applying a second stimulus to the cell of (a-i), wherein the second stimulus induces the third biosensor of claim 1 such that the protease cleavage site becomes accessible; or
- (b-i) providing a cell expressing the set of nucleic acid molecules of claim 10;
- (b-ii) applying a first stimulus to the cell of (b-i), wherein the first stimulus induces the first inducible interaction module of claim 1;
- (b-iii) applying a second stimulus to the cell of (b-i), wherein the second stimulus induces the second inducible interaction module of claim 1 and
- (b-iv) applying a third stimulus to the cell of (b-i), wherein the third stimulus induces the third biosensor of claim 1 such that the protease cleavage site becomes accessible;

thereby effecting a biological response due to an activation of the effector molecule o of claim 1.

15. A method for monitoring intracellular signaling, the method comprising: (a-i) providing a cell expressing the set of nucleic acid molecules of claim 9;
- (a-ii) applying a first stimulus to the cell of (a-i), wherein the first stimulus induces the first inducible interaction module of claim 1; and
- (a-iii) applying a second stimulus to the cell of (a-i), wherein the second stimulus induces the third biosensor of claim 1 such that the protease cleavage site becomes accessible; or
- (b-i) providing a cell expressing the set of nucleic acid molecules of claim 10;
- (b-ii) applying a first stimulus to the cell of (b-i), wherein the first stimulus induces the first inducible interaction module of claim 1;
- (b-iii) applying a second stimulus to the cell of (b-i), wherein the second stimulus induces the second inducible interaction module of claim 1; and
- (b-iv) applying a third stimulus to the cell of (b-i), wherein the third stimulus induces the third biosensor of claim 1 such that the protease cleavage site becomes accessible; and (c) detecting a biological response effected by the effector molecule of claim 1.

16. The set of nucleic acid molecules according to claim 10, comprised in one or more vectors.

17. A host cell or host expressing the set of nucleic acid molecules according to claim 10.

* * * * *

SEQUENCE LISTING

<160> NUMBER OF SEQ ID NOS: 108

<210> SEQ ID NO 1
<211> LENGTH: 1428
<212> TYPE: DNA
<213> ORGANISM: Artificial Sequence
<220> FEATURE:
<223> OTHER INFORMATION: CIBN ? TEV-N ? AsLOV2? TEVseq

<400> SEQUENCE: 1

```
atgaatggag ctataggagg tgaccttttg ctcaattttc ctgacatgtc ggtcctagag      60
cgccaaaggg ctcacctcaa gtacctcaat cccacctttg attctcctct cgccggcttc     120
tttgccgatt cttcaatgat taccggcggc gagatggaca gctatctttc gactgccggt     180
ttgaatcttc cgatgatgta cggtgagacg acggtggaag gtgattcaag actctcaatt     240
tcgccggaaa cgacgcttgg gactggaaat ttcaaggcag cgaagtttga tacagagact     300
aaggattgta atgaggcggc gaagaagatg acgatgaaca gagatgacct agtagaagaa     360
ggagaagaag agaagtcgaa aataacagag caaaacaatg ggagcacaaa aagcatcaag     420
aagatgaaac acaaagccaa gaaagaagag aacaatttct ctaatgattc atctaaagtg     480
acgaaggaat tggagaaaac ggattatatt catgcatgcg gtggcggtgg ctctggaggt     540
ggtgggtccg gaggaggcgg ccgctccggt ggatccatgc ttcaacttcc tcctcttgaa     600
cgtcttactc tcgagatggg cgagagcctg ttcaagggac ctaggactct caacccctatc     660 agtagcacaa tttgtcacct gaccaacgag agtgatggcc acacaacaag cctgtacggc     720
atcgggttcg gaccctttat catcaccaac aagcacctgt tcaggcggaa taatggcact     780
ctgctggtgc agagcctgca cggggtgttc aaagtgaaga acacaaccac tctgcagcag     840
cacctgatcg atgggcggga tatgatcatc attaggatgc ccaaggactt cccccctttt     900
cctcagaaac tgaagttccg agagccccag agagaggaga gaatctgtct ggtgaccaca     960
aactttcagg agctcggtag tggtagtggg gagtttctgg caaccacact ggaacggatc    1020
gagaaaaatt tcgtgattac tgatccgaga ctgcctgaca cccaatcat ttttgcgagc    1080 gattccttcc tgcagctgac agaatattct cgggaagaga tcctggggcg caattgccgt    1140
tttctgcagg gacccgagac agaccgtgcc actgttcgga aaatcagaga tgctattgac    1200
```

-continued

```
aaccagactg aagtgaccgt tcagctgatc aattatacca agagcggcaa gaagttctgg    1260
aacgtgttcc acctgcagcc gatgcgcgat tataagggcg acgtccagta cttcattggc    1320
gtgcagctgg atggcaccga acgtcttcat ggcgccgctg agcgtgaggc ggtctgcctg    1380
atcaaaaaga cagccttttca gattgctgag aacctgtact tccagggc                1428
```

<210> SEQ ID NO 2
<211> LENGTH: 476
<212> TYPE: PRT
<213> ORGANISM: Artificial Sequence
<220> FEATURE:
<223> OTHER INFORMATION: CIBN ? TEV-N ? AsLOV2? TEVseq

<400> SEQUENCE: 2

```
Met Asn Gly Ala Ile Gly Gly Asp Leu Leu Asn Phe Pro Asp Met
1               5                   10                  15

Ser Val Leu Glu Arg Gln Arg Ala His Leu Lys Tyr Leu Asn Pro Thr
            20                  25                  30

Phe Asp Ser Pro Leu Ala Gly Phe Phe Ala Asp Ser Ser Met Ile Thr
        35                  40                  45

Gly Gly Glu Met Asp Ser Tyr Leu Ser Thr Ala Gly Leu Asn Leu Pro
    50                  55                  60

Met Met Tyr Gly Glu Thr Thr Val Glu Gly Asp Ser Arg Leu Ser Ile
65                  70                  75                  80

Ser Pro Glu Thr Thr Leu Gly Thr Gly Asn Phe Lys Ala Ala Lys Phe
                85                  90                  95

Asp Thr Glu Thr Lys Asp Cys Asn Glu Ala Ala Lys Lys Met Thr Met
            100                 105                 110

Asn Arg Asp Asp Leu Val Glu Glu Gly Glu Glu Glu Lys Ser Lys Ile
        115                 120                 125

Thr Glu Gln Asn Asn Gly Ser Thr Lys Ser Ile Lys Lys Met Lys His
    130                 135                 140

Lys Ala Lys Lys Glu Glu Asn Asn Phe Ser Asn Asp Ser Ser Lys Val
145                 150                 155                 160

Thr Lys Glu Leu Glu Lys Thr Asp Tyr Ile His Ala Cys Gly Gly Gly
                165                 170                 175

Gly Ser Gly Gly Gly Gly Ser Gly Gly Gly Gly Arg Ser Gly Gly Ser
            180                 185                 190

Met Leu Gln Leu Pro Pro Leu Glu Arg Leu Thr Leu Glu Met Gly Glu
        195                 200                 205

Ser Leu Phe Lys Gly Pro Arg Asp Tyr Asn Pro Ile Ser Ser Thr Ile
    210                 215                 220

Cys His Leu Thr Asn Glu Ser Asp Gly His Thr Thr Ser Leu Tyr Gly
225                 230                 235                 240

Ile Gly Phe Gly Pro Phe Ile Ile Thr Asn Lys His Leu Phe Arg Arg
                245                 250                 255

Asn Asn Gly Thr Leu Leu Val Gln Ser Leu His Gly Val Phe Lys Val
            260                 265                 270

Lys Asn Thr Thr Thr Leu Gln Gln His Leu Ile Asp Gly Arg Asp Met
        275                 280                 285

Ile Ile Ile Arg Met Pro Lys Asp Phe Pro Pro Phe Pro Gln Lys Leu
    290                 295                 300

Lys Phe Arg Glu Pro Gln Arg Glu Glu Arg Ile Cys Leu Val Thr Thr
305                 310                 315                 320
```

-continued

```
Asn Phe Gln Glu Leu Gly Ser Gly Ser Gly Glu Phe Leu Ala Thr Thr
            325                 330                 335

Leu Glu Arg Ile Glu Lys Asn Phe Val Ile Thr Asp Pro Arg Leu Pro
        340                 345                 350

Asp Asn Pro Ile Ile Phe Ala Ser Asp Ser Phe Leu Gln Leu Thr Glu
    355                 360                 365

Tyr Ser Arg Glu Glu Ile Leu Gly Arg Asn Cys Arg Phe Leu Gln Gly
370                 375                 380

Pro Glu Thr Asp Arg Ala Thr Val Arg Lys Ile Arg Asp Ala Ile Asp
385                 390                 395                 400

Asn Gln Thr Glu Val Thr Val Gln Leu Ile Asn Tyr Thr Lys Ser Gly
                405                 410                 415

Lys Lys Phe Trp Asn Val Phe His Leu Gln Pro Met Arg Asp Tyr Lys
            420                 425                 430

Gly Asp Val Gln Tyr Phe Ile Gly Val Gln Leu Asp Gly Thr Glu Arg
        435                 440                 445

Leu His Gly Ala Ala Glu Arg Glu Ala Val Cys Leu Ile Lys Lys Thr
    450                 455                 460

Ala Phe Gln Ile Ala Glu Asn Leu Tyr Phe Gln Gly
465                 470                 475

<210> SEQ ID NO 3
<211> LENGTH: 948
<212> TYPE: DNA
<213> ORGANISM: Artificial Sequence
<220> FEATURE:
<223> OTHER INFORMATION: V2tail ? TEV-N ? AsLOV2(BLITz-1)? TEVseq

<400> SEQUENCE: 3
ggacgcaccc cacccagcct gggtccccaa gatgagtcct gcaccaccgc cagctcctcc        60
ctggccaagg acacttcatc gcttcaactt cctcctcttg aacgtcttac tctcggtggc       120
tctggaggtc tcgagatggg cgagagcctg ttcaagggac ctaggactaa caaccctatc       180
agtagcacaa tttgtcacct gaccaacgag agtgatggcc acacaacaag cctgtacggc       240
atcgggttcg acccttat catcaccaac aagcacctgt tcaggcggaa taatggcact        300
ctgctggtgc agagcctgca cggggtgttc aaagtgaaga acacaaccac tctgcagcag       360
cacctgatcg atgggcggga tatgatcatc attaggatgc ccaaggactt cccccctttt       420
cctcagaaac tgaagttccg agagcccag agagaggaga gaatctgtct ggtgaccaca       480
aactttcagg agctcggtag tggtagtggg gagtttctgg caaccacact ggaacggatc       540
gagaaaaatt tcgtgattac tgatccgaga ctgcctgaca acccaatcat tttgcgagc       600 gattccttcc tgcagctgac agaatattct cgggaagaga tcctgggcg caattgccgt        660 tttctgcagg gacccgagac agaccgtgcc actgttcgga aaatcagaga tgctattgac       720
aaccagactg aagtgaccgt tcagctgatc aattatacca agagcggcaa gaagttctgg       780
aacgtgttcc acctgcagcc gatgcgcgat tataagggcg acgtccagta cttcattggc       840
gtgcagctgg atggcaccga acgtcttcat ggcgccgctg agcgtgaggc ggtctgcctg       900
atcaaaaaga cagcctttca gattgctgag aacctgtact ccagggc                   948

<210> SEQ ID NO 4
<211> LENGTH: 316
<212> TYPE: PRT
<213> ORGANISM: Artificial Sequence
<220> FEATURE:
<223> OTHER INFORMATION: V2tail ? TEV-N ? AsLOV2(BLITz-1)? TEVseq
```

<400> SEQUENCE: 4

```
Gly Arg Thr Pro Pro Ser Leu Gly Pro Gln Asp Glu Ser Cys Thr Thr
1               5                   10                  15
Ala Ser Ser Ser Leu Ala Lys Asp Thr Ser Ser Leu Gln Leu Pro Pro
            20                  25                  30
Leu Glu Arg Leu Thr Leu Gly Gly Ser Gly Gly Leu Glu Met Gly Glu
        35                  40                  45
Ser Leu Phe Lys Gly Pro Arg Asp Tyr Asn Pro Ile Ser Ser Thr Ile
    50                  55                  60
Cys His Leu Thr Asn Glu Ser Asp Gly His Thr Thr Ser Leu Tyr Gly
65                  70                  75                  80
Ile Gly Phe Gly Pro Phe Ile Ile Thr Asn Lys His Leu Phe Arg Arg
                85                  90                  95
Asn Asn Gly Thr Leu Leu Val Gln Ser Leu His Gly Val Phe Lys Val
            100                 105                 110
Lys Asn Thr Thr Thr Leu Gln Gln His Leu Ile Asp Gly Arg Asp Met
        115                 120                 125
Ile Ile Ile Arg Met Pro Lys Asp Phe Pro Pro Phe Pro Gln Lys Leu
130                 135                 140
Lys Phe Arg Glu Pro Gln Arg Glu Glu Arg Ile Cys Leu Val Thr Thr
145                 150                 155                 160
Asn Phe Gln Glu Leu Gly Ser Gly Ser Gly Glu Phe Leu Ala Thr Thr
                165                 170                 175
Leu Glu Arg Ile Glu Lys Asn Phe Val Ile Thr Asp Pro Arg Leu Pro
            180                 185                 190
Asp Asn Pro Ile Ile Phe Ala Ser Asp Ser Phe Leu Gln Leu Thr Glu
        195                 200                 205
Tyr Ser Arg Glu Glu Ile Leu Gly Arg Asn Cys Arg Phe Leu Gln Gly
    210                 215                 220
Pro Glu Thr Asp Arg Ala Thr Val Arg Lys Ile Arg Asp Ala Ile Asp
225                 230                 235                 240
Asn Gln Thr Glu Val Thr Val Gln Leu Ile Asn Tyr Thr Lys Ser Gly
                245                 250                 255
Lys Lys Phe Trp Asn Val Phe His Leu Gln Pro Met Arg Asp Tyr Lys
            260                 265                 270
Gly Asp Val Gln Tyr Phe Ile Gly Val Gln Leu Asp Gly Thr Glu Arg
        275                 280                 285
Leu His Gly Ala Ala Glu Arg Glu Ala Val Cys Leu Ile Lys Lys Thr
    290                 295                 300
Ala Phe Gln Ile Ala Glu Asn Leu Tyr Phe Gln Gly
305                 310                 315
```

<210> SEQ ID NO 5
<211> LENGTH: 1110
<212> TYPE: DNA
<213> ORGANISM: Artificial Sequence
<220> FEATURE:
<223> OTHER INFORMATION: V2tail ? CIBN ? AsLOV2(BLITz-6) ? TEVseq

<400> SEQUENCE: 5

```
ggacgcaccc cacccagcct gggtccccaa gatgagtcct gcaccaccgc cagctcctcc      60
ctggccaagg acacttcatc gcttcaactt cctcctcttg aacgtcttac tctcggtggc     120
tctggaggtc tcgagggaat gaatggagct ataggaggtg accttttgct caatttttcct   180
```

```
gacatgtcgg tcctagagcg ccaaagggct cacctcaagt acctcaatcc cacctttgat    240
tctcctctcg ccggcttctt tgccgattct tcaatgatta ccggcggcga gatggacagc    300
tatctttcga ctgccggttt gaatcttccg atgatgtacg gtgagacgac ggtggaaggt    360
gattcaagac tctcaatttc gccggaaacg acgcttggga ctggaaattt caaggcagcg    420
aagtttgata cagagactaa ggattgtaat gaggcggcga agaagatgac gatgaacaga    480
gatgacctag tagaagaagg agaagaagag aagtcgaaaa taacagagca aaacaatggg    540
agcacaaaaa gcatcaagaa gatgaaacac aaagccaaga agaagagaa caatttctct    600 aatgattcat ctaaagtgac gaaggaattg gagaaaacgg attatattca tgcatgcggt    660
agtggtagtg gggagtttct ggcaaccaca ctggaacgga tcgagaaaaa tttcgtgatt    720
actgatccga gactgcctga caacccaatc atttttgcga gcgattcctt cctgcagctg    780
acagaatatt ctcgggaaga gatcctgggg cgcaattgcc gttttctgca gggacccgag    840
acagaccgtg ccactgttcg gaaaatcaga gatgctattg acaaccagac tgaagtgacc    900
gttcagctga tcaattatac caagagcggc aagaagttct ggaacgtgtt ccacctgcag    960
ccgatgcgcg attataaggg cgacgtccag tacttcattg gcgtgcagct ggatggcacc   1020
gaacgtcttc atggcgccgc tgagcgtgag gcggtctgcc tgatcaaaaa gacagccttt   1080
cagattgctg agaacctgta cttccagggc                                    1110
```

<210> SEQ ID NO 6
<211> LENGTH: 369
<212> TYPE: PRT
<213> ORGANISM: Artificial Sequence
<220> FEATURE:
<223> OTHER INFORMATION: V2tail ? CIBN ? AsLOV2(BLITz-6) ? TEVseq

<400> SEQUENCE: 6

Gly Arg Thr Pro Pro Ser Leu Gly Pro Gln Asp Glu Ser Cys Thr Thr
1               5                   10                  15

Ala Ser Ser Ser Leu Ala Lys Asp Thr Ser Ser Leu Gln Leu Pro Pro
            20                  25                  30

Leu Glu Arg Leu Thr Leu Gly Gly Ser Gly Gly Leu Glu Gly Met Asn
        35                  40                  45

Gly Ala Ile Gly Gly Asp Leu Leu Asn Phe Pro Asp Met Ser Val
    50                  55                  60

Leu Glu Arg Gln Arg Ala His Leu Lys Tyr Leu Asn Pro Thr Phe Asp
65                  70                  75                  80

Ser Pro Leu Ala Gly Phe Phe Ala Asp Ser Ser Met Ile Thr Gly Gly
                85                  90                  95

Glu Met Asp Ser Tyr Leu Ser Thr Ala Gly Leu Asn Leu Pro Met Met
            100                 105                 110

Tyr Gly Glu Thr Thr Val Glu Gly Asp Ser Arg Leu Ser Ile Ser Pro
        115                 120                 125

Glu Thr Thr Leu Gly Thr Gly Asn Phe Lys Ala Ala Lys Phe Asp Thr
    130                 135                 140

Glu Thr Lys Asp Cys Asn Glu Ala Ala Lys Lys Met Thr Met Asn Arg
145                 150                 155                 160

Asp Asp Leu Val Glu Glu Gly Glu Glu Glu Lys Ser Lys Ile Thr Glu
                165                 170                 175

Gln Asn Asn Gly Ser Thr Lys Ser Ile Lys Lys Met Lys His Lys Ala
            180                 185                 190

Lys Lys Glu Glu Asn Asn Phe Ser Asn Asp Ser Ser Lys Val Thr Lys

```
            195                 200                 205
Glu Leu Glu Lys Thr Asp Tyr Ile His Ala Cys Gly Ser Gly Ser Gly
    210                 215                 220

Glu Phe Leu Ala Thr Thr Leu Glu Arg Ile Glu Lys Asn Phe Val Ile
225                 230                 235                 240

Thr Asp Pro Arg Leu Pro Asp Asn Pro Ile Ile Phe Ala Ser Asp Ser
                245                 250                 255

Phe Leu Gln Leu Thr Glu Tyr Ser Arg Glu Glu Ile Leu Gly Arg Asn
            260                 265                 270

Cys Arg Phe Leu Gln Gly Pro Glu Thr Asp Arg Ala Thr Val Arg Lys
        275                 280                 285

Ile Arg Asp Ala Ile Asp Asn Gln Thr Glu Val Thr Val Gln Leu Ile
    290                 295                 300

Asn Tyr Thr Lys Ser Gly Lys Lys Phe Trp Asn Val Phe His Leu Gln
305                 310                 315                 320

Pro Met Arg Asp Tyr Lys Gly Asp Val Gln Tyr Phe Ile Gly Val Gln
                325                 330                 335

Leu Asp Gly Thr Glu Arg Leu His Gly Ala Ala Glu Arg Glu Ala Val
            340                 345                 350

Cys Leu Ile Lys Lys Thr Ala Phe Gln Ile Glu Asn Leu Tyr Phe Gln
        355                 360                 365

Gly

<210> SEQ ID NO 7
<211> LENGTH: 801
<212> TYPE: DNA
<213> ORGANISM: Artificial Sequence
<220> FEATURE:
<223> OTHER INFORMATION: Backbone Sequence A

<400> SEQUENCE: 7
aagctttcat ttaggtgaca ctatagaata caagctactt gttctatgga gacagacaca    60
ctcctgctat gggtactgct gctctgggtt ccaggttcca ctggtgacga caaaaaactc   120
atctcagaag aggatctgaa tgctgtgggc aggacacgc aggaggtcat cgtggtgcca   180
cactccttgc cctttaaggt ggtggtgatc tcagccatcc tggccctggt ggtgctcacc   240
atcatctccc ttatcatcct catcatgctt tggcagaaga agccacgtgg tggctctgga   300
ggtctcgagg gagcatgcgg tggcggtggc tctggaggtg gtgggtccgg aggaggcggc   360
cgctccggtg gatccatgct tcaacttcct cctcttgaac gtcttactct cgagatgggc   420
gagagcctgt tcaagggacc tagggactac aaccctatca gtagcacaat tgtcacctg   480 accaacgaga gtgatggcca cacaacaagc ctgtacggca tcgggttcgg accctttatc   540
atcaccaaca agcacctgtt caggcggaat aatggcactc tgctggtgca gagcctgcac   600
ggggtgttca agtgaagaa cacaaccact ctgcagcagc acctgatcga tgggcgggat   660
atgatcatca ttaggatgcc caaggacttc ccccctttc ctcagaaact gaagttccga   720
agcccccaga gagaggagag aatctgtctg gtgaccacaa actttcagga gctcggtagt   780
ggtagtgggt ctagagctag c                                            801

<210> SEQ ID NO 8
<211> LENGTH: 1308
<212> TYPE: DNA
<213> ORGANISM: Artificial Sequence
<220> FEATURE:
<223> OTHER INFORMATION: CaM ? TEV-N ? AsLOV2(BLITz-6)? TEVseq
```

-continued

<400> SEQUENCE: 8

```
atgccggacc aactgactga agagcagatc gcagaattta agaggcttt ctccctattt     60
gacaaggacg gggatgggac aataacaacc aaggagctgg ggacggtgat gcggtctctg    120
gggcagaacc ccacagaagc agagctgcaa gacatgatca atgaagtaga tgccgacggt    180
gacggcacaa tcgacttccc tgagttcctg acaatgatgg caagaaaaat gaaatacagg    240
gacacggaag aagaaattag agaagcgttc ggtgtgtttg ataaggatgg caatggctac    300
atcagtgcag cagagcttcg ccacgtgatg acaaaccttg gagagaagtt aacagatgaa    360
gaggttgatg aaatgatcag ggaagcagac atcgatgggg atggtcaggt aaactacgaa    420
gagtttgtac aaatgatgac agcgaaggca tgcggtggcg gtggctctgg aggtggtggg    480
tccggaggag gcggccgcat gggcgagagc ctgttcaagg gacctaggga ctacaaccct    540
atcagtagca caatttgtca cctgaccaac gagagtgatg ccacacaac aagcctgtac    600
ggcatcgggt tcggacccct tatcatcacc aacaagcacc tgttcaggcg aataatggc     660
actctgctgg tgcagagcct gcacggggtg ttcaaagtga gaacacaac cactctgcag    720
cagcacctga tcgatgggcg ggatatgatc atcattagga tgcccaagga cttccccct     780
tttcctcaga aactgaagtt ccgagagccc agagagagg agagaatctg tctggtgacc    840
acaaacttc aggagctcgg tagtggtagt ggggagtttc tggcaaccac actgaacgg    900
atcgagaaaa atttcgtgat tactgatccg agactgcctg acaacccaat catttttgcg    960
agcgattcct cctgcagct gacagaatat tctcgggaag gatcctgggg gcgcaattgc    1020
cgttttctgc agggacccga cagaccgt gccactgttc ggaaaatcag agatgctatt    1080
gacaaccaga ctgaagtgac cgttcagctg atcaattata ccaagagcgg caagaagttc    1140
tggaacgtgt tccacctgca gccgatgcgc gattataagg gcgacgtcca gtacttcatt    1200
ggcgtgcagc tggatggcac cgaacgtctt catggcgccg ctgagcgtga ggcggtctgc    1260
ctgatcaaaa agacagcctt tcagattgag aacctgtact tccagggc                1308
```

<210> SEQ ID NO 9
<211> LENGTH: 436
<212> TYPE: PRT
<213> ORGANISM: Artificial Sequence
<220> FEATURE:
<223> OTHER INFORMATION: CaM ? TEV-N ? AsLOV2(BLITz-6)? TEVseq

<400> SEQUENCE: 9

```
Met Pro Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
            20                  25                  30

Leu Gly Thr Val Met Arg Ser Leu Gly Gln Asn Pro Thr Glu Ala Glu
        35                  40                  45

Leu Gln Asp Met Ile Asn Glu Val Asp Ala Asp Gly Asp Gly Thr Ile
    50                  55                  60

Asp Phe Pro Glu Phe Leu Thr Met Met Ala Arg Lys Met Lys Tyr Arg
65                  70                  75                  80

Asp Thr Glu Glu Glu Ile Arg Glu Ala Phe Gly Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
```

```
            115                 120                 125
Ala Asp Ile Asp Gly Asp Gly Gln Val Asn Tyr Glu Glu Phe Val Gln
130                 135                 140

Met Met Thr Ala Lys Ala Cys Gly Gly Gly Ser Gly Gly Gly Gly
145                 150                 155                 160

Ser Gly Gly Gly Gly Arg Met Gly Glu Ser Leu Phe Lys Gly Pro Arg
                165                 170                 175

Asp Tyr Asn Pro Ile Ser Ser Thr Ile Cys His Leu Thr Asn Glu Ser
            180                 185                 190

Asp Gly His Thr Thr Ser Leu Tyr Gly Ile Gly Phe Gly Pro Phe Ile
        195                 200                 205

Ile Thr Asn Lys His Leu Phe Arg Arg Asn Asn Gly Thr Leu Leu Val
    210                 215                 220

Gln Ser Leu His Gly Val Phe Lys Val Lys Asn Thr Thr Thr Leu Gln
225                 230                 235                 240

Gln His Leu Ile Asp Gly Arg Asp Met Ile Ile Ile Arg Met Pro Lys
                245                 250                 255

Asp Phe Pro Pro Phe Pro Gln Lys Leu Lys Phe Arg Glu Pro Gln Arg
            260                 265                 270

Glu Glu Arg Ile Cys Leu Val Thr Asn Phe Gln Glu Leu Gly Ser
        275                 280                 285

Gly Ser Gly Glu Phe Leu Ala Thr Thr Leu Glu Arg Ile Glu Lys Asn
290                 295                 300

Phe Val Ile Thr Asp Pro Arg Leu Pro Asp Asn Pro Ile Ile Phe Ala
305                 310                 315                 320

Ser Asp Ser Phe Leu Gln Leu Thr Glu Tyr Ser Arg Glu Glu Ile Leu
                325                 330                 335

Gly Arg Asn Cys Arg Phe Leu Gln Gly Pro Glu Thr Asp Arg Ala Thr
            340                 345                 350

Val Arg Lys Ile Arg Asp Ala Ile Asp Asn Gln Thr Glu Val Thr Val
        355                 360                 365

Gln Leu Ile Asn Tyr Thr Lys Ser Gly Lys Lys Phe Trp Asn Val Phe
    370                 375                 380

His Leu Gln Pro Met Arg Asp Tyr Lys Gly Asp Val Gln Tyr Phe Ile
385                 390                 395                 400

Gly Val Gln Leu Asp Gly Thr Glu Arg Leu His Gly Ala Ala Glu Arg
                405                 410                 415

Glu Ala Val Cys Leu Ile Lys Lys Thr Ala Phe Gln Ile Glu Asn Leu
            420                 425                 430

Tyr Phe Gln Gly
        435

<210> SEQ ID NO 10
<211> LENGTH: 1002
<212> TYPE: DNA
<213> ORGANISM: Artificial Sequence
<220> FEATURE:
<223> OTHER INFORMATION: TetR-VP16

<400> SEQUENCE: 10
tctagattag ataaaagtaa agtgattaac agcgcattag agctgcttaa tgaggtcgga      60
atcgaaggtt taacaacccg taaactcgcc cagaagctag gtgtagagca gcctacattg     120
tattggcatg taaaaaataa gcgggctttg ctcgacgcct tagccattga gatgttagat     180
aggcaccata ctcactttg cccttttagaa ggggaaagct ggcaagattt tttacgtaat     240
```

```
aacgctaaaa gttttagatg tgctttacta agtcatcgcg atggagcaaa agtacattta    300
ggtacacggc ctacagaaaa acagtatgaa actctcgaaa atcaattagc ctttttatgc    360
caacaaggtt tttcactaga gaatgcatta tatgcactca gcgctgtggg gcattttact    420
ttaggttgcg tattggaaga tcaagagcat caagtcgcta aagaagaaag ggaaacacct    480
actactgata gtatgccgcc attattacga caagctatcg aattatttga tcaccaaggt    540
gcagagccag ccttcttatt cggccttgaa ttgatcatat gcggattaga aaaacaactt    600
aaatgtgaaa gtgggtccgc gtacagccgc gcgcgtacga aaaacaatta cgggtctacc    660
atcgagggcc tgctcgatct cccggacgac gacgcccccg aagaggcggg gctggcggct    720
ccgcgcctgt cctttctccc cgcgggacac acgcgcagac tgtcgacggc ccccccgacc    780
gatgtcagcc tggggacga gctccactta gacggcgagg acgtggcgat ggcgcatgcc    840
gacgcgctag acgatttcga tctggacatg ttgggggacg gggattcccc gggtccggga    900
tttacccccc acgactccgc cccctacggc gctctggata tggccgactt cgagtttgag    960
cagatgttta ccgatgccct tggaattgac gagtacggtg gg                     1002
```

<210> SEQ ID NO 11
<211> LENGTH: 334
<212> TYPE: PRT
<213> ORGANISM: Artificial Sequence
<220> FEATURE:
<223> OTHER INFORMATION: TetR-VP16

<400> SEQUENCE: 11

```
Ser Arg Leu Asp Lys Ser Lys Val Ile Asn Ser Ala Leu Glu Leu Leu
1               5                   10                  15

Asn Glu Val Gly Ile Glu Gly Leu Thr Thr Arg Lys Leu Ala Gln Lys
            20                  25                  30

Leu Gly Val Glu Gln Pro Thr Leu Tyr Trp His Val Lys Asn Lys Arg
        35                  40                  45

Ala Leu Leu Asp Ala Leu Ala Ile Glu Met Leu Asp Arg His His Thr
    50                  55                  60

His Phe Cys Pro Leu Glu Gly Glu Ser Trp Gln Asp Phe Leu Arg Asn
65                  70                  75                  80

Asn Ala Lys Ser Phe Arg Cys Ala Leu Leu Ser His Arg Asp Gly Ala
                85                  90                  95

Lys Val His Leu Gly Thr Arg Pro Thr Glu Lys Gln Tyr Glu Thr Leu
            100                 105                 110

Glu Asn Gln Leu Ala Phe Leu Cys Gln Gln Gly Phe Ser Leu Glu Asn
        115                 120                 125

Ala Leu Tyr Ala Leu Ser Ala Val Gly His Phe Thr Leu Gly Cys Val
    130                 135                 140

Leu Glu Asp Gln Glu His Gln Val Ala Lys Glu Glu Arg Glu Thr Pro
145                 150                 155                 160

Thr Thr Asp Ser Met Pro Pro Leu Leu Arg Gln Ala Ile Glu Leu Phe
                165                 170                 175

Asp His Gln Gly Ala Glu Pro Ala Phe Leu Phe Gly Leu Glu Leu Ile
            180                 185                 190

Ile Cys Gly Leu Glu Lys Gln Leu Lys Cys Glu Ser Gly Ser Ala Tyr
        195                 200                 205

Ser Arg Ala Arg Thr Lys Asn Asn Tyr Gly Ser Thr Ile Glu Gly Leu
    210                 215                 220
```

Leu Asp Leu Pro Asp Asp Ala Pro Glu Glu Ala Gly Leu Ala Ala
225                 230                 235                 240

Pro Arg Leu Ser Phe Leu Pro Ala Gly His Thr Arg Arg Leu Ser Thr
            245                 250                 255

Ala Pro Pro Thr Asp Val Ser Leu Gly Asp Glu Leu His Leu Asp Gly
        260                 265                 270

Glu Asp Val Ala Met Ala His Ala Asp Ala Leu Asp Asp Phe Asp Leu
    275                 280                 285

Asp Met Leu Gly Asp Gly Asp Ser Pro Gly Pro Gly Phe Thr Pro His
    290                 295                 300

Asp Ser Ala Pro Tyr Gly Ala Leu Asp Met Ala Asp Phe Glu Phe Glu
305                 310                 315                 320

Gln Met Phe Thr Asp Ala Leu Gly Ile Asp Glu Tyr Gly Gly
                325                 330

<210> SEQ ID NO 12
<211> LENGTH: 4101
<212> TYPE: DNA
<213> ORGANISM: Artificial Sequence
<220> FEATURE:
<223> OTHER INFORMATION: Cas9

<400> SEQUENCE: 12
gacaagaagt acagcatcgg cctggacatc ggcaccaact ctgtgggctg ggccgtgatc      60
accgacgagt acaaggtgcc cagcaagaaa ttcaaggtgc tgggcaacac cgaccggcac     120
agcatcaaga gaaacctgat cggagccctg ctgttcgaca gcggcgaaac agccgaggcc     180
acccggctga agagaaccgc cagaagaaga taccaccgac ggaagaaccg gatctgctat     240
ctgcaagaga tcttcagcaa cgagatggcc aaggtggacg acagcttctt ccacagactg     300
gaagagtcct tcctggtgga agaggataag aagcacgagc ggcaccccat cttcggcaac     360
atcgtggacg aggtggccta ccacgagaag taccccacca tctaccacct gagaaagaaa     420
ctggtggaca gcaccgacaa ggccgacctg cggctgatct atctggccct ggcccacatg     480
atcaagttcc ggggccactt cctgatcgag ggcgacctga accccgacaa cagcgacgtg     540
gacaagctgt tcatccagct ggtgcagacc tacaaccagc tgttcgagga aaaccccatc     600
aacgccagcg gcgtggacgc caaggccatc ctgtctgcca gactgagcaa gagcagacgg     660
ctggaaaatc tgatcgccca gctgcccggc gagaagaaga tggcctgttc ggaaacctg      720 attgccctga gcctgggcct gacccccaac ttcaagagca cttcgacct ggccgaggat     780 gccaaactgc agctgagcaa ggacacctac gacgacgacc tggacaacct gctggcccag     840
atcggcgacc agtacgccga cctgtttctg gccgccaaga acctgtccga cgccatcctg     900
ctgagcgaca tcctgagagt gaacaccgag atcaccaagg cccccctgag cgcctctatg     960
atcaagagat acgacgagca ccaccaggac ctgaccctgc tgaaagctct cgtgcggcag    1020
cagctgcctg agaagtacaa agagattttc ttcgaccaga gcaagaacgg ctacgccggc    1080
tacattgacg gcggagccag ccaggaagag ttctacaagt tcatcaagcc catcctggaa    1140
aagatggacg gcaccgagga actgctcgtg aagctgaaca gagaggacct gctgcggaag    1200
cagcggacct tcgacaacgg cagcatcccc caccagatcc acctgggaga gctgcacgcc    1260
attctgcggc ggcaggaaga ttttttaccca ttcctgaagg acaaccggga aaagatcgag    1320
aagatcctga ccttccgcat cccctactac gtgggccctc tggccagggg aaacagcaga    1380
ttcgcctgga tgaccagaaa gagcgaggaa accatcaccc cctggaactt cgaggaagtg    1440

```
gtggacaagg gcgcttccgc ccagagcttc atcgagcgga tgaccaactt cgataagaac    1500
ctgcccaacg agaaggtgct gcccaagcac agcctgctgt acgagtactt caccgtgtat    1560
aacgagctga ccaaagtgaa atacgtgacc gagggaatga aaagcccgc cttcctgagc     1620 ggcgagcaga aaaaggccat cgtggacctg ctgttcaaga ccaaccggaa agtgaccgtg    1680
aagcagctga agaggactac cttcaagaaa atcgagtgct tcgactccgt ggaaatctcc    1740
ggcgtggaag atcggttcaa cgcctccctg ggcacatacc acgatctgct gaaaattatc    1800
aaggacaagg acttcctgga caatgaggaa acgaggaca ttctggaaga tatcgtgctg     1860
accctgacac tgtttgagga cagagagatg atcgaggaac ggctgaaaac ctatgcccac    1920
ctgttcgacg acaaagtgat gaagcagctg aagcggcgga gatacaccgg ctggggcagg    1980
ctgagccgga agctgatcaa cggcatccgg gacaagcagt ccggcaagac aatcctggat    2040
ttcctgaagt ccgacggctt cgccaacaga aacttcatgc agctgatcca cgacgacagc    2100 ctgacctttta agaggacat ccagaaagcc caggtgtccg ccagggcga tagcctgcac     2160 gagcacattg ccaatctggc cggcagcccc gccattaaga agggcatcct gcagacagtg    2220
aaggtggtgg acgagctcgt gaaagtgatg ggccggcaca agcccgagaa catcgtgatc    2280
gaaatggcca gagagaacca gaccacccag aaggacagag agaacagccg cgagagaatg    2340
aagcggatcg aagagggcat caaagagctg ggcagccaga tcctgaaaga acaccccgtg    2400 gaaacaccc agctgcagaa cgagaagctg tacctgtact acctgcagaa tgggcgggat    2460
atgtacgtgg accaggaact ggacatcaac cggctgtccg actacgatgt ggaccatatc    2520
gtgcctcaga gctttctgaa ggacgactcc atcgacaaca aggtgctgac cagaagcgac    2580
aagaaccggg gcaagagcga caacgtgccc tccgaagagg tcgtgaagaa gatgaagaac    2640
tactggcggc agctgctgaa cgccaagctg attacccaga gaaagttcga caatctgacc    2700
aaggccgaga gaggcggcct gagcgaactg gataaggccg gcttcatcaa gagacagctg    2760
gtggaaaccc ggcagatcac aaagcacgtg gcacagatcc tggactcccg gatgaacact    2820
aagtacgacg agaatgacaa gctgatccgg gaagtgaaag tgatcaccct gaagtccaag    2880
ctggtgtccg atttccggaa ggatttccag ttttacaaag tgcgcgagat caacaactac    2940
caccacgccc acgacgccta cctgaacgcc gtcgtgggaa ccgccctgat caaaaagtac    3000
cctaagctgg aaagcgagtt cgtgtacggc gactacaagg tgtacgacgt gcggaagatg    3060
atcgccaaga gcgagcagga aatcggcaag gctaccgcca agtacttctt ctacagcaac    3120
atcatgaact ttttcaagac cgagattacc ctggccaacg cgagatccg gaagcggcct    3180 ctgatcgaga caaacggcga aaccggggag atcgtgtggg ataagggccg ggatttttgcc    3240 accgtgcgga aagtgctgag catgcccca gtgaatatcg tgaaaaagac cgaggtgcag    3300
acaggcggct tcagcaaaga gtctatcctg cccaagagga cagcgataa gctgatcgcc    3360 agaaagaagg actgggaccc taagaagtac ggcggcttcg acagcccac cgtggcctat    3420 tctgtgctgg tggtggccaa agtggaaaag ggcaagtcca gaaactgaa gagtgtgaaa    3480 gagctgctgg gcatcaccat catggaaaga agcagcttcg agaagaatcc catcgacttt    3540
ctggaagcca gggctacaa agaagtgaaa aaggacctga tcatcaagct gcctaagtac    3600 tcccctgttcg agctggaaaa cggccggaag agaatgctgg cctctgccgg cgaactgcag    3660
aagggaaacg aactggccct gccctccaaa tatgtgaact tcctgtacct ggccagccac    3720
tatgagaagc tgaagggctc ccccgaggat aatgagcaga acagctgtt tgtgaacag    3780 cacaagcact acctggacga gatcatcgag cagatcagcg agttctccaa gagagtgatc    3840
```

```
ctggccgacg ctaatctgga caaagtgctg tccgcctaca acaagcaccg ggataagccc    3900
atcagagagc aggccgagaa tatcatccac ctgtttaccc tgaccaatct gggagcccct    3960
gccgccttca gtactttga caccaccatc gaccggaaga ggtacaccag caccaaagag     4020
gtgctggacg ccaccctgat ccaccagagc atcaccggcc tgtacgagac acggatcgac    4080
ctgtctcagc tgggaggcga c                                               4101
```

<210> SEQ ID NO 13
<211> LENGTH: 1367
<212> TYPE: PRT
<213> ORGANISM: Artificial Sequence
<220> FEATURE:
<223> OTHER INFORMATION: Cas9

<400> SEQUENCE: 13

```
Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
```

```
            305                 310                 315                 320
        Ile Lys Arg Tyr Asp Glu His His Gln Asp Leu Thr Leu Leu Lys Ala
                        325                 330                 335
        Leu Val Arg Gln Gln Leu Pro Glu Lys Tyr Lys Glu Ile Phe Phe Asp
                        340                 345                 350
        Gln Ser Lys Asn Gly Tyr Ala Gly Tyr Ile Asp Gly Gly Ala Ser Gln
                        355                 360                 365
        Glu Glu Phe Tyr Lys Phe Ile Lys Pro Ile Leu Glu Lys Met Asp Gly
                        370                 375                 380
        Thr Glu Glu Leu Leu Val Lys Leu Asn Arg Glu Asp Leu Leu Arg Lys
        385                 390                 395                 400
        Gln Arg Thr Phe Asp Asn Gly Ser Ile Pro His Gln Ile His Leu Gly
                        405                 410                 415
        Glu Leu His Ala Ile Leu Arg Arg Gln Glu Asp Phe Tyr Pro Phe Leu
                        420                 425                 430
        Lys Asp Asn Arg Glu Lys Ile Glu Lys Ile Leu Thr Phe Arg Ile Pro
                        435                 440                 445
        Tyr Tyr Val Gly Pro Leu Ala Arg Gly Asn Ser Arg Phe Ala Trp Met
        450                 455                 460
        Thr Arg Lys Ser Glu Glu Thr Ile Thr Pro Trp Asn Phe Glu Glu Val
        465                 470                 475                 480
        Val Asp Lys Gly Ala Ser Ala Gln Ser Phe Ile Glu Arg Met Thr Asn
                        485                 490                 495
        Phe Asp Lys Asn Leu Pro Asn Glu Lys Val Leu Pro Lys His Ser Leu
                        500                 505                 510
        Leu Tyr Glu Tyr Phe Thr Val Tyr Asn Glu Leu Thr Lys Val Lys Tyr
                        515                 520                 525
        Val Thr Glu Gly Met Arg Lys Pro Ala Phe Leu Ser Gly Glu Gln Lys
                        530                 535                 540
        Lys Ala Ile Val Asp Leu Leu Phe Lys Thr Asn Arg Lys Val Thr Val
        545                 550                 555                 560
        Lys Gln Leu Lys Glu Asp Tyr Phe Lys Lys Ile Glu Cys Phe Asp Ser
                        565                 570                 575
        Val Glu Ile Ser Gly Val Glu Asp Arg Phe Asn Ala Ser Leu Gly Thr
                        580                 585                 590
        Tyr His Asp Leu Leu Lys Ile Ile Lys Asp Lys Asp Phe Leu Asp Asn
                        595                 600                 605
        Glu Glu Asn Glu Asp Ile Leu Glu Asp Ile Val Leu Thr Leu Thr Leu
                        610                 615                 620
        Phe Glu Asp Arg Glu Met Ile Glu Glu Arg Leu Lys Thr Tyr Ala His
        625                 630                 635                 640
        Leu Phe Asp Asp Lys Val Met Lys Gln Leu Lys Arg Arg Arg Tyr Thr
                        645                 650                 655
        Gly Trp Gly Arg Leu Ser Arg Lys Leu Ile Asn Gly Ile Arg Asp Lys
                        660                 665                 670
        Gln Ser Gly Lys Thr Ile Leu Asp Phe Leu Lys Ser Asp Gly Phe Ala
                        675                 680                 685
        Asn Arg Asn Phe Met Gln Leu Ile His Asp Asp Ser Leu Thr Phe Lys
                        690                 695                 700
        Glu Asp Ile Gln Lys Ala Gln Val Ser Gly Gln Gly Asp Ser Leu His
        705                 710                 715                 720
        Glu His Ile Ala Asn Leu Ala Gly Ser Pro Ala Ile Lys Lys Gly Ile
                        725                 730                 735
```

```
Leu Gln Thr Val Lys Val Asp Glu Leu Val Lys Val Met Gly Arg
            740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
            805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
            835                 840                 845

Asp Ser Ile Asp Asn Lys Val Leu Thr Arg Ser Asp Lys Asn Arg Gly
            850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys Ser
            1010                1015                1020

Glu Gln Glu Ile Gly Lys Ala Thr Ala Lys Tyr Phe Phe Tyr Ser Asn
1025                1030                1035                1040

Ile Met Asn Phe Phe Lys Thr Glu Ile Thr Leu Ala Asn Gly Glu Ile
            1045                1050                1055

Arg Lys Arg Pro Leu Ile Glu Thr Asn Gly Glu Thr Gly Glu Ile Val
            1060                1065                1070

Trp Asp Lys Gly Arg Asp Phe Ala Thr Val Arg Lys Val Leu Ser Met
            1075                1080                1085

Pro Gln Val Asn Ile Val Lys Lys Thr Glu Val Gln Thr Gly Gly Phe
            1090                1095                1100

Ser Lys Glu Ser Ile Leu Pro Lys Arg Asn Ser Asp Lys Leu Ile Ala
1105                1110                1115                1120

Arg Lys Lys Asp Trp Asp Pro Lys Lys Tyr Gly Gly Phe Asp Ser Pro
            1125                1130                1135

Thr Val Ala Tyr Ser Val Leu Val Val Ala Lys Val Glu Lys Gly Lys
            1140                1145                1150
```

| | | | | | | | | | | | | |
|---|---|---|---|---|---|---|---|---|---|---|---|---|
|Ser|Lys|Lys|Leu|Lys|Ser|Val|Lys|Glu|Leu|Leu|Gly|Ile Thr Ile Met|
| |1155| | | |1160| | | |1165| | | |

Ser Lys Lys Leu Lys Ser Val Lys Glu Leu Leu Gly Ile Thr Ile Met
         1155                1160                1165

Glu Arg Ser Ser Phe Glu Lys Asn Pro Ile Asp Phe Leu Glu Ala Lys
    1170                1175                1180

Gly Tyr Lys Glu Val Lys Lys Asp Leu Ile Ile Lys Leu Pro Lys Tyr
1185                1190                1195                1200

Ser Leu Phe Glu Leu Glu Asn Gly Arg Lys Arg Met Leu Ala Ser Ala
        1205                1210                1215

Gly Glu Leu Gln Lys Gly Asn Glu Leu Ala Leu Pro Ser Lys Tyr Val
            1220                1225                1230

Asn Phe Leu Tyr Leu Ala Ser His Tyr Glu Lys Leu Lys Gly Ser Pro
        1235                1240                1245

Glu Asp Asn Glu Gln Lys Gln Leu Phe Val Glu Gln His Lys His Tyr
    1250                1255                1260

Leu Asp Glu Ile Ile Glu Gln Ile Ser Glu Phe Ser Lys Arg Val Ile
1265                1270                1275                1280

Leu Ala Asp Ala Asn Leu Asp Lys Val Leu Ser Ala Tyr Asn Lys His
            1285                1290                1295

Arg Asp Lys Pro Ile Arg Glu Gln Ala Glu Asn Ile Ile His Leu Phe
        1300                1305                1310

Thr Leu Thr Asn Leu Gly Ala Pro Ala Ala Phe Lys Tyr Phe Asp Thr
    1315                1320                1325

Thr Ile Asp Arg Lys Arg Tyr Thr Ser Thr Lys Glu Val Leu Asp Ala
    1330                1335                1340

Thr Leu Ile His Gln Ser Ile Thr Gly Leu Tyr Glu Thr Arg Ile Asp
1345                1350                1355                1360

Leu Ser Gln Leu Gly Gly Asp
            1365

<210> SEQ ID NO 14
<211> LENGTH: 1032
<212> TYPE: DNA
<213> ORGANISM: Artificial Sequence
<220> FEATURE:
<223> OTHER INFORMATION: CRE recombinase

<400> SEQUENCE: 14

```
atggccaatt tactgaccgt acaccaaaat tgcctgcat  taccggtcga tgcaacgagt    60
gatgaggttc gcaagaacct gatggacatg ttcagggatc gccaggcgtt ttctgagcat   120
acctggaaaa tgcttctgtc cgtttgccgg tcgtgggcgg catggtgcaa gttgaataac   180
cggaaatggt tcccgcaga  acctgaagat gttcgcgatt atcttctata tcttcaggcg   240
cgcggtctgg cagtaaaaac tatccagcaa catttgggcc agctaaacat gcttcatcgt   300
cggtccgggc tgccacgacc aagtgacagc aatgctgttt cactggttat gcggcggatc   360
cgaaaagaaa acgttgatgc cggtgaacgt gcaaaacagg ctctagcgtt cgaacgcact   420
gatttcgacc aggttcgttc actcatggaa atagcgatc  gctgccagga tatacgtaat   480
ctggcatttc tggggattgc ttataacacc ctgttacgta tagccgaaat tgccaggatc   540
agggttaaag atatctcacg tactgacggt gggagaatgt taatccatat ggcagaacg   600 aaaacgctgg ttagcaccgc aggtgtagag aaggcactta gcctgggggt aactaaactg   660
gtcgagcgat ggatttccgt ctctggtgta gctgatgatc cgaataacta cctgttttgc   720
cgggtcagaa aaatggtgt  tgccgcgcca tctgccacca gccagctatc aactcgcgcc   780
ctggaaggga ttttgaagc  aactcatcga ttgatttacg gcgctaagga tgactctggt   840
```

```
cagagatacc tggcctggtc tggacacagt gcccgtgtcg gagccgcgcg agatatggcc    900
cgcgctggag tttcaatacc ggagatcatg caagctggtg gctggaccaa tgtaaatatt    960
gtcatgaact atatccgtaa cctggatagt gaaacagggg caatggtgcg cctgctggaa   1020
gatggcgatt aa                                                       1032
```

```
<210> SEQ ID NO 15
<211> LENGTH: 343
<212> TYPE: PRT
<213> ORGANISM: Artificial Sequence
<220> FEATURE:
<223> OTHER INFORMATION: CRE recombinase

<400> SEQUENCE: 15
```

| | | | | | | | | | | | | | | |
|---|---|---|---|---|---|---|---|---|---|---|---|---|---|---|
| Met | Ala | Asn | Leu | Leu | Thr | Val | His | Gln | Asn | Leu | Pro | Ala | Leu | Pro | Val |
| 1 | | | | 5 | | | | | 10 | | | | | 15 | |
| Asp | Ala | Thr | Ser | Asp | Glu | Val | Arg | Lys | Asn | Leu | Met | Asp | Met | Phe | Arg |
| | | | 20 | | | | | 25 | | | | | 30 | | |
| Asp | Arg | Gln | Ala | Phe | Ser | Glu | His | Thr | Trp | Lys | Met | Leu | Leu | Ser | Val |
| | | 35 | | | | | 40 | | | | | 45 | | | |
| Cys | Arg | Ser | Trp | Ala | Ala | Trp | Cys | Lys | Leu | Asn | Asn | Arg | Lys | Trp | Phe |
| 50 | | | | | 55 | | | | | 60 | | | | | |
| Pro | Ala | Glu | Pro | Glu | Asp | Val | Arg | Asp | Tyr | Leu | Leu | Tyr | Leu | Gln | Ala |
| 65 | | | | | 70 | | | | | 75 | | | | | 80 |
| Arg | Gly | Leu | Ala | Val | Lys | Thr | Ile | Gln | Gln | His | Leu | Gly | Gln | Leu | Asn |
| | | | | 85 | | | | | 90 | | | | | 95 | |
| Met | Leu | His | Arg | Arg | Ser | Gly | Leu | Pro | Arg | Pro | Ser | Asp | Ser | Asn | Ala |
| | | | 100 | | | | | 105 | | | | | 110 | | |
| Val | Ser | Leu | Val | Met | Arg | Arg | Ile | Arg | Lys | Glu | Asn | Val | Asp | Ala | Gly |
| | | 115 | | | | | 120 | | | | | 125 | | | |
| Glu | Arg | Ala | Lys | Gln | Ala | Leu | Ala | Phe | Glu | Arg | Thr | Asp | Phe | Asp | Gln |
| 130 | | | | | 135 | | | | | 140 | | | | | |
| Val | Arg | Ser | Leu | Met | Glu | Asn | Ser | Asp | Arg | Cys | Gln | Asp | Ile | Arg | Asn |
| 145 | | | | | 150 | | | | | 155 | | | | | 160 |
| Leu | Ala | Phe | Leu | Gly | Ile | Ala | Tyr | Asn | Thr | Leu | Leu | Arg | Ile | Ala | Glu |
| | | | | 165 | | | | | 170 | | | | | 175 | |
| Ile | Ala | Arg | Ile | Arg | Val | Lys | Asp | Ile | Ser | Arg | Thr | Asp | Gly | Gly | Arg |
| | | | 180 | | | | | 185 | | | | | 190 | | |
| Met | Leu | Ile | His | Ile | Gly | Arg | Thr | Lys | Thr | Leu | Val | Ser | Thr | Ala | Gly |
| | | 195 | | | | | 200 | | | | | 205 | | | |
| Val | Glu | Lys | Ala | Leu | Ser | Leu | Gly | Val | Thr | Lys | Leu | Val | Glu | Arg | Trp |
| 210 | | | | | 215 | | | | | 220 | | | | | |
| Ile | Ser | Val | Ser | Gly | Val | Ala | Asp | Asp | Pro | Asn | Asn | Tyr | Leu | Phe | Cys |
| 225 | | | | | 230 | | | | | 235 | | | | | 240 |
| Arg | Val | Arg | Lys | Asn | Gly | Val | Ala | Ala | Pro | Ser | Ala | Thr | Ser | Gln | Leu |
| | | | | 245 | | | | | 250 | | | | | 255 | |
| Ser | Thr | Arg | Ala | Leu | Glu | Gly | Ile | Phe | Glu | Ala | Thr | His | Arg | Leu | Ile |
| | | | 260 | | | | | 265 | | | | | 270 | | |
| Tyr | Gly | Ala | Lys | Asp | Asp | Ser | Gly | Gln | Arg | Tyr | Leu | Ala | Trp | Ser | Gly |
| | | 275 | | | | | 280 | | | | | 285 | | | |
| His | Ser | Ala | Arg | Val | Gly | Ala | Ala | Arg | Asp | Met | Ala | Arg | Ala | Gly | Val |
| | 290 | | | | | 295 | | | | | 300 | | | | |
| Ser | Ile | Pro | Glu | Ile | Met | Gln | Ala | Gly | Gly | Trp | Thr | Asn | Val | Asn | Ile |
| 305 | | | | | 310 | | | | | 315 | | | | | 320 |

Val Met Asn Tyr Ile Arg Asn Leu Asp Ser Glu Thr Gly Ala Met Val
            325                 330                 335

Arg Leu Leu Glu Asp Gly Asp
            340

<210> SEQ ID NO 16
<211> LENGTH: 2433
<212> TYPE: DNA
<213> ORGANISM: Artificial Sequence
<220> FEATURE:
<223> OTHER INFORMATION: CIBN ? TEV-N ? AsLOV2 ? TEVseq ? TetR-VP16(tTA)

<400> SEQUENCE: 16

| | |
|---|---:|
| atgaatggag ctataggagg tgacctttg ctcaattttc ctgacatgtc ggtcctagag | 60 |
| cgccaaaggg ctcacctcaa gtacctcaat cccacctttg attctcctct cgccggcttc | 120 |
| tttgccgatt cttcaatgat taccggcggc gagatggaca gctatctttc gactgccggt | 180 |
| ttgaatcttc cgatgatgta cggtgagacg acggtggaag gtgattcaag actctcaatt | 240 |
| tcgccggaaa cgacgcttgg gactggaaat ttcaaggcag cgaagtttga tacagagact | 300 |
| aaggattgta atgaggcggc gaagaagatg acgatgaaca gagatgaccT agtagaagaa | 360 |
| ggagaagaag agaagtcgaa aataacagag caaaacaatg ggagcacaaa aagcatcaag | 420 |
| aagatgaaac acaaagccaa gaagaagag aacaatttct ctaatgattc atctaaagtg | 480 |
| acgaaggaat tggagaaaac ggattatatt catgcatgcg gtggcggtgg ctctggaggt | 540 |
| ggtgggtccg gaggaggcgg ccgctccggt ggatccatgc ttcaacttcc tcctcttgaa | 600 |
| cgtcttactc tcgagatggg cgagagcctg ttcaagggac ctaggactaa caaccctatc | 660 |
| agtagcacaa tttgtcacct gaccaacgag agtgatggcc acacaacaag cctgtacggc | 720 |
| atcgggttcg gaccctttat catcaccaac aagcacctgt tcaggcggaa taatggcact | 780 |
| ctgctggtgc agagcctgca cggggtgttc aaagtgaaga cacaaccac tctgcagcag | 840 |
| cacctgatcg atgggcggga tatgatcatc attaggatgc ccaaggactt ccccccttt | 900 |
| cctcagaaac tgaagttccg agagcccag agagaggaga gaatctgtct ggtgaccaca | 960 |
| aactttcagg agctcggtag tggtagtggg agtttctgg caaccacact ggaacggatc | 1020 |
| gagaaaaatt tcgtgattac tgatccgaga ctgcctgaca acccaatcat ttttgcgagc | 1080 |
| gattccttcc tgcagctgac agaatattct cgggaagaga tcctgggggcg caattgccgt | 1140 |
| tttctgcagg gacccgagac agaccgtgcc actgttcgga aaatcagaga tgctattgac | 1200 |
| aaccagactg aagtgaccgt tcagctgatc aattatacca gagcggcaa gaagttctgg | 1260 |
| aacgtgttcc acctgcagcc gatgcgcgat tataagggcg acgtccagta cttcattggc | 1320 |
| gtgcagctgg atggcaccga acgtcttcat ggcgccgctg agcgtgaggc ggtctgcctg | 1380 |
| atcaaaaaga cagcctttca gattgctgag aacctgtact ccagggctc tagattagat | 1440 |
| aaaagtaaag tgattaacag cgcattgag ctgcttaatg aggtcggaat cgaaggttta | 1500 |
| acaacccgta actcgcccca gaagctaggt gtagagcagc ctacattgta ttggcatgta | 1560 |
| aaaaataagc gggctttgct cgacgcctta gccattgaga tgttagatag gcaccatact | 1620 |
| cacttttgcc ctttagaagg ggaaagctgg caagattttt acgtaataa cgctaaaagt | 1680 |
| tttagatgtg ctttactaag tcatcgcgat ggagcaaaag tacattagg tacacggcct | 1740 |
| acagaaaaac agtatgaaac tctcgaaaat caattagcct tttatgcca acaaggtttt | 1800 |
| tcactagaga atgcattata tgcactcagc gctgtggggc attttacttt aggttgcgta | 1860 |
| ttggaagatc aagagcatca agtcgctaaa gaagaaaggg aaacacctac tactgatagt | 1920 |

-continued

```
atgccgccat tattacgaca agctatcgaa ttatttgatc accaaggtgc agagccagcc   1980
ttcttattcg gccttgaatt gatcatatgc ggattagaaa aacaacttaa atgtgaaagt   2040
gggtccgcgt acagccgcgc gcgtacgaaa aacaattacg ggtctaccat cgagggcctg   2100
ctcgatctcc cggacgacga cgcccccgaa gaggcgggc tggcggctcc gcgcctgtcc    2160
tttctccccg cgggacacac gcgcagactg tcgacggccc cccgaccga tgtcagcctg    2220 ggggacgagc tccacttaga cggcgaggac gtggcgatgg cgcatgccga cgcgctagac   2280
gatttcgatc tggacatgtt gggggacggg gattccccgg gtccgggatt accccccac    2340 gactccgccc cctacggcgc tctggatatg gccgacttcg agtttgagca atgtttacc    2400 gatgcccttg gaattgacga gtacggtggg tag                                2433
```

<210> SEQ ID NO 17
<211> LENGTH: 810
<212> TYPE: PRT
<213> ORGANISM: Artificial Sequence
<220> FEATURE:
<223> OTHER INFORMATION: CIBN ? TEV-N ? AsLOV2 ? TEVseq ? TetR-VP16(tTA)

<400> SEQUENCE: 17

```
Met Asn Gly Ala Ile Gly Gly Asp Leu Leu Leu Asn Phe Pro Asp Met
1               5                   10                  15

Ser Val Leu Glu Arg Gln Arg Ala His Leu Lys Tyr Leu Asn Pro Thr
            20                  25                  30

Phe Asp Ser Pro Leu Ala Gly Phe Phe Ala Asp Ser Ser Met Ile Thr
        35                  40                  45

Gly Gly Glu Met Asp Ser Tyr Leu Ser Thr Ala Gly Leu Asn Leu Pro
    50                  55                  60

Met Met Tyr Gly Glu Thr Thr Val Glu Gly Asp Ser Arg Leu Ser Ile
65                  70                  75                  80

Ser Pro Glu Thr Thr Leu Gly Thr Gly Asn Phe Lys Ala Ala Lys Phe
                85                  90                  95

Asp Thr Glu Thr Lys Asp Cys Asn Glu Ala Ala Lys Lys Met Thr Met
            100                 105                 110

Asn Arg Asp Asp Leu Val Glu Glu Gly Glu Glu Lys Ser Lys Ile
        115                 120                 125

Thr Glu Gln Asn Asn Gly Ser Thr Lys Ser Ile Lys Lys Met Lys His
    130                 135                 140

Lys Ala Lys Lys Glu Glu Asn Asn Phe Ser Asn Asp Ser Ser Lys Val
145                 150                 155                 160

Thr Lys Glu Leu Glu Lys Thr Asp Tyr Ile His Ala Cys Gly Gly Gly
                165                 170                 175

Gly Ser Gly Gly Gly Gly Ser Gly Gly Gly Arg Ser Gly Gly Ser
            180                 185                 190

Met Leu Gln Leu Pro Pro Leu Glu Arg Leu Thr Leu Glu Met Gly Glu
        195                 200                 205

Ser Leu Phe Lys Gly Pro Arg Asp Tyr Asn Pro Ile Ser Ser Thr Ile
    210                 215                 220

Cys His Leu Thr Asn Glu Ser Asp Gly His Thr Thr Ser Leu Tyr Gly
225                 230                 235                 240

Ile Gly Phe Gly Pro Phe Ile Ile Thr Asn Lys His Leu Phe Arg Arg
                245                 250                 255

Asn Asn Gly Thr Leu Leu Val Gln Ser Leu His Gly Val Phe Lys Val
            260                 265                 270
```

```
Lys Asn Thr Thr Thr Leu Gln Gln His Leu Ile Asp Gly Arg Asp Met
            275                 280                 285

Ile Ile Ile Arg Met Pro Lys Asp Phe Pro Pro Phe Pro Gln Lys Leu
290                 295                 300

Lys Phe Arg Glu Pro Gln Arg Glu Arg Ile Cys Leu Val Thr Thr
305                 310                 315                 320

Asn Phe Gln Glu Leu Gly Ser Gly Ser Gly Glu Phe Leu Ala Thr Thr
                325                 330                 335

Leu Glu Arg Ile Glu Lys Asn Phe Val Ile Thr Asp Pro Arg Leu Pro
                340                 345                 350

Asp Asn Pro Ile Ile Phe Ala Ser Asp Ser Phe Leu Gln Leu Thr Glu
                355                 360                 365

Tyr Ser Arg Glu Glu Ile Leu Gly Arg Asn Cys Arg Phe Leu Gln Gly
                370                 375                 380

Pro Glu Thr Asp Arg Ala Thr Val Arg Lys Ile Arg Asp Ala Ile Asp
385                 390                 395                 400

Asn Gln Thr Glu Val Thr Val Gln Leu Ile Asn Tyr Thr Lys Ser Gly
                405                 410                 415

Lys Lys Phe Trp Asn Val Phe His Leu Gln Pro Met Arg Asp Tyr Lys
                420                 425                 430

Gly Asp Val Gln Tyr Phe Ile Gly Val Gln Leu Asp Gly Thr Glu Arg
                435                 440                 445

Leu His Gly Ala Ala Glu Arg Glu Ala Val Cys Leu Ile Lys Lys Thr
                450                 455                 460

Ala Phe Gln Ile Ala Glu Asn Leu Tyr Phe Gln Gly Ser Arg Leu Asp
465                 470                 475                 480

Lys Ser Lys Val Ile Asn Ser Ala Leu Glu Leu Leu Asn Glu Val Gly
                485                 490                 495

Ile Glu Gly Leu Thr Thr Arg Lys Leu Ala Gln Lys Leu Gly Val Glu
                500                 505                 510

Gln Pro Thr Leu Tyr Trp His Val Lys Asn Lys Arg Ala Leu Leu Asp
                515                 520                 525

Ala Leu Ala Ile Glu Met Leu Asp Arg His His Thr His Phe Cys Pro
                530                 535                 540

Leu Glu Gly Glu Ser Trp Gln Asp Phe Leu Arg Asn Asn Ala Lys Ser
545                 550                 555                 560

Phe Arg Cys Ala Leu Leu Ser His Arg Asp Gly Ala Lys Val His Leu
                565                 570                 575

Gly Thr Arg Pro Thr Glu Lys Gln Tyr Glu Thr Leu Glu Asn Gln Leu
                580                 585                 590

Ala Phe Leu Cys Gln Gln Gly Phe Ser Leu Glu Asn Ala Leu Tyr Ala
                595                 600                 605

Leu Ser Ala Val Gly His Phe Thr Leu Gly Cys Val Leu Glu Asp Gln
                610                 615                 620

Glu His Gln Val Ala Lys Glu Glu Arg Glu Thr Pro Thr Thr Asp Ser
625                 630                 635                 640

Met Pro Pro Leu Leu Arg Gln Ala Ile Glu Leu Phe Asp His Gln Gly
                645                 650                 655

Ala Glu Pro Ala Phe Leu Phe Gly Leu Glu Leu Ile Ile Cys Gly Leu
                660                 665                 670

Glu Lys Gln Leu Lys Cys Glu Ser Gly Ser Ala Tyr Ser Arg Ala Arg
                675                 680                 685
```

|       |     |     |     |     |     |     |     |     |     |
|-------|-----|-----|-----|-----|-----|-----|-----|-----|-----|
| Thr   | Lys | Asn | Asn | Tyr | Gly | Ser | Thr | Ile | Glu | Gly | Leu | Leu | Asp | Leu | Pro |

Thr Lys Asn Asn Tyr Gly Ser Thr Ile Glu Gly Leu Leu Asp Leu Pro
690                 695                 700

Asp Asp Asp Ala Pro Glu Glu Ala Gly Leu Ala Ala Pro Arg Leu Ser
705                 710                 715                 720

Phe Leu Pro Ala Gly His Thr Arg Arg Leu Ser Thr Ala Pro Pro Thr
            725                 730                 735

Asp Val Ser Leu Gly Asp Glu Leu His Leu Asp Gly Glu Asp Val Ala
            740                 745                 750

Met Ala His Ala Asp Ala Leu Asp Asp Phe Asp Leu Asp Met Leu Gly
        755                 760                 765

Asp Gly Asp Ser Pro Gly Pro Gly Phe Thr Pro His Asp Ser Ala Pro
770                 775                 780

Tyr Gly Ala Leu Asp Met Ala Asp Phe Glu Phe Glu Gln Met Phe Thr
785                 790                 795                 800

Asp Ala Leu Gly Ile Asp Glu Tyr Gly Gly
                805                 810

<210> SEQ ID NO 18
<211> LENGTH: 1953
<212> TYPE: DNA
<213> ORGANISM: Artificial Sequence
<220> FEATURE:
<223> OTHER INFORMATION: V2tail ? TEV-N ? AsLOV2 ?TEVseq ? TetR-
      VP16(tTA)

<400> SEQUENCE: 18

```
ggacgcaccc cacccagcct gggtccccaa gatgagtcct gcaccaccgc cagctcctcc      60
ctggccaagg acacttcatc gcttcaactt cctcctcttg aacgtcttac tctcggtggc     120
tctggaggtc tcgagatggg cgagagcctg ttcaagggac taggactaa caacccat       180
agtagcacaa tttgtcacct gaccaacgag agtgatggcc acacaacaag cctgtacggc    240
atcgggttcg accctttat catcaccaac aagcacctgt tcaggcggaa aatggcact      300
ctgctggtgc agagcctgca cggggtgttc aaagtgaaga acacaaccac tctgcagcag    360
cacctgatcg atgggcggga tatgatcatc attaggatgc caaggactt cccccctttt   420
cctcagaaac tgaagttccg agagcccag agagaggaga gaatctgtct ggtgaccaca    480
aactttcagg agctcggtag tggtagtggg gagtttctgg caaccacact ggaacggatc    540
gagaaaaatt tcgtgattac tgatccgaga ctgcctgaca cccaatcat ttttgcgagc   600
gattccttcc tgcagctgac agaatattct cgggaagaga tcctggggcg caattgccgt    660
tttctgcagg gacccgagac agaccgtgcc actgttcgga aaatcagaga tgctattgac    720
aaccagactg aagtgaccgt tcagctgatc aattatacca agagcggcaa gaagttctgg    780
aacgtgttcc acctgcagcc gatgcgcgat tataagggcg acgtccagta cttcattggc    840
gtgcagctgg atggcaccga acgtcttcat ggcgccgctg agcgtgaggc ggtctgcctg    900
atcaaaaaga cagcctttca gattgctgag aacctgtact ccagggctc tagattagat    960
aaaagtaaag tgattaacag cgcattagag ctgcttaatg aggtcggaat cgaaggttta   1020
acaacccgta aactcgccca gaagctaggt gtagagcagc ctacattgta ttggcatgta   1080
aaaaataagc gggctttgct cgacgcctta gccattgaga tgttagatag gcaccatact   1140
cactttttgc ctttagaagg ggaaagctgg caagattttt tacgtaataa cgctaaaagt   1200
tttagatgtg cttactaag tcatcgcgat ggagcaaaag tacatttagg tacacggcct   1260
acagaaaaac agtatgaaac tctcgaaaat caattagcct ttttatgcca acaaggtttt   1320
```

-continued

```
tcactagaga atgcattata tgcactcagc gctgtggggc attttacttt aggttgcgta    1380
ttggaagatc aagagcatca agtcgctaaa gaagaaaggg aaacacctac tactgatagt    1440
atgccgccat tattacgaca agctatcgaa ttatttgatc accaaggtgc agagccagcc    1500
ttcttattcg gccttgaatt gatcatatgc ggattagaaa acaacttaa atgtgaaagt     1560 gggtccgcgt acagccgcgc gcgtacgaaa aacaattacg ggtctaccat cgagggcctg    1620
ctcgatctcc cggacgacga cgcccccgaa gaggcgggc tggcggctcc gcgcctgtcc     1680
tttctccccg cgggacacac gcgcagactg tcgacggccc cccgaccga tgtcagcctg     1740 ggggacgagc tccacttaga cggcgaggac gtggcgatgg cgcatgccga cgcgctagac    1800
gatttcgatc tggacatgtt ggggggacggg gattccccgg gtccgggatt tacccccac    1860 gactccgccc cctacggcgc tctggatatg gccgacttcg agtttgagca atgtttacc     1920 gatgcccttg gaattgacga gtacggtggg tag                                  1953
```

<210> SEQ ID NO 19
<211> LENGTH: 650
<212> TYPE: PRT
<213> ORGANISM: Artificial Sequence
<220> FEATURE:
<223> OTHER INFORMATION: V2tail ? TEV-N ? AsLOV2 ?TEVseq ? TetR-VP16(tTA)

<400> SEQUENCE: 19

```
Gly Arg Thr Pro Pro Ser Leu Gly Pro Gln Asp Glu Ser Cys Thr Thr
1               5                   10                  15

Ala Ser Ser Ser Leu Ala Lys Asp Thr Ser Ser Leu Gln Leu Pro Pro
            20                  25                  30

Leu Glu Arg Leu Thr Leu Gly Gly Ser Gly Gly Leu Glu Met Gly Glu
        35                  40                  45

Ser Leu Phe Lys Gly Pro Arg Asp Tyr Asn Pro Ile Ser Ser Thr Ile
    50                  55                  60

Cys His Leu Thr Asn Glu Ser Asp Gly His Thr Thr Ser Leu Tyr Gly
65                  70                  75                  80

Ile Gly Phe Gly Pro Phe Ile Ile Thr Asn Lys His Leu Phe Arg Arg
                85                  90                  95

Asn Asn Gly Thr Leu Leu Val Gln Ser Leu His Gly Val Phe Lys Val
            100                 105                 110

Lys Asn Thr Thr Thr Leu Gln Gln His Leu Ile Asp Gly Arg Asp Met
        115                 120                 125

Ile Ile Ile Arg Met Pro Lys Asp Phe Pro Pro Phe Pro Gln Lys Leu
    130                 135                 140

Lys Phe Arg Glu Pro Gln Arg Glu Glu Arg Ile Cys Leu Val Thr Thr
145                 150                 155                 160

Asn Phe Gln Glu Leu Gly Ser Gly Ser Gly Glu Phe Leu Ala Thr Thr
                165                 170                 175

Leu Glu Arg Ile Glu Lys Asn Phe Val Ile Thr Asp Pro Arg Leu Pro
            180                 185                 190

Asp Asn Pro Ile Ile Phe Ala Ser Asp Ser Phe Leu Gln Leu Thr Glu
        195                 200                 205

Tyr Ser Arg Glu Glu Ile Leu Gly Arg Asn Cys Arg Phe Leu Gln Gly
    210                 215                 220

Pro Glu Thr Asp Arg Ala Thr Val Arg Lys Ile Arg Asp Ala Ile Asp
225                 230                 235                 240

Asn Gln Thr Glu Val Thr Val Gln Leu Ile Asn Tyr Thr Lys Ser Gly
```

```
            245                 250                 255
Lys Lys Phe Trp Asn Val Phe His Leu Gln Pro Met Arg Asp Tyr Lys
            260                 265                 270

Gly Asp Val Gln Tyr Phe Ile Gly Val Gln Leu Asp Gly Thr Glu Arg
            275                 280                 285

Leu His Gly Ala Ala Glu Arg Glu Ala Val Cys Leu Ile Lys Lys Thr
290                 295                 300

Ala Phe Gln Ile Ala Glu Asn Leu Tyr Phe Gln Gly Ser Arg Leu Asp
305                 310                 315                 320

Lys Ser Lys Val Ile Asn Ser Ala Leu Glu Leu Leu Asn Glu Val Gly
            325                 330                 335

Ile Glu Gly Leu Thr Thr Arg Lys Leu Ala Gln Lys Leu Gly Val Glu
            340                 345                 350

Gln Pro Thr Leu Tyr Trp His Val Lys Asn Lys Arg Ala Leu Leu Asp
            355                 360                 365

Ala Leu Ala Ile Glu Met Leu Asp Arg His His Thr His Phe Cys Pro
370                 375                 380

Leu Glu Gly Glu Ser Trp Gln Asp Phe Leu Arg Asn Asn Ala Lys Ser
385                 390                 395                 400

Phe Arg Cys Ala Leu Leu Ser His Arg Asp Gly Ala Lys Val His Leu
            405                 410                 415

Gly Thr Arg Pro Thr Glu Lys Gln Tyr Glu Thr Leu Glu Asn Gln Leu
            420                 425                 430

Ala Phe Leu Cys Gln Gln Gly Phe Ser Leu Glu Asn Ala Leu Tyr Ala
            435                 440                 445

Leu Ser Ala Val Gly His Phe Thr Leu Gly Cys Val Leu Glu Asp Gln
450                 455                 460

Glu His Gln Val Ala Lys Glu Arg Glu Thr Pro Thr Thr Asp Ser
465                 470                 475                 480

Met Pro Pro Leu Leu Arg Gln Ala Ile Glu Leu Phe Asp His Gln Gly
            485                 490                 495

Ala Glu Pro Ala Phe Leu Phe Gly Leu Glu Leu Ile Ile Cys Gly Leu
            500                 505                 510

Glu Lys Gln Leu Lys Cys Glu Ser Gly Ser Ala Tyr Ser Arg Ala Arg
            515                 520                 525

Thr Lys Asn Asn Tyr Gly Ser Thr Ile Glu Gly Leu Leu Asp Leu Pro
            530                 535                 540

Asp Asp Asp Ala Pro Glu Glu Ala Gly Leu Ala Ala Pro Arg Leu Ser
545                 550                 555                 560

Phe Leu Pro Ala Gly His Thr Arg Arg Leu Ser Thr Ala Pro Pro Thr
            565                 570                 575

Asp Val Ser Leu Gly Asp Glu Leu His Leu Asp Gly Glu Asp Val Ala
            580                 585                 590

Met Ala His Ala Asp Ala Leu Asp Asp Phe Asp Leu Asp Met Leu Gly
            595                 600                 605

Asp Gly Asp Ser Pro Gly Pro Gly Phe Thr Pro His Asp Ser Ala Pro
            610                 615                 620

Tyr Gly Ala Leu Asp Met Ala Asp Phe Glu Phe Glu Gln Met Phe Thr
625                 630                 635                 640

Asp Ala Leu Gly Ile Asp Glu Tyr Gly Gly
            645                 650

<210> SEQ ID NO 20
```

<211> LENGTH: 2112
<212> TYPE: DNA
<213> ORGANISM: Artificial Sequence
<220> FEATURE:
<223> OTHER INFORMATION: V2tail ? CIBN ? AsLOV2 ? TEVseq ? TetR-
      VP16(tTA)

<400> SEQUENCE: 20

| | | | | | | |
|---|---|---|---|---|---|---|
| ggacgcaccc | cacccagcct | gggtccccaa | gatgagtcct | gcaccaccgc | cagctcctcc | 60 |
| ctggccaagg | acacttcatc | gcttcaactt | cctcctcttg | aacgtcttac | tctcggtggc | 120 |
| tctggaggtc | tcgagatgaa | tggagctata | ggaggtgacc | ttttgctcaa | ttttcctgac | 180 |
| atgtcggtcc | tagagcgcca | aagggctcac | ctcaagtacc | tcaatcccac | ctttgattct | 240 |
| cctctcgccg | gcttctttgc | cgattcttca | atgattaccg | gcggcgagat | ggacagctat | 300 |
| cttcgactg | ccggtttgaa | tcttccgatg | atgtacggtg | agacgacggt | ggaaggtgat | 360 |
| tcaagactct | caatttcgcc | ggaaacgacg | cttgggactg | gaaatttcaa | ggcagcgaag | 420 |
| tttgatacag | agactaagga | ttgtaatgag | gcggcgaaga | gatgacgat | gaacagagat | 480 |
| gacctagtag | aagaaggaga | agaagagaag | tcgaaaataa | cagagcaaaa | caatgggagc | 540 |
| acaaaaagca | tcaagaagat | gaaacacaaa | gccaagaaag | aagagaacaa | tttctctaat | 600 |
| gattcatcta | aagtgacgaa | ggaattggag | aaaacggatt | atattcatga | gctcggtagt | 660 |
| ggtagtgggg | agtttctggc | aaccacactg | gaacggatcg | agaaaaattt | cgtgattact | 720 |
| gatccgagac | tgcctgacaa | cccaatcatt | tttgcgagcg | attccttcct | gcagctgaca | 780 |
| gaatattctc | gggaagagat | cctggggcgc | aattgccgtt | ttctgcaggg | acccgagaca | 840 |
| gaccgtgcca | ctgttcggaa | aatcagagat | gctattgaca | ccagactga | agtgaccgtt | 900 |
| cagctgatca | attataccaa | gagcggcaag | aagttctgga | acgtgttcca | cctgcagccg | 960 |
| atgcgcgatt | ataagggcga | cgtccagtac | ttcattggcg | tgcagctgga | tggcaccgaa | 1020 |
| cgtcttcatg | gcgccgctga | gcgtgaggcg | gtctgcctga | tcaaaaagac | agcctttcag | 1080 |
| attgctgaga | acctgtactt | ccagggctct | agattagata | aaagtaaagt | gattaacagc | 1140 |
| gcattagagc | tgcttaatga | ggtcggaatc | gaaggtttaa | caacccgtaa | actcgcccag | 1200 |
| aagctaggtg | tagagcagcc | tacattgtat | tggcatgtaa | aaaataagcg | ggcttttgctc | 1260 |
| gacgccttag | ccattgagat | gttagatagg | caccatactc | acttttgccc | tttagaaggg | 1320 |
| gaaagctggc | aagattttttt | acgtaataac | gctaaaagtt | ttagatgtgc | tttactaagt | 1380 |
| catcgcgatg | gagcaaaagt | acatttaggt | acacggccta | cagaaaaaca | gtatgaaact | 1440 |
| ctcgaaaatc | aattagcctt | tttatgccaa | caaggttttt | cactagagaa | tgcattatat | 1500 |
| gcactcagcg | ctgtggggca | ttttactta | ggttgcgtat | ggaagatca | agagcatcaa | 1560 |
| gtcgctaaag | aagaaaggga | aacacctact | actgatagta | tgccgccatt | attacgacaa | 1620 |
| gctatcgaat | tatttgatca | ccaaggtgca | gagccagcct | tcttattcgg | ccttgaattg | 1680 |
| atcatatgcg | gattagaaaa | acaacttaaa | tgtgaaagtg | gtccgcgta | cagccgcgcg | 1740 |
| cgtacgaaaa | acaattacgg | gtctaccatc | gagggcctgc | tcgatctccc | ggacgacgac | 1800 |
| gccccgaag | aggcggggct | ggcggctccg | cgcctgtcct | ttctcccgc | gggacacacg | 1860 |
| cgcagactgt | cgacggcccc | cccgaccgat | gtcagcctgg | ggacgagct | ccacttagac | 1920 |
| ggcgaggacg | tggcgatggc | gcatgccgac | gcgctagacg | atttcgatct | ggacatgttg | 1980 |
| ggggacgggg | attccccggg | tccgggattt | accccccacg | actccgcccc | ctacggcgct | 2040 |
| ctggatatgg | ccgacttcga | gtttgagcag | atgtttaccg | atgcccttgg | aattgacgag | 2100 |

-continued tacggtgggt ag                                                     2112

<210> SEQ ID NO 21
<211> LENGTH: 703
<212> TYPE: PRT
<213> ORGANISM: Artificial Sequence
<220> FEATURE:
<223> OTHER INFORMATION: V2tail ? CIBN ? AsLOV2 ? TEVseq ? TetR-
      VP16(tTA)

<400> SEQUENCE: 21

Gly Arg Thr Pro Pro Ser Leu Gly Pro Gln Asp Glu Ser Cys Thr Thr
1               5                   10                  15

Ala Ser Ser Ser Leu Ala Lys Asp Thr Ser Ser Leu Gln Leu Pro Pro
            20                  25                  30

Leu Glu Arg Leu Thr Leu Gly Gly Ser Gly Gly Leu Glu Met Asn Gly
        35                  40                  45

Ala Ile Gly Gly Asp Leu Leu Leu Asn Phe Pro Asp Met Ser Val Leu
    50                  55                  60

Glu Arg Gln Arg Ala His Leu Lys Tyr Leu Asn Pro Thr Phe Asp Ser
65                  70                  75                  80

Pro Leu Ala Gly Phe Phe Ala Asp Ser Ser Met Ile Thr Gly Gly Glu
                85                  90                  95

Met Asp Ser Tyr Leu Ser Thr Ala Gly Leu Asn Leu Pro Met Met Tyr
            100                 105                 110

Gly Glu Thr Thr Val Glu Gly Asp Ser Arg Leu Ser Ile Ser Pro Glu
        115                 120                 125

Thr Thr Leu Gly Thr Gly Asn Phe Lys Ala Ala Lys Phe Asp Thr Glu
    130                 135                 140

Thr Lys Asp Cys Asn Glu Ala Ala Lys Lys Met Thr Met Asn Arg Asp
145                 150                 155                 160

Asp Leu Val Glu Glu Gly Glu Glu Lys Ser Lys Ile Thr Glu Gln
                165                 170                 175

Asn Asn Gly Ser Thr Lys Ser Ile Lys Lys Met Lys His Lys Ala Lys
            180                 185                 190

Lys Glu Glu Asn Asn Phe Ser Asn Asp Ser Ser Lys Val Thr Lys Glu
        195                 200                 205

Leu Glu Lys Thr Asp Tyr Ile His Glu Leu Gly Ser Gly Ser Gly Glu
    210                 215                 220

Phe Leu Ala Thr Thr Leu Glu Arg Ile Glu Lys Asn Phe Val Ile Thr
225                 230                 235                 240

Asp Pro Arg Leu Pro Asp Asn Pro Ile Ile Phe Ala Ser Asp Ser Phe
                245                 250                 255

Leu Gln Leu Thr Glu Tyr Ser Arg Glu Glu Ile Leu Gly Arg Asn Cys
            260                 265                 270

Arg Phe Leu Gln Gly Pro Glu Thr Asp Arg Ala Thr Val Arg Lys Ile
        275                 280                 285

Arg Asp Ala Ile Asp Asn Gln Thr Glu Val Thr Val Gln Leu Ile Asn
    290                 295                 300

Tyr Thr Lys Ser Gly Lys Lys Phe Trp Asn Val Phe His Leu Gln Pro
305                 310                 315                 320

Met Arg Asp Tyr Lys Gly Asp Val Gln Tyr Phe Ile Gly Val Gln Leu
                325                 330                 335

Asp Gly Thr Glu Arg Leu His Gly Ala Ala Glu Arg Glu Ala Val Cys
            340                 345                 350

-continued

| | | | | | | | | | | | |
|---|---|---|---|---|---|---|---|---|---|---|---|
|Leu|Ile|Lys|Lys|Thr|Ala|Phe|Gln|Ile|Ala|Glu|Asn|Leu|Tyr|Phe|Gln|
| | |355| | | |360| | | |365| |

Gly Ser Arg Leu Asp Lys Ser Lys Val Ile Asn Ser Ala Leu Glu Leu
370                 375                 380

Leu Asn Glu Val Gly Ile Glu Gly Leu Thr Thr Arg Lys Leu Ala Gln
385                 390                 395                 400

Lys Leu Gly Val Glu Gln Pro Thr Leu Tyr Trp His Val Lys Asn Lys
            405                 410                 415

Arg Ala Leu Leu Asp Ala Leu Ala Ile Glu Met Leu Asp Arg His His
            420                 425                 430

Thr His Phe Cys Pro Leu Glu Gly Glu Ser Trp Gln Asp Phe Leu Arg
        435                 440                 445

Asn Asn Ala Lys Ser Phe Arg Cys Ala Leu Leu Ser His Arg Asp Gly
    450                 455                 460

Ala Lys Val His Leu Gly Thr Arg Pro Thr Glu Lys Gln Tyr Glu Thr
465                 470                 475                 480

Leu Glu Asn Gln Leu Ala Phe Leu Cys Gln Gln Gly Phe Ser Leu Glu
                485                 490                 495

Asn Ala Leu Tyr Ala Leu Ser Ala Val Gly His Phe Thr Leu Gly Cys
            500                 505                 510

Val Leu Glu Asp Gln Glu His Gln Val Ala Lys Glu Glu Arg Glu Thr
        515                 520                 525

Pro Thr Thr Asp Ser Met Pro Pro Leu Leu Arg Gln Ala Ile Glu Leu
    530                 535                 540

Phe Asp His Gln Gly Ala Glu Pro Ala Phe Leu Phe Gly Leu Glu Leu
545                 550                 555                 560

Ile Ile Cys Gly Leu Glu Lys Gln Leu Lys Cys Glu Ser Gly Ser Ala
                565                 570                 575

Tyr Ser Arg Ala Arg Thr Lys Asn Asn Tyr Gly Ser Thr Ile Glu Gly
            580                 585                 590

Leu Leu Asp Leu Pro Asp Asp Ala Pro Glu Glu Ala Gly Leu Ala
        595                 600                 605

Ala Pro Arg Leu Ser Phe Leu Pro Ala Gly His Thr Arg Arg Leu Ser
    610                 615                 620

Thr Ala Pro Pro Thr Asp Val Ser Leu Gly Asp Glu Leu His Leu Asp
625                 630                 635                 640

Gly Glu Asp Val Ala Met Ala His Ala Asp Ala Leu Asp Asp Phe Asp
                645                 650                 655

Leu Asp Met Leu Gly Asp Gly Asp Ser Pro Gly Pro Gly Phe Thr Pro
            660                 665                 670

His Asp Ser Ala Pro Tyr Gly Ala Leu Asp Met Ala Asp Phe Glu Phe
        675                 680                 685

Glu Gln Met Phe Thr Asp Ala Leu Gly Ile Asp Glu Tyr Gly Gly
    690                 695                 700

<210> SEQ ID NO 22
<211> LENGTH: 2319
<212> TYPE: DNA
<213> ORGANISM: Artificial Sequence
<220> FEATURE:
<223> OTHER INFORMATION: CaM ? TEV-N ? AsLOV2 ?TEVseq ? TetR-VP16(tTA)

<400> SEQUENCE: 22
atgccggacc aactgactga agagcagatc gcagaattta aagaggcttt ctccctattt     60
gacaaggacg gggatgggac aataacaacc aaggagctgg ggacggtgat gcggtctctg    120

```
gggcagaacc ccacagaagc agagctgcaa gacatgatca atgaagtaga tgccgacggt    180
gacggcacaa tcgacttccc tgagttcctg acaatgatgg caagaaaaat gaaatacagg    240
gacacggaag aagaaattag agaagcgttc ggtgtgtttg ataaggatgg caatggctac    300
atcagtgcag cagagcttcg ccacgtgatg acaaaccttg agagaagtt aacagatgaa     360
gaggttgatg aaatgatcag ggaagcagac atcgatgggg atggtcaggt aaactacgaa    420
gagtttgtac aaatgatgac agcgaagctt caacttcctc ctcttgaacg tcttactctc    480
ggtggctctg gaggtctcga gatgggcgag agcctgttca agggacctag ggactacaac    540
cctatcagta gcacaatttg tcacctgacc aacgagagtg atggccacac aacaagcctg    600
tacggcatcg ggttcggacc ctttatcatc accaacaagc acctgttcag gcggaataat    660
ggcactctgc tggtgcagag cctgcacggg gtgttcaaag tgaagaacac aaccactctg    720
cagcagcacc tgatcgatgg gcgggatatg atcatcatta ggatgcccaa ggacttcccc    780
ccttttcctc agaaactgaa gttccgagag ccccagagag aggagagaat ctgtctggtg    840
accacaaact ttcaggagct cggtagtggt agtgggagt ttctggcaac cacactggaa      900
cggatcgaga aaaatttcgt gattactgat ccgagactgc ctgacaaccc aatcattttt    960
gcgagcgatt ccttcctgca gctgacagaa tattctcggg aagagatcct ggggcgcaat    1020
tgccgttttc tgcagggacc cgagacagac cgtgccactg ttcggaaaat cagagatgct    1080
attgacaacc agactgaagt gaccgttcag ctgatcaatt ataccaagag cggcaagaag    1140
ttctggaacg tgttccacct gcagccgatg cgcgattata agggcgacgt ccagtacttc    1200
attggcgtgc agctggatgg caccgaacgt cttcatggcg ccgctgagcg tgaggcggtc    1260
tgcctgatca aaaagacagc ctttcagatt gctgagaacc tgtacttcca gggctctaga    1320
ttagataaaa gtaaagtgat taacagcgca ttagagctgc ttaatgaggt cggaatcgaa    1380
ggtttaacaa cccgtaaact cgcccagaag ctaggtgtag agcagcctac attgtattgg    1440
catgtaaaaa ataagcgggc tttgctcgac gccttagcca ttgagatgtt agataggcac    1500
catactcact tttgcccttt agaagggaa agctggcaag atttttacg taataacgct       1560
aaaagttta gatgtgcttt actaagtcat cgcgatggag caaaagtaca tttaggtaca     1620
cggcctacag aaaaacagta tgaaactctc gaaaatcaat tagccttttt atgccaacaa    1680
ggttttcac tagagaatgc attatatgca ctcagcgctg tggggcattt tacttaggt      1740
tgcgtattgg aagatcaaga gcatcaagtc gctaagaag aaagggaaac acctactact     1800
gatagtatgc cgccattatt acgacaagct atcgaattat ttgatcacca aggtgcagag    1860
ccagccttct tattcggcct tgaattgatc atatgcggat tagaaaaaca acttaaatgt    1920
gaaagtgggt ccgcgtacag ccgcgcgcgt acgaaaaaca attacgggtc taccatcgag    1980
ggcctgctcg atctcccgga cgacgacgcc cccgaagagg cggggctggc ggctccgcgc    2040
ctgtcctttc tccccgcggg acacacgcgc agactgtcga cggccccccc gaccgatgtc    2100
agcctggggg acgagctcca cttagacggc gaggacgtgg cgatggcgca tgccgacgcg    2160
ctagacgatt tcgatctgga catgttgggg gacggggatt ccccgggtcc gggatttacc    2220
ccccacgact ccgcccccta cggcgctctg gatatgccg acttcgagtt tgagcagatg     2280
tttaccgatg cccttggaat tgacgagtac ggtgggtag                           2319
```

<210> SEQ ID NO 23
<211> LENGTH: 772
<212> TYPE: PRT

<213> ORGANISM: Artificial Sequence
<220> FEATURE:
<223> OTHER INFORMATION: CaM ? TEV-N ? AsLOV2 ?TEVseq ? TetR-VP16(tTA)

<400> SEQUENCE: 23

```
Met Pro Asp Gln Leu Thr Glu Glu Ile Ala Glu Phe Lys Glu Ala
1               5                   10                  15

Phe Ser Leu Phe Asp Lys Asp Gly Asp Gly Thr Ile Thr Thr Lys Glu
            20                  25                  30

Leu Gly Thr Val Met Arg Ser Leu Gly Gln Asn Pro Thr Glu Ala Glu
        35                  40                  45

Leu Gln Asp Met Ile Asn Glu Val Asp Ala Asp Gly Asp Gly Thr Ile
50                  55                  60

Asp Phe Pro Glu Phe Leu Thr Met Met Ala Arg Lys Met Lys Tyr Arg
65                  70                  75                  80

Asp Thr Glu Glu Glu Ile Arg Glu Ala Phe Gly Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
        115                 120                 125

Ala Asp Ile Asp Gly Asp Gly Gln Val Asn Tyr Glu Glu Phe Val Gln
130                 135                 140

Met Met Thr Ala Lys Leu Gln Leu Pro Pro Leu Glu Arg Leu Thr Leu
145                 150                 155                 160

Gly Gly Ser Gly Gly Leu Glu Met Gly Glu Ser Leu Phe Lys Gly Pro
                165                 170                 175

Arg Asp Tyr Asn Pro Ile Ser Ser Thr Ile Cys His Leu Thr Asn Glu
            180                 185                 190

Ser Asp Gly His Thr Thr Ser Leu Tyr Gly Ile Gly Phe Gly Pro Phe
        195                 200                 205

Ile Ile Thr Asn Lys His Leu Phe Arg Arg Asn Asn Gly Thr Leu Leu
210                 215                 220

Val Gln Ser Leu His Gly Val Phe Lys Val Lys Asn Thr Thr Thr Leu
225                 230                 235                 240

Gln Gln His Leu Ile Asp Gly Arg Asp Met Ile Ile Ile Arg Met Pro
                245                 250                 255

Lys Asp Phe Pro Pro Phe Pro Gln Lys Leu Lys Phe Arg Glu Pro Gln
            260                 265                 270

Arg Glu Glu Arg Ile Cys Leu Val Thr Thr Asn Phe Gln Glu Leu Gly
        275                 280                 285

Ser Gly Ser Gly Glu Phe Leu Ala Thr Thr Leu Glu Arg Ile Glu Lys
290                 295                 300

Asn Phe Val Ile Thr Asp Pro Arg Leu Pro Asp Asn Pro Ile Ile Phe
305                 310                 315                 320

Ala Ser Asp Ser Phe Leu Gln Leu Thr Glu Tyr Ser Arg Glu Glu Ile
                325                 330                 335

Leu Gly Arg Asn Cys Arg Phe Leu Gln Gly Pro Glu Thr Asp Arg Ala
            340                 345                 350

Thr Val Arg Lys Ile Arg Asp Ala Ile Asp Asn Gln Thr Glu Val Thr
        355                 360                 365

Val Gln Leu Ile Asn Tyr Thr Lys Ser Gly Lys Lys Phe Trp Asn Val
370                 375                 380

Phe His Leu Gln Pro Met Arg Asp Tyr Lys Gly Asp Val Gln Tyr Phe
```

```
                385                 390                 395                 400
        Ile Gly Val Gln Leu Asp Gly Thr Glu Arg Leu His Gly Ala Ala Glu
                            405                 410                 415

Arg Glu Ala Val Cys Leu Ile Lys Lys Thr Ala Phe Gln Ile Ala Glu
                            420                 425                 430

Asn Leu Tyr Phe Gln Gly Ser Arg Leu Asp Lys Ser Lys Val Ile Asn
                            435                 440                 445

Ser Ala Leu Glu Leu Leu Asn Glu Val Gly Ile Glu Gly Leu Thr Thr
                            450                 455                 460

Arg Lys Leu Ala Gln Lys Leu Gly Val Glu Gln Pro Thr Leu Tyr Trp
        465                 470                 475                 480

His Val Lys Asn Lys Arg Ala Leu Leu Asp Ala Leu Ala Ile Glu Met
                            485                 490                 495

Leu Asp Arg His His Thr His Phe Cys Pro Leu Glu Gly Glu Ser Trp
                            500                 505                 510

Gln Asp Phe Leu Arg Asn Asn Ala Lys Ser Phe Arg Cys Ala Leu Leu
                            515                 520                 525

Ser His Arg Asp Gly Ala Lys Val His Leu Gly Thr Arg Pro Thr Glu
                            530                 535                 540

Lys Gln Tyr Glu Thr Leu Glu Asn Gln Leu Ala Phe Leu Cys Gln Gln
        545                 550                 555                 560

Gly Phe Ser Leu Glu Asn Ala Leu Tyr Ala Leu Ser Ala Val Gly His
                            565                 570                 575

Phe Thr Leu Gly Cys Val Leu Glu Asp Gln Glu His Gln Val Ala Lys
                            580                 585                 590

Glu Glu Arg Glu Thr Pro Thr Thr Asp Ser Met Pro Pro Leu Leu Arg
                            595                 600                 605

Gln Ala Ile Glu Leu Phe Asp His Gln Gly Ala Glu Pro Ala Phe Leu
                            610                 615                 620

Phe Gly Leu Glu Leu Ile Ile Cys Gly Leu Glu Lys Gln Leu Lys Cys
        625                 630                 635                 640

Glu Ser Gly Ser Ala Tyr Ser Arg Ala Arg Thr Lys Asn Asn Tyr Gly
                            645                 650                 655

Ser Thr Ile Glu Gly Leu Leu Asp Leu Pro Asp Asp Ala Pro Glu
                            660                 665                 670

Glu Ala Gly Leu Ala Ala Pro Arg Leu Ser Phe Leu Pro Ala Gly His
                            675                 680                 685

Thr Arg Arg Leu Ser Thr Ala Pro Pro Thr Asp Val Ser Leu Gly Asp
        690                 695                 700

Glu Leu His Leu Asp Gly Glu Asp Val Ala Met Ala His Ala Asp Ala
        705                 710                 715                 720

Leu Asp Asp Phe Asp Leu Asp Met Leu Gly Asp Gly Asp Ser Pro Gly
                            725                 730                 735

Pro Gly Phe Thr Pro His Asp Ser Ala Pro Tyr Gly Ala Leu Asp Met
                            740                 745                 750

Ala Asp Phe Glu Phe Glu Gln Met Phe Thr Asp Ala Leu Gly Ile Asp
                            755                 760                 765

Glu Tyr Gly Gly
            770

<210> SEQ ID NO 24
<211> LENGTH: 118
<212> TYPE: PRT
<213> ORGANISM: Artificial Sequence
```

```
<220> FEATURE:
<223> OTHER INFORMATION: TEV-N

<400> SEQUENCE: 24

Met Gly Glu Ser Leu Phe Lys Gly Pro Arg Asp Tyr Asn Pro Ile Ser
1               5                  10                  15

Ser Thr Ile Cys His Leu Thr Asn Glu Ser Asp Gly His Thr Thr Ser
            20                  25                  30

Leu Tyr Gly Ile Gly Phe Gly Pro Phe Ile Ile Thr Asn Lys His Leu
        35                  40                  45

Phe Arg Arg Asn Asn Gly Thr Leu Leu Val Gln Ser Leu His Gly Val
    50                  55                  60

Phe Lys Val Lys Asn Thr Thr Thr Leu Gln Gln His Leu Ile Asp Gly
65                  70                  75                  80

Arg Asp Met Ile Ile Ile Arg Met Pro Lys Asp Phe Pro Pro Phe Pro
                85                  90                  95

Gln Lys Leu Lys Phe Arg Glu Pro Gln Arg Glu Glu Arg Ile Cys Leu
            100                 105                 110

Val Thr Thr Asn Phe Gln
            115

<210> SEQ ID NO 25
<211> LENGTH: 99
<212> TYPE: PRT
<213> ORGANISM: Artificial Sequence
<220> FEATURE:
<223> OTHER INFORMATION: TEV-C

<400> SEQUENCE: 25

Met Ser Ser Met Val Ser Asp Thr Ser Cys Thr Phe Pro Ser Ser Asp
1               5                  10                  15

Gly Ile Phe Trp Lys His Trp Ile Gln Thr Lys Asp Gly Gln Cys Gly
            20                  25                  30

Ser Pro Leu Val Ser Thr Arg Asp Gly Phe Ile Val Gly Ile His Ser
        35                  40                  45

Ala Ser Asn Phe Thr Asn Thr Asn Asn Tyr Phe Thr Ser Val Pro Lys
    50                  55                  60

Asn Phe Met Glu Leu Leu Thr Asn Gln Glu Ala Gln Gln Trp Val Ser
65                  70                  75                  80

Gly Trp Arg Leu Asn Ala Asp Ser Val Leu Trp Gly Gly His Lys Val
                85                  90                  95

Phe Met Val

<210> SEQ ID NO 26
<211> LENGTH: 11
<212> TYPE: PRT
<213> ORGANISM: Artificial Sequence
<220> FEATURE:
<223> OTHER INFORMATION: T7 tag

<400> SEQUENCE: 26

Met Ala Ser Met Thr Gly Gly Gln Gln Met Gly
1               5                  10

<210> SEQ ID NO 27
<211> LENGTH: 8
<212> TYPE: PRT
<213> ORGANISM: Artificial Sequence
<220> FEATURE:
<223> OTHER INFORMATION: Xpress tag
```

```
<400> SEQUENCE: 27

Asp Leu Tyr Asp Asp Asp Lys
1               5

<210> SEQ ID NO 28
<211> LENGTH: 10
<212> TYPE: PRT
<213> ORGANISM: Artificial Sequence
<220> FEATURE:
<223> OTHER INFORMATION: Myc tag

<400> SEQUENCE: 28

Glu Gln Lys Leu Ile Ser Glu Glu Asp Leu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: NES (Nuclear Export Sequence)

<400> SEQUENCE: 29

Leu Gln Leu Pro Pro Leu Glu Arg Leu Thr Leu Glu
1               5                   10

<210> SEQ ID NO 30
<211> LENGTH: 21
<212> TYPE: PRT
<213> ORGANISM: Artificial Sequence
<220> FEATURE:
<223> OTHER INFORMATION: IgK leader sequence

<400> SEQUENCE: 30

Met Glu Thr Asp Thr Leu Leu Leu Trp Val Leu Leu Leu Trp Val Pro
1               5                   10                  15

Gly Ser Thr Gly Asp
            20

<210> SEQ ID NO 31
<211> LENGTH: 19
<212> TYPE: PRT
<213> ORGANISM: Artificial Sequence
<220> FEATURE:
<223> OTHER INFORMATION: P2A sequence (for bicistronic system)

<400> SEQUENCE: 31

Ala Thr Asn Phe Ser Leu Leu Lys Gln Ala Gly Asp Val Glu Glu Asn
1               5                   10                  15

Pro Gly Pro

<210> SEQ ID NO 32
<211> LENGTH: 19
<212> TYPE: PRT
<213> ORGANISM: Artificial Sequence
<220> FEATURE:
<223> OTHER INFORMATION: linker sequence

<400> SEQUENCE: 32

Gly Gly Gly Gly Ser Gly Gly Gly Ser Gly Gly Gly Gly Arg Ser
1               5                   10                  15

Gly Gly Ser
```

```
<210> SEQ ID NO 33
<211> LENGTH: 8
<212> TYPE: PRT
<213> ORGANISM: Artificial Sequence
<220> FEATURE:
<223> OTHER INFORMATION: linker sequence

<400> SEQUENCE: 33

Gly Gly Ser Gly Gly Leu Glu Gly
1               5

<210> SEQ ID NO 34
<211> LENGTH: 11
<212> TYPE: PRT
<213> ORGANISM: Artificial Sequence
<220> FEATURE:
<223> OTHER INFORMATION: linker sequence

<400> SEQUENCE: 34

Gly Gly Gly Gly Arg Ser Gly Gly Gly Gly Ser
1               5                   10

<210> SEQ ID NO 35
<211> LENGTH: 14
<212> TYPE: PRT
<213> ORGANISM: Artificial Sequence
<220> FEATURE:
<223> OTHER INFORMATION: linker sequence

<400> SEQUENCE: 35

Gly Gly Gly Gly Ser Gly Gly Gly Ser Gly Gly Gly Gly
1               5                   10

<210> SEQ ID NO 36
<211> LENGTH: 5
<212> TYPE: PRT
<213> ORGANISM: Artificial Sequence
<220> FEATURE:
<223> OTHER INFORMATION: linker sequence

<400> SEQUENCE: 36

Gly Ser Gly Ser Gly
1               5

<210> SEQ ID NO 37
<211> LENGTH: 78
<212> TYPE: DNA
<213> ORGANISM: Artificial Sequence
<220> FEATURE:
<223> OTHER INFORMATION: CD28 transmembrane domain

<400> SEQUENCE: 37
aagctttttt gggcactggt cgtggttgct ggagtcctgt tttgttatgg cttgctagtg    60
acagtggctc tttgtgtt                                                  78

<210> SEQ ID NO 38
<211> LENGTH: 26
<212> TYPE: PRT
<213> ORGANISM: Artificial Sequence
<220> FEATURE:
<223> OTHER INFORMATION: CD28 transmembrane domain

<400> SEQUENCE: 38

Lys Leu Phe Trp Ala Leu Val Val Val Ala Gly Val Leu Phe Cys Tyr
1               5                   10                  15

Gly Leu Leu Val Thr Val Ala Leu Cys Val
```

<210> SEQ ID NO 39
<211> LENGTH: 75
<212> TYPE: DNA
<213> ORGANISM: Artificial Sequence
<220> FEATURE:
<223> OTHER INFORMATION: CD 8a transmembrane domain

<400> SEQUENCE: 39

```
atttacatct gggcacccdt ggccggaatc tgcgtggccc ttctgctgtc cttgatcatc    60
actctcatct gctac                                                     75
```

<210> SEQ ID NO 40
<211> LENGTH: 25
<212> TYPE: PRT
<213> ORGANISM: Artificial Sequence
<220> FEATURE:
<223> OTHER INFORMATION: CD 8a transmembrane domain

<400> SEQUENCE: 40

```
Ile Tyr Ile Trp Ala Pro Leu Ala Gly Ile Cys Val Ala Leu Leu Leu
1               5                   10                  15

Ser Leu Ile Ile Thr Leu Ile Cys Tyr
            20                  25
```

<210> SEQ ID NO 41
<211> LENGTH: 267
<212> TYPE: DNA
<213> ORGANISM: Artificial Sequence
<220> FEATURE:
<223> OTHER INFORMATION: TM-domain (IgK leader sequence / Myc tag / PDGFR sequence)

<400> SEQUENCE: 41

```
atggagacag acacactcct gctatgggta ctgctgctct gggttccagg ttccactggt    60
gacgaacaaa aactcatctc agaagaggat ctgaatgctg tgggccagga cacgcaggag   120
gtcatcgtgg tgccacactc cttgcccttt aaggtggtgg tgatctcagc catcctggcc   180
ctggtggtgc tcaccatcat ctcccttatc atcctcatca tgctttggca gaagaagcca   240
cgtggtggct ctggaggtct cgaggga                                       267
```

<210> SEQ ID NO 42
<211> LENGTH: 89
<212> TYPE: PRT
<213> ORGANISM: Artificial Sequence
<220> FEATURE:
<223> OTHER INFORMATION: TM-domain (IgK leader sequence / Myc tag / PDGFR sequence)

<400> SEQUENCE: 42

```
Met Glu Thr Asp Thr Leu Leu Leu Trp Val Leu Leu Leu Trp Val Pro
1               5                   10                  15

Gly Ser Thr Gly Asp Glu Gln Lys Leu Ile Ser Glu Glu Asp Leu Asn
            20                  25                  30

Ala Val Gly Gln Asp Thr Gln Glu Val Ile Val Val Pro His Ser Leu
        35                  40                  45

Pro Phe Lys Val Val Val Ile Ser Ala Ile Leu Ala Leu Val Val Leu
    50                  55                  60

Thr Ile Ile Ser Leu Ile Ile Leu Ile Met Leu Trp Gln Lys Lys Pro
65                  70                  75                  80
```

Arg Gly Gly Ser Gly Gly Leu Glu Gly
            85

<210> SEQ ID NO 43
<211> LENGTH: 34
<212> TYPE: PRT
<213> ORGANISM: Artificial Sequence
<220> FEATURE:
<223> OTHER INFORMATION: linking sequence in SEQ ID NO: 1

<400> SEQUENCE: 43

Ala Cys Gly Gly Gly Gly Ser Gly Gly Gly Gly Ser Gly Gly Gly Gly
1               5                   10                  15

Arg Ser Gly Gly Ser Met Leu Gln Leu Pro Pro Leu Glu Arg Leu Thr
            20                  25                  30

Leu Glu

<210> SEQ ID NO 44
<211> LENGTH: 18
<212> TYPE: PRT
<213> ORGANISM: Artificial Sequence
<220> FEATURE:
<223> OTHER INFORMATION: linking sequence in SEQ ID NO: 3

<400> SEQUENCE: 44

Leu Gln Leu Pro Pro Leu Glu Arg Leu Thr Leu Gly Gly Ser Gly Gly
1               5                   10                  15

Leu Glu

<210> SEQ ID NO 45
<211> LENGTH: 19
<212> TYPE: PRT
<213> ORGANISM: Artificial Sequence
<220> FEATURE:
<223> OTHER INFORMATION: linking sequence in SEQ ID NO: 5

<400> SEQUENCE: 45

Leu Gln Leu Pro Pro Leu Glu Arg Leu Thr Leu Gly Gly Ser Gly Gly
1               5                   10                  15

Leu Glu Gly

<210> SEQ ID NO 46
<211> LENGTH: 17
<212> TYPE: PRT
<213> ORGANISM: Artificial Sequence
<220> FEATURE:
<223> OTHER INFORMATION: linking sequence in SEQ ID NO: 8

<400> SEQUENCE: 46

Ala Cys Gly Gly Gly Gly Ser Gly Gly Gly Gly Ser Gly Gly Gly Gly
1               5                   10                  15

Arg

<210> SEQ ID NO 47
<211> LENGTH: 462
<212> TYPE: DNA
<213> ORGANISM: Artificial Sequence
<220> FEATURE:
<223> OTHER INFORMATION: Backbone Sequence B

<400> SEQUENCE: 47
aagcttgatt taggtgacac tatagaatac aagctacttg ttcttttgc aggatccatg     60 cttcaacttc ctcctcttga acgtcttact ctcgaggcca ccctgcagga gctcggtgga   120

```
ggcggccgct ccggtggcgg tggctctact aagagcatgt ccagcatggt gagcgatact    180
agctgtacct tcccatcatc tgacggaatc ttctggaagc actggattca gactaaggac    240
ggccagtgtg gcagcccact ggtgagcaca cgagacggat tcatcgtggg gattcacagc    300
gcctccaact ttacaaacac caataactat ttcacctcag tgccaaagaa ctttatggag    360
ctgctgacca accaggaggc ccagcagtgg gtgagcgggt ggcgcctgaa cgccgattcc    420
gtgctgtggg gcgggcacaa ggtgtttatg gtgtgagcta gc                      462
```

<210> SEQ ID NO 48
<211> LENGTH: 275
<212> TYPE: DNA
<213> ORGANISM: Artificial Sequence
<220> FEATURE:
<223> OTHER INFORMATION: Backbone Sequence C

<400> SEQUENCE: 48

```
aagcttgatt taggtgacac tatagaatac aagctacttg ttcttttgc aatgaagacg      60 atcatcgccc tgagctacat cttctgcctg gtattcgccg actacaagga cgatgatgac    120
gccagcatgg atccgaattc ggacgcaccc cacccagcct gggtccccaa gatgagtcct    180
gcaccaccgc cagctcctcc ctggccaagg acacttcatc gcttcaactt cctcctcttg    240
aacgtcttac tctcggtggc tctggaggtc tcgag                               275
```

<210> SEQ ID NO 49
<211> LENGTH: 138
<212> TYPE: PRT
<213> ORGANISM: Artificial Sequence
<220> FEATURE:
<223> OTHER INFORMATION: BLITz-6: AsLOV2 (1-138 A.A.)

<400> SEQUENCE: 49

Glu Phe Leu Ala Thr Thr Leu Glu Arg Ile Glu Lys Asn Phe Val Ile
1               5                   10                  15

Thr Asp Pro Arg Leu Pro Asp Asn Pro Ile Ile Phe Ala Ser Asp Ser
            20                  25                  30

Phe Leu Gln Leu Thr Glu Tyr Ser Arg Glu Glu Ile Leu Gly Arg Asn
        35                  40                  45

Cys Arg Phe Leu Gln Gly Pro Glu Thr Asp Arg Ala Thr Val Arg Lys
    50                  55                  60

Ile Arg Asp Ala Ile Asp Asn Gln Thr Glu Val Thr Val Gln Leu Ile
65                  70                  75                  80

Asn Tyr Thr Lys Ser Gly Lys Lys Phe Trp Asn Val Phe His Leu Gln
                85                  90                  95

Pro Met Arg Asp Tyr Lys Gly Asp Val Gln Tyr Phe Ile Gly Val Gln
            100                 105                 110

Leu Asp Gly Thr Glu Arg Leu His Gly Ala Ala Glu Arg Glu Ala Val
        115                 120                 125

Cys Leu Ile Lys Lys Thr Ala Phe Gln Ile
    130                 135

<210> SEQ ID NO 50
<211> LENGTH: 414
<212> TYPE: DNA
<213> ORGANISM: Artificial Sequence
<220> FEATURE:
<223> OTHER INFORMATION: BLITz-6: AsLOV2 (1-138 A.A.)

<400> SEQUENCE: 50

```
gagtttctgg caaccacact ggaacggatc gagaaaaatt tcgtgattac tgatccgaga    60
ctgcctgaca acccaatcat ttttgcgagc gattccttcc tgcagctgac agaatattct   120
cgggaagaga tcctggggcg caattgccgt tttctgcagg acccgagac agaccgtgcc    180 actgttcgga aaatcagaga tgctattgac aaccagactg aagtgaccgt tcagctgatc   240
aattatacca agagcggcaa gaagttctgg aacgtgttcc acctgcagcc gatgcgcgat   300
tataagggcg acgtccagta cttcattggc gtgcagctgg atggcaccga acgtcttcat   360
ggcgccgctg agcgtgaggc ggtctgcctg atcaaaaaga cagcctttca gatt          414
```

<210> SEQ ID NO 51
<211> LENGTH: 139
<212> TYPE: PRT
<213> ORGANISM: Artificial Sequence
<220> FEATURE:
<223> OTHER INFORMATION: BLITz-1: AsLOV2 (1-139 A.A.)

<400> SEQUENCE: 51

```
Glu Phe Leu Ala Thr Thr Leu Glu Arg Ile Glu Lys Asn Phe Val Ile
1               5                   10                  15

Thr Asp Pro Arg Leu Pro Asp Asn Pro Ile Ile Phe Ala Ser Asp Ser
            20                  25                  30

Phe Leu Gln Leu Thr Glu Tyr Ser Arg Glu Glu Ile Leu Gly Arg Asn
        35                  40                  45

Cys Arg Phe Leu Gln Gly Pro Glu Thr Asp Arg Ala Thr Val Arg Lys
    50                  55                  60

Ile Arg Asp Ala Ile Asp Asn Gln Thr Glu Val Thr Val Gln Leu Ile
65                  70                  75                  80

Asn Tyr Thr Lys Ser Gly Lys Lys Phe Trp Asn Val Phe His Leu Gln
                85                  90                  95

Pro Met Arg Asp Tyr Lys Gly Asp Val Gln Tyr Phe Ile Gly Val Gln
            100                 105                 110

Leu Asp Gly Thr Glu Arg Leu His Gly Ala Ala Glu Arg Glu Ala Val
        115                 120                 125

Cys Leu Ile Lys Lys Thr Ala Phe Gln Ile Ala
    130                 135
```

<210> SEQ ID NO 52
<211> LENGTH: 417
<212> TYPE: DNA
<213> ORGANISM: Artificial Sequence
<220> FEATURE:
<223> OTHER INFORMATION: BLITz-1: AsLOV2 (1-139 A.A.)

<400> SEQUENCE: 52

```
gagtttctgg caaccacact ggaacggatc gagaaaaatt tcgtgattac tgatccgaga    60
ctgcctgaca acccaatcat ttttgcgagc gattccttcc tgcagctgac agaatattct   120
cgggaagaga tcctggggcg caattgccgt tttctgcagg acccgagac agaccgtgcc    180 actgttcgga aaatcagaga tgctattgac aaccagactg aagtgaccgt tcagctgatc   240
aattatacca agagcggcaa gaagttctgg aacgtgttcc acctgcagcc gatgcgcgat   300
tataagggcg acgtccagta cttcattggc gtgcagctgg atggcaccga acgtcttcat   360
ggcgccgctg agcgtgaggc ggtctgcctg atcaaaaaga cagcctttca gattgct       417
```

<210> SEQ ID NO 53
<211> LENGTH: 7

```
<212> TYPE: PRT
<213> ORGANISM: Artificial Sequence
<220> FEATURE:
<223> OTHER INFORMATION: TEV cleavage site

<400> SEQUENCE: 53

Glu Asn Leu Tyr Phe Gln Gly
1               5

<210> SEQ ID NO 54
<211> LENGTH: 7
<212> TYPE: PRT
<213> ORGANISM: Artificial Sequence
<220> FEATURE:
<223> OTHER INFORMATION: TEV cleavage site

<400> SEQUENCE: 54

Glu Ala Leu Tyr Phe Gln Gly
1               5

<210> SEQ ID NO 55
<211> LENGTH: 21
<212> TYPE: DNA
<213> ORGANISM: Artificial Sequence
<220> FEATURE:
<223> OTHER INFORMATION: TEV cleavage site

<400> SEQUENCE: 55
gagaacctgt acttccaggg c                                              21

<210> SEQ ID NO 56
<211> LENGTH: 21
<212> TYPE: DNA
<213> ORGANISM: Artificial Sequence
<220> FEATURE:
<223> OTHER INFORMATION: TEV protease cleavage site EALYFQG

<400> SEQUENCE: 56
gaggccctgt acttccaggg c                                              21

<210> SEQ ID NO 57
<211> LENGTH: 1887
<212> TYPE: DNA
<213> ORGANISM: Artificial Sequence
<220> FEATURE:
<223> OTHER INFORMATION: CRY2PHR ? TEV-C

<400> SEQUENCE: 57
cttcaacttc ctcctcttga acgtcttact ctcgaggcca ccatgaagat ggacaaaaag    60
actatagttt ggtttagaag agacctaagg attgaggata tcctgcatt agcagcagct    120 gctcacgaag atctgttttt cctgtcttc atttggtgtc ctgaagaaga aggacagttt   180
tatcctggaa gagcttcaag atggtggatg aaacaatcac ttgctcactt atctcaatcc   240
ttgaaggctc ttggatctga cctcacttta atcaaaaccc acaacacgat tcagcgatc    300 ttggattgta tccgcgttac cggtgctaca aaagtcgtct taaccacct ctatgatcct    360 gtttcgttag ttcgggacca taccgtaaag gagaagctgg tggaacgtgg gatctctgtg   420
caaagctaca tggagatct attgtatgaa ccgtgggaga tatactgcga aaagggcaaa   480
ccttttacga gtttcaattc ttactggaag aaatgcttag atatgtcgat tgaatccgtt   540
atgcttcctc ctccttggcg gttgatgcca ataactgcag cggctgaagc gatttgggcg   600
tgttcgattg aagaactagg gctggagaat gaggccgaga aaccgagcaa tgcgttgtta   660
```

```
actagagctt ggtctccagg atggagcaat gctgataagt tactaaatga gttcatcgag    720
aagcagttga tagattatgc aaagaacagc aagaaagttg ttgggaattc tacttcacta    780
cttcctccgt atctccattt cggggaaata agcgtcagac acgttttcca gtgtgcccgg    840
atgaaacaaa ttatatgggc aagagataag aacagtgaag gagaagaaag tgcagatctt    900
tttcttaggg gaatcggttt aagagagtat tctcggtata tatgtttcaa cttcccgttt    960
actcacgagc aatcgttgtt gagtcatctt cggttttttcc cttgggatgc tgatgttgat   1020
aagttcaagg cctggagaca aggcaggacc ggttatccgt ggtggatgc cggaatgaga    1080
gagctttggg ctaccggatg gatgcataac agaataagag tgattgtttc aagctttgct   1140
gtgaagtttc ttctccttcc atggaaatgg ggaatgaagt atttctggga tacacttttg   1200
gatgctgatt ggaatgtgaa catccttggc tggcagtata tctctgggag tatccccgat   1260
ggccacgagc ttgatcgctt ggacaatccc gcgttacaag gcgccaaata tgacccagaa   1320
ggtgagtaca taaggcaatg gcttcccgag cttgcgagat tgccaactga atggatccat   1380
catccatggg acgtcccttt aaccgtactc aaagcttctg gtgtggaact cggaacaaac   1440
tatgcgaaac ccattgtaga catcgacaca gctcgtgagc tactagctaa agctatttca   1500
agaaccgtg aagcacagat catgatcgga gcagcactgc aggagctcgg tggaggcggc   1560
cgctccggtg gcggtggctc tactaagagc atgtccagca tggtgagcga tactagctgt   1620
accttcccat catctgacgg aatcttctgg aagcactgga ttcagactaa ggacggccag   1680
tgtggcagcc cactggtgag cacacgagac ggattcatcg tggggattca cagcgcctcc   1740
aactttacaa acaccaataa ctatttcacc tcagtgccaa agaactttat ggagctgctg   1800
accaaccagg aggcccagca gtgggtgagc gggtggcgcc tgaacgccga ttccgtgctg   1860
tggggcgggc acaaggtgtt tatggtg                                       1887

<210> SEQ ID NO 58
<211> LENGTH: 630
<212> TYPE: PRT
<213> ORGANISM: Artificial Sequence
<220> FEATURE:
<223> OTHER INFORMATION: CRY2PHR ? TEV-C

<400> SEQUENCE: 58

Met Leu Gln Leu Pro Pro Leu Glu Arg Leu Thr Leu Glu Ala Thr Met
1               5                   10                  15

Lys Met Asp Lys Lys Thr Ile Val Trp Phe Arg Arg Asp Leu Arg Ile
            20                  25                  30

Glu Asp Asn Pro Ala Leu Ala Ala Ala His Glu Gly Ser Val Phe
        35                  40                  45

Pro Val Phe Ile Trp Cys Pro Glu Glu Gly Gln Phe Tyr Pro Gly
    50                  55                  60

Arg Ala Ser Arg Trp Trp Met Lys Gln Ser Leu Ala His Leu Ser Gln
65                  70                  75                  80

Ser Leu Lys Ala Leu Gly Ser Asp Leu Thr Leu Ile Lys Thr His Asn
                85                  90                  95

Thr Ile Ser Ala Ile Leu Asp Cys Ile Arg Val Thr Gly Ala Thr Lys
            100                 105                 110

Val Val Phe Asn His Leu Tyr Asp Pro Val Ser Leu Val Arg Asp His
        115                 120                 125

Thr Val Lys Glu Lys Leu Val Glu Arg Gly Ile Ser Val Gln Ser Tyr
    130                 135                 140
```

```
Asn Gly Asp Leu Leu Tyr Glu Pro Trp Glu Ile Tyr Cys Glu Lys Gly
145                 150                 155                 160

Lys Pro Phe Thr Ser Phe Asn Ser Tyr Trp Lys Lys Cys Leu Asp Met
            165                 170                 175

Ser Ile Glu Ser Val Met Leu Pro Pro Pro Trp Arg Leu Met Pro Ile
        180                 185                 190

Thr Ala Ala Ala Glu Ala Ile Trp Ala Cys Ser Ile Glu Glu Leu Gly
    195                 200                 205

Leu Glu Asn Glu Ala Glu Lys Pro Ser Asn Ala Leu Leu Thr Arg Ala
210                 215                 220

Trp Ser Pro Gly Trp Ser Asn Ala Asp Lys Leu Leu Asn Glu Phe Ile
225                 230                 235                 240

Glu Lys Gln Leu Ile Asp Tyr Ala Lys Asn Ser Lys Lys Val Val Gly
            245                 250                 255

Asn Ser Thr Ser Leu Leu Ser Pro Tyr Leu His Phe Gly Glu Ile Ser
            260                 265                 270

Val Arg His Val Phe Gln Cys Ala Arg Met Lys Gln Ile Ile Trp Ala
        275                 280                 285

Arg Asp Lys Asn Ser Glu Gly Glu Ser Ala Asp Leu Phe Leu Arg
290                 295                 300

Gly Ile Gly Leu Arg Glu Tyr Ser Arg Tyr Ile Cys Phe Asn Phe Pro
305                 310                 315                 320

Phe Thr His Glu Gln Ser Leu Leu Ser His Leu Arg Phe Phe Pro Trp
            325                 330                 335

Asp Ala Asp Val Asp Lys Phe Lys Ala Trp Arg Gln Gly Arg Thr Gly
            340                 345                 350

Tyr Pro Leu Val Asp Ala Gly Met Arg Glu Leu Trp Ala Thr Gly Trp
            355                 360                 365

Met His Asn Arg Ile Arg Val Ile Val Ser Ser Phe Ala Val Lys Phe
        370                 375                 380

Leu Leu Leu Pro Trp Lys Trp Gly Met Lys Tyr Phe Trp Asp Thr Leu
385                 390                 395                 400

Leu Asp Ala Asp Leu Glu Cys Asp Ile Leu Gly Trp Gln Tyr Ile Ser
            405                 410                 415

Gly Ser Ile Pro Asp Gly His Glu Leu Asp Arg Leu Asp Asn Pro Ala
            420                 425                 430

Leu Gln Gly Ala Lys Tyr Asp Pro Glu Gly Glu Tyr Ile Arg Gln Trp
            435                 440                 445

Leu Pro Glu Leu Ala Arg Leu Pro Thr Glu Trp Ile His His Pro Trp
450                 455                 460

Asp Ala Pro Leu Thr Val Leu Lys Ala Ser Gly Val Glu Leu Gly Thr
465                 470                 475                 480

Asn Tyr Ala Lys Pro Ile Val Asp Ile Asp Thr Ala Arg Glu Leu Leu
            485                 490                 495

Ala Lys Ala Ile Ser Arg Thr Arg Glu Ala Gln Ile Met Ile Gly Ala
        500                 505                 510

Ala Leu Gln Glu Leu Gly Gly Gly Arg Ser Gly Gly Gly Ser
        515                 520                 525

Thr Lys Ser Met Ser Ser Met Val Ser Asp Thr Ser Cys Thr Phe Pro
        530                 535                 540

Ser Ser Asp Gly Ile Phe Trp Lys His Trp Ile Gln Thr Lys Asp Gly
545                 550                 555                 560

Gln Cys Gly Ser Pro Leu Val Ser Thr Arg Asp Gly Phe Ile Val Gly
```

|     | 565 |     |     |     | 570 |     |     |     | 575 |     |     |
| --- | --- | --- | --- | --- | --- | --- | --- | --- | --- | --- | --- |

Ile His Ser Ala Ser Asn Phe Thr Asn Thr Asn Asn Tyr Phe Thr Ser
            580                    585                    590

Val Pro Lys Asn Phe Met Glu Leu Leu Thr Asn Gln Glu Ala Gln Gln
      595                    600                    605

Trp Val Ser Gly Trp Arg Leu Asn Ala Asp Ser Val Leu Trp Gly Gly
    610                    615                    620

His Lys Val Phe Met Val
625              630

<210> SEQ ID NO 59
<211> LENGTH: 3093
<212> TYPE: DNA
<213> ORGANISM: Artificial Sequence
<220> FEATURE:
<223> OTHER INFORMATION: bArr2 ? TEV-C ? TdTomato

<400> SEQUENCE: 59

| | |
|---|---|
| atgggtgaaa aacccgggac caggtcttc aagaagtcga gccctaactg caagctcacc | 60 |
| gtgtacttgg gcaagcgtga ctttgtggat cacttggaca agtggatcc tgtcgatggt | 120 |
| gtggtgcttg tggatcctga ctacttgaag accggaaag tgtttgtgac cctcacctgt | 180 |
| gccttccgct atggccgaga agacctggat gtactgggcc tgtctttccg caaagatctg | 240 |
| ttcatcgcca cctaccaggc cttcccccc atgcccaacc cacctcggcc ccccacccgc | 300 |
| ctacaggacc gactgctgaa gaagttgggc cagcacgccc accctttttt tttcacaata | 360 |
| ccccagaatt tgccttgctc cgtcacactg cagccaggac cggaggacac agggaaggcc | 420 |
| tgtggagtag actttgagat cgagccttc tgtgccaaat ctatagaaga aaaaagccac | 480 |
| aaaaggaact ccgtgcggct tatcatcaga aggtacagtt tgctcctga cacccggc | 540 |
| ccccagccat cagctgaaac cacacgccac ttcctcatgt ctgaccggag gtccctgcac | 600 |
| ctagaggctt ccctggacaa agagctgtac taccatgggg aacccctcaa tgtcaacgtc | 660 |
| cacgtcacca acaattctgc caagaccgtc aagaagatca gagtgtctgt gagacagtat | 720 |
| gccgacattt gcctcttcag caccgcgcag tacaagtgtc ctgtggctca gcttgaacaa | 780 |
| gatgaccagg tgtctcccag ttccacattc tgcaaggtgt acaccataac ccgctgctc | 840 |
| agtgacaacc gagagaagcg tggccttgcc cttgatgggc aactcaagca cgaagacacc | 900 |
| aacctggctt ccagcaccat tgtgaaggag ggagccaaca aggaggtgct gggaatccta | 960 |
| gtatcctaca gggtcaaggt gaagctggtg gtgtctcgag gcggggatgt ctccgtggag | 1020 |
| ctacctttcg tcctaatgca ccccaagccc cacgaccaca tcacccttcc ccgacccag | 1080 |
| tcagcccccc gggaaataga catccctgtg gataccaacc tcattgaatt cgataccaac | 1140 |
| tatgccacag acgacgacat cgtgtttgag acttgcga ggcttcggct gaaggggatg | 1200 |
| aaggatgacg actgtgatga ccagttctgc ctgagctcac tcgaaggtgg cggtggctct | 1260 |
| ggaggtggtg ggtccggagg aggcggcatc gagatgtcca gcatggtgag cgatactagc | 1320 |
| tgtaccttcc catcatctga cggaatcttc tggaagcact ggattcagac taggacggc | 1380 |
| cagtgtggca gcccactggt gagcacacga gacggattca tcgtgggat tcacagcgcc | 1440 |
| tccaaccttta caaacaccaa taactatttc acctcagtgc caagaactt tatggagctg | 1500 |
| ctgaccaacc aggaggccca gcagggtg agcgggtggc gcctgaacgc cgattccgtg | 1560 |
| ctgtggggcg gcacaaggt gtttatggca tgccgaagcg gagctactaa cttcagcctg | 1620 |
| ctgaagcagg ctggagacgt ggaggagaac cctggacctg aattcatggt gagcaagggc | 1680 |

```
gaggaggtca tcaaagagtt catgcgcttc aaggtgcgca tggagggctc catgaacggc    1740
cacgagttcg agatcgaggg cgagggcgag ggccgcccct acgagggcac ccagaccgcc    1800
aagctgaagg tgaccaaggg cggccccctg cccttcgcct gggacatcct gtcccccag     1860 ttcatgtacg gctccaaggc gtacgtgaag caccccgccg acatcccga ttacaagaag     1920 ctgtccttcc ccgagggctt caagtgggag cgcgtgatga acttcgagga cggcggtctg    1980
gtgaccgtga cccaggactc ctccctgcag gacggcacgc tgatctacaa ggtgaagatg    2040
cgcggcacca acttccccc cgacggcccc gtaatgcaga gaagaccat gggctgggag      2100 gcctccaccg agcgcctgta cccccgcgac ggcgtgctga agggcgagat ccaccaggcc    2160
ctgaagctga aggacggcgg ccgctacctg gtggagttca gaccatcta catggccaag     2220 aagcccgtgc aactgcccgg ctactactac gtggacacca gctggacat cacctcccac     2280 aacgaggact acaccatcgt ggaacagtac gagcgctccg agggccgcca ccacctgttc    2340
ctggggcatg gcaccggcag caccggcagc ggcagttccg gcaccgcctc ctccgaggac    2400
aacaacatgg ccgtcatcaa agagttcatg cgcttcaagg tgcgcatgga gggctccatg    2460 aacgccacg agttcgagat cgagggcgag ggcgagggcc gcccctacga gggcacccag     2520
accgccaagc tgaaggtgac caagggcggc cccctgccct cgcctggga catcctgtcc    2580 ccccagttca tgtacggctc caaggcgtac gtgaagcacc ccgccgacat ccccgattac   2640
aagaagctgt ccttccccga gggcttcaag tgggagcgcg tgatgaactt cgaggacggc    2700
ggtctggtga ccgtgaccca ggactcctcc ctgcaggacg gcacgctgat ctacaaggtg    2760
aagatgcgcg gcaccaactt ccccccgac ggccccgtaa tgcagaagaa gaccatgggc     2820
tgggaggcct ccaccgagcg cctgtacccc cgcgacggcg tgctgaaggg cgagatccac    2880
caggccctga agctgaagga cggcggccgc tacctggtgg agttcaagac catctacatg    2940
gccaagaagc ccgtgcaact gcccggctac tactacgtgg acaccaagct ggacatcacc    3000
tcccacaacg aggactacac catcgtggaa cagtacgagc gctccgaggg ccgccaccac    3060
ctgttcctgt acggcatgga cgagctgtac aag                                 3093
```

<210> SEQ ID NO 60
<211> LENGTH: 1031
<212> TYPE: PRT
<213> ORGANISM: Artificial Sequence
<220> FEATURE:
<223> OTHER INFORMATION: bArr2 ? TEV-C ? TdTomato

<400> SEQUENCE: 60

```
Met Gly Glu Lys Pro Gly Thr Arg Val Phe Lys Lys Ser Ser Pro Asn
1               5                   10                  15

Cys Lys Leu Thr Val Tyr Leu Gly Lys Arg Asp Phe Val Asp His Leu
                20                  25                  30

Asp Lys Val Asp Pro Val Asp Gly Val Val Leu Val Asp Pro Asp Tyr
            35                  40                  45

Leu Lys Asp Arg Lys Val Phe Val Thr Leu Thr Cys Ala Phe Arg Tyr
        50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Met Pro Asn Pro Pro Arg
                85                  90                  95

Pro Pro Thr Arg Leu Gln Asp Arg Leu Leu Lys Lys Leu Gly Gln His
            100                 105                 110
```

```
Ala His Pro Phe Phe Phe Thr Ile Pro Gln Asn Leu Pro Cys Ser Val
        115                 120                 125

Thr Leu Gln Pro Gly Pro Glu Asp Thr Gly Lys Ala Cys Gly Val Asp
    130                 135                 140

Phe Glu Ile Arg Ala Phe Cys Ala Lys Ser Ile Glu Glu Lys Ser His
145                 150                 155                 160

Lys Arg Asn Ser Val Arg Leu Ile Ile Arg Lys Val Gln Phe Ala Pro
                165                 170                 175

Glu Thr Pro Gly Pro Gln Pro Ser Ala Glu Thr Thr Arg His Phe Leu
                180                 185                 190

Met Ser Asp Arg Arg Ser Leu His Leu Glu Ala Ser Leu Asp Lys Glu
            195                 200                 205

Leu Tyr Tyr His Gly Glu Pro Leu Asn Val Asn Val His Val Thr Asn
        210                 215                 220

Asn Ser Ala Lys Thr Val Lys Lys Ile Arg Val Ser Val Arg Gln Tyr
225                 230                 235                 240

Ala Asp Ile Cys Leu Phe Ser Thr Ala Gln Tyr Lys Cys Pro Val Ala
                245                 250                 255

Gln Leu Glu Gln Asp Asp Gln Val Ser Pro Ser Ser Thr Phe Cys Lys
            260                 265                 270

Val Tyr Thr Ile Thr Pro Leu Leu Ser Asp Asn Arg Glu Lys Arg Gly
        275                 280                 285

Leu Ala Leu Asp Gly Gln Leu Lys His Glu Asp Thr Asn Leu Ala Ser
        290                 295                 300

Ser Thr Ile Val Lys Glu Gly Ala Asn Lys Glu Val Leu Gly Ile Leu
305                 310                 315                 320

Val Ser Tyr Arg Val Lys Val Lys Leu Val Val Ser Arg Gly Gly Asp
                325                 330                 335

Val Ser Val Glu Leu Pro Phe Val Leu Met His Pro Lys Pro His Asp
            340                 345                 350

His Ile Thr Leu Pro Arg Pro Gln Ser Ala Pro Arg Glu Ile Asp Ile
        355                 360                 365

Pro Val Asp Thr Asn Leu Ile Glu Phe Asp Thr Asn Tyr Ala Thr Asp
        370                 375                 380

Asp Asp Ile Val Phe Glu Asp Phe Ala Arg Leu Arg Leu Lys Gly Met
385                 390                 395                 400

Lys Asp Asp Asp Cys Asp Asp Gln Phe Cys Leu Ser Ser Leu Glu Gly
                405                 410                 415

Gly Gly Gly Ser Gly Gly Gly Ser Gly Gly Gly Ile Glu Met
                420                 425                 430

Ser Ser Met Val Ser Asp Thr Ser Cys Thr Phe Pro Ser Ser Asp Gly
        435                 440                 445

Ile Phe Trp Lys His Trp Ile Gln Thr Lys Asp Gly Gln Cys Gly Ser
        450                 455                 460

Pro Leu Val Ser Thr Arg Asp Gly Phe Ile Val Gly Ile His Ser Ala
465                 470                 475                 480

Ser Asn Phe Thr Asn Thr Asn Asn Tyr Phe Thr Ser Val Pro Lys Asn
                485                 490                 495

Phe Met Glu Leu Leu Thr Asn Gln Glu Ala Gln Gln Trp Val Ser Gly
            500                 505                 510

Trp Arg Leu Asn Ala Asp Ser Val Leu Trp Gly Gly His Lys Val Phe
        515                 520                 525
```

```
Met Ala Cys Gly Ser Gly Ala Thr Asn Phe Ser Leu Leu Lys Gln Ala
            530                 535                 540

Gly Asp Val Glu Glu Asn Pro Gly Pro Glu Phe Met Val Ser Lys Gly
545                 550                 555                 560

Glu Glu Val Ile Lys Glu Phe Met Arg Phe Lys Val Arg Met Glu Gly
                565                 570                 575

Ser Met Asn Gly His Glu Phe Glu Ile Glu Gly Glu Gly Glu Gly Arg
            580                 585                 590

Pro Tyr Glu Gly Thr Gln Thr Ala Lys Leu Lys Val Thr Lys Gly Gly
        595                 600                 605

Pro Leu Pro Phe Ala Trp Asp Ile Leu Ser Pro Gln Phe Met Tyr Gly
610                 615                 620

Ser Lys Ala Tyr Val Lys His Pro Ala Asp Ile Pro Asp Tyr Lys Lys
625                 630                 635                 640

Leu Ser Phe Pro Glu Gly Phe Lys Trp Glu Arg Val Met Asn Phe Glu
                645                 650                 655

Asp Gly Gly Leu Val Thr Val Thr Gln Asp Ser Ser Leu Gln Asp Gly
            660                 665                 670

Thr Leu Ile Tyr Lys Val Lys Met Arg Gly Thr Asn Phe Pro Pro Asp
        675                 680                 685

Gly Pro Val Met Gln Lys Lys Thr Met Gly Trp Glu Ala Ser Thr Glu
690                 695                 700

Arg Leu Tyr Pro Arg Asp Gly Val Leu Lys Gly Glu Ile His Gln Ala
705                 710                 715                 720

Leu Lys Leu Lys Asp Gly Gly Arg Tyr Leu Val Glu Phe Lys Thr Ile
                725                 730                 735

Tyr Met Ala Lys Lys Pro Val Gln Leu Pro Gly Tyr Tyr Tyr Val Asp
            740                 745                 750

Thr Lys Leu Asp Ile Thr Ser His Asn Glu Asp Tyr Thr Ile Val Glu
        755                 760                 765

Gln Tyr Glu Arg Ser Glu Gly Arg His His Leu Phe Leu Gly His Gly
770                 775                 780

Thr Gly Ser Thr Gly Ser Gly Ser Ser Gly Thr Ala Ser Ser Glu Asp
785                 790                 795                 800

Asn Asn Met Ala Val Ile Lys Glu Phe Met Arg Phe Lys Val Arg Met
                805                 810                 815

Glu Gly Ser Met Asn Gly His Glu Phe Glu Ile Glu Gly Glu Gly Glu
            820                 825                 830

Gly Arg Pro Tyr Glu Gly Thr Gln Thr Ala Lys Leu Lys Val Thr Lys
        835                 840                 845

Gly Gly Pro Leu Pro Phe Ala Trp Asp Ile Leu Ser Pro Gln Phe Met
850                 855                 860

Tyr Gly Ser Lys Ala Tyr Val Lys His Pro Ala Asp Ile Pro Asp Tyr
865                 870                 875                 880

Lys Lys Leu Ser Phe Pro Glu Gly Phe Lys Trp Glu Arg Val Met Asn
                885                 890                 895

Phe Glu Asp Gly Gly Leu Val Thr Val Thr Gln Asp Ser Ser Leu Gln
            900                 905                 910

Asp Gly Thr Leu Ile Tyr Lys Val Lys Met Arg Gly Thr Asn Phe Pro
        915                 920                 925

Pro Asp Gly Pro Val Met Gln Lys Lys Thr Met Gly Trp Glu Ala Ser
930                 935                 940

Thr Glu Arg Leu Tyr Pro Arg Asp Gly Val Leu Lys Gly Glu Ile His
```

```
                945                 950                 955                 960
Gln Ala Leu Lys Leu Lys Asp Gly Gly Arg Tyr Leu Val Glu Phe Lys
                    965                 970                 975
Thr Ile Tyr Met Ala Lys Lys Pro Val Gln Leu Pro Gly Tyr Tyr Tyr
                    980                 985                 990
Val Asp Thr Lys Leu Asp Ile Thr Ser His Asn Glu Asp Tyr Thr Ile
                    995                 1000                1005
Val Glu Gln Tyr Glu Arg Ser Glu Gly Arg His His Leu Phe Leu Tyr
                    1010                1015                1020
Gly Met Asp Glu Leu Tyr Lys
1025                1030

<210> SEQ ID NO 61
<211> LENGTH: 591
<212> TYPE: DNA
<213> ORGANISM: Artificial Sequence
<220> FEATURE:
<223> OTHER INFORMATION: TEV-C-M13

<400> SEQUENCE: 61
gctactaact tcagcctgct gaagcaggct ggagacgtgg aggagaaccc tggacctctt      60
caacttcctc ctcttgaacg tcttactctc ccatggaccg gtatgtccag catggtgagc     120
gatactagct gtaccttccc atcatctgac ggaatcttct ggaagcactg gattcagact     180
aaggacggcc agtgtggcag cccactggtg agcacacgag acggattcat cgtggggatt     240
cacagcgcct ccaactttac aaacaccaat aactatttca cctcagtgcc aaagaacttt     300
atggagctgc tgaccaacca ggaggcccag cagtgggtga gcgggtggcg cctgaacgcc     360
gattccgtgc tgtggggcgg gcacaaggtg tttatggcat gcggtggcgg tggctctgga     420
ggtggtgggt ccggaggagg cggccgcatg gcaagcatga ctggtggaca gcaaatgggt     480
cgggatctgt acgacgatga cgataaggat ctcgccacca tggtcgactc atcacgtcgt     540
aagtggaata agacaggtca cgcagtcaga gctataggtc ggctgagttc a              591

<210> SEQ ID NO 62
<211> LENGTH: 197
<212> TYPE: PRT
<213> ORGANISM: Artificial Sequence
<220> FEATURE:
<223> OTHER INFORMATION: TEV-C-M13

<400> SEQUENCE: 62

Ala Thr Asn Phe Ser Leu Leu Lys Gln Ala Gly Asp Val Glu Glu Asn
1               5                   10                  15

Pro Gly Pro Leu Gln Leu Pro Pro Leu Glu Arg Leu Thr Leu Pro Trp
                20                  25                  30

Thr Gly Met Ser Ser Met Val Ser Asp Thr Ser Cys Thr Phe Pro Ser
                35                  40                  45

Ser Asp Gly Ile Phe Trp Lys His Trp Ile Gln Thr Lys Asp Gly Gln
            50                  55                  60

Cys Gly Ser Pro Leu Val Ser Thr Arg Asp Gly Phe Ile Val Gly Ile
65                  70                  75                  80

His Ser Ala Ser Asn Phe Thr Asn Thr Asn Asn Tyr Phe Thr Ser Val
                85                  90                  95

Pro Lys Asn Phe Met Glu Leu Leu Thr Asn Gln Glu Ala Gln Gln Trp
                100                 105                 110

Val Ser Gly Trp Arg Leu Asn Ala Asp Ser Val Leu Trp Gly Gly His
```

```
            115                 120                 125
Lys Val Phe Met Ala Cys Gly Gly Gly Ser Gly Gly Gly Ser
        130                 135                 140

Gly Gly Gly Gly Arg Met Ala Ser Met Thr Gly Gln Gln Met Gly
145                 150                 155                 160

Arg Asp Leu Tyr Asp Asp Asp Lys Asp Leu Ala Thr Met Val Asp
                165                 170                 175

Ser Ser Arg Arg Lys Trp Asn Lys Thr Gly His Ala Val Arg Ala Ile
            180                 185                 190

Gly Arg Leu Ser Ser
        195

<210> SEQ ID NO 63
<211> LENGTH: 1587
<212> TYPE: DNA
<213> ORGANISM: Artificial Sequence
<220> FEATURE:
<223> OTHER INFORMATION: ?-arrestin2-TEV-C

<400> SEQUENCE: 63
atgggtgaaa acccgggac  cagggtcttc aagaagtcga  gccctaactg caagctcacc    60
gtgtacttgg gcaagcgtga ctttgtggat cacttggaca aagtggatcc tgtcgatggt   120
gtggtgcttg tggatcctga ctacttgaag gaccggaaag tgtttgtgac cctcacctgt   180
gccttccgct atggccgaga agacctggat gtactgggcc tgtcttttcg caaagatctg   240
ttcatcgcca cctaccaggc cttcccccc  atgcccaacc cacctcggcc ccccacccgc   300
ctacaggacc gactgctgaa gaagttgggc cagcacgccc ccccttttt  tttcacaata   360 ccccagaatt tgccttgctc cgtcacactg cagccaggac cggaggacac agggaaggcc   420
tgtggagtag actttgagat cgagccttc  tgtgccaaat ctatagaaga aaaaagccac   480
aaaaggaact ccgtgcggct tatcatcaga aaggtacagt ttgctcctga cacccggc    540 ccccagccat cagctgaaac cacacgccac ttcctcatgt ctgaccggag gtccctgcac   600
ctagaggctt ccctggacaa agagctgtac taccatgggg aacccctcaa tgtcaacgtc   660
cacgtcacca acaattctgc caagaccgtc aagaagatca gagtgtctgt gagacagtat   720
gccgacattt gcctcttcag caccgcgcag tacaagtgtc ctgtggctca gcttgaacaa   780
gatgaccagg tgtctcccag ttccacattc tgcaaggtgt acaccataac cccgctgctc   840
agtgacaacc gagagaagcg tggccttgcc cttgatgggc aactcaagca cgaagacacc   900
aacctggctt ccagcaccat tgtgaaggag ggagccaaca aggaggtgct gggaatccta   960
gtatcctaca gggtcaaggt gaagctggtg gtgtctcgag gcgggatgt  ctccgtggag  1020 ctacctttcg tcctaatgca ccccaagccc acgaccaca  tcacccttcc ccgacccag  1080 tcagcccccc gggaaatag  catccctgtg gataccaacc tcattgaatt cgataccaac  1140
tatgccacag cgacgacat  cgtgtttgag actttgcga  ggcttcggct gaaggggatg  1200
aaggatgacg actgtgatga ccagttctgc ctgagctcac tcgaaggtgg cggtggctct  1260
ggaggtggtg gtccggagg  aggcggcatc gagatgtcca gcatggtgag cgatactagc  1320
tgtaccttcc catcatctga cggaatcttc tggaagcact ggattcagac taaggacggc  1380
cagtgtggca gcccactggt gagcacacga gacggattca tcgtgggat  tcacagcgcc  1440 tccaactta  caaacaccaa taactatttc acctcagtgc aaagaactt  tatggagctg  1500 ctgaccaacc aggaggccca gcagtgggtg agcgggtggc gctgaacgc  cgattccgtg  1560
```
ctgtggggcg ggcacaaggt gtttatg                                          1587

<210> SEQ ID NO 64
<211> LENGTH: 529
<212> TYPE: PRT
<213> ORGANISM: Artificial Sequence
<220> FEATURE:
<223> OTHER INFORMATION: ?-arrestin2-TEV-C
<400> SEQUENCE: 64

```
Met Gly Glu Lys Pro Gly Thr Arg Val Phe Lys Ser Ser Pro Asn
1               5                   10                  15

Cys Lys Leu Thr Val Tyr Leu Gly Lys Arg Asp Phe Val Asp His Leu
            20                  25                  30

Asp Lys Val Asp Pro Val Asp Gly Val Val Leu Val Asp Pro Asp Tyr
        35                  40                  45

Leu Lys Asp Arg Lys Val Phe Val Thr Leu Thr Cys Ala Phe Arg Tyr
    50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Met Pro Asn Pro Pro Arg
                85                  90                  95

Pro Pro Thr Arg Leu Gln Asp Arg Leu Leu Lys Lys Leu Gly Gln His
            100                 105                 110

Ala His Pro Phe Phe Thr Ile Pro Gln Asn Leu Pro Cys Ser Val
        115                 120                 125

Thr Leu Gln Pro Gly Pro Glu Asp Thr Gly Lys Ala Cys Gly Val Asp
130                 135                 140

Phe Glu Ile Arg Ala Phe Cys Ala Lys Ser Ile Glu Glu Lys Ser His
145                 150                 155                 160

Lys Arg Asn Ser Val Arg Leu Ile Ile Arg Lys Val Gln Phe Ala Pro
                165                 170                 175

Glu Thr Pro Gly Pro Gln Pro Ser Ala Glu Thr Thr Arg His Phe Leu
            180                 185                 190

Met Ser Asp Arg Arg Ser Leu His Leu Glu Ala Ser Leu Asp Lys Glu
        195                 200                 205

Leu Tyr Tyr His Gly Glu Pro Leu Asn Val Asn Val His Val Thr Asn
    210                 215                 220

Asn Ser Ala Lys Thr Val Lys Lys Ile Arg Val Ser Val Arg Gln Tyr
225                 230                 235                 240

Ala Asp Ile Cys Leu Phe Ser Thr Ala Gln Tyr Lys Cys Pro Val Ala
                245                 250                 255

Gln Leu Glu Gln Asp Asp Gln Val Ser Pro Ser Ser Thr Phe Cys Lys
            260                 265                 270

Val Tyr Thr Ile Thr Pro Leu Leu Ser Asp Asn Arg Glu Lys Arg Gly
        275                 280                 285

Leu Ala Leu Asp Gly Gln Leu Lys His Glu Asp Thr Asn Leu Ala Ser
    290                 295                 300

Ser Thr Ile Val Lys Glu Gly Ala Asn Lys Glu Val Leu Gly Ile Leu
305                 310                 315                 320

Val Ser Tyr Arg Val Lys Val Lys Leu Val Val Ser Arg Gly Gly Asp
                325                 330                 335

Val Ser Val Glu Leu Pro Phe Val Leu Met His Pro Lys Pro His Asp
            340                 345                 350

His Ile Thr Leu Pro Arg Pro Gln Ser Ala Pro Arg Glu Ile Asp Ile
```

```
                355                 360                 365
Pro Val Asp Thr Asn Leu Ile Glu Phe Asp Thr Asn Tyr Ala Thr Asp
    370                 375                 380

Asp Asp Ile Val Phe Glu Asp Phe Ala Arg Leu Arg Leu Lys Gly Met
385                 390                 395                 400

Lys Asp Asp Cys Asp Gln Phe Cys Leu Ser Ser Leu Glu Gly
                405                 410                 415

Gly Gly Gly Ser Gly Gly Gly Ser Gly Gly Gly Ile Glu Met
            420                 425                 430

Ser Ser Met Val Ser Asp Thr Ser Cys Thr Phe Pro Ser Asp Gly
                435                 440                 445

Ile Phe Trp Lys His Trp Ile Gln Thr Lys Asp Gly Gln Cys Gly Ser
    450                 455                 460

Pro Leu Val Ser Thr Arg Asp Gly Phe Ile Val Gly Ile His Ser Ala
465                 470                 475                 480

Ser Asn Phe Thr Asn Thr Asn Tyr Phe Thr Ser Val Pro Lys Asn
                485                 490                 495

Phe Met Glu Leu Leu Thr Asn Gln Glu Ala Gln Gln Trp Val Ser Gly
                500                 505                 510

Trp Arg Leu Asn Ala Asp Ser Val Leu Trp Gly Gly His Lys Val Phe
    515                 520                 525
Met
```

<210> SEQ ID NO 65
<211> LENGTH: 3165
<212> TYPE: DNA
<213> ORGANISM: Artificial Sequence
<220> FEATURE:
<223> OTHER INFORMATION: bArr2 ? TEV-N ? TdTomato

<400> SEQUENCE: 65

```
atgggtgaaa acccgggac  cagggtcttc aagaagtcga gccctaactg caagctcacc    60
gtgtacttgg gcaagcgtga ctttgtggat cacttggaca agtggatcc  tgtcgatggt   120
gtggtgcttg tggatcctga ctacttgaag accggaaag  tgtttgtgac cctcacctgt   180
gccttccgct atggccgaga gacctggat  gtactgggcc tgtctttccg caaagatctg   240
ttcatcgcca cctaccaggc cttcccccc  atgcccaacc cacctcggcc cccaccccgc   300
ctacaggacc gactgctgaa gaagttgggc cagcatgccc accctttttt tttcacaata   360
ccccagaatt tgccttgctc cgtcacactg cagccaggac cggaggacac agggaaggcc   420
tgtggagtag actttgagat cgagccttc  tgtgccaaat ctatagaaga aaaaagccac   480
aaaaggaact ccgtgcggct tatcatcaga aaggtacagt ttgctcctga cacccggc    540
ccccagccat cagctgaaac cacacgccac ttcctcatgt ctgaccggag gtccctgcac   600
ctagaggctt ccctggacaa agagctgtac taccatgggg aacccctcaa tgtcaacgtc   660
cacgtcacca caattctgc  caagaccgtc aagaagatca gagtgtctgt gagacagtat   720
gccgacattt gcctcttcag caccgcgcag tacaagtgtc ctgtggctca gcttgaacaa   780
gatgaccagg tgtctcccag ttccacattc tgcaaggtgt acaccataac ccgctgctc   840
agtgacaacc gagagaagcg tggccttgcc cttgatgggc aactcaagca cgaagacacc   900
aacctggctt ccagcaccat tgtgaaggag ggagccaaca aggaggtgct gggaatccta   960
gtatcctaca gggtcaaggt gaagctggtg gtgtctcgag cggggatgt  ctccgtggag  1020
ctaccttttcg tcctaatgca cccaagccc  cacgaccaca tcacccttcc ccgaccccag  1080
```

```
tcagccccccc gggaaataga catccctgtg gataccaacc tcattgaatt cgataccaac    1140
tatgccacag acgacgacat cgtgtttgag gactttgcga ggcttcggct gaagggatg     1200 aaggatgacg actgtgatga ccagttctgc ctgagctcac tcgaaggtgg cggtggctct    1260
ggaggtggtg ggtccggagg aggcggcatc gagggtatgg gcgagagcct gttcaaggga    1320
cctagggact acaaccctat cagtagcaca atttgtcacc tgaccaacga gagtgatggc    1380
cacacaacaa gcctgtacgg catcgggttc ggacccttta tcatcaccaa caagcacctg    1440
ttcaggcgga ataatggcac tctgctggtg cagagcctgc acggggtgtt caaagtgaag    1500
aacacaacca ctctgcagca gcacctgatc gatgggcggg atatgatcat cattaggatg    1560
cccaaggact cccccccttt tcctcagaaa ctgaagttcc gagagcccca gagagaggag    1620
agaatctgtc tggtgaccac aaactttcag gcatgcggaa gcggagctac taacttcagc    1680
ctgctgaagc aggctggaga cgtggaggag aaccctggac tgaattcat ggtgagcaag     1740 ggcgaggagg tcatcaaaga gttcatgcgc ttcaaggtgc gcatggaggg ctccatgaac    1800
ggccacgagt tcgagatcga gggcgagggc gagggccgcc cctacgaggg cacccagacc    1860
gccaagctga aggtgaccaa gggcggcccc ctgcccttcg cctgggacat cctgtccccc    1920
cagttcatgt acggctccaa ggcgtacgtg aagcaccccg ccgacatccc cgattacaag    1980
aagctgtcct tccccgaggg cttcaagtgg gagcgcgtga tgaacttcga ggacggcggt    2040
ctggtgaccg tgacccagga ctcctccctg caggacggca cgctgatcta caaggtgaag    2100
atgcgcggca ccaacttccc ccccgacggc ccgtaatgc agaagaagac catgggctgg    2160
gaggcctcca ccgagcgcct gtaccccgc gacgcgtgc tgaagggcga gatccaccag     2220
gccctgaagc tgaaggacgg cggccgctac ctggtggagt tcaagaccat ctacatggcc    2280
aagaagcccg tgcaactgcc cggctactac tacgtggaca ccaagctgga catcacctcc    2340
cacaacgagg actacaccat cgtggaacag tacgagcgct ccgagggccg ccaccacctg    2400
ttcctggggc atggcaccgg cagcaccggc agcggcagtt ccggcaccgc ctcctccgag    2460
gacaacaaca tggccgtcat caaagagttc atgcgcttca aggtgcgcat ggagggctcc    2520
atgaacggcc acgagttcga gatcgagggc gagggcgagg gccgccccta cgagggcacc    2580
cagaccgcca agctgaaggt gaccaagggc ggccccctgc ccttcgcctg gacatcctg     2640 tccccccagt tcatgtacgg ctccaaggcg tacgtgaagc accccgccga catccccgat    2700
tacaagaagc tgtccttccc cgagggcttc aagtgggagc gcgtgatgaa cttcgaggac    2760
ggcggtctgg tgaccgtgac ccaggactcc tccctgcagg acggcacgct gatctacaag    2820
gtgaagatgc gcggcaccaa cttccccccc gacggccccg taatgcagaa gaagaccatg    2880
ggctgggagg cctccaccga gcgcctgtac cccgcgacg gcgtgctgaa gggcgagatc     2940
caccaggccc tgaagctgaa ggacggcggc cgctacctgg tggagttcaa gaccatctac    3000
atggccaaga gcccgtgca actgcccggc tactactacg tggacaccaa gctggacatc     3060
acctcccaca acgaggacta caccatcgtg aacagtacg agcgctccga gggccgccac     3120
cacctgttcc tgtacggcat ggacgagctg tacaagtgtg gcggc                    3165
```

<210> SEQ ID NO 66
<211> LENGTH: 1055
<212> TYPE: PRT
<213> ORGANISM: Artificial Sequence
<220> FEATURE:
<223> OTHER INFORMATION: bArr2 ? TEV-N ? TdTomato

<400> SEQUENCE: 66

```
Met Gly Glu Lys Pro Gly Thr Arg Val Phe Lys Lys Ser Ser Pro Asn
1               5                   10                  15

Cys Lys Leu Thr Val Tyr Leu Gly Lys Arg Asp Phe Val Asp His Leu
            20                  25                  30

Asp Lys Val Asp Pro Val Asp Gly Val Val Leu Val Asp Pro Asp Tyr
        35                  40                  45

Leu Lys Asp Arg Lys Val Phe Val Thr Leu Thr Cys Ala Phe Arg Tyr
    50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Met Pro Asn Pro Pro Arg
                85                  90                  95

Pro Pro Thr Arg Leu Gln Asp Arg Leu Leu Lys Lys Leu Gly Gln His
            100                 105                 110

Ala His Pro Phe Phe Phe Thr Ile Pro Gln Asn Leu Pro Cys Ser Val
        115                 120                 125

Thr Leu Gln Pro Gly Pro Glu Asp Thr Gly Lys Ala Cys Gly Val Asp
    130                 135                 140

Phe Glu Ile Arg Ala Phe Cys Ala Lys Ser Ile Glu Glu Lys Ser His
145                 150                 155                 160

Lys Arg Asn Ser Val Arg Leu Ile Ile Arg Lys Val Gln Phe Ala Pro
                165                 170                 175

Glu Thr Pro Gly Pro Gln Pro Ser Ala Glu Thr Thr Arg His Phe Leu
            180                 185                 190

Met Ser Asp Arg Arg Ser Leu His Leu Glu Ala Ser Leu Asp Lys Glu
        195                 200                 205

Leu Tyr Tyr His Gly Glu Pro Leu Asn Val Asn Val His Val Thr Asn
    210                 215                 220

Asn Ser Ala Lys Thr Val Lys Lys Ile Arg Val Ser Val Arg Gln Tyr
225                 230                 235                 240

Ala Asp Ile Cys Leu Phe Ser Thr Ala Gln Tyr Lys Cys Pro Val Ala
                245                 250                 255

Gln Leu Glu Gln Asp Asp Gln Val Ser Pro Ser Ser Thr Phe Cys Lys
            260                 265                 270

Val Tyr Thr Ile Thr Pro Leu Leu Ser Asp Asn Arg Glu Lys Arg Gly
        275                 280                 285

Leu Ala Leu Asp Gly Gln Leu Lys His Glu Asp Thr Asn Leu Ala Ser
    290                 295                 300

Ser Thr Ile Val Lys Glu Gly Ala Asn Lys Glu Val Leu Gly Ile Leu
305                 310                 315                 320

Val Ser Tyr Arg Val Lys Val Lys Leu Val Val Ser Arg Gly Gly Asp
                325                 330                 335

Val Ser Val Glu Leu Pro Phe Val Leu Met His Pro Lys Pro His Asp
            340                 345                 350

His Ile Thr Leu Pro Arg Pro Gln Ser Ala Pro Arg Glu Ile Asp Ile
        355                 360                 365

Pro Val Asp Thr Asn Leu Ile Glu Phe Asp Thr Asn Tyr Ala Thr Asp
    370                 375                 380

Asp Asp Ile Val Phe Glu Asp Phe Ala Arg Leu Arg Leu Lys Gly Met
385                 390                 395                 400

Lys Asp Asp Asp Cys Asp Asp Gln Phe Cys Leu Ser Ser Leu Glu Gly
                405                 410                 415
```

```
Gly Gly Gly Ser Gly Gly Gly Ser Gly Gly Gly Ile Glu Gly
            420                 425             430

Met Gly Glu Ser Leu Phe Lys Gly Pro Arg Asp Tyr Asn Pro Ile Ser
                435                 440             445

Ser Thr Ile Cys His Leu Thr Asn Glu Ser Asp Gly His Thr Thr Ser
450                 455                 460

Leu Tyr Gly Ile Gly Phe Gly Pro Phe Ile Ile Thr Asn Lys His Leu
465                 470                 475                 480

Phe Arg Arg Asn Asn Gly Thr Leu Leu Val Gln Ser Leu His Gly Val
                485                 490                 495

Phe Lys Val Lys Asn Thr Thr Thr Leu Gln Gln His Leu Ile Asp Gly
                500                 505                 510

Arg Asp Met Ile Ile Ile Arg Met Pro Lys Asp Phe Pro Pro Phe Pro
            515                 520                 525

Gln Lys Leu Lys Phe Arg Glu Pro Gln Arg Glu Glu Arg Ile Cys Leu
530                 535                 540

Val Thr Thr Asn Phe Gln Ala Cys Gly Ser Gly Ala Thr Asn Phe Ser
545                 550                 555                 560

Leu Leu Lys Gln Ala Gly Asp Val Glu Glu Asn Pro Gly Pro Glu Phe
                565                 570                 575

Met Val Ser Lys Gly Glu Glu Val Ile Lys Glu Phe Met Arg Phe Lys
                580                 585                 590

Val Arg Met Glu Gly Ser Met Asn Gly His Glu Phe Glu Ile Glu Gly
                595                 600                 605

Glu Gly Glu Gly Arg Pro Tyr Glu Gly Thr Gln Thr Ala Lys Leu Lys
            610                 615                 620

Val Thr Lys Gly Gly Pro Leu Pro Phe Ala Trp Asp Ile Leu Ser Pro
625                 630                 635                 640

Gln Phe Met Tyr Gly Ser Lys Ala Tyr Val Lys His Pro Ala Asp Ile
                645                 650                 655

Pro Asp Tyr Lys Lys Leu Ser Phe Pro Glu Gly Phe Lys Trp Glu Arg
                660                 665                 670

Val Met Asn Phe Glu Asp Gly Gly Leu Val Thr Val Thr Gln Asp Ser
            675                 680                 685

Ser Leu Gln Asp Gly Thr Leu Ile Tyr Lys Val Lys Met Arg Gly Thr
            690                 695                 700

Asn Phe Pro Pro Asp Gly Pro Val Met Gln Lys Lys Thr Met Gly Trp
705                 710                 715                 720

Glu Ala Ser Thr Glu Arg Leu Tyr Pro Arg Asp Gly Val Leu Lys Gly
                725                 730                 735

Glu Ile His Gln Ala Leu Lys Leu Lys Asp Gly Gly Arg Tyr Leu Val
                740                 745                 750

Glu Phe Lys Thr Ile Tyr Met Ala Lys Lys Pro Val Gln Leu Pro Gly
                755                 760                 765

Tyr Tyr Tyr Val Asp Thr Lys Leu Asp Ile Thr Ser His Asn Glu Asp
                770                 775                 780

Tyr Thr Ile Val Glu Gln Tyr Glu Arg Ser Glu Gly Arg His His Leu
785                 790                 795                 800

Phe Leu Gly His Gly Thr Gly Ser Thr Gly Ser Gly Ser Ser Gly Thr
                805                 810                 815

Ala Ser Ser Glu Asp Asn Asn Met Ala Val Ile Lys Glu Phe Met Arg
            820                 825                 830
```

| Phe | Lys | Val | Arg | Met | Glu | Gly | Ser | Met | Asn | Gly | His | Glu | Phe | Glu | Ile |
|  |  | 835 |  |  |  |  | 840 |  |  |  |  | 845 |  |  |  |

| Glu | Gly | Glu | Gly | Glu | Gly | Arg | Pro | Tyr | Glu | Gly | Thr | Gln | Thr | Ala | Lys |
| 850 |  |  |  |  |  | 855 |  |  |  |  | 860 |  |  |  |  |

| Leu | Lys | Val | Thr | Lys | Gly | Gly | Pro | Leu | Pro | Phe | Ala | Trp | Asp | Ile | Leu |
| 865 |  |  |  | 870 |  |  |  | 875 |  |  |  |  |  |  | 880 |

| Ser | Pro | Gln | Phe | Met | Tyr | Gly | Ser | Lys | Ala | Tyr | Val | Lys | His | Pro | Ala |
|  |  |  |  | 885 |  |  |  | 890 |  |  |  |  | 895 |  |  |

| Asp | Ile | Pro | Asp | Tyr | Lys | Lys | Leu | Ser | Phe | Pro | Glu | Gly | Phe | Lys | Trp |
|  |  |  | 900 |  |  |  |  | 905 |  |  |  | 910 |  |  |  |

| Glu | Arg | Val | Met | Asn | Phe | Glu | Asp | Gly | Gly | Leu | Val | Thr | Val | Thr | Gln |
|  |  | 915 |  |  |  |  | 920 |  |  |  |  | 925 |  |  |  |

| Asp | Ser | Ser | Leu | Gln | Asp | Gly | Thr | Leu | Ile | Tyr | Lys | Val | Lys | Met | Arg |
|  | 930 |  |  |  |  | 935 |  |  |  |  | 940 |  |  |  |  |

| Gly | Thr | Asn | Phe | Pro | Pro | Asp | Gly | Pro | Val | Met | Gln | Lys | Lys | Thr | Met |
| 945 |  |  |  |  | 950 |  |  |  |  | 955 |  |  |  |  | 960 |

| Gly | Trp | Glu | Ala | Ser | Thr | Glu | Arg | Leu | Tyr | Pro | Arg | Asp | Gly | Val | Leu |
|  |  |  |  | 965 |  |  |  |  | 970 |  |  |  |  | 975 |  |

| Lys | Gly | Glu | Ile | His | Gln | Ala | Leu | Lys | Leu | Lys | Asp | Gly | Gly | Arg | Tyr |
|  |  |  | 980 |  |  |  |  | 985 |  |  |  |  | 990 |  |  |

| Leu | Val | Glu | Phe | Lys | Thr | Ile | Tyr | Met | Ala | Lys | Lys | Pro | Val | Gln | Leu |
|  |  |  | 995 |  |  |  |  | 1000 |  |  |  |  | 1005 |  |  |

| Pro | Gly | Tyr | Tyr | Tyr | Val | Asp | Thr | Lys | Leu | Asp | Ile | Thr | Ser | His | Asn |
|  |  | 1010 |  |  |  |  | 1015 |  |  |  |  | 1020 |  |  |  |

| Glu | Asp | Tyr | Thr | Ile | Val | Glu | Gln | Tyr | Glu | Arg | Ser | Glu | Gly | Arg | His |
| 1025 |  |  |  |  | 1030 |  |  |  |  | 1035 |  |  |  |  | 1040 |

| His | Leu | Phe | Leu | Tyr | Gly | Met | Asp | Glu | Leu | Tyr | Lys | Cys | Gly | Gly |  |
|  |  |  |  | 1045 |  |  |  |  | 1050 |  |  |  | 1055 |  |  |

<210> SEQ ID NO 67
<211> LENGTH: 1650
<212> TYPE: DNA
<213> ORGANISM: Artificial Sequence
<220> FEATURE:
<223> OTHER INFORMATION: ?-arrestin2-TEV-N

<400> SEQUENCE: 67

```
atgggtgaaa aacccgggac cagggtcttc aagaagtcga gccctaactg caagctcacc      60
gtgtacttgg gcaagcgtga ctttgtggat cacttggaca agtggatccc tgtcgatggt     120
gtggtgcttg tggatcctga ctacttgaag gaccggaaag tgtttgtgac cctcacctgt     180
gccttccgct atggccgaga agacctggat gtactgggcc tgtctttccg caaagatctg     240
ttcatcgcca cctaccaggc cttccccccc atgcccaacc cacctcggcc ccccacccgc     300
ctacaggacc gactgctgaa gaagttgggc cagcatgccc acccttttt tttcacaata      360
ccccagaatt tgccttgctc cgtcacactg cagccaggac cggaggacac agggaaggcc     420
tgtggagtag actttgagat cgagcccttc tgtgccaaat ctatagaaga aaaagccac      480
aaaaggaact ccgtgcggct tatcatcaga aaggtacagt ttgctcctga cacccggc       540
ccccagccat cagctgaaac cacacgccac ttcctcatgt ctgaccggag gtccctgcac     600
ctagaggctt ccctggacaa agagctgtac taccatgggg aaccccctcaa tgtcaacgtc    660
cacgtcacca caattctgc caagaccgtc aagaagatca gagtgtctgt gagacagtat     720
gccgacattt gcctcttcag caccgcgcag tacaagtgtc ctgtggctca gcttgaacaa     780
gatgaccagg tgtctcccag ttccacattc tgcaaggtgt acaccataac cccgctgctc     840
```

```
agtgacaacc gagagaagcg tggccttgcc cttgatgggc aactcaagca cgaagacacc    900
aacctggctt ccagcaccat tgtgaaggag ggagccaaca aggaggtgct gggaatccta    960
gtatcctaca gggtcaaggt gaagctggtg gtgtctcgag gcggggatgt ctccgtggag   1020
ctacctttcg tcctaatgca ccccaagccc cacgaccaca tcaccctctcc ccgaccccag   1080
tcagcccccc gggaaataga catccctgtg gataccaacc tcattgaatt cgataccaac   1140
tatgccacag acgacgacat cgtgtttgag gactttgcga ggcttcggct gaaggggatg   1200
aaggatgacg actgtgatga ccagttctgc ctgagctcac tcgaaggtgg cggtggctct   1260
ggaggtggtg ggtccggagg aggcggcatc gagggtatgg gcgagagcct gttcaaggga   1320
cctagggact acaaccctat cagtagcaca atttgtcacc tgaccaacga gagtgatggc   1380
cacacaacaa gcctgtacgg catcgggttc ggacccttta tcatcaccaa caagcacctg   1440
ttcaggcgga ataatggcac tctgctggtg cagagcctgc acggggtgtt caaagtgaag   1500
aacacaacca ctctgcagca gcacctgatc gatgggcggg atatgatcat cattaggatg   1560
cccaaggact tccccccttt tcctcagaaa ctgaagttcc gagagcccca gagagaggag   1620
agaatctgtc tggtgaccac aaactttcag                                    1650
```

<210> SEQ ID NO 68
<211> LENGTH: 550
<212> TYPE: PRT
<213> ORGANISM: Artificial Sequence
<220> FEATURE:
<223> OTHER INFORMATION: ?-arrestin2-TEV-N

<400> SEQUENCE: 68

```
Met Gly Glu Lys Pro Gly Thr Arg Val Phe Lys Lys Ser Ser Pro Asn
1               5                   10                  15

Cys Lys Leu Thr Val Tyr Leu Gly Lys Arg Asp Phe Val Asp His Leu
            20                  25                  30

Asp Lys Val Asp Pro Val Asp Gly Val Val Leu Val Asp Pro Asp Tyr
        35                  40                  45

Leu Lys Asp Arg Lys Val Phe Val Thr Leu Thr Cys Ala Phe Arg Tyr
    50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Met Pro Asn Pro Pro Arg
                85                  90                  95

Pro Pro Thr Arg Leu Gln Asp Arg Leu Leu Lys Lys Leu Gly Gln His
            100                 105                 110

Ala His Pro Phe Phe Phe Thr Ile Pro Gln Asn Leu Pro Cys Ser Val
        115                 120                 125

Thr Leu Gln Pro Gly Pro Glu Asp Thr Gly Lys Ala Cys Gly Val Asp
    130                 135                 140

Phe Glu Ile Arg Ala Phe Cys Ala Lys Ser Ile Glu Glu Lys Ser His
145                 150                 155                 160

Lys Arg Asn Ser Val Arg Leu Ile Ile Arg Lys Val Gln Phe Ala Pro
                165                 170                 175

Glu Thr Pro Gly Pro Gln Pro Ser Ala Glu Thr Arg His Phe Leu
            180                 185                 190

Met Ser Asp Arg Arg Ser Leu His Leu Glu Ala Ser Leu Asp Lys Glu
        195                 200                 205

Leu Tyr Tyr His Gly Glu Pro Leu Asn Val Asn Val His Val Thr Asn
```

Asn Ser Ala Lys Thr Val Lys Lys Ile Arg Val Ser Val Arg Gln Tyr
225                 230                 235                 240

Ala Asp Ile Cys Leu Phe Ser Thr Ala Gln Tyr Lys Cys Pro Val Ala
            245                 250                 255

Gln Leu Glu Gln Asp Asp Gln Val Ser Pro Ser Ser Thr Phe Cys Lys
        260                 265                 270

Val Tyr Thr Ile Thr Pro Leu Leu Ser Asp Asn Arg Glu Lys Arg Gly
            275                 280                 285

Leu Ala Leu Asp Gly Gln Leu Lys His Glu Asp Thr Asn Leu Ala Ser
        290                 295                 300

Ser Thr Ile Val Lys Glu Gly Ala Asn Lys Glu Val Leu Gly Ile Leu
305                 310                 315                 320

Val Ser Tyr Arg Val Lys Val Lys Leu Val Val Ser Arg Gly Gly Asp
            325                 330                 335

Val Ser Val Glu Leu Pro Phe Val Leu Met His Pro Lys Pro His Asp
        340                 345                 350

His Ile Thr Leu Pro Arg Pro Gln Ser Ala Pro Arg Glu Ile Asp Ile
            355                 360                 365

Pro Val Asp Thr Asn Leu Ile Glu Phe Asp Thr Asn Tyr Ala Thr Asp
    370                 375                 380

Asp Asp Ile Val Phe Glu Asp Phe Ala Arg Leu Arg Leu Lys Gly Met
385                 390                 395                 400

Lys Asp Asp Asp Cys Asp Asp Gln Phe Cys Leu Ser Ser Leu Glu Gly
            405                 410                 415

Gly Gly Gly Ser Gly Gly Gly Ser Gly Gly Gly Ile Glu Gly
        420                 425                 430

Met Gly Glu Ser Leu Phe Lys Gly Pro Arg Asp Tyr Asn Pro Ile Ser
            435                 440                 445

Ser Thr Ile Cys His Leu Thr Asn Glu Ser Asp Gly His Thr Thr Ser
        450                 455                 460

Leu Tyr Gly Ile Gly Phe Gly Pro Phe Ile Ile Thr Asn Lys His Leu
465                 470                 475                 480

Phe Arg Arg Asn Asn Gly Thr Leu Leu Val Gln Ser Leu His Gly Val
            485                 490                 495

Phe Lys Val Lys Asn Thr Thr Thr Leu Gln Gln His Leu Ile Asp Gly
        500                 505                 510

Arg Asp Met Ile Ile Ile Arg Met Pro Lys Asp Phe Pro Pro Phe Pro
        515                 520                 525

Gln Lys Leu Lys Phe Arg Glu Pro Gln Arg Glu Glu Arg Ile Cys Leu
        530                 535                 540

Val Thr Thr Asn Phe Gln
545                 550

<210> SEQ ID NO 69
<211> LENGTH: 1887
<212> TYPE: DNA
<213> ORGANISM: Artificial Sequence
<220> FEATURE:
<223> OTHER INFORMATION: CRY2PHR ? TEV-C

<400> SEQUENCE: 69
cttcaacttc ctcctcttga acgtcttact ctcgaggcca ccatgaagat ggacaaaaag      60
actatagttt ggtttagaag agacctaagg attgaggata atcctgcatt agcagcagct     120

```
gctcacgaag gatctgtttt tcctgtcttc atttggtgtc ctgaagaaga aggacagttt    180
tatcctggaa gagcttcaag atggtggatg aaacaatcac ttgctcactt atctcaatcc    240
ttgaaggctc ttggatctga cctcactttta atcaaaaccc acaacacgat ttcagcgatc    300
ttggattgta tccgcgttac cggtgctaca aaagtcgtct ttaaccacct ctatgatcct    360
gtttcgttag ttcgggacca taccgtaaag gagaagctgg tggaacgtgg gatctctgtg    420
caaagctaca atggagatct attgtatgaa ccgtgggaga tatactgcga aaagggcaaa    480
ccttttacga gtttcaattc ttactggaag aaatgcttag atatgtcgat tgaatccgtt    540
atgcttcctc ctccttggcg gttgatgcca ataactgcag cggctgaagc gatttgggcg    600
tgttcgattg aagaactagg gctggagaat gaggccgaga accgagcaa tgcgttgtta    660 actagagctt ggtctccagg atggagcaat gctgataagt tactaaatga gttcatcgag    720
aagcagttga tagattatgc aaagaacagc aagaaagttg ttgggaattc tacttcacta    780 cttctccgt atctccattt cggggaaata agcgtcagac acgttttcca gtgtgcccgg    840
atgaaacaaa ttatatgggc aagagataag aacagtgaag gagaagaaag tgcagatctt    900
tttcttaggg gaatcggttt aagagagtat tctcggtata tatgttttca acttcccgttt    960 actcacgagc aatcgttgtt gagtcatctt cggttttttcc cttgggatgc tgatgttgat   1020
aagttcaagg cctggagaca aggcaggacc ggttatccgt tggtggatgc cggaatgaga   1080
gagctttggg ctaccggatg gatgcataac agaataagag tgattgtttc aagctttgct   1140
gtgaagtttc ttctccttcc atggaaatgg ggaatgaagt atttctggga tacacttttg   1200
gatgctgatt tggaatgtga catccttggc tggcagtata tctctgggag tatccccgat   1260
ggccacgagc ttgatcgctt ggacaatccc gcgttacaag gcgccaaata tgacccagaa   1320
ggtgagtaca taaggcaatg gcttcccgag cttgcgagat tgccaactga atggatccat   1380
catccatggg acgctccttt aaccgtactc aaagcttctg gtgtggaact cggaacaaac   1440
tatgcgaaac ccattgtaga catcgacaca gctcgtgagc tactagctaa agctatttca   1500
agaacccgtg aagcacagat catgatcgga gcagcactgc aggagctcgg tggaggcggc   1560
cgctccggtg gcggtggctc tactaagagc atgtccagca tggtgagcga tactagctgt   1620
accttcccat catctgacgg aatcttctgg aagcactgga ttcagactaa ggacggccag   1680
tgtggcagcc cactggtgag cacacgagac ggattcatcg tggggattca cagcgcctcc   1740
aactttacaa acaccaataa ctatttcacc tcagtgccaa agaactttat ggagctgctg   1800
accaaccagg aggcccagca gtgggtgagc gggtggcgcc tgaacgccga ttccgtgctg   1860
tggggcgggc acaaggtgtt tatggtg                                       1887
```

<210> SEQ ID NO 70
<211> LENGTH: 630
<212> TYPE: PRT
<213> ORGANISM: Artificial Sequence
<220> FEATURE:
<223> OTHER INFORMATION: CRY2PHR ? TEV-C

<400> SEQUENCE: 70

```
Met Leu Gln Leu Pro Pro Leu Glu Arg Leu Thr Leu Glu Ala Thr Met
1               5                   10                  15

Lys Met Asp Lys Lys Thr Ile Val Trp Phe Arg Arg Asp Leu Arg Ile
            20                  25                  30

Glu Asp Asn Pro Ala Leu Ala Ala Ala His Glu Gly Ser Val Phe
        35                  40                  45
```

-continued

```
Pro Val Phe Ile Trp Cys Pro Glu Glu Gly Gln Phe Tyr Pro Gly
    50                  55                  60

Arg Ala Ser Arg Trp Trp Met Lys Gln Ser Leu Ala His Leu Ser Gln
65                  70                  75                  80

Ser Leu Lys Ala Leu Gly Ser Asp Leu Thr Leu Ile Lys Thr His Asn
                85                  90                  95

Thr Ile Ser Ala Ile Leu Asp Cys Ile Arg Val Thr Gly Ala Thr Lys
            100                 105                 110

Val Val Phe Asn His Leu Tyr Asp Pro Val Ser Leu Val Arg Asp His
                115                 120                 125

Thr Val Lys Glu Lys Leu Val Glu Arg Gly Ile Ser Val Gln Ser Tyr
130                 135                 140

Asn Gly Asp Leu Leu Tyr Glu Pro Trp Glu Ile Tyr Cys Glu Lys Gly
145                 150                 155                 160

Lys Pro Phe Thr Ser Phe Asn Ser Tyr Trp Lys Lys Cys Leu Asp Met
                165                 170                 175

Ser Ile Glu Ser Val Met Leu Pro Pro Trp Arg Leu Met Pro Ile
            180                 185                 190

Thr Ala Ala Glu Ala Ile Trp Ala Cys Ser Ile Glu Glu Leu Gly
            195                 200                 205

Leu Glu Asn Glu Ala Glu Lys Pro Ser Asn Ala Leu Leu Thr Arg Ala
210                 215                 220

Trp Ser Pro Gly Trp Ser Asn Ala Asp Lys Leu Leu Asn Glu Phe Ile
225                 230                 235                 240

Glu Lys Gln Leu Ile Asp Tyr Ala Lys Asn Ser Lys Lys Val Val Gly
                245                 250                 255

Asn Ser Thr Ser Leu Leu Ser Pro Tyr Leu His Phe Gly Glu Ile Ser
                260                 265                 270

Val Arg His Val Phe Gln Cys Ala Arg Met Lys Gln Ile Ile Trp Ala
            275                 280                 285

Arg Asp Lys Asn Ser Glu Gly Glu Glu Ser Ala Asp Leu Phe Leu Arg
290                 295                 300

Gly Ile Gly Leu Arg Glu Tyr Ser Arg Tyr Ile Cys Phe Asn Phe Pro
305                 310                 315                 320

Phe Thr His Glu Gln Ser Leu Leu Ser His Leu Arg Phe Phe Pro Trp
                325                 330                 335

Asp Ala Asp Val Asp Lys Phe Lys Ala Trp Arg Gln Gly Arg Thr Gly
                340                 345                 350

Tyr Pro Leu Val Asp Ala Gly Met Arg Glu Leu Trp Ala Thr Gly Trp
                355                 360                 365

Met His Asn Arg Ile Arg Val Ile Val Ser Ser Phe Ala Val Lys Phe
370                 375                 380

Leu Leu Leu Pro Trp Lys Trp Gly Met Lys Tyr Phe Trp Asp Thr Leu
385                 390                 395                 400

Leu Asp Ala Asp Leu Glu Cys Asp Ile Leu Gly Trp Gln Tyr Ile Ser
                405                 410                 415

Gly Ser Ile Pro Asp Gly His Glu Leu Asp Arg Leu Asp Asn Pro Ala
                420                 425                 430

Leu Gln Gly Ala Lys Tyr Asp Pro Glu Gly Glu Tyr Ile Arg Gln Trp
                435                 440                 445

Leu Pro Glu Leu Ala Arg Leu Pro Thr Glu Trp Ile His His Pro Trp
450                 455                 460

Asp Ala Pro Leu Thr Val Leu Lys Ala Ser Gly Val Glu Leu Gly Thr
```

```
                465                 470                 475                 480
Asn Tyr Ala Lys Pro Ile Val Asp Ile Asp Thr Ala Arg Glu Leu Leu
                    485                 490                 495
Ala Lys Ala Ile Ser Arg Thr Arg Glu Ala Gln Ile Met Ile Gly Ala
                500                 505                 510
Ala Leu Gln Glu Leu Gly Gly Gly Gly Arg Ser Gly Gly Gly Gly Ser
            515                 520                 525
Thr Lys Ser Met Ser Ser Met Val Ser Asp Ser Cys Thr Phe Pro
        530                 535                 540
Ser Ser Asp Gly Ile Phe Trp Lys His Trp Ile Gln Thr Lys Asp Gly
545                 550                 555                 560
Gln Cys Gly Ser Pro Leu Val Ser Thr Arg Asp Gly Phe Ile Val Gly
                565                 570                 575
Ile His Ser Ala Ser Asn Phe Thr Asn Thr Asn Tyr Phe Thr Ser
                580                 585                 590
Val Pro Lys Asn Phe Met Glu Leu Leu Thr Asn Gln Glu Ala Gln Gln
            595                 600                 605
Trp Val Ser Gly Trp Arg Leu Asn Ala Asp Ser Val Leu Trp Gly Gly
        610                 615                 620
His Lys Val Phe Met Val
625                 630

<210> SEQ ID NO 71
<211> LENGTH: 1332
<212> TYPE: DNA
<213> ORGANISM: Artificial Sequence
<220> FEATURE:
<223> OTHER INFORMATION: DRD2 (Dopamine receptor D2)

<400> SEQUENCE: 71
atggatccac tgaacctgtc ctggtacgat gacgatctgg agaggcagaa ctggagccgg     60
cccttcaatg ggtcagaagg gaaggcagac aggccccact acaactacta tgccatgctg    120
ctcacccctc tcatctttat catcgtcttt ggcaatgtgc tggtgtgcat ggctgtatcc    180
cgagagaagg ctttgcagac caccaccaac tacttgatag tcagccttgc cgtggctgat    240
cttctggtgg ccacactggt aatgccgtgg gttgtctacc tggaggtggt gggtgagtgg    300
aaattcagca ggattcactg tgacatcttt gtcactctgg atgtcatgat gtgcacagca    360
agcatcctga acctgtgtgc catcagcatt gacaggtaca gctgtggc aatgcccatg    420
ctgtataaca cacgctacag ctccaagcgc gagttactg tcatgattgc cattgtctgg    480
gtcctgtcct tcaccatctc ctgcccactg ctcttcggac tcaacaatac agaccagaat    540
gagtgtatca ttgccaaccc tgcctttgtg gtctactcct ccattgtctc attctacgtg    600
cccttcatcg tcactctgct ggtctatatc aaaatctaca tcgtcctccg gaagcgccgg    660
aagcgggtca acaccaagcg cagcagtcga gctttcagag ccaacctgaa gacaccactc    720
aagggcaact gtacccaccc tgaggacatg aaactctgca ccgttatcat gaagtctaat    780
gggagtttcc cagtgaacag gcggagaatg gatgctgccc gccgagctca ggagctggaa    840
atggagatgc tgtcaagcac cagtccccca gagaggaccc ggtatagccc catccctccc    900
agtcaccacc agctcactct ccctgatcca tccaccacg gcctacatag caaccctgac    960
agtcctgcca aaccagagaa gaatgggcac gccaagattg tcaatccag gattgccaag   1020
ttctttgaga tccagaccat gcccaatggc aaaacccgga cctcccttaa gacgatgagc   1080
cgcagaaagc tctcccagca gaaggagaag aaagccactc agatgcttgc cattgttctc   1140
```

```
ggtgtgttca tcatctgctg gctgcccttc ttcatcacgc acatcctgaa tatacactgt    1200
gattgcaaca tcccaccagt cctctacagc gccttcacat ggctgggcta tgtcaacagt    1260
gccgtcaacc ccatcatcta caccaccttc aacatcgagt ccgcaaggc cttcatgaag    1320 atcttgcact gc                                                        1332
```

<210> SEQ ID NO 72
<211> LENGTH: 444
<212> TYPE: PRT
<213> ORGANISM: Artificial Sequence
<220> FEATURE:
<223> OTHER INFORMATION: DRD2 (Dopamine receptor D2)

<400> SEQUENCE: 72

```
Met Asp Pro Leu Asn Leu Ser Trp Tyr Asp Asp Leu Glu Arg Gln
1               5                  10                  15

Asn Trp Ser Arg Pro Phe Asn Gly Ser Glu Gly Lys Ala Asp Arg Pro
            20                  25                  30

His Tyr Asn Tyr Tyr Ala Met Leu Leu Thr Leu Leu Ile Phe Ile Ile
            35                  40                  45

Val Phe Gly Asn Val Leu Val Cys Met Ala Val Ser Arg Glu Lys Ala
    50                  55                  60

Leu Gln Thr Thr Thr Asn Tyr Leu Ile Val Ser Leu Ala Val Ala Asp
65                  70                  75                  80

Leu Leu Val Ala Thr Leu Val Met Pro Trp Val Val Tyr Leu Glu Val
                85                  90                  95

Val Gly Glu Trp Lys Phe Ser Arg Ile His Cys Asp Ile Phe Val Thr
            100                 105                 110

Leu Asp Val Met Met Cys Thr Ala Ser Ile Leu Asn Leu Cys Ala Ile
            115                 120                 125

Ser Ile Asp Arg Tyr Thr Ala Val Ala Met Pro Met Leu Tyr Asn Thr
        130                 135                 140

Arg Tyr Ser Ser Lys Arg Arg Val Thr Val Met Ile Ala Ile Val Trp
145                 150                 155                 160

Val Leu Ser Phe Thr Ile Ser Cys Pro Leu Leu Phe Gly Leu Asn Asn
                165                 170                 175

Thr Asp Gln Asn Glu Cys Ile Ile Ala Asn Pro Ala Phe Val Val Tyr
            180                 185                 190

Ser Ser Ile Val Ser Phe Tyr Val Pro Phe Ile Val Thr Leu Leu Val
        195                 200                 205

Tyr Ile Lys Ile Tyr Ile Val Leu Arg Lys Arg Arg Lys Arg Val Asn
        210                 215                 220

Thr Lys Arg Ser Ser Arg Ala Phe Arg Ala Asn Leu Lys Thr Pro Leu
225                 230                 235                 240

Lys Gly Asn Cys Thr His Pro Glu Asp Met Lys Leu Cys Thr Val Ile
                245                 250                 255

Met Lys Ser Asn Gly Ser Phe Pro Val Asn Arg Arg Arg Met Asp Ala
            260                 265                 270

Ala Arg Arg Ala Gln Glu Leu Glu Met Glu Met Leu Ser Ser Thr Ser
        275                 280                 285

Pro Pro Glu Arg Thr Arg Tyr Ser Pro Ile Pro Pro Ser His His Gln
        290                 295                 300

Leu Thr Leu Pro Asp Pro Ser His His Gly Leu His Ser Asn Pro Asp
305                 310                 315                 320
```

```
Ser Pro Ala Lys Pro Glu Lys Asn Gly His Ala Lys Ile Val Asn Pro
                325                 330                 335

Arg Ile Ala Lys Phe Phe Glu Ile Gln Thr Met Pro Asn Gly Lys Thr
            340                 345                 350

Arg Thr Ser Leu Lys Thr Met Ser Arg Arg Lys Leu Ser Gln Gln Lys
        355                 360                 365

Glu Lys Lys Ala Thr Gln Met Leu Ala Ile Val Leu Gly Val Phe Ile
    370                 375                 380

Ile Cys Trp Leu Pro Phe Phe Ile Thr His Ile Leu Asn Ile His Cys
385                 390                 395                 400

Asp Cys Asn Ile Pro Pro Val Leu Tyr Ser Ala Phe Thr Trp Leu Gly
                405                 410                 415

Tyr Val Asn Ser Ala Val Asn Pro Ile Ile Tyr Thr Thr Phe Asn Ile
            420                 425                 430

Glu Phe Arg Lys Ala Phe Met Lys Ile Leu His Cys
        435                 440

<210> SEQ ID NO 73
<211> LENGTH: 1431
<212> TYPE: DNA
<213> ORGANISM: Artificial Sequence
<220> FEATURE:
<223> OTHER INFORMATION: TdTomato

<400> SEQUENCE: 73
atggtgagca agggcgagga ggtcatcaaa gagttcatgc gcttcaaggt gcgcatggag      60
ggctccatga acggccacga gttcgagatc gagggcgagg cgagggccg ccctacgag      120 ggcacccaga ccgccaagct gaaggtgacc aagggcggcc ccctgccctt cgcctgggac      180
atcctgtccc cccagttcat gtacggctcc aaggcgtacg tgaagcaccc cgccgacatc      240
cccgattaca agaagctgtc cttccccgag ggcttcaagt gggagcgcgt gatgaacttc      300
gaggacggcg gtctggtgac cgtgacccag gactcctccc tgcaggacgg cacgctgatc      360
tacaaggtga agatgcgcgg caccaacttc cccccgacg gccccgtaat gcagaagaag      420
accatgggct gggaggcctc caccgagcgc ctgtaccccc gcgacggcgt gctgaagggc      480
gagatccacc aggccctgaa gctgaaggac ggcggccgct acctggtgga gttcaagacc      540
atctacatgg ccaagaagcc cgtgcaactg cccggctact actacgtgga caccaagctg      600
gacatcacct cccacaacga ggactacacc atcgtggaac agtacgagcg ctccgagggc      660
cgccaccacc tgttcctggg catggacacc ggcagcaccg gcagcggcag ttccggcacc      720
gcctcctccg aggacaacaa catggccgtc atcaaagagt tcatgcgctt caaggtgcgc      780
atggagggct ccatgaacgg ccacgagttc gagatcgagg gcgagggcga gggccgcccc      840
tacgagggca cccagaccgc caagctgaag gtgaccaagg gcggccccct gcccttcgcc      900
tgggacatcc tgtcccccca gttcatgtac ggctccaagg cgtacgtgaa gcaccccgcc      960
gacatccccg attacaagaa gctgtccttc cccgagggct tcaagtggga gcgcgtgatg     1020
aacttcgagg acggcggtct ggtgaccgtg acccaggact cctccctgca ggacggcacg     1080
ctgatctaca aggtgaagat gcgcggcacc aacttccccc cgacggccc cgtaatgcag     1140 aagaagacca tgggctggga ggcctccacc gagcgcctgt accccgcga cggcgtgctg     1200 aagggcgaga tccaccaggc cctgaagctg aaggacggcg gccgctacct ggtggagttc     1260
aagaccatct acatggccaa gaagcccgtg caactgcccg gctactacta cgtggacacc     1320
aagctggaca tcacctccca caacgaggac tacaccatcg tggaacagta cgagcgctcc     1380
```

```
gagggccgcc accacctgtt cctgtacggc atggacgagc tgtacaagta g         1431
```

```
<210> SEQ ID NO 74
<211> LENGTH: 476
<212> TYPE: PRT
<213> ORGANISM: Artificial Sequence
<220> FEATURE:
<223> OTHER INFORMATION: TdTomato

<400> SEQUENCE: 74
```

| | | | | | | | | | | | | | | |
|---|---|---|---|---|---|---|---|---|---|---|---|---|---|---|
| Met | Val | Ser | Lys | Gly | Glu | Glu | Val | Ile | Lys | Glu | Phe | Met | Arg | Phe | Lys |
| 1 | | | | 5 | | | | | 10 | | | | | 15 | |
| Val | Arg | Met | Glu | Gly | Ser | Met | Asn | Gly | His | Glu | Phe | Glu | Ile | Glu | Gly |
| | | | 20 | | | | | 25 | | | | | 30 | | |
| Glu | Gly | Glu | Gly | Arg | Pro | Tyr | Glu | Gly | Thr | Gln | Thr | Ala | Lys | Leu | Lys |
| | | 35 | | | | | 40 | | | | | 45 | | | |
| Val | Thr | Lys | Gly | Gly | Pro | Leu | Pro | Phe | Ala | Trp | Asp | Ile | Leu | Ser | Pro |
| 50 | | | | | 55 | | | | | 60 | | | | | |
| Gln | Phe | Met | Tyr | Gly | Ser | Lys | Ala | Tyr | Val | Lys | His | Pro | Ala | Asp | Ile |
| 65 | | | | | 70 | | | | | 75 | | | | | 80 |
| Pro | Asp | Tyr | Lys | Lys | Leu | Ser | Phe | Pro | Glu | Gly | Phe | Lys | Trp | Glu | Arg |
| | | | | 85 | | | | | 90 | | | | | 95 | |
| Val | Met | Asn | Phe | Glu | Asp | Gly | Gly | Leu | Val | Thr | Val | Thr | Gln | Asp | Ser |
| | | | 100 | | | | | 105 | | | | | 110 | | |
| Ser | Leu | Gln | Asp | Gly | Thr | Leu | Ile | Tyr | Lys | Val | Lys | Met | Arg | Gly | Thr |
| | | 115 | | | | | 120 | | | | | 125 | | | |
| Asn | Phe | Pro | Pro | Asp | Gly | Pro | Val | Met | Gln | Lys | Lys | Thr | Met | Gly | Trp |
| 130 | | | | | 135 | | | | | 140 | | | | | |
| Glu | Ala | Ser | Thr | Glu | Arg | Leu | Tyr | Pro | Arg | Asp | Gly | Val | Leu | Lys | Gly |
| 145 | | | | | 150 | | | | | 155 | | | | | 160 |
| Glu | Ile | His | Gln | Ala | Leu | Lys | Leu | Lys | Asp | Gly | Gly | Arg | Tyr | Leu | Val |
| | | | | 165 | | | | | 170 | | | | | 175 | |
| Glu | Phe | Lys | Thr | Ile | Tyr | Met | Ala | Lys | Lys | Pro | Val | Gln | Leu | Pro | Gly |
| | | | 180 | | | | | 185 | | | | | 190 | | |
| Tyr | Tyr | Tyr | Val | Asp | Thr | Lys | Leu | Asp | Ile | Thr | Ser | His | Asn | Glu | Asp |
| | | 195 | | | | | 200 | | | | | 205 | | | |
| Tyr | Thr | Ile | Val | Glu | Gln | Tyr | Glu | Arg | Ser | Glu | Gly | Arg | His | His | Leu |
| 210 | | | | | 215 | | | | | 220 | | | | | |
| Phe | Leu | Gly | His | Gly | Thr | Gly | Ser | Thr | Gly | Ser | Gly | Ser | Ser | Gly | Thr |
| 225 | | | | | 230 | | | | | 235 | | | | | 240 |
| Ala | Ser | Ser | Glu | Asp | Asn | Asn | Met | Ala | Val | Ile | Lys | Glu | Phe | Met | Arg |
| | | | | 245 | | | | | 250 | | | | | 255 | |
| Phe | Lys | Val | Arg | Met | Glu | Gly | Ser | Met | Asn | Gly | His | Glu | Phe | Glu | Ile |
| | | | 260 | | | | | 265 | | | | | 270 | | |
| Glu | Gly | Glu | Gly | Glu | Gly | Arg | Pro | Tyr | Glu | Gly | Thr | Gln | Thr | Ala | Lys |
| | | 275 | | | | | 280 | | | | | 285 | | | |
| Leu | Lys | Val | Thr | Lys | Gly | Gly | Pro | Leu | Pro | Phe | Ala | Trp | Asp | Ile | Leu |
| | 290 | | | | | 295 | | | | | 300 | | | | |
| Ser | Pro | Gln | Phe | Met | Tyr | Gly | Ser | Lys | Ala | Tyr | Val | Lys | His | Pro | Ala |
| 305 | | | | | 310 | | | | | 315 | | | | | 320 |
| Asp | Ile | Pro | Asp | Tyr | Lys | Lys | Leu | Ser | Phe | Pro | Glu | Gly | Phe | Lys | Trp |
| | | | | 325 | | | | | 330 | | | | | 335 | |
| Glu | Arg | Val | Met | Asn | Phe | Glu | Asp | Gly | Gly | Leu | Val | Thr | Val | Thr | Gln |
| | | | 340 | | | | | 345 | | | | | 350 | | |

```
Asp Ser Ser Leu Gln Asp Gly Thr Leu Ile Tyr Lys Val Lys Met Arg
            355                 360                 365
Gly Thr Asn Phe Pro Pro Asp Gly Pro Val Met Gln Lys Lys Thr Met
        370                 375                 380
Gly Trp Glu Ala Ser Thr Glu Arg Leu Tyr Pro Arg Asp Gly Val Leu
385                 390                 395                 400
Lys Gly Glu Ile His Gln Ala Leu Lys Leu Lys Asp Gly Gly Arg Tyr
                405                 410                 415
Leu Val Glu Phe Lys Thr Ile Tyr Met Ala Lys Lys Pro Val Gln Leu
            420                 425                 430
Pro Gly Tyr Tyr Tyr Val Asp Thr Lys Leu Asp Ile Thr Ser His Asn
        435                 440                 445
Glu Asp Tyr Thr Ile Val Glu Gln Tyr Glu Arg Ser Glu Gly Arg His
    450                 455                 460
His Leu Phe Leu Tyr Gly Met Asp Glu Leu Tyr Lys
465                 470                 475

<210> SEQ ID NO 75
<211> LENGTH: 37
<212> TYPE: DNA
<213> ORGANISM: Artificial Sequence
<220> FEATURE:
<223> OTHER INFORMATION: primer XhoI-CIBN-FW

<400> SEQUENCE: 75
attctcgagg gtggaatgaa tggagctata ggaggtg                            37

<210> SEQ ID NO 76
<211> LENGTH: 30
<212> TYPE: DNA
<213> ORGANISM: Artificial Sequence
<220> FEATURE:
<223> OTHER INFORMATION: primer CIBN-SphI-RV

<400> SEQUENCE: 76
tttgcatgca tgaatataat ccgttttctc                                    30

<210> SEQ ID NO 77
<211> LENGTH: 35
<212> TYPE: DNA
<213> ORGANISM: Artificial Sequence
<220> FEATURE:
<223> OTHER INFORMATION: primer SacI-AsLOV2 FW

<400> SEQUENCE: 77
aaagagctcg gtagtggtag tggggagttt ctggc                              35

<210> SEQ ID NO 78
<211> LENGTH: 62
<212> TYPE: DNA
<213> ORGANISM: Artificial Sequence
<220> FEATURE:
<223> OTHER INFORMATION: primer BLITz-1-TEV-XbaI-RV

<400> SEQUENCE: 78
ttttctagag ccctggaagt acaggttctc agcaatctga aaggctgtct ttttgatcag   60
gc                                                                  62

<210> SEQ ID NO 79
<211> LENGTH: 60
<212> TYPE: DNA
<213> ORGANISM: Artificial Sequence
```

<220> FEATURE:
<223> OTHER INFORMATION: primer BLITz-2-TEV-XbaI-RV

<400> SEQUENCE: 79
ttttctagag ccctggaagt acaggttctc aaaggctgtc tttttgatca ggcagaccgc    60

<210> SEQ ID NO 80
<211> LENGTH: 40
<212> TYPE: DNA
<213> ORGANISM: Artificial Sequence
<220> FEATURE:
<223> OTHER INFORMATION: primer BLITz-3-TEV-XbaI-RV

<400> SEQUENCE: 80
atctagagcc ctggaagtac aaattttcgt cgttcgctgc    40

<210> SEQ ID NO 81
<211> LENGTH: 36
<212> TYPE: DNA
<213> ORGANISM: Artificial Sequence
<220> FEATURE:
<223> OTHER INFORMATION: primer XbaI-tTA-FW

<400> SEQUENCE: 81
atgtctagat tagataaaag taaagtgatt aacagc    36

<210> SEQ ID NO 82
<211> LENGTH: 36
<212> TYPE: DNA
<213> ORGANISM: Artificial Sequence
<220> FEATURE:
<223> OTHER INFORMATION: primer tTA-NheI-RV

<400> SEQUENCE: 82
tttgctagcc tacccaccgt actcgtcaat tccaag    36

<210> SEQ ID NO 83
<211> LENGTH: 38
<212> TYPE: DNA
<213> ORGANISM: Artificial Sequence
<220> FEATURE:
<223> OTHER INFORMATION: primer BLITz-4-FW

<400> SEQUENCE: 83
cctttcagat tgctgaggct gagaacctgt acttccag    38

<210> SEQ ID NO 84
<211> LENGTH: 40
<212> TYPE: DNA
<213> ORGANISM: Artificial Sequence
<220> FEATURE:
<223> OTHER INFORMATION: primer BLITz-4-RV

<400> SEQUENCE: 84
caggttctca gcctcagcaa tctgaaaggc tgtctttttg    40

<210> SEQ ID NO 85
<211> LENGTH: 40
<212> TYPE: DNA
<213> ORGANISM: Artificial Sequence
<220> FEATURE:
<223> OTHER INFORMATION: primer BLITz-5-FW

<400> SEQUENCE: 85
cagattgctg aggccctgta cttccagggc tctagattag    40

<210> SEQ ID NO 86
<211> LENGTH: 40
<212> TYPE: DNA
<213> ORGANISM: Artificial Sequence
<220> FEATURE:
<223> OTHER INFORMATION: primer BLITz-5-RV

<400> SEQUENCE: 86
gaagtacagg gcctcagcaa tctgaaaggc tgtcttttg    40

<210> SEQ ID NO 87
<211> LENGTH: 38
<212> TYPE: DNA
<213> ORGANISM: Artificial Sequence
<220> FEATURE:
<223> OTHER INFORMATION: primer BLITz-6-FW

<400> SEQUENCE: 87
gcctttcaga ttgagaacct gtacttccag ggctctag    38

<210> SEQ ID NO 88
<211> LENGTH: 38
<212> TYPE: DNA
<213> ORGANISM: Artificial Sequence
<220> FEATURE:
<223> OTHER INFORMATION: primer BLITz-6-RV

<400> SEQUENCE: 88
caggttctca atctgaaagg ctgtcttttt gatcaggc    38

<210> SEQ ID NO 89
<211> LENGTH: 35
<212> TYPE: DNA
<213> ORGANISM: Artificial Sequence
<220> FEATURE:
<223> OTHER INFORMATION: primer XhoI-CRY2PHR-FW

<400> SEQUENCE: 89
aaactcgagg ccaccatgaa gatggacaaa aagac    35

<210> SEQ ID NO 90
<211> LENGTH: 30
<212> TYPE: DNA
<213> ORGANISM: Artificial Sequence
<220> FEATURE:
<223> OTHER INFORMATION: primer CRY2PHR-PstI-RV

<400> SEQUENCE: 90
tttgctagct gctgctccga tcatgatctg    30

<210> SEQ ID NO 91
<211> LENGTH: 27
<212> TYPE: DNA
<213> ORGANISM: Artificial Sequence
<220> FEATURE:
<223> OTHER INFORMATION: primer SphI-AsLOV2-FW

<400> SEQUENCE: 91
aaagcatgcg gtagtggtag tggggag    27

<210> SEQ ID NO 92
<211> LENGTH: 36
<212> TYPE: DNA
<213> ORGANISM: Artificial Sequence
<220> FEATURE:
<223> OTHER INFORMATION: primer tTA-NheI-RV

<400> SEQUENCE: 92
tttgctagcc tacccaccgt actcgtcaat tccaag                36

<210> SEQ ID NO 93
<211> LENGTH: 33
<212> TYPE: DNA
<213> ORGANISM: Artificial Sequence
<220> FEATURE:
<223> OTHER INFORMATION: primer BamHI-DRD2-FW

<400> SEQUENCE: 93
tttaagctta tggatccact gaacctgtcc tgg                   33

<210> SEQ ID NO 94
<211> LENGTH: 34
<212> TYPE: DNA
<213> ORGANISM: Artificial Sequence
<220> FEATURE:
<223> OTHER INFORMATION: primer DRD2-EcoRI-RV

<400> SEQUENCE: 94
tttgaattcg cagtgcaaga tcttcatgaa ggcc                  34

<210> SEQ ID NO 95
<211> LENGTH: 27
<212> TYPE: DNA
<213> ORGANISM: Artificial Sequence
<220> FEATURE:
<223> OTHER INFORMATION: primer EcoRI-TdTomato-FW

<400> SEQUENCE: 95
cctgaattca tggtgagcaa gggcgag                          27

<210> SEQ ID NO 96
<211> LENGTH: 28
<212> TYPE: DNA
<213> ORGANISM: Artificial Sequence
<220> FEATURE:
<223> OTHER INFORMATION: primer TdTomato-XbaI-RV

<400> SEQUENCE: 96
ctatctagac tacttgtaca gctcgtcc                         28

<210> SEQ ID NO 97
<211> LENGTH: 39
<212> TYPE: DNA
<213> ORGANISM: Artificial Sequence
<220> FEATURE:
<223> OTHER INFORMATION: primer SacI-LK-TEV-N-FW

<400> SEQUENCE: 97
aaagagctca ctcgaaggtg gcggtggctc tggaggtgg             39

<210> SEQ ID NO 98
<211> LENGTH: 32
<212> TYPE: DNA
<213> ORGANISM: Artificial Sequence
<220> FEATURE:
<223> OTHER INFORMATION: primer TEV-N-SphI RV

<400> SEQUENCE: 98
tttgcatgcc tgaaagtttg tggtcaccag ac                    32

<210> SEQ ID NO 99

```
<211> LENGTH: 34
<212> TYPE: DNA
<213> ORGANISM: Artificial Sequence
<220> FEATURE:
<223> OTHER INFORMATION: primer Hind3-?- Arr2-FW

<400> SEQUENCE: 99
tttaagctta tgggtgaaaa acccgggacc aggg                              34

<210> SEQ ID NO 100
<211> LENGTH: 35
<212> TYPE: DNA
<213> ORGANISM: Artificial Sequence
<220> FEATURE:
<223> OTHER INFORMATION: primer ?-Arr2-SacI-RV

<400> SEQUENCE: 100
aaagagctca ggcagaactg gtcatcacag tcgtc                             35

<210> SEQ ID NO 101
<211> LENGTH: 35
<212> TYPE: DNA
<213> ORGANISM: Artificial Sequence
<220> FEATURE:
<223> OTHER INFORMATION: primer XhoI-TEV-N FW

<400> SEQUENCE: 101
aaactcgagg gtatgggcga gagcctgttc aaggg                             35

<210> SEQ ID NO 102
<211> LENGTH: 62
<212> TYPE: DNA
<213> ORGANISM: Artificial Sequence
<220> FEATURE:
<223> OTHER INFORMATION: primer BLITz-1-TEV-XbaI-RV

<400> SEQUENCE: 102
ttttctagag ccctggaagt acaggttctc agcaatctga aggctgtct ttttgatcag   60 gc                                                                 62

<210> SEQ ID NO 103
<211> LENGTH: 37
<212> TYPE: DNA
<213> ORGANISM: Artificial Sequence
<220> FEATURE:
<223> OTHER INFORMATION: primer SacI-TEV-C-FW

<400> SEQUENCE: 103
aaagagctca ggtggcggtg gctctggagg tggtggg                           37

<210> SEQ ID NO 104
<211> LENGTH: 34
<212> TYPE: DNA
<213> ORGANISM: Artificial Sequence
<220> FEATURE:
<223> OTHER INFORMATION: primer TEV-C-SphI-RV

<400> SEQUENCE: 104
tttgcatgca ccccggcgcc tcctgcgatt catc                              34

<210> SEQ ID NO 105
<211> LENGTH: 28
<212> TYPE: DNA
<213> ORGANISM: Artificial Sequence
<220> FEATURE:
<223> OTHER INFORMATION: primer EcoRI-EGFP-FW
```

```
<400> SEQUENCE: 105
cctgaattca tggtgagcaa gggcgagg                                          28

<210> SEQ ID NO 106
<211> LENGTH: 34
<212> TYPE: DNA
<213> ORGANISM: Artificial Sequence
<220> FEATURE:
<223> OTHER INFORMATION: primer EGFP-NheI-RV

<400> SEQUENCE: 106
taagctagcc tacttgtaca gctcgtccat gccg                                   34

<210> SEQ ID NO 107
<211> LENGTH: 354
<212> TYPE: DNA
<213> ORGANISM: Artificial Sequence
<220> FEATURE:
<223> OTHER INFORMATION: TEV-N

<400> SEQUENCE: 107
atgggcgaga gcctgttcaa gggacctagg gactacaacc ctatcagtag cacaatttgt       60
cacctgacca acgagagtga tggccacaca acaagcctgt acggcatcgg gttcggaccc      120
tttatcatca ccaacaagca cctgttcagg cggaataatg gcactctgct ggtgcagagc      180
ctgcacgggg tgttcaaagt gaagaacaca accactctgc agcagcacct gatcgatggg      240
cgggatatga tcatcattag gatgcccaag gacttccccc cttttcctca gaaactgaag      300
ttccgagagc cccagagaga ggagagaatc tgtctggtga ccacaaactt tcag            354

<210> SEQ ID NO 108
<211> LENGTH: 294
<212> TYPE: DNA
<213> ORGANISM: Artificial Sequence
<220> FEATURE:
<223> OTHER INFORMATION: TEV-C

<400> SEQUENCE: 108
atgtccagca tggtgagcga tactagctgt accttcccat catctgacgg aatcttctgg       60
aagcactgga ttcagactaa ggacggccag tgtggcagcc cactggtgag cacacgagac      120
ggattcatcg tggggattca cagcgcctcc aactttacaa acaccaataa ctatttcacc      180
tcagtgccaa agaactttat ggagctgctg accaaccagg aggcccagca gtgggtgagc      240
gggtggcgcc tgaacgccga ttccgtgctg tggggcgggc acaaggtgtt tatg            294
```